US007279316B2

(12) United States Patent
Short et al.

(10) Patent No.: US 7,279,316 B2
(45) Date of Patent: Oct. 9, 2007

(54) ENZYMES HAVING GLYCOSIDASE ACTIVITY AND METHODS OF USE THEREOF

(75) Inventors: Jay M. Short, Rancho Santa Fe, CA (US); Edward Bylina, San Diego, CA (US); Ronald V. Swanson, La Jolla, CA (US); Eric J. Mathur, Carlsbad, CA (US); David E. Lam, Carlsbad, CA (US)

(73) Assignee: Verenium Corporation, Cambridge, MA (US)

( * ) Notice: Subject to any disclaimer, the term of this patent is extended or adjusted under 35 U.S.C. 154(b) by 14 days.

(21) Appl. No.: 10/093,037

(22) Filed: Mar. 6, 2002

(65) Prior Publication Data

US 2003/0078397 A1 Apr. 24, 2003

Related U.S. Application Data

(63) Continuation of application No. 09/910,579, filed on Jul. 20, 2001, now abandoned, which is a continuation-in-part of application No. 09/134,078, filed on Aug. 13, 1998, now Pat. No. 6,368,844, which is a continuation of application No. 08/949,026, filed on Oct. 10, 1997, now abandoned.

(60) Provisional application No. 60/056,916, filed on Dec. 6, 1996.

(51) Int. Cl.
*C12N 9/00* (2006.01)
*C12N 9/44* (2006.01)
*C12P 21/06* (2006.01)
*C07H 21/04* (2006.01)

(52) U.S. Cl. .............................. 435/210; 435/4; 435/6; 435/69.1; 435/183; 435/200; 435/252.3; 435/320.1; 435/41; 435/262; 536/23.2; 536/23.4; 536/23.5; 536/23.74; 536/24.31

(58) Field of Classification Search .................... 435/4, 435/6, 69.1, 183, 200, 252–3, 320.1; 530/350; 536/23.2, 23.4, 23.7, 24.1, 24.31, 24.32, 536/24.33
See application file for complete search history.

(56) References Cited

U.S. PATENT DOCUMENTS

| 4,557,927 A | 12/1985 | Miyake et al. |
| 5,395,541 A | 3/1995 | Carpenter et al. |
| 5,731,174 A * | 3/1998 | DeWeer et al. ............... 435/99 |

FOREIGN PATENT DOCUMENTS

| WO | WO 97/20918 | 6/1997 |
| WO | WO 97/44361 | 11/1997 |

OTHER PUBLICATIONS

Bronnenmeier, et al., "Purification of *Thermotoga maritima* Enzymes for the Degradation of Cellulosic Materials", *Applied and Environmental Microbiology*, vol. 61, No. 4, pp. 1399-1407, Apr. 1995.

Canganella, et al., "Characterization of amylolytic and pullulytic enzymes from thermophilic archaea and from a new *Fervidobacterium* species", *Appl. Microbiol. Biotechnol.*, vol. 42, pp. 239-245, 1994.

Dakhova, et al., "*Thermotoga neapolitana* bg1A gene" EMBL Sequence Database, Jul. 1, 1997, AC Z97212.

Bauer, et al., "Beta mannosidase" EMBL Sequence Dataase Nov. 1, 1996, AC Q51733.

Dakhova, et al., "Cloning and Expression in *Escherichia coli* of *Thermotoga neapolitana* Genes Coding for Enzymes of Carbohydrate Substrate Degradation", *Biochemical and Biophysical Research Communications*, vol. 194, No. 3, pp. 1359-1364, 1993.

Bauer, et al., *Pyrococcus furiosus* beta-mannosidase (bmnA) gene, complete cds. AC U60214, Jul. 2, 1996.

Scheirlinck, et al., "Cloning and expression of cellulase and xylanase genes in *Lactobacillus plantarum*", *Appl. Microbiol. Biotechnol.*, vol. 33, No. 5, pp. 534-541, Oct. 1990.

Scheirlinck, et al., "Integratoin and Expression of α-Amylase and Endoglucanase Genes in the *Lactobacillus plantarum* Chromosome", *Applied and Environmental Microbiology*, vol. 55, No. , pp. 2130-2137, Sep. 1989.

Sim, et al., "Microbial Conversion of Spent Brewery Grains into Soluble Sugars and Proteins", *Microbial Utilization of Renewable Resources*, vol. 6, pp. 220-227, Mar. 1989.

Signoretti, et al., "Evaluation of Corn Germ Meal in the Feeding of Dairy Calves", *Revista Brasileira de Zootecnia*, vol. 26, No. 3, pp. 616-622, May-Jun. 1997 (English abstract only).

Bhat, "Cellulases and related enzymes in biotechnology", *Biotechnology Advances*, vol. 18, pp. 355-383, Jan. 2000.

Caransa et al., "A novel enzyme application for corn wet milling", Starch/Starke, Wiley-VCH Verlag, Weinheim, DE, vol. 40, No. II, 1988, pp. 409-411. XP002030182.

Cubellis et al, Gene 94:89-94 (1990).

Dakhova et al, "Cloning and expression of *Escherichia coli* of *Thermotoga neapolitana* genes coding for enzymes of carbohydrate substrate degradation", Biochem. Biophys. Res. Commun. 194:1359-1364 (1993), EMBL TNLAMABGL, XP002154623.

Liebl et al, "Comparative amino acid sequence analysis of *Thermotoga maritima* beta-glucosidase (BglA) deduced from the nucleotide sequence of the gene indicates distant relationship between beta-glucosidases of the BGA family and other families of beta-1,4-glycosyl hydrolases", Mol Gen Genet. Jan. 1994; 242(1):111-5.

(Continued)

*Primary Examiner*—Manjunath Rao
(74) *Attorney, Agent, or Firm*—Verenium Corporation; Lynn M. Linkowski

(57) ABSTRACT

The invention relates to glycosidases and to polynucleotides encoding the glycosidases. In addition methods of designing new glycosidases and method of use thereof are also provided. The glycosidases have increased activity and stability at increased pH and temperature.

50 Claims, 51 Drawing Sheets

OTHER PUBLICATIONS

Liebl, et al, "Analysis of a *Thermotoga maritima* DNA fragment encoding two similar thermostable cellulases, CelA and CelB, and characterization of the recombinant enzymes", Microbiology (Reading, Engl.) 142:2532-2542(1996), EMBL TMCELAB.

Stroeher, et al, "Serotype conversion in Vibrio cholerae O1", Proc. Natl. Acad. Sci. U.S.A. 89 (7), 2566-2570 (1992), Genbank X59554.1.

* cited by examiner

M11TL GLYCOSIDASE – 29G
COMPLETE GENE SEQUENCE – 9/95

| | | | | | | | | | | | | | | | | |
|---|---|---|---|---|---|---|---|---|---|---|---|---|---|---|---|---|
| TTG | AAA | TTC | CCC | AAA | GAC | TTC | ATG | ATA | GGC | TAC | TCA | TCT | TCA | CCG | TTT | 48 |
| Leu | Lys | Phe | Pro | Lys | Asp | Phe | Met | Ile | Gly | Tyr | Ser | Ser | Ser | Pro | Phe | |
| 1 | | | | 5 | | | | | 10 | | | | | 15 | | |
| CAA | TTT | GAA | GCT | GGT | ATT | CCC | GGG | TCC | GAG | GAT | CCG | AAT | AGT | GAT | TGG | 96 |
| Gln | Phe | Glu | Ala | Gly | Ile | Pro | Gly | Ser | Glu | Asp | Pro | Asn | Ser | Asp | Trp | |
| | | | | 20 | | | | | 25 | | | | | 30 | | |
| TGG | GTA | TGG | GTG | CAT | GAT | CCG | GAG | AAC | ACA | GCA | GCT | GGA | CTA | GTC | AGC | 144 |
| Trp | Val | Trp | Val | His | Asp | Pro | Glu | Asn | Thr | Ala | Ala | Gly | Leu | Val | Ser | |
| | | 35 | | | | | 40 | | | | | 45 | | | | |
| GGC | GAT | TTT | CCC | GAG | AAC | GGC | CCA | GGT | TAC | TGG | AAT | TTA | AAC | CAA | AAT | 192 |
| Gly | Asp | Phe | Pro | Glu | Asn | Gly | Pro | Gly | Tyr | Trp | Asn | Leu | Asn | Gln | Asn | |
| | 50 | | | | | 55 | | | | | 60 | | | | | |
| GAC | CAC | GAC | CTG | GCT | GAG | AAG | CTG | GGG | GTT | AAC | ACT | ATT | AGA | GTA | GGC | 240 |
| Asp | His | Asp | Leu | Ala | Glu | Lys | Leu | Gly | Val | Asn | Thr | Ile | Arg | Val | Gly | |
| 65 | | | | | 70 | | | | | 75 | | | | | 80 | |
| GTT | GAG | TGG | AGT | AGG | ATT | TTT | CCA | AAG | CCA | ACT | TTC | AAT | GTT | AAA | GTC | 288 |
| Val | Glu | Trp | Ser | Arg | Ile | Phe | Pro | Lys | Pro | Thr | Phe | Asn | Val | Lys | Val | |
| | | | | 85 | | | | | 90 | | | | | 95 | | |
| CCT | GTA | GAG | AGA | GAT | GAG | AAC | GGC | AGC | ATT | GTT | CAC | GTA | GAT | GTC | GAT | 336 |
| Pro | Val | Glu | Arg | Asp | Glu | Asn | Gly | Ser | Ile | Val | His | Val | Asp | Val | Asp | |
| | | | 100 | | | | | 105 | | | | | 110 | | | |
| GAT | AAA | GCG | GTT | GAA | AGA | CTT | GAT | GAA | TTA | GCC | AAC | AAG | GAG | GCC | GTA | 384 |
| Asp | Lys | Ala | Val | Glu | Arg | Leu | Asp | Glu | Leu | Ala | Asn | Lys | Glu | Ala | Val | |
| | | 115 | | | | | 120 | | | | | 125 | | | | |
| AAC | CAT | TAC | GTA | GAA | ATG | TAT | AAA | GAC | TGG | GTT | GAA | AGA | GGT | AGA | AAA | 432 |
| Asn | His | Tyr | Val | Glu | Met | Tyr | Lys | Asp | Trp | Val | Glu | Arg | Gly | Arg | Lys | |
| | 130 | | | | | 135 | | | | | 140 | | | | | |
| CTT | ATA | CTC | AAT | TTA | TAC | CAT | TGG | CCC | CTG | CCT | CTC | TGG | CTT | CAC | AAC | 480 |
| Leu | Ile | Leu | Asn | Leu | Tyr | His | Trp | Pro | Leu | Pro | Leu | Trp | Leu | His | Asn | |
| 145 | | | | | 150 | | | | | 155 | | | | | 160 | |
| CCA | ATC | ATG | GTG | AGA | AGA | ATG | GGC | CCG | GAC | AGA | GCG | CCC | TCA | GGC | TGG | 528 |
| Pro | Ile | Met | Val | Arg | Arg | Met | Gly | Pro | Asp | Arg | Ala | Pro | Ser | Gly | Trp | |
| | | | | 165 | | | | | 170 | | | | | 175 | | |
| CTT | AAC | GAG | GAG | TCC | GTG | GTG | GAG | TTT | GCC | AAA | TAC | GCC | GCA | TAC | ATT | 576 |
| Leu | Asn | Glu | Glu | Ser | Val | Val | Glu | Phe | Ala | Lys | Tyr | Ala | Ala | Tyr | Ile | |
| | | | 180 | | | | | 185 | | | | | 190 | | | |
| GCT | TGG | AAA | ATG | GGC | GAG | CTA | CCT | GTT | ATG | TGG | AGC | ACC | ATG | AAC | GAA | 624 |
| Ala | Trp | Lys | Met | Gly | Glu | Leu | Pro | Val | Met | Trp | Ser | Thr | Met | Asn | Glu | |
| | | 195 | | | | | 200 | | | | | 205 | | | | |
| CCC | AAC | GTC | GTT | TAT | GAG | CAA | GGA | TAC | ATG | TTC | GTT | AAA | GGG | GGT | TTC | 672 |
| Pro | Asn | Val | Val | Tyr | Glu | Gln | Gly | Tyr | Met | Phe | Val | Lys | Gly | Gly | Phe | |
| | 210 | | | | | 215 | | | | | 220 | | | | | |
| CCA | CCC | GGC | TAC | TTG | AGT | TTG | GAA | GCT | GCT | GAT | AAG | GCC | AGG | AGA | AAT | 720 |
| Pro | Pro | Gly | Tyr | Leu | Ser | Leu | Glu | Ala | Ala | Asp | Lys | Ala | Arg | Arg | Asn | |
| 225 | | | | | 230 | | | | | 235 | | | | | 240 | |
| ATG | ATC | CAG | GCT | CAT | GCA | CGG | GCC | TAT | GAC | AAT | ATT | AAA | CGC | TTC | AGT | 768 |
| Met | Ile | Gln | Ala | His | Ala | Arg | Ala | Tyr | Asp | Asn | Ile | Lys | Arg | Phe | Ser | |
| | | | | 245 | | | | | 250 | | | | | 255 | | |

FIG. 5a

| | |
|---|---|
| AAG AAA CCT GTT GGA CTA ATA TAC GCT TTC CAA TGG TTC GAA CTA TTA<br>Lys Lys Pro Val Gly Leu Ile Tyr Ala Phe Gln Trp Phe Glu Leu Leu<br>260                    265                    270 | 816 |
| GAG GGT CCA GCA GAA GTA TTT GAT AAG TTT AAG AGC TCT AAG TTA TAC<br>Glu Gly Pro Ala Glu Val Phe Asp Lys Phe Lys Ser Ser Lys Leu Tyr<br>275                    280                    285 | 864 |
| TAT TTC ACA GAC ATA GTA TCG AAG GGT AGT TCA ATC ATC AAT GTT GAA<br>Tyr Phe Thr Asp Ile Val Ser Lys Gly Ser Ser Ile Ile Asn Val Glu<br>290                    295                    300 | 912 |
| TAC AGG AGA GAT CTT GCC AAT AGG CTA GAC TGG TTG GGC GTT AAC TAC<br>Tyr Arg Arg Asp Leu Ala Asn Arg Leu Asp Trp Leu Gly Val Asn Tyr<br>305                    310                    315                    320 | 960 |
| TAT AGC CGT TTA GTC TAC AAA ATC GTC GAT GAC AAA CCT ATA ATC CTG<br>Tyr Ser Arg Leu Val Tyr Lys Ile Val Asp Asp Lys Pro Ile Ile Leu<br>325                    330                    335 | 1008 |
| CAC GGG TAT GGA TTC CTT TGT ACA CCT GGG GGG ATC AGC CCG GCT GAA<br>His Gly Tyr Gly Phe Leu Cys Thr Pro Gly Gly Ile Ser Pro Ala Glu<br>340                    345                    350 | 1056 |
| AAT CCT TGT AGC GAT TTT GGG TGG GAG GTG TAT CCT GAA GGA CTC TAC<br>Asn Pro Cys Ser Asp Phe Gly Trp Glu Val Tyr Pro Glu Gly Leu Tyr<br>355                    360                    365 | 1104 |
| CTA CTT CTA AAA GAA CTT TAC AAC CGA TAC GGG GTA GAC TTG ATC GTG<br>Leu Leu Leu Lys Glu Leu Tyr Asn Arg Tyr Gly Val Asp Leu Ile Val<br>370                    375                    380 | 1152 |
| ACC GAG AAC GGT GTT TCA GAC AGC AGG GAT GCG TTG AGA CCG GCA TAC<br>Thr Glu Asn Gly Val Ser Asp Ser Arg Asp Ala Leu Arg Pro Ala Tyr<br>385                    390                    395                    400 | 1200 |
| CTG GTC TCG CAT GTT TAC AGC GTA TGG AAA GCC GCT AAC GAG GGC ATT<br>Leu Val Ser His Val Tyr Ser Val Trp Lys Ala Ala Asn Glu Gly Ile<br>405                    410                    415 | 1248 |
| CCC GTC AAA GGC TAC CTC CAC TGG AGC TTG ACA GAC AAT TAC GAG TGG<br>Pro Val Lys Gly Tyr Leu His Trp Ser Leu Thr Asp Asn Tyr Glu Trp<br>420                    425                    430 | 1296 |
| GCC CAG GGC TTC AGG CAG AAA TTC GGT TTA GTC ATG GTT GAC TTC AAA<br>Ala Gln Gly Phe Arg Gln Lys Phe Gly Leu Val Met Val Asp Phe Lys<br>435                    440                    445 | 1344 |
| ACT AAG AAA AGG TAT CTC CGC CCA AGC GCC CTA GTG TTC CGG GAG ATC<br>Thr Lys Lys Arg Tyr Leu Arg Pro Ser Ala Leu Val Phe Arg Glu Ile<br>450                    455                    460 | 1392 |
| GCA ACG CAT AAC GGA ATA CCG GAT GAG CTA CAG CAT CTT ACA CTG ATC<br>Ala Thr His Asn Gly Ile Pro Asp Glu Leu Gln His Leu Thr Leu Ile<br>465                    470                    475                    480 | 1440 |
| CAG TAA<br>Gln | 1446 |

FIG. 5b

OC1/4 GLYCOSIDASE – 33G/B
COMPLETE GENE SEQUENCE – 9/95

| | | | | | | | | | | | | | | | | |
|---|---|---|---|---|---|---|---|---|---|---|---|---|---|---|---|---|
| ATG | ATA | AGA | AGG | TCC | GAT | TTT | CCA | AAA | GAT | TTT | ATC | TTC | GGA | ACG | GCT | 48 |
| Met | Ile | Arg | Arg | Ser | Asp | Phe | Pro | Lys | Asp | Phe | Ile | Phe | Gly | Thr | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ACG | GCA | GCA | TAC | CAG | ATT | GAA | GGT | GCA | GCA | AAC | GAA | GAT | GGC | AGA | GGG | 96 |
| Thr | Ala | Ala | Tyr | Gln | Ile | Glu | Gly | Ala | Ala | Asn | Glu | Asp | Gly | Arg | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| CCA | TCA | ATT | TGG | GAT | GTC | TTT | TCA | CAC | ACG | CCT | GGC | AAA | ACC | CTG | AAC | 144 |
| Pro | Ser | Ile | Trp | Asp | Val | Phe | Ser | His | Thr | Pro | Gly | Lys | Thr | Leu | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| GGT | GAC | ACA | GGA | GAC | GTT | GCG | TGT | GAC | CAT | TAT | CAC | CGA | TAC | AAG | GAA | 192 |
| Gly | Asp | Thr | Gly | Asp | Val | Ala | Cys | Asp | His | Tyr | His | Arg | Tyr | Lys | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| GAT | ATC | CAG | CTG | ATG | AAA | GAA | ATA | GGG | TTA | GAC | GCT | TAC | AGG | TTC | TCT | 240 |
| Asp | Ile | Gln | Leu | Met | Lys | Glu | Ile | Gly | Leu | Asp | Ala | Tyr | Arg | Phe | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATC | TCC | TGG | CCC | AGA | ATT | ATG | CCA | GAT | GGG | AAG | AAC | ATC | AAC | CAA | AAG | 288 |
| Ile | Ser | Trp | Pro | Arg | Ile | Met | Pro | Asp | Gly | Lys | Asn | Ile | Asn | Gln | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| GGT | GTG | GAT | TTC | TAC | AAC | AGA | CTC | GTT | GAT | GAG | CTT | TTG | AAG | AAT | GAT | 336 |
| Gly | Val | Asp | Phe | Tyr | Asn | Arg | Leu | Val | Asp | Glu | Leu | Leu | Lys | Asn | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ATC | ATA | CCA | TTC | GTA | ACA | CTC | TAT | CAC | TGG | GAC | TTA | CCC | TAC | GCA | CTT | 384 |
| Ile | Ile | Pro | Phe | Val | Thr | Leu | Tyr | His | Trp | Asp | Leu | Pro | Tyr | Ala | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| TAT | GAA | AAA | GGT | GGA | TGG | CTT | AAC | CCA | GAT | ATA | GCG | CTC | TAT | TTC | AGA | 432 |
| Tyr | Glu | Lys | Gly | Gly | Trp | Leu | Asn | Pro | Asp | Ile | Ala | Leu | Tyr | Phe | Arg | |
| | 130 | | | | | 135 | | | | | 140 | | | | | |

| | | | | | | | | | | | | | | | | |
|---|---|---|---|---|---|---|---|---|---|---|---|---|---|---|---|---|
| GCA | TAC | GCA | ACG | TTT | ATG | TTC | AAC | GAA | CTC | GGT | GAT | CGT | GTG | AAA | CAT | 480 |
| Ala | Tyr | Ala | Thr | Phe | Met | Phe | Asn | Glu | Leu | Gly | Asp | Arg | Val | Lys | His | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TGG | ATT | ACA | CTG | AAC | GAA | CCA | TGG | TGT | TCT | TCT | TTC | TCG | GGT | TAT | TAC | 528 |
| Trp | Ile | Thr | Leu | Asn | Glu | Pro | Trp | Cys | Ser | Ser | Phe | Ser | Gly | Tyr | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ACG | GGA | GAG | CAT | GCC | CCG | GGT | CAT | CAA | AAT | TTA | CAA | GAA | GCG | ATA | ATC | 576 |
| Thr | Gly | Glu | His | Ala | Pro | Gly | His | Gln | Asn | Leu | Gln | Glu | Ala | Ile | Ile | |
| | | | 180 | | | | | 185 | | | | | 190 | | | |

| | | | | | | | | | | | | | | | | |
|---|---|---|---|---|---|---|---|---|---|---|---|---|---|---|---|---|
| GCG | GCG | CAC | AAC | CTG | TTG | AGG | GAA | CAT | GGA | CAT | GCC | GTC | CAG | GCG | TCC | 624 |
| Ala | Ala | His | Asn | Leu | Leu | Arg | Glu | His | Gly | His | Ala | Val | Gln | Ala | Ser | |
| | | | 195 | | | | | 200 | | | | | 205 | | | |

| | | | | | | | | | | | | | | | | |
|---|---|---|---|---|---|---|---|---|---|---|---|---|---|---|---|---|
| AGA | GAA | GAA | GTA | AAA | GAT | GGG | GAA | GTT | GGC | TTA | ACC | AAC | GTT | GTG | ATG | 672 |
| Arg | Glu | Glu | Val | Lys | Asp | Gly | Glu | Val | Gly | Leu | Thr | Asn | Val | Val | Met | |
| | 210 | | | | | 215 | | | | | 220 | | | | | |

| | | | | | | | | | | | | | | | | |
|---|---|---|---|---|---|---|---|---|---|---|---|---|---|---|---|---|
| AAA | ATA | GAA | CCG | GGC | GAT | GCA | AAA | CCC | GAA | AGT | TTC | TTG | GTC | GCA | AGT | 720 |
| Lys | Ile | Glu | Pro | Gly | Asp | Ala | Lys | Pro | Glu | Ser | Phe | Leu | Val | Ala | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| CTT | GTT | GAT | AAG | TTC | GTT | AAT | GCA | TGG | TCC | CAT | GAC | CCT | GTT | GTT | TTC | 768 |
| Leu | Val | Asp | Lys | Phe | Val | Asn | Ala | Trp | Ser | His | Asp | Pro | Val | Val | Phe | |
| | | | | 245 | | | | | 250 | | | | | 255 | | |

FIG. 6a

```
GGA AAA TAT CCC GAA GAA GCA GTT GCA CTT TAT ACG GAA AAA GGG TTG      816
Gly Lys Tyr Pro Glu Glu Ala Val Ala Leu Tyr Thr Glu Lys Gly Leu
            260             265             270

CAA GTT CTC GAT AGC GAT ATG AAT ATT ATT TCG ACT CCT ATA GAC TTC      864
Gln Val Leu Asp Ser Asp Met Asn Ile Ile Ser Thr Pro Ile Asp Phe
            275             280             285

TTT GGT GTG AAT TAT TAC ACA AGA ACA CTT GTT GTT TTT GAT ATG AAC      912
Phe Gly Val Asn Tyr Tyr Thr Arg Thr Leu Val Val Phe Asp Met Asn
            290             295             300

AAT CCT CTT GGA TTT TCG TAT GTT CAG GGA GAC CTT CCC AAA ACG GAG      960
Asn Pro Leu Gly Phe Ser Tyr Val Gln Gly Asp Leu Pro Lys Thr Glu
305             310             315             320

ATG GGA TGG GAA ATC TAC CCG CAG GGA TTA TTT GAT ATG CTG GTC TAT     1008
Met Gly Trp Glu Ile Tyr Pro Gln Gly Leu Phe Asp Met Leu Val Tyr
            325             330             335

CTG AAG GAA AGA TAT AAA CTA CCA CTT TAT ATC ACA GAG AAC GGG ATG     1056
Leu Lys Glu Arg Tyr Lys Leu Pro Leu Tyr Ile Thr Glu Asn Gly Met
            340             345             350

GCT GGA CCT GAT AAA TTG GAA AAC GGA AGA GTT CAT GAT AAT TAC CGA     1104
Ala Gly Pro Asp Lys Leu Glu Asn Gly Arg Val His Asp Asn Tyr Arg
            355             360             365

ATT GAA TAT TTG GAA AAG CAC TTT GAA AAA GCA CTT GAA GCA ATC AAT     1152
Ile Glu Tyr Leu Glu Lys His Phe Glu Lys Ala Leu Glu Ala Ile Asn
            370             375             380

GCA GAT GTT GAT TTG AAA GGT TAC TTC ATT TGG TCT TTG ATG GAT AAC     1200
Ala Asp Val Asp Leu Lys Gly Tyr Phe Ile Trp Ser Leu Met Asp Asn
385             390             395             400

TTC GAA TGG GCG TGC GGA TAC TCC AAA CGT TTC GGT ATA ATC TAC GTA     1248
Phe Glu Trp Ala Cys Gly Tyr Ser Lys Arg Phe Gly Ile Ile Tyr Val
            405             410             415

GAT TAC AAT ACC CCA AAA AGG ATA TTG AAA GAT TCA GCG ATG TGG TTG     1296
Asp Tyr Asn Thr Pro Lys Arg Ile Leu Lys Asp Ser Ala Met Trp Leu
            420             425             430

AAG GAA TTT CTA AAA TCT TAA                                         1317
Lys Glu Phe Leu Lys Ser
            435
```

FIG. 6b

STAPHYLOTHERMUS MARINUS GLYCOSIDASE – 12G
COMPLETE GENE SEQUENCE 9/95

```
TTG ATA AGG TTT CCT GAT TAT TTC TTG TTT GGA ACA GCT ACA TCA TCG         48
Leu Ile Arg Phe Pro Asp Tyr Phe Leu Phe Gly Thr Ala Thr Ser Ser
 1           5                   10                  15

CAC CAG ATC GAG GGT AAT AAC ATA TTT AAT GAT TGG TGG GAG TGG GAG         96
His Gln Ile Glu Gly Asn Asn Ile Phe Asn Asp Trp Trp Glu Trp Glu
             20                  25                  30

ACT AAA GGC AGG ATT AAG GTG AGA TCG GGT AAG GCA TGT AAT CAT TGG        144
Thr Lys Gly Arg Ile Lys Val Arg Ser Gly Lys Ala Cys Asn His Trp
         35                  40                  45

GAA CTC TAT AAA GAA GAC ATA GAG CTT ATG GCT GAG CTG GGA TAT AAT        192
Glu Leu Tyr Lys Glu Asp Ile Glu Leu Met Ala Glu Leu Gly Tyr Asn
     50                  55                  60

GCT TAT AGG TTC TCC ATA GAG TGG AGT AGA ATA TTT CCC AGA AAA GAT        240
Ala Tyr Arg Phe Ser Ile Glu Trp Ser Arg Ile Phe Pro Arg Lys Asp
 65              70                  75                  80

CAT ATA GAT TAT GAG TCG CTT AAT AAG TAT AAG GAA ATA GTT AAT CTA        288
His Ile Asp Tyr Glu Ser Leu Asn Lys Tyr Lys Glu Ile Val Asn Leu
             85                  90                  95

CTT AGA AAA TAC GGG ATA GAA CCT GTA ATC ACT CTT CAC CAC TTC ACA        336
Leu Arg Lys Tyr Gly Ile Glu Pro Val Ile Thr Leu His His Phe Thr
         100                 105                 110

AAC CCG CAA TGG TTT ATG AAA ATT GGT GGA TGG ACT AGG GAA GAG AAC        384
Asn Pro Gln Trp Phe Met Lys Ile Gly Gly Trp Thr Arg Glu Glu Asn
     115                 120                 125

ATA AAA TAT TTT ATA AAA TAT GTA GAA CTT ATA GCT TCC GAG ATA AAA        432
Ile Lys Tyr Phe Ile Lys Tyr Val Glu Leu Ile Ala Ser Glu Ile Lys
 130                 135                 140

GAC GTG AAA ATA TGG ATC ACT ATT AAT GAA CCA ATA ATA TAT GTT TTA        480
Asp Val Lys Ile Trp Ile Thr Ile Asn Glu Pro Ile Ile Tyr Val Leu
145                 150                 155                 160

CAA GGA TAT ATT TCC GGC GAA TGG CCA CCT GGA ATT AAA AAT TTA AAA        528
Gln Gly Tyr Ile Ser Gly Glu Trp Pro Pro Gly Ile Lys Asn Leu Lys
             165                 170                 175

ATA GCT GAT CAA GTA ACT AAG AAT CTT TTA AAA GCA CAT AAT GAA GCC        576
Ile Ala Asp Gln Val Thr Lys Asn Leu Leu Lys Ala His Asn Glu Ala
         180                 185                 190

TAT AAT ATA CTT CAT AAA CAC GGT ATT GTA GGC ATA GCT AAA AAC ATG        624
Tyr Asn Ile Leu His Lys His Gly Ile Val Gly Ile Ala Lys Asn Met
     195                 200                 205

ATA GCA TTT AAA CCA GGA TCT AAT AGA GGA AAA GAC ATT AAT ATT TAT        672
Ile Ala Phe Lys Pro Gly Ser Asn Arg Gly Lys Asp Ile Asn Ile Tyr
 210                 215                 220

CAT AAA GTC GAT AAA GCA TTC AAC TGG GGA TTT CTC AAC GGA ATA TTA        720
His Lys Val Asp Lys Ala Phe Asn Trp Gly Phe Leu Asn Gly Ile Leu
225                 230                 235                 240

AGG GGA GAA CTA GAA ACT CTC CGT GGA AAA TAC CGA GTT GAG CCC GGA        768
Arg Gly Glu Leu Glu Thr Leu Arg Gly Lys Tyr Arg Val Glu Pro Gly
             245                 250                 255
```

FIG. 7a

```
AAT ATT GAT TTC ATA GGC ATA AAC TAT TAT TCA TCA TAT ATT GTA AAA    816
Asn Ile Asp Phe Ile Gly Ile Asn Tyr Tyr Ser Ser Tyr Ile Val Lys
            260                 265                 270

TAT ACT TGG AAT CCT TTT AAA CTA CAT ATT AAA GTC GAA CCA TTA GAT    864
Tyr Thr Trp Asn Pro Phe Lys Leu His Ile Lys Val Glu Pro Leu Asp
        275                 280                 285

ACA GGT CTA TGG ACA ACT ATG GGT TAC TGC ATA TAT CCT AGA GGA ATA    912
Thr Gly Leu Trp Thr Thr Met Gly Tyr Cys Ile Tyr Pro Arg Gly Ile
    290                 295                 300

TAT GAA GTT GTA ATG AAA ACT CAT GAG AAA TAC GGC AAA GAA ATA ATC    960
Tyr Glu Val Val Met Lys Thr His Glu Lys Tyr Gly Lys Glu Ile Ile
305                 310                 315                 320

ATT ACA GAG AAC GGT GTT GCA GTA GAA AAT GAT GAA TTA AGG ATT TTA   1008
Ile Thr Glu Asn Gly Val Ala Val Glu Asn Asp Glu Leu Arg Ile Leu
                325                 330                 335

TCC ATT ATC AGG CAC TTA CAA TAC TTA TAT AAA GCC ATG AAT GAA GGA   1056
Ser Ile Ile Arg His Leu Gln Tyr Leu Tyr Lys Ala Met Asn Glu Gly
            340                 345                 350

GCA AAG GTG AAA GGA TAT TTC TAC TGG AGC TTC ATG GAT AAT TTT GAG   1104
Ala Lys Val Lys Gly Tyr Phe Tyr Trp Ser Phe Met Asp Asn Phe Glu
        355                 360                 365

TGG GAT AAA GGA TTT AAC CAA AGG TTC GGA CTA GTA GAA GTT GAT TAT   1152
Trp Asp Lys Gly Phe Asn Gln Arg Phe Gly Leu Val Glu Val Asp Tyr
    370                 375                 380

AAG ACT TTT GAG AGA AAA CCT AGA AAA AGC GCA TAT GTA TAT AGT CAA   1200
Lys Thr Phe Glu Arg Lys Pro Arg Lys Ser Ala Tyr Val Tyr Ser Gln
385                 390                 395                 400

ATA GCA CGT ACC AAG ACT ATA AGT GAT GAA TAC CTA GAA AAA TAT GGA   1248
Ile Ala Arg Thr Lys Thr Ile Ser Asp Glu Tyr Leu Glu Lys Tyr Gly
                405                 410                 415

TTA AAG AAC CTC GAA TAA                                           1266
Leu Lys Asn Leu Glu
                420
```

FIG. 7b

THERMOCOCCUS 9N2 GLYCOSIDASE – 3IB/G
COMPLETE GENE SEQUENCE 9/95

```
ATG CTA CCA GAA GGC TTT CTC TGG GGC GTG TCC CAG TCC GGC TTT CAG        48
Met Leu Pro Glu Gly Phe Leu Trp Gly Val Ser Gln Ser Gly Phe Gln
 1           5                   10                  15

TTC GAG ATG GGC GAC AAG CTC AGG AGG AAC ATT GAT CCG AAC ACA GAC        96
Phe Glu Met Gly Asp Lys Leu Arg Arg Asn Ile Asp Pro Asn Thr Asp
                 20                  25                  30

TGG TGG AAG TGG GTC AGG GAT CCC TTC AAC ATA AAG AGG GAA CTC GTC       144
Trp Trp Lys Trp Val Arg Asp Pro Phe Asn Ile Lys Arg Glu Leu Val
             35                  40                  45

AGC GGC GAC CTG CCC GAG GAG GGG ATA AAC AAC TAC GAA CTT TAC GAG       192
Ser Gly Asp Leu Pro Glu Glu Gly Ile Asn Asn Tyr Glu Leu Tyr Glu
         50                  55                  60

AAG GAT CAC CGC CTC GCC AGA GAC CTC GGT CTG AAC GTT TAC AGG ATT       240
Lys Asp His Arg Leu Ala Arg Asp Leu Gly Leu Asn Val Tyr Arg Ile
 65                  70                  75                  80

GGA ATA GAG TGG AGC AGG ATC TTT CCC TGG CCA ACG TGG TTT GTG GAG       288
Gly Ile Glu Trp Ser Arg Ile Phe Pro Trp Pro Thr Trp Phe Val Glu
                 85                  90                  95

GTT GAC GTT GAG CGG GAC AGC TAC GGA CTC GTG AAG GAC GTC AAA ATC       336
Val Asp Val Glu Arg Asp Ser Tyr Gly Leu Val Lys Asp Val Lys Ile
                100                 105                 110

GAT AAA GAC ACG CTC GAA GAG CTC GAC GAG ATA GCG AAT CAT CAG GAG       384
Asp Lys Asp Thr Leu Glu Glu Leu Asp Glu Ile Ala Asn His Gln Glu
             115                 120                 125

ATA GCC TAC TAC CGC CGC GTT ATA GAG CAC CTC AGG GAG CTG GGC TTC       432
Ile Ala Tyr Tyr Arg Arg Val Ile Glu His Leu Arg Glu Leu Gly Phe
         130                 135                 140

AAG GTC ATC GTG AAC CTC AAC CAC TTC ACG CTC CCC CTC TGG CTT CAC       480
Lys Val Ile Val Asn Leu Asn His Phe Thr Leu Pro Leu Trp Leu His
145                 150                 155                 160

GAT CCG ATA ATC GCG AGG GAG AAG GCC CTC ACC AAC GGT AGG ATT GGC       528
Asp Pro Ile Ile Ala Arg Glu Lys Ala Leu Thr Asn Gly Arg Ile Gly
                 165                 170                 175

TGG GTC GGG CAG GAG AGC GTG GTG GAG TTC GCC AAG TAC GCG GCG TAC       576
Trp Val Gly Gln Glu Ser Val Val Glu Phe Ala Lys Tyr Ala Ala Tyr
             180                 185                 190

ATC GCG AAC GCA CTC GGG GAC CTC GTT GAT ATG TGG AGC ACC TTC AAC       624
Ile Ala Asn Ala Leu Gly Asp Leu Val Asp Met Trp Ser Thr Phe Asn
         195                 200                 205

GAG CCG ATG GTC GTT GTG GAG CTC GGT TAC CTC GCG CCC TAC TCC GGC       672
Glu Pro Met Val Val Val Glu Leu Gly Tyr Leu Ala Pro Tyr Ser Gly
     210                 215                 220

TTT CCG CCG GGG GTT ATG AAC CCC GAG GCG GCA AAG CTG GCA ATC CTC       720
Phe Pro Pro Gly Val Met Asn Pro Glu Ala Ala Lys Leu Ala Ile Leu
225                 230                 235                 240

AAC ATG ATA AAC GCC CAC GCA CTG GCC TAC AAG ATG ATA AAG AAG TTC       768
Asn Met Ile Asn Ala His Ala Leu Ala Tyr Lys Met Ile Lys Lys Phe
                 245                 250                 255
```

FIG. 8a

```
GAC AGG GTA AAG GCC GAT AAG GAT TCC CGC TCC GAG GCC GAG GTC GGG    816
Asp Arg Val Lys Ala Asp Lys Asp Ser Arg Ser Glu Ala Glu Val Gly
            260                 265                 270

ATA ATC TAC AAC AAC ATA GGC GTT GCC TAT CCA TAC GAC TCC AAC GAC    864
Ile Ile Tyr Asn Asn Ile Gly Val Ala Tyr Pro Tyr Asp Ser Asn Asp
            275                 280                 285

CCA AAG GAC GTG AAA GCT GCA GAA AAC GAC AAC TAC TTC CAC AGC GGG    912
Pro Lys Asp Val Lys Ala Ala Glu Asn Asp Asn Tyr Phe His Ser Gly
            290                 295                 300

CTC TTC TTC GAC GCA ATC CAC AAG GGC AAG CTC AAC ATC GAG TTC GAC    960
Leu Phe Phe Asp Ala Ile His Lys Gly Lys Leu Asn Ile Glu Phe Asp
305                 310                 315                 320

GGT GAG ACC TTC GTC AAA GTT CGG CAT CTC AGG GGG AAC GAC TGG ATA   1008
Gly Glu Thr Phe Val Lys Val Arg His Leu Arg Gly Asn Asp Trp Ile
            325                 330                 335

GGC GTT AAC TAC TAC ACG AGA GAA GTC GTC AGG TAT TCG GAG CCC AAG   1056
Gly Val Asn Tyr Tyr Thr Arg Glu Val Val Arg Tyr Ser Glu Pro Lys
            340                 345                 350

TTC CCG AGC ATA CCC CTG ATA TCC TTC CGG GGA GTT CAC AAC TAC GGC   1104
Phe Pro Ser Ile Pro Leu Ile Ser Phe Arg Gly Val His Asn Tyr Gly
            355                 360                 365

TAC GCC TGC AGG CCC GGG AGT TCT TCC GCC GAC GGA AGG CCC GTA AGC   1152
Tyr Ala Cys Arg Pro Gly Ser Ser Ser Ala Asp Gly Arg Pro Val Ser
            370                 375                 380

GAC ATC GGC TGG GAG ATC TAT CCG GAG GGG ATC TAC GAC TCG ATA AGA   1200
Asp Ile Gly Trp Glu Ile Tyr Pro Glu Gly Ile Tyr Asp Ser Ile Arg
385                 390                 395                 400

GAG GCC AAC AAA TAC GGG GTC CCG GTT TAC GTC ACC GAA AAC GGA ATA   1248
Glu Ala Asn Lys Tyr Gly Val Pro Val Tyr Val Thr Glu Asn Gly Ile
            405                 410                 415

GCC GAT TCA ACT GAC ACC CTG CGG CCG TAC TAC CTC GCG AGC CAT GTA   1296
Ala Asp Ser Thr Asp Thr Leu Arg Pro Tyr Tyr Leu Ala Ser His Val
            420                 425                 430

GCG AAG ATT GAG GAG GCG TAC GAG GCG GGT TAC GAC GTC AGG GGC TAC   1344
Ala Lys Ile Glu Glu Ala Tyr Glu Ala Gly Tyr Asp Val Arg Gly Tyr
            435                 440                 445

CTC TAC TGG GCG CTG ACC GAC AAC TAC GAG TGG GCC CTC GGT TTC AGG   1392
Leu Tyr Trp Ala Leu Thr Asp Asn Tyr Glu Trp Ala Leu Gly Phe Arg
450                 455                 460

ATG AGG TTC GGC CTC TAT AAA GTG GAT CTC ATA ACC AAG GAG AGA ACA   1440
Met Arg Phe Gly Leu Tyr Lys Val Asp Leu Ile Thr Lys Glu Arg Thr
465                 470                 475                 480

CCG CGG GAG GAA AGC GTA AAG GTT TAT AGG GGC ATC GTG GAG AAC AAC   1488
Pro Arg Glu Glu Ser Val Lys Val Tyr Arg Gly Ile Val Glu Asn Asn
            485                 490                 495

GGA GTG AGC AAG GAA ATC CGG GAG AAG TTC GGA CTT GGG TGA           1530
Gly Val Ser Lys Glu Ile Arg Glu Lys Phe Gly Leu Gly
            500                 505
```

FIG. 8b

```
ATG GAA AGG ATC GAT GAA ATT CTC TCT CAG TTA ACT ACA GAG GAA AAG    48
Met Glu Arg Ile Asp Glu Ile Leu Ser Gln Leu Thr Thr Glu Glu Lys
 1               5                  10                  15

GTG AAG CTC GTT GTG GGG GTT GGT CTT CCA GGA CTT TTT GGG AAC CCA    96
Val Lys Leu Val Val Gly Val Gly Leu Pro Gly Leu Phe Gly Asn Pro
             20                  25                  30

CAT TCC AGA GTG GCG GGT GCG GCT GGA GAA ACA CAT CCC GTT CCA AGA   144
His Ser Arg Val Ala Gly Ala Ala Gly Glu Thr His Pro Val Pro Arg
         35                  40                  45

CTT GGA ATT CCT GCG TTT GTC CTG GCA GAT GGT CCC GCA GGA CTC AGA   192
Leu Gly Ile Pro Ala Phe Val Leu Ala Asp Gly Pro Ala Gly Leu Arg
     50                  55                  60

ATA AAT CCC ACA AGG GAA AAC GAT GAA AAC ACT TAC TAC ACG ACG GCA   240
Ile Asn Pro Thr Arg Glu Asn Asp Glu Asn Thr Tyr Tyr Thr Thr Ala
 65                  70                  75                  80

TTT CCC GTT GAA ATC ATG CTC GCT TCT ACC TGG AAC AGA GAC CTT CTG   288
Phe Pro Val Glu Ile Met Leu Ala Ser Thr Trp Asn Arg Asp Leu Leu
                 85                  90                  95

GAA GAA GTG GGA AAA GCC ATG GGA GAA GAA GTT AGG GAA TAC GGT GTC   336
Glu Glu Val Gly Lys Ala Met Gly Glu Glu Val Arg Glu Tyr Gly Val
            100                 105                 110

GAT GTG CTT CTT GCA CCT GCG ATG AAC ATT CAC AGA AAC CCT CTT TGT   384
Asp Val Leu Leu Ala Pro Ala Met Asn Ile His Arg Asn Pro Leu Cys
        115                 120                 125

GGA AGG AAT TTC GAG TAC TAC TCA GAA GAT CCT GTC CTT TCC GGT GAA   432
Gly Arg Asn Phe Glu Tyr Tyr Ser Glu Asp Pro Val Leu Ser Gly Glu
    130                 135                 140

ATG GCT TCA GCC TTT GTC AAG GGA GTT CAA TCT CAA GGG GTG GGA GCC   480
Met Ala Ser Ala Phe Val Lys Gly Val Gln Ser Gln Gly Val Gly Ala
145                 150                 155                 160

TGC ATA AAA CAC TTT GTC GCG AAC AAC CAG GAA ACG AAC AGG ATG GTA   528
Cys Ile Lys His Phe Val Ala Asn Asn Gln Glu Thr Asn Arg Met Val
                165                 170                 175

GTG GAC ACG ATC GTG TCC GAG CGA GCC CTC AGA GAA ATA TAT CTG AAA   576
Val Asp Thr Ile Val Ser Glu Arg Ala Leu Arg Glu Ile Tyr Leu Lys
            180                 185                 190

GGT TTT GAA ATT GCT GTC AAG AAA GCA AGA CCC TGG ACC GTG ATG AGC   624
Gly Phe Glu Ile Ala Val Lys Lys Ala Arg Pro Trp Thr Val Met Ser
        195                 200                 205

GCT TAC AAC AAA CTG AAT GGA AAA TAC TGT TCA CAG AAC GAA TGG CTT   672
Ala Tyr Asn Lys Leu Asn Gly Lys Tyr Cys Ser Gln Asn Glu Trp Leu
    210                 215                 220

TTG AAG AAG GTT CTC AGG GAA GAA TGG GGA TTT GGC GGT TTC GTG ATG   720
Leu Lys Lys Val Leu Arg Glu Glu Trp Gly Phe Gly Gly Phe Val Met
225                 230                 235                 240

AGC GAC TGG TAC GCG GGA GAC AAC CCT GTA GAA CAG CTC AAG GCC GGA   768
Ser Asp Trp Tyr Ala Gly Asp Asn Pro Val Glu Gln Leu Lys Ala Gly
                245                 250                 255
```

FIG. 9a

| | | | | | | | | | | | | | | | |
|---|---|---|---|---|---|---|---|---|---|---|---|---|---|---|---|
| AAC | GAT | ATG | ATC | ATG | CCT | GGG | AAA | GCG | TAT | CAG | GTG | AAC | ACA | GAA | AGA | 816 |
| Asn | Asp | Met | Ile | Met | Pro | Gly | Lys | Ala | Tyr | Gln | Val | Asn | Thr | Glu | Arg |
| | | | 260 | | | | 265 | | | | | 270 | | | |
| AGA | GAT | GAA | ATA | GAA | GAA | ATC | ATG | GAG | GCG | TTG | AAG | GAG | GGA | AAA | TTG | 864 |
| Arg | Asp | Glu | Ile | Glu | Glu | Ile | Met | Glu | Ala | Leu | Lys | Glu | Gly | Lys | Leu |
| | | 275 | | | | | 280 | | | | | 285 | | | |
| AGT | GAG | GAG | GTT | CTC | GAT | GAG | TGT | GTG | AGA | AAC | ATT | CTC | AAA | GTT | CTT | 912 |
| Ser | Glu | Glu | Val | Leu | Asp | Glu | Cys | Val | Arg | Asn | Ile | Leu | Lys | Val | Leu |
| | 290 | | | | | 295 | | | | | 300 | | | | |
| GTG | AAC | GCG | CCT | TCC | TTC | AAA | GGG | TAC | AGG | TAC | TCA | AAC | AAG | CCG | GAT | 960 |
| Val | Asn | Ala | Pro | Ser | Phe | Lys | Gly | Tyr | Arg | Tyr | Ser | Asn | Lys | Pro | Asp |
| 305 | | | | | 310 | | | | | 315 | | | | | 320 |
| CTC | GAA | TCT | CAC | GCG | GAA | GTC | GCC | TAC | GAA | GCA | GGT | GCG | GAG | GGT | GTT | 1008 |
| Leu | Glu | Ser | His | Ala | Glu | Val | Ala | Tyr | Glu | Ala | Gly | Ala | Glu | Gly | Val |
| | | | | 325 | | | | | 330 | | | | | 335 | |
| GTC | CTT | CTT | GAG | AAC | AAC | GGT | GTT | CTT | CCG | TTC | GAT | GAA | AAT | ACC | CAT | 1056 |
| Val | Leu | Leu | Glu | Asn | Asn | Gly | Val | Leu | Pro | Phe | Asp | Glu | Asn | Thr | His |
| | | | 340 | | | | | 345 | | | | | 350 | | |
| GTC | GCC | GTC | TTT | GGC | ACC | GGT | CAA | ATC | GAA | ACA | ATA | AAG | GGA | GGA | ACG | 1104 |
| Val | Ala | Val | Phe | Gly | Thr | Gly | Gln | Ile | Glu | Thr | Ile | Lys | Gly | Gly | Thr |
| | | 355 | | | | | 360 | | | | | 365 | | | |
| GGA | AGT | GGA | GAC | ACC | CAT | CCG | AGA | TAC | ACG | ATC | TCT | ATC | CTT | GAA | GGC | 1152 |
| Gly | Ser | Gly | Asp | Thr | His | Pro | Arg | Tyr | Thr | Ile | Ser | Ile | Leu | Glu | Gly |
| | 370 | | | | | 375 | | | | | 380 | | | | |
| ATA | AAA | GAA | AGA | AAC | ATG | AAG | TTC | GAC | GAA | GAA | CTC | GCT | TCC | ACT | TAT | 1200 |
| Ile | Lys | Glu | Arg | Asn | Met | Lys | Phe | Asp | Glu | Glu | Leu | Ala | Ser | Thr | Tyr |
| 385 | | | | | 390 | | | | | 395 | | | | | 400 |
| GAG | GAG | TAC | ATA | AAA | AAG | ATG | AGA | GAA | ACA | GAG | GAA | TAT | AAA | CCC | AGA | 1248 |
| Glu | Glu | Tyr | Ile | Lys | Lys | Met | Arg | Glu | Thr | Glu | Glu | Tyr | Lys | Pro | Arg |
| | | | | 405 | | | | | 410 | | | | | 415 | |
| ACC | GAC | TCT | TGG | GGA | ACG | GTC | ATA | AAA | CCG | AAA | CTC | CCA | GAG | AAT | TTC | 1296 |
| Thr | Asp | Ser | Trp | Gly | Thr | Val | Ile | Lys | Pro | Lys | Leu | Pro | Glu | Asn | Phe |
| | | | 420 | | | | | 425 | | | | | 430 | | |
| CTC | TCA | GAA | AAA | GAG | ATA | AAG | AAA | CCT | CCA | AAG | AAA | AAC | GAT | GTT | GCA | 1344 |
| Leu | Ser | Glu | Lys | Glu | Ile | Lys | Lys | Pro | Pro | Lys | Lys | Asn | Asp | Val | Ala |
| | | 435 | | | | | 440 | | | | | 445 | | | |
| GTT | GTT | GTG | ATC | AGT | AGG | ATC | TCC | GGT | GAG | GGA | TAC | GAC | AGA | AAG | CCG | 1392 |
| Val | Val | Val | Ile | Ser | Arg | Ile | Ser | Gly | Glu | Gly | Tyr | Asp | Arg | Lys | Pro |
| | 450 | | | | | 455 | | | | | 460 | | | | |
| GTG | AAA | GGT | GAC | TTC | TAC | CTC | TCC | GAT | GAC | GAG | CTG | GAA | CTC | ATA | AAA | 1440 |
| Val | Lys | Gly | Asp | Phe | Tyr | Leu | Ser | Asp | Asp | Glu | Leu | Glu | Leu | Ile | Lys |
| 465 | | | | | 470 | | | | | 475 | | | | | 480 |
| ACC | GTC | TCG | AAA | GAA | TTC | CAC | GAT | CAG | GGT | AAG | AAA | GTT | GTG | GTT | CTT | 1488 |
| Thr | Val | Ser | Lys | Glu | Phe | His | Asp | Gln | Gly | Lys | Lys | Val | Val | Val | Leu |
| | | | | 485 | | | | | 490 | | | | | 495 | |
| CTG | AAC | ATC | GGA | AGT | CCC | ATC | GAA | GTC | GCA | AGC | TGG | AGA | GAC | CTT | GTG | 1536 |
| Leu | Asn | Ile | Gly | Ser | Pro | Ile | Glu | Val | Ala | Ser | Trp | Arg | Asp | Leu | Val |

FIG. 9b

|     |     |     |     |     | 500 |     |     |     |     | 505 |     |     |     |     | 510 |     |      |
|-----|-----|-----|-----|-----|-----|-----|-----|-----|-----|-----|-----|-----|-----|-----|-----|-----|------|
| GAT | GGA | ATT | CTT | CTC | GTC | TGG | CAG | GCG | GGA | CAG | GAG | ATG | GGA | AGA | ATA |     | 1584 |
| Asp | Gly | Ile | Leu | Leu | Val | Trp | Gln | Ala | Gly | Gln | Glu | Met | Gly | Arg | Ile |     |      |
|     |     | 515 |     |     |     |     | 520 |     |     |     |     | 525 |     |     |     |     |      |

```
        GTG GCC GAT GTT CTT GTG GGA AAG ATT AAT CCC TCC GGA AAA CTT CCA       1632
        Val Ala Asp Val Leu Val Gly Lys Ile Asn Pro Ser Gly Lys Leu Pro
            530             535             540

ACG ACC TTC CCG AAG GAT TAC TCG GAC GTT CCA TCC TGG ACG TTC CCA       1680
        Thr Thr Phe Pro Lys Asp Tyr Ser Asp Val Pro Ser Trp Thr Phe Pro
        545             550             555             560

GGA GAG CCA AAG GAC AAT CCG CAA AGA GTG GTG TAC GAG GAA GAC ATC       1728
        Gly Glu Pro Lys Asp Asn Pro Gln Arg Val Val Tyr Glu Glu Asp Ile
                        565             570             575

TAC GTG GGA TAC AGG TAC TAC GAC ACC TTC GGT GTG GAA CCT GCC TAC       1776
        Tyr Val Gly Tyr Arg Tyr Tyr Asp Thr Phe Gly Val Glu Pro Ala Tyr
                    580             585             590

GAA TTC GGC TAC GGC CTC TCT TAC ACA AAG TTT GAA TAC AAA GAT TTA       1824
        Glu Phe Gly Tyr Gly Leu Ser Tyr Thr Lys Phe Glu Tyr Lys Asp Leu
                595             600             605

AAA ATC GCT ATC GAC GGT GAG ACG CTC AGA GTG TCG TAC ACG ATC ACA       1872
        Lys Ile Ala Ile Asp Gly Glu Thr Leu Arg Val Ser Tyr Thr Ile Thr
            610             615             620

AAC ACT GGG GAC AGA GCT GGA AAG GAA GTC TCA CAG GTC TAC ATC AAA       1920
        Asn Thr Gly Asp Arg Ala Gly Lys Glu Val Ser Gln Val Tyr Ile Lys
        625             630             635             640

GCT CCA AAA GGA AAA ATA GAC AAA CCC TTC CAG GAG CTG AAA GCG TTT       1968
        Ala Pro Lys Gly Lys Ile Asp Lys Pro Phe Gln Glu Leu Lys Ala Phe
                        645             650             655

CAC AAA ACA AAA CTT TTG AAC CCG GGT GAA TCA GAA GAA ATC TCC TTG       2016
        His Lys Thr Lys Leu Leu Asn Pro Gly Glu Ser Glu Glu Ile Ser Leu
                    660             665             670

GAA ATT CCT CTC AGA GAT CTT GCG AGT TTC GAT GGG AAA GAA TGG GTT       2064
        Glu Ile Pro Leu Arg Asp Leu Ala Ser Phe Asp Gly Lys Glu Trp Val
                675             680             685

GTC GAG TCA GGA GAA TAC GAG GTC AGG GTC GGT GCA TCT TCG AGG GAT       2112
        Val Glu Ser Gly Glu Tyr Glu Val Arg Val Gly Ala Ser Ser Arg Asp
            690             695             700

ATA AGG TTG AGA GAT ATT TTT CTG GTT GAG GGA GAG AAG AGA TTC AAA       2160
        Ile Arg Leu Arg Asp Ile Phe Leu Val Glu Gly Glu Lys Arg Phe Lys
        705             710             715             720

CCA TGA                                                               2166
        Pro
```

FIG. 9c

THERMOCOCCUS AEDII12RA GLYCOSIDASE (18B/G)
COMPLETE GENE SEQUENCE – 9/95

| | | | | | | | | | | | | | | | | |
|---|---|---|---|---|---|---|---|---|---|---|---|---|---|---|---|---|
| ATG | ATC | CAC | TGC | CCG | GTT | AAA | GGG | ATT | ATA | TCT | GAG | GCT | CGC | GGC | ATA | 48 |
| Met | Ile | His | Cys | Pro | Val | Lys | Gly | Ile | Ile | Ser | Glu | Ala | Arg | Gly | Ile | |
| 1 | | | 5 | | | | | 10 | | | | | 15 | | | |

| | | | | | | | | | | | | | | | | |
|---|---|---|---|---|---|---|---|---|---|---|---|---|---|---|---|---|
| ACC | ATC | ACA | ATA | GAT | TTA | AGT | TTT | CAA | GGC | CAA | ATA | AAT | AAT | TTG | GTG | 96 |
| Thr | Ile | Thr | Ile | Asp | Leu | Ser | Phe | Gln | Gly | Gln | Ile | Asn | Asn | Leu | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| AAT | GCT | ATG | ATT | GTC | TTT | CCG | GAG | TTC | TTC | CTC | TTT | GGA | ACC | GCC | ACA | 144 |
| Asn | Ala | Met | Ile | Val | Phe | Pro | Glu | Phe | Phe | Leu | Phe | Gly | Thr | Ala | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| TCT | TCT | CAT | CAG | ATC | GAG | GGA | GAT | AAT | AAA | TGG | AAC | GAC | TGG | TGG | TAT | 192 |
| Ser | Ser | His | Gln | Ile | Glu | Gly | Asp | Asn | Lys | Trp | Asn | Asp | Trp | Trp | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| TAT | GAG | GAG | ATA | GGT | AAG | CTC | CCC | TAC | AAA | TCC | GGT | AAA | GCC | TGC | AAT | 240 |
| Tyr | Glu | Glu | Ile | Gly | Lys | Leu | Pro | Tyr | Lys | Ser | Gly | Lys | Ala | Cys | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CAC | TGG | GAG | CTT | TAC | AGG | GAA | GAT | ATA | GAG | CTA | ATG | GCA | CAG | CTC | GGC | 288 |
| His | Trp | Glu | Leu | Tyr | Arg | Glu | Asp | Ile | Glu | Leu | Met | Ala | Gln | Leu | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| TAC | AAT | GCC | TAC | CGC | TTT | TCG | ATA | GAG | TGG | AGC | CGT | CTC | TTC | CCG | GAA | 336 |
| Tyr | Asn | Ala | Tyr | Arg | Phe | Ser | Ile | Glu | Trp | Ser | Arg | Leu | Phe | Pro | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| GAG | GGC | AAA | TTC | AAT | GAA | GAA | GCC | TTC | AAC | CGC | TAC | CGT | GAA | ATA | ATT | 384 |
| Glu | Gly | Lys | Phe | Asn | Glu | Glu | Ala | Phe | Asn | Arg | Tyr | Arg | Glu | Ile | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| GAA | ATC | CTC | CTT | GAG | AAG | GGG | ATT | ACT | CCA | AAC | GTT | ACA | CTG | CAC | CAC | 432 |
| Glu | Ile | Leu | Leu | Glu | Lys | Gly | Ile | Thr | Pro | Asn | Val | Thr | Leu | His | His | |
| | 130 | | | | | 135 | | | | | 140 | | | | | |

| | | | | | | | | | | | | | | | | |
|---|---|---|---|---|---|---|---|---|---|---|---|---|---|---|---|---|
| TTC | ACA | TCA | CCG | CTG | TGG | TTC | ATG | CGG | AAG | GGA | GGC | TTT | TTG | AAG | GAA | 480 |
| Phe | Thr | Ser | Pro | Leu | Trp | Phe | Met | Arg | Lys | Gly | Gly | Phe | Leu | Lys | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GAA | AAC | CTC | AAG | TAC | TGG | GAG | CAG | TAC | GTT | GAT | AAA | GCC | GCG | GAG | CTC | 528 |
| Glu | Asn | Leu | Lys | Tyr | Trp | Glu | Gln | Tyr | Val | Asp | Lys | Ala | Ala | Glu | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| CTC | AAG | GGA | GTC | AAG | CTT | GTA | GCT | ACA | TTC | AAC | GAG | CCG | ATG | GTC | TAT | 576 |
| Leu | Lys | Gly | Val | Lys | Leu | Val | Ala | Thr | Phe | Asn | Glu | Pro | Met | Val | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| GTT | ATG | ATG | GGC | TAC | CTC | ACA | GCC | TAC | TGG | CCG | CCC | TTC | ATC | AAG | AGT | 624 |
| Val | Met | Met | Gly | Tyr | Leu | Thr | Ala | Tyr | Trp | Pro | Pro | Phe | Ile | Lys | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| CCC | TTT | AAA | GCC | TTT | AAA | GTT | GCC | GCA | AAC | CTC | CTT | AAG | GCC | CAT | GCA | 672 |
| Pro | Phe | Lys | Ala | Phe | Lys | Val | Ala | Ala | Asn | Leu | Leu | Lys | Ala | His | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| ATG | GCA | TAT | GAT | ATC | CTC | CAT | GGT | AAC | TTT | GAT | GTG | GGG | ATA | GTT | AAA | 720 |
| Met | Ala | Tyr | Asp | Ile | Leu | His | Gly | Asn | Phe | Asp | Val | Gly | Ile | Val | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| AAC | ATC | CCC | ATA | ATG | CTC | CCT | GCA | AGC | AAC | AGA | GAG | AAA | GAC | GTA | GAA | 768 |
| Asn | Ile | Pro | Ile | Met | Leu | Pro | Ala | Ser | Asn | Arg | Glu | Lys | Asp | Val | Glu | |
| | | | | 245 | | | | | 250 | | | | | 255 | | |

FIG. 10a

```
GCT GCC CAA AAG GCG GAT AAC CTC TTT AAC TGG AAC TTC CTT GAT GCA          816
Ala Ala Gln Lys Ala Asp Asn Leu Phe Asn Trp Asn Phe Leu Asp Ala
            260                 265                 270

ATA TGG AGC GGA AAA TAT AAA GGA GCT TTT GGA ACT TAC AAA ACT CCA          864
Ile Trp Ser Gly Lys Tyr Lys Gly Ala Phe Gly Thr Tyr Lys Thr Pro
            275                 280                 285

GAA AGC GAT GCA GAC TTC ATA GGG ATA AAC TAC TAC ACA GCC AGC GAG          912
Glu Ser Asp Ala Asp Phe Ile Gly Ile Asn Tyr Tyr Thr Ala Ser Glu
            290                 295                 300

GTA AGG CAT AGC TGG AAT CCG CTA AAG TTT TTC TTC GAT GCC AAG CTT          960
Val Arg His Ser Trp Asn Pro Leu Lys Phe Phe Phe Asp Ala Lys Leu
305                 310                 315                 320

GCA GAC TTA AGC GAG AGA AAA ACA GAT ATG GGT TGG AGT GTC TAT CCA         1008
Ala Asp Leu Ser Glu Arg Lys Thr Asp Met Gly Trp Ser Val Tyr Pro
            325                 330                 335

AAG GGC ATA TAC GAA GCT ATA GCA AAG GTT TCA CAC TAC GGA AAG CCA         1056
Lys Gly Ile Tyr Glu Ala Ile Ala Lys Val Ser His Tyr Gly Lys Pro
            340                 345                 350

ATG TAC ATC ACG GAA AAC GGG ATA GCT ACC TTA GAC GAT GAG TGG AGG         1104
Met Tyr Ile Thr Glu Asn Gly Ile Ala Thr Leu Asp Asp Glu Trp Arg
            355                 360                 365

ATA GAG TTT ATC ATC CAG CAC CTC CAG TAC GTT CAC AAA GCC TTA AAC         1152
Ile Glu Phe Ile Ile Gln His Leu Gln Tyr Val His Lys Ala Leu Asn
            370                 375                 380

GAT GGC TTT GAC TTG AGA GGC TAC TTC TAT TGG TCT TTT ATG GAT AAC         1200
Asp Gly Phe Asp Leu Arg Gly Tyr Phe Tyr Trp Ser Phe Met Asp Asn
385                 390                 395                 400

TTC GAG TGG GCT GAG GGT TTT AGA CCA CGC TTT GGG CTG GTC GAG GTG         1248
Phe Glu Trp Ala Glu Gly Phe Arg Pro Arg Phe Gly Leu Val Glu Val
            405                 410                 415

GAC TAC ACG ACC TTC AAG AGG AGA CCG AGA AAG AGT GCT TAC ATA TAT         1296
Asp Tyr Thr Thr Phe Lys Arg Arg Pro Arg Lys Ser Ala Tyr Ile Tyr
            420                 425                 430

GGA GAA ATT GCA AGG GAA AAG AAA ATA AAA GAC GAA CTG CTG GCA AAG         1344
Gly Glu Ile Ala Arg Glu Lys Lys Ile Lys Asp Glu Leu Leu Ala Lys
            435                 440                 445

TAT GGG CTT CCG GAG CTA TGA                                             1365
Tyr Gly Leu Pro Glu Leu
450
```

FIG. 10b

THERMOCOCCUS CHITONOPHAGUS GLYCOSIDASE – 22G
COMPLETE SEQUENCE – 9/95

```
TTG CTT CCA GAG AAC TTT CTC TGG GGA GTT TCA CAG TCC GGA TTC CAG      48
Leu Leu Pro Glu Asn Phe Leu Trp Gly Val Ser Gln Ser Gly Phe Gln
 1            5                   10                  15

TTT GAA ATG GGG GAC AGA CTG AGG AGG CAC ATT GAT CCA AAC ACA GAT      96
Phe Glu Met Gly Asp Arg Leu Arg Arg His Ile Asp Pro Asn Thr Asp
                 20                  25                  30

TGG TGG TAC TGG GTA AGA GAT GAA TAT AAT ATC AAA AAA GGA CTA GTA     144
Trp Trp Tyr Trp Val Arg Asp Glu Tyr Asn Ile Lys Lys Gly Leu Val
             35                  40                  45

AGT GGG GAT CTT CCC GAA GAC GGT ATA AAT TCA TAT GAA TTA TAT GAG     192
Ser Gly Asp Leu Pro Glu Asp Gly Ile Asn Ser Tyr Glu Leu Tyr Glu
         50                  55                  60

AGA GAC CAA GAA ATT GCA AAG GAT TTA GGG CTC AAC ACA TAT AGG ATC     240
Arg Asp Gln Glu Ile Ala Lys Asp Leu Gly Leu Asn Thr Tyr Arg Ile
 65                  70                  75                  80

GGA ATT GAA TGG AGC AGA GTA TTT CCA TGG CCA ACG ACT TTT GTC GAC     288
Gly Ile Glu Trp Ser Arg Val Phe Pro Trp Pro Thr Thr Phe Val Asp
                 85                  90                  95

GTG GAG TAT GAA ATT GAT GAG TCT TAC GGG TTG GTA AAG GAT GTG AAG     336
Val Glu Tyr Glu Ile Asp Glu Ser Tyr Gly Leu Val Lys Asp Val Lys
                100                 105                 110

ATT TCT AAA GAC GCA TTA GAA AAA CTT GAT GAA ATC GCT AAC CAA AGG     384
Ile Ser Lys Asp Ala Leu Glu Lys Leu Asp Glu Ile Ala Asn Gln Arg
             115                 120                 125

GAA ATA ATA TAT TAT AGG AAC CTA ATA AAT TCC CTA AGA AAG AGG GGT     432
Glu Ile Ile Tyr Tyr Arg Asn Leu Ile Asn Ser Leu Arg Lys Arg Gly
         130                 135                 140

TTT AAG GTA ATA CTA AAC CTA AAT CAT TTT ACC CTC CCA ATA TGG CTT     480
Phe Lys Val Ile Leu Asn Leu Asn His Phe Thr Leu Pro Ile Trp Leu
145                 150                 155                 160

CAT GAT CCT ATC GAA TCT AGA GAA AAA GCC CTG ACC AAT AAG AGA AAC     528
His Asp Pro Ile Glu Ser Arg Glu Lys Ala Leu Thr Asn Lys Arg Asn
                 165                 170                 175

GGA TGG GTA AGC GAA AGG AGT GTT ATA GAG TTT GCA AAA TTT GCC GCG     576
Gly Trp Val Ser Glu Arg Ser Val Ile Glu Phe Ala Lys Phe Ala Ala
             180                 185                 190

TAT TTA GCA TAT AAA TTC GGA GAC ATA GTA GAC ATG TGG AGC ACA TTT     624
Tyr Leu Ala Tyr Lys Phe Gly Asp Ile Val Asp Met Trp Ser Thr Phe
         195                 200                 205

AAT GAA CCT ATG GTG GTC GCC GAG TTG GGG TAT TTA GCC CCA TAC TCA     672
Asn Glu Pro Met Val Val Ala Glu Leu Gly Tyr Leu Ala Pro Tyr Ser
210                 215                 220

GGA TTC CCC CCG GGA GTC ATG AAT CCA GAA GCA GCA AAG TTA GTT ATG     720
Gly Phe Pro Pro Gly Val Met Asn Pro Glu Ala Ala Lys Leu Val Met
225                 230                 235                 240

CTA CAT ATG ATA AAC GCC CAT GCT TTA GCA TAT AGG ATG ATA AAG AAA     768
Leu His Met Ile Asn Ala His Ala Leu Ala Tyr Arg Met Ile Lys Lys
                 245                 250                 255
```

FIG. 11a

```
TTT GAC AGA AAA AAA GCT GAT CCA GAA TCA AAA GAA CCA GCT GAA ATA          816
Phe Asp Arg Lys Lys Ala Asp Pro Glu Ser Lys Glu Pro Ala Glu Ile
            260                 265                 270

GGA ATT ATA TAC AAT AAC ATC GGC GTC ACA TAT CCG TTT AAT CCG AAA          864
Gly Ile Ile Tyr Asn Asn Ile Gly Val Thr Tyr Pro Phe Asn Pro Lys
            275                 280                 285

GAC TCA AAG GAT CTA CAA GCA TCC GAT AAT GCC AAT TTC TTC CAC AGT          912
Asp Ser Lys Asp Leu Gln Ala Ser Asp Asn Ala Asn Phe Phe His Ser
            290                 295                 300

GGG CTA TTC TTA ACG GCT ATC CAC AGG GGA AAA TTA AAT ATC GAA TTT          960
Gly Leu Phe Leu Thr Ala Ile His Arg Gly Lys Leu Asn Ile Glu Phe
305                 310                 315                 320

GAC GGA GAG ACA TTT GTT TAC CTT CCA TAT TTA AAG GGC AAT GAT TGG         1008
Asp Gly Glu Thr Phe Val Tyr Leu Pro Tyr Leu Lys Gly Asn Asp Trp
                    325                 330                 335

CTG GGA GTG AAT TAT TAT ACA AGA GAA GTC GTT AAA TAC CAA GAT CCC         1056
Leu Gly Val Asn Tyr Tyr Thr Arg Glu Val Val Lys Tyr Gln Asp Pro
                340                 345                 350

ATG TTT CCA AGT ATC CCT CTC ATA AGC TTC AAG GGC GTT CCA GAT TAT         1104
Met Phe Pro Ser Ile Pro Leu Ile Ser Phe Lys Gly Val Pro Asp Tyr
            355                 360                 365

GGA TAC GGA TGT AGA CCA GGA ACG ACG TCA AAG GAC GGT AAT CCT GTT         1152
Gly Tyr Gly Cys Arg Pro Gly Thr Thr Ser Lys Asp Gly Asn Pro Val
            370                 375                 380

AGT GAC ATT GGA TGG GAG GTA TAT CCC AAA GGC ATG TAC GAC TCT ATA         1200
Ser Asp Ile Gly Trp Glu Val Tyr Pro Lys Gly Met Tyr Asp Ser Ile
385                 390                 395                 400

GTA GCT GCC AAT GAA TAT GGA GTT CCT GTA TAC GTA ACA GAA AAC GGA         1248
Val Ala Ala Asn Glu Tyr Gly Val Pro Val Tyr Val Thr Glu Asn Gly
                    405                 410                 415

ATA GCA GAT TCA AAA GAT GTA TTA AGG CCC TAT TAC ATC GCA TCT CAC         1296
Ile Ala Asp Ser Lys Asp Val Leu Arg Pro Tyr Tyr Ile Ala Ser His
                420                 425                 430

ATT GAA GCC ATG GAA GAG GCT TAC GAA AAT GGT TAT GAC GTG AGA GGA         1344
Ile Glu Ala Met Glu Glu Ala Tyr Glu Asn Gly Tyr Asp Val Arg Gly
            435                 440                 445

TAC TTA CAC TGG GCA TTA ACC GAT AAT TAC GAA TGG GCC TTA GGG TTC         1392
Tyr Leu His Trp Ala Leu Thr Asp Asn Tyr Glu Trp Ala Leu Gly Phe
            450                 455                 460

AGA ATG AGG TTT GGC TTG TAC GAA GTA AAC TTG ATA ACC AAA GAG AGA         1440
Arg Met Arg Phe Gly Leu Tyr Glu Val Asn Leu Ile Thr Lys Glu Arg
465                 470                 475                 480

AAA CCC AGG AAA AAG AGT GTA AGA GTA TTC AGA GAG ATA GTT ATT AAT         1488
Lys Pro Arg Lys Lys Ser Val Arg Val Phe Arg Glu Ile Val Ile Asn
                    485                 490                 495

AAT GGG CTA ACA AGC AAC ATC AGG AAA GAG ATC TTA GAG GAG GGG TAG         1536
Asn Gly Leu Thr Ser Asn Ile Arg Lys Glu Ile Leu Glu Glu Gly
                500                 505                 510
```

FIG. 11b

PYROCOCCUS FURIOSUS GLYCOSIDASE – 7G1
COMPLETE GENE SEQUENCE – 10/95

```
ATG TTC CCT GAA AAG TTC CTT TGG GGT GTG GCA CAA TCG GGT TTT CAG        48
Met Phe Pro Glu Lys Phe Leu Trp Gly Val Ala Gln Ser Gly Phe Gln
 1            5                    10                  15

TTT GAA ATG GGG GAT AAA CTC AGG AGG AAT ATT GAC ACT AAC ACT GAT        96
Phe Glu Met Gly Asp Lys Leu Arg Arg Asn Ile Asp Thr Asn Thr Asp
              20                  25                  30

TGG TGG CAC TGG GTA AGG GAT AAG ACA AAT ATA GAG AAA GGC CTC GTT       144
Trp Trp His Trp Val Arg Asp Lys Thr Asn Ile Glu Lys Gly Leu Val
              35                  40                  45

AGT GGA GAT CTT CCC GAG GAG GGG ATT AAC AAT TAC GAG CTT TAT GAG       192
Ser Gly Asp Leu Pro Glu Glu Gly Ile Asn Asn Tyr Glu Leu Tyr Glu
      50                  55                  60

AAG GAC CAT GAG ATT GCA AGA AAG CTG GGT CTT AAT GCT TAC AGA ATA       240
Lys Asp His Glu Ile Ala Arg Lys Leu Gly Leu Asn Ala Tyr Arg Ile
 65                  70                  75                  80

GGC ATA GAG TGG AGC AGA ATA TTC CCA TGG CCA ACG ACA TTT ATT GAT       288
Gly Ile Glu Trp Ser Arg Ile Phe Pro Trp Pro Thr Thr Phe Ile Asp
                  85                  90                  95

GTT GAT TAT AGC TAT AAT GAA TCA TAT AAC CTT ATA GAA GAT GTA AAG       336
Val Asp Tyr Ser Tyr Asn Glu Ser Tyr Asn Leu Ile Glu Asp Val Lys
              100                 105                 110

ATC ACC AAG GAC ACT TTG GAG GAG TTA GAT GAG ATC GCC AAC AAG AGG       384
Ile Thr Lys Asp Thr Leu Glu Glu Leu Asp Glu Ile Ala Asn Lys Arg
              115                 120                 125

GAG GTG GCC TAC TAT AGG TCA GTC ATA AAC AGC CTG AGG AGC AAG GGG       432
Glu Val Ala Tyr Tyr Arg Ser Val Ile Asn Ser Leu Arg Ser Lys Gly
              130                 135                 140

TTT AAG GTT ATA GTT AAT CTA AAT CAC TTC ACC CTT CCA TAT TGG TTG       480
Phe Lys Val Ile Val Asn Leu Asn His Phe Thr Leu Pro Tyr Trp Leu
145                 150                 155                 160

CAT GAT CCC ATT GAG GCT AGG GAG AGG GCG TTA ACT AAT AAG AGG AAC       528
His Asp Pro Ile Glu Ala Arg Glu Arg Ala Leu Thr Asn Lys Arg Asn
              165                 170                 175

GGC TGG GTT AAC CCA AGA ACA GTT ATA GAG TTT GCA AAG TAT GCC GCT       576
Gly Trp Val Asn Pro Arg Thr Val Ile Glu Phe Ala Lys Tyr Ala Ala
              180                 185                 190

TAC ATA GCC TAT AAG TTT GGA GAT ATA GTG GAT ATG TGG AGC ACG TTT       624
Tyr Ile Ala Tyr Lys Phe Gly Asp Ile Val Asp Met Trp Ser Thr Phe
              195                 200                 205

AAT GAG CCT ATG GTG GTT GTT GAG CTT GGC TAC CTA GCC CCC TAC TCT       672
Asn Glu Pro Met Val Val Val Glu Leu Gly Tyr Leu Ala Pro Tyr Ser
210                 215                 220

GGC TTC CCT CCA GGG GTT CTA AAT CCA GAG GCC GCA AAG CTG GCG ATA       720
Gly Phe Pro Pro Gly Val Leu Asn Pro Glu Ala Ala Lys Leu Ala Ile
225                 230                 235                 240

CTT CAC ATG ATA AAT GCA CAT GCT TTA GCT TAT AGG CAG ATA AAG AAG       768
Leu His Met Ile Asn Ala His Ala Leu Ala Tyr Arg Gln Ile Lys Lys
              245                 250                 255
```

FIG. 12a

```
TTT GAC ACT GAG AAA GCT GAT AAG GAT TCT AAA GAG CCT GCA GAA GTT    816
Phe Asp Thr Glu Lys Ala Asp Lys Asp Ser Lys Glu Pro Ala Glu Val
            260                 265                 270

GGT ATA ATT TAC AAC AAC ATT GGA GTT GCT TAT CCC AAG GAT CCG AAC    864
Gly Ile Ile Tyr Asn Asn Ile Gly Val Ala Tyr Pro Lys Asp Pro Asn
            275                 280                 285

GAT TCC AAG GAT GTT AAG GCA GCA GAA AAC GAC AAC TTC TTC CAC TCA    912
Asp Ser Lys Asp Val Lys Ala Ala Glu Asn Asp Asn Phe Phe His Ser
            290                 295                 300

GGG CTG TTC TTC GAG GCC ATA CAC AAA GGA AAA CTT AAT ATA GAG TTT    960
Gly Leu Phe Phe Glu Ala Ile His Lys Gly Lys Leu Asn Ile Glu Phe
305                 310                 315                 320

GAC GGT GAA ACG TTT ATA GAT GCC CCC TAT CTA AAG GGC AAT GAC TGG   1008
Asp Gly Glu Thr Phe Ile Asp Ala Pro Tyr Leu Lys Gly Asn Asp Trp
            325                 330                 335

ATA GGG GTT AAT TAC TAC ACA AGG GAA GTA GTT ACG TAT CAG GAA CCA   1056
Ile Gly Val Asn Tyr Tyr Thr Arg Glu Val Val Thr Tyr Gln Glu Pro
            340                 345                 350

ATG TTT CCT TCA ATC CCG CTG ATC ACC TTT AAG GGA GTT CAA GGA TAT   1104
Met Phe Pro Ser Ile Pro Leu Ile Thr Phe Lys Gly Val Gln Gly Tyr
            355                 360                 365

GGC TAT GCC TGC AGA CCT GGA ACT CTG TCA AAG GAT GAC AGA CCC GTC   1152
Gly Tyr Ala Cys Arg Pro Gly Thr Leu Ser Lys Asp Asp Arg Pro Val
            370                 375                 380

AGC GAC ATA GGA TGG GAA CTC TAT CCA GAG GGG ATG TAC GAT TCA ATA   1200
Ser Asp Ile Gly Trp Glu Leu Tyr Pro Glu Gly Met Tyr Asp Ser Ile
385                 390                 395                 400

GTT GAA GCT CAC AAG TAC GGC GTT CCA GTT TAC GTG ACG GAG AAC GGA   1248
Val Glu Ala His Lys Tyr Gly Val Pro Val Tyr Val Thr Glu Asn Gly
            405                 410                 415

ATA GCG GAT TCA AAG GAC ATC CTA AGA CCT TAC TAC ATA GCG AGC CAC   1296
Ile Ala Asp Ser Lys Asp Ile Leu Arg Pro Tyr Tyr Ile Ala Ser His
            420                 425                 430

ATA AAG ATG ATA GAG AAG GCC TTT GAG GAT GGG TAT GAA GTT AAG GGC   1344
Ile Lys Met Ile Glu Lys Ala Phe Glu Asp Gly Tyr Glu Val Lys Gly
            435                 440                 445

TAC TTC CAC TGG GCA TTA ACT GAC AAC TTC GAG TGG GCT CTC GGG TTT   1392
Tyr Phe His Trp Ala Leu Thr Asp Asn Phe Glu Trp Ala Leu Gly Phe
            450                 455                 460

AGA ATG CGC TTT GGC CTC TAC GAA GTC AAC CTA ATT ACA AAG GAG AGA   1440
Arg Met Arg Phe Gly Leu Tyr Glu Val Asn Leu Ile Thr Lys Glu Arg
465                 470                 475                 480

ATT CCC AGG GAG AAG AGC GTG TCG ATA TTC AGA GAG ATA GTA GCC AAT   1488
Ile Pro Arg Glu Lys Ser Val Ser Ile Phe Arg Glu Ile Val Ala Asn
            485                 490                 495

AAT GGT GTT ACG AAA AAG ATT GAA GAG GAA TTG CTG AGG GGA TGA      1533
Asn Gly Val Thr Lys Lys Ile Glu Glu Glu Leu Leu Arg Gly
            500                 505                 510
```

FIG. 12b

BANKIA GOULDI ENDOGLUCANASE (37GF1)

```
ATG AGA ATA CGT TTA GCG ACG CTC GCG CTC TGC GCA GCG CTG AGC CCA        48
Met Arg Ile Arg Leu Ala Thr Leu Ala Leu Cys Ala Ala Leu Ser Pro
 1               5                  10                  15

GTC ACC TTT GCA GAT AAT GTA ACC GTA CAA ATC GAC GCC GAC GGC GGT        96
Val Thr Phe Ala Asp Asn Val Thr Val Gln Ile Asp Ala Asp Gly Gly
                 20                  25                  30

AAA AAA CTC ATC AGC CGA GCC CTT TAC GGC ATG AAT AAC TCC AAC GCA       144
Lys Lys Leu Ile Ser Arg Ala Leu Tyr Gly Met Asn Asn Ser Asn Ala
             35                  40                  45

GAA AGC CTT ACC GAT ACT GAC TGG CAG CGT TTT CGC GAT GCA GGT GTG       192
Glu Ser Leu Thr Asp Thr Asp Trp Gln Arg Phe Arg Asp Ala Gly Val
         50                  55                  60

CGC ATG CTG CGG GAA AAT GGC GGC AAC AAC AGC ACC AAA TAT AAC TGG       240
Arg Met Leu Arg Glu Asn Gly Gly Asn Asn Ser Thr Lys Tyr Asn Trp
 65                  70                  75                  80

CAA CTG CAC CTG AGC AGT CAT CCG GAT TGG TAC AAC AAT GTC TAC GCC       288
Gln Leu His Leu Ser Ser His Pro Asp Trp Tyr Asn Asn Val Tyr Ala
                 85                  90                  95

GGC AAC AAC AAC TGG GAC AAC CGG GTA GCC CTG ATT CAG GAA AAC CTG       336
Gly Asn Asn Asn Trp Asp Asn Arg Val Ala Leu Ile Gln Glu Asn Leu
             100                 105                 110

CCC GGC GCC GAC ACC ATG TGG GCA TTC CAG CTC ATC GGT AAG GTC GCG       384
Pro Gly Ala Asp Thr Met Trp Ala Phe Gln Leu Ile Gly Lys Val Ala
         115                 120                 125

GCG ACT TCT GCC TAC AAC TTT AAC GAT TGG GAA TTC AAC CAG TCG CAA       432
Ala Thr Ser Ala Tyr Asn Phe Asn Asp Trp Glu Phe Asn Gln Ser Gln
130                 135                 140

TGG TGG ACC GGC GTC GCT CAG AAT CTC GCT GGC GGC GGT GAA CCC AAT       480
Trp Trp Thr Gly Val Ala Gln Asn Leu Ala Gly Gly Gly Glu Pro Asn
145                 150                 155                 160

CTG GAC GGC GGC GGC GAA GCG CTG GTT GAA GGA GAC CCC AAT CTC TAC       528
Leu Asp Gly Gly Gly Glu Ala Leu Val Glu Gly Asp Pro Asn Leu Tyr
                 165                 170                 175

CTC ATG GAT TGG TCG CCA GCC GAC ACT GTG GGT ATT CTC GAC CAC TGG       576
Leu Met Asp Trp Ser Pro Ala Asp Thr Val Gly Ile Leu Asp His Trp
             180                 185                 190

TTT GGC GTA AAC GGG CTG GGC GTG CGG CGT GGC AAA GCC AAA TAC TGG       624
Phe Gly Val Asn Gly Leu Gly Val Arg Arg Gly Lys Ala Lys Tyr Trp
         195                 200                 205

AGT ATG GAT AAC GAG CCC GGC ATC TGG GTT GGC ACC CAC GAC GAT GTA       672
Ser Met Asp Asn Glu Pro Gly Ile Trp Val Gly Thr His Asp Asp Val
210                 215                 220

GTG AAA GAA CAA ACG CCG GTA GAA GAT TTC CTG CAC ACC TAT TTC GAA       720
Val Lys Glu Gln Thr Pro Val Glu Asp Phe Leu His Thr Tyr Phe Glu
225                 230                 235                 240

ACC GCC AAA AAA GCC CGC GCC AAA TTT CCC GGT ATT AAA ATC ACC GGT       768
Thr Ala Lys Lys Ala Arg Ala Lys Phe Pro Gly Ile Lys Ile Thr Gly
```

FIG. 13a

BANKIA GOULDI ENDOGLUCANASE (37GF1) (continued)

```
              245                         250                         255
CCG GTG CCC GCT AAT GAG TGG CAG TGG TAT GCC TGG GGC GGT TTC TCG        816
Pro Val Pro Ala Asn Glu Trp Gln Trp Tyr Ala Trp Gly Gly Phe Ser
            260                         265                 270

GTA CCC CAG GAA CAA GGG TTT ATG AGC TGG ATG GAG TAT TTC ATC AAG        864
Val Pro Gln Glu Gln Gly Phe Met Ser Trp Met Glu Tyr Phe Ile Lys
        275                         280                         285

CGG GTG TCT GAA GAG CAA CGC GCA AGT GGT GTT CGC CTC CTC GAT GTA        912
Arg Val Ser Glu Glu Gln Arg Ala Ser Gly Val Arg Leu Leu Asp Val
    290                         295                         300

CTC GAT CTG CAC TAC TAC CCC GGC GCT TAC AAT GCG GAA GAT ATC GTG        960
Leu Asp Leu His Tyr Tyr Pro Gly Ala Tyr Asn Ala Glu Asp Ile Val
305                         310                         315         320

CAA TTA CAT CGC ACG TTC TTC GAC CGC GAC TTT GTT TCA CTG GAT GCC       1008
Gln Leu His Arg Thr Phe Phe Asp Arg Asp Phe Val Ser Leu Asp Ala
                325                         330                 335

AAC GGG GTG AAA ATG GTA GAA GGT GGC TGG GAT GAC AGC ATC AAC AAG       1056
Asn Gly Val Lys Met Val Glu Gly Gly Trp Asp Asp Ser Ile Asn Lys
            340                         345                 350

GAA TAT ATT TTC GGG CGA GTG AAC GAT TGG CTC GAG GAA TAT ATG GGG       1104
Glu Tyr Ile Phe Gly Arg Val Asn Asp Trp Leu Glu Glu Tyr Met Gly
        355                         360                         365

CCA GAC CAT GGT GTA ACC CTG GGC TTA ACC GAA ATG TGC GTG CGC AAT       1152
Pro Asp His Gly Val Thr Leu Gly Leu Thr Glu Met Cys Val Arg Asn
    370                         375                         380

GTG AAT CCG ATG ACT ACC GCC ATC TGG TAT GCC TCC ATG CTC GGC ACC       1200
Val Asn Pro Met Thr Thr Ala Ile Trp Tyr Ala Ser Met Leu Gly Thr
385                         390                         395         400

TTC GCG GAT AAC GGC GTC GAA ATA TTC ACC CCA TGG TGC TGG AAC ACC       1248
Phe Ala Asp Asn Gly Val Glu Ile Phe Thr Pro Trp Cys Trp Asn Thr
                405                         410                 415

GGA ATG TGG GAA ACA CTC CAC CTC TTC AGC CGC TAC AAC AAA CCT TAT       1296
Gly Met Trp Glu Thr Leu His Leu Phe Ser Arg Tyr Asn Lys Pro Tyr
            420                         425                 430

CGG GTC GCC TCC AGC TCC AGT CTT GAA GAG TTT GTC AGC GCC TAC AGC       1344
Arg Val Ala Ser Ser Ser Ser Leu Glu Glu Phe Val Ser Ala Tyr Ser
        435                         440                         445

TCC ATT AAC GAA GCA GAA GAC GCC ATG ACG GTA CTT CTG GTG AAT CGT       1392
Ser Ile Asn Glu Ala Glu Asp Ala Met Thr Val Leu Leu Val Asn Arg
    450                         455                         460

TCC ACT AGC GAG ACC CAC ACC GCC ACT GTC GCT ATC GAC GAT TTC CCA       1440
Ser Thr Ser Glu Thr His Thr Ala Thr Val Ala Ile Asp Asp Phe Pro
465                         470                         475         480

CTG GAT GGC CCC TAC CGC ACC CTG CGC TTA CAC AAC CTG CCG GGG GAG       1488
Leu Asp Gly Pro Tyr Arg Thr Leu Arg Leu His Asn Leu Pro Gly Glu
                485                         490                 495
```

FIG. 13b

BANKIA GOULDI ENDOGLUCANASE (37GF1) (continued)

```
GAA ACC TTC GTA TCT CAC CGA GAC AAC GCC CTG GAA AAA GGT ACA GTG      1536
Glu Thr Phe Val Ser His Arg Asp Asn Ala Leu Glu Lys Gly Thr Val
            500                 505                 510

CGC GCC AGC GAC AAT ACG GTA ACA CTG GAG TTG CCC CCT CTG TCC GTT      1584
Arg Ala Ser Asp Asn Thr Val Thr Leu Glu Leu Pro Pro Leu Ser Val
            515                 520                 525

ACT GCA ATA TTG CTC AAG GCC CGG CCC TAA                              1614
Thr Ala Ile Leu Leu Lys Ala Arg Pro
            530                 535
```

FIG. 13c

THERMOTOGA MARITIMA ALPHA-GALACTOSIDASE
COMPLETE GENE SEQUENCE (1 OF 3)

| | | | | | | | | | | | | | | | | |
|---|---|---|---|---|---|---|---|---|---|---|---|---|---|---|---|---|
| GTG | ATC | TGT | GTG | GAA | ATA | TTC | GGA | AAG | ACC | TTC | AGA | GAG | GGA | AGA | TTC | 48 |
| Val | Ile | Cys | Val | Glu | Ile | Phe | Gly | Lys | Thr | Phe | Arg | Glu | Gly | Arg | Phe | |
| 1 | | | | 5 | | | | | 10 | | | | | 15 | | |
| GTT | CTC | AAA | GAG | AAA | AAC | TTC | ACA | GTT | GAG | TTC | GCG | GTG | GAG | AAG | ATA | 96 |
| Val | Leu | Lys | Glu | Lys | Asn | Phe | Thr | Val | Glu | Phe | Ala | Val | Glu | Lys | Ile | |
| | | | 20 | | | | | 25 | | | | | 30 | | | |
| CAC | CTT | GGC | TGG | AAG | ATC | TCC | GGC | AGG | GTG | AAG | GGA | AGT | CCG | GGA | AGG | 144 |
| His | Leu | Gly | Trp | Lys | Ile | Ser | Gly | Arg | Val | Lys | Gly | Ser | Pro | Gly | Arg | |
| | | 35 | | | | | 40 | | | | | 45 | | | | |
| CTT | GAG | GTT | CTT | CGA | ACG | AAA | GCA | CCG | GAA | AAG | GTA | CTT | GTG | AAC | AAC | 192 |
| Leu | Glu | Val | Leu | Arg | Thr | Lys | Ala | Pro | Glu | Lys | Val | Leu | Val | Asn | Asn | |
| | 50 | | | | | 55 | | | | | 60 | | | | | |
| TGG | CAG | TCC | TGG | GGA | CCG | TGC | AGG | GTG | GTC | GAT | GCC | TTT | TCT | TTC | AAA | 240 |
| Trp | Gln | Ser | Trp | Gly | Pro | Cys | Arg | Val | Val | Asp | Ala | Phe | Ser | Phe | Lys | |
| 65 | | | | | 70 | | | | | 75 | | | | | 80 | |
| CCA | CCT | GAA | ATA | GAT | CCG | AAC | TGG | AGA | TAC | ACC | GCT | TCG | GTG | GTG | CCC | 288 |
| Pro | Pro | Glu | Ile | Asp | Pro | Asn | Trp | Arg | Tyr | Thr | Ala | Ser | Val | Val | Pro | |
| | | | | 85 | | | | | 90 | | | | | 95 | | |
| GAT | GTA | CTT | GAA | AGG | AAC | CTC | CAG | AGC | GAC | TAT | TTC | GTG | GCT | GAA | GAA | 336 |
| Asp | Val | Leu | Glu | Arg | Asn | Leu | Gln | Ser | Asp | Tyr | Phe | Val | Ala | Glu | Glu | |
| | | | 100 | | | | | 105 | | | | | 110 | | | |
| GGA | AAA | GTG | TAC | GGT | TTT | CTG | AGT | TCG | AAA | ATC | GCA | CAT | CCT | TTC | TTC | 384 |
| Gly | Lys | Val | Tyr | Gly | Phe | Leu | Ser | Ser | Lys | Ile | Ala | His | Pro | Phe | Phe | |
| | | 115 | | | | | 120 | | | | | 125 | | | | |
| GCT | GTG | GAA | GAT | GGG | GAA | CTT | GTG | GCA | TAC | CTC | GAA | TAT | TTC | GAT | GTC | 432 |
| Ala | Val | Glu | Asp | Gly | Glu | Leu | Val | Ala | Tyr | Leu | Glu | Tyr | Phe | Asp | Val | |
| | 130 | | | | | 135 | | | | | 140 | | | | | |
| GAG | TTC | GAC | GAC | TTT | GTT | CCT | CTT | GAA | CCT | CTC | GTT | GTA | CTC | GAG | GAT | 480 |
| Glu | Phe | Asp | Asp | Phe | Val | Pro | Leu | Glu | Pro | Leu | Val | Val | Leu | Glu | Asp | |
| 145 | | | | | 150 | | | | | 155 | | | | | 160 | |
| CCC | AAC | ACA | CCC | CTT | CTT | CTG | GAG | AAA | TAC | GCG | GAA | CTC | GTC | GGA | ATG | 528 |
| Pro | Asn | Thr | Pro | Leu | Leu | Leu | Glu | Lys | Tyr | Ala | Glu | Leu | Val | Gly | Met | |
| | | | | 165 | | | | | 170 | | | | | 175 | | |
| GAA | AAC | AAC | GCG | AGA | GTT | CCA | AAA | CAC | ACA | CCC | ACT | GGA | TGG | TGC | AGC | 576 |
| Glu | Asn | Asn | Ala | Arg | Val | Pro | Lys | His | Thr | Pro | Thr | Gly | Trp | Cys | Ser | |
| | | | 180 | | | | | 185 | | | | | 190 | | | |
| TGG | TAC | CAT | TAC | TTC | CTT | GAT | CTC | ACC | TGG | GAA | GAG | ACC | CTC | AAG | AAC | 624 |
| Trp | Tyr | His | Tyr | Phe | Leu | Asp | Leu | Thr | Trp | Glu | Glu | Thr | Leu | Lys | Asn | |
| | | 195 | | | | | 200 | | | | | 205 | | | | |
| CTG | AAG | CTC | GCG | AAG | AAT | TTC | CCG | TTC | GAG | GTC | TTC | CAG | ATA | GAC | GAC | 672 |
| Leu | Lys | Leu | Ala | Lys | Asn | Phe | Pro | Phe | Glu | Val | Phe | Gln | Ile | Asp | Asp | |
| | 210 | | | | | 215 | | | | | 220 | | | | | |
| GCC | TAC | GAA | AAG | GAC | ATA | GGT | GAC | TGG | CTC | GTG | ACA | AGA | GGA | GAC | TTT | 720 |
| Ala | Tyr | Glu | Lys | Asp | Ile | Gly | Asp | Trp | Leu | Val | Thr | Arg | Gly | Asp | Phe | |
| 225 | | | | | 230 | | | | | 235 | | | | | 240 | |
| CCA | TCG | GTG | GAA | GAG | ATG | GCA | AAA | GTT | ATA | GCG | GAA | AAC | GGT | TTC | ATC | 768 |
| Pro | Ser | Val | Glu | Glu | Met | Ala | Lys | Val | Ile | Ala | Glu | Asn | Gly | Phe | Ile | |
| | | | | 245 | | | | | 250 | | | | | 255 | | |

FIG. 14a

THERMOTOGA MARITIMA ALPHA-GALACTOSIDASE
COMPLETE GENE SEQUENCE (2 OF 3)

```
CCG GGC ATA TGG ACC GCC CCG TTC AGT GTT TCT GAA ACC TCG GAT GTA     816
Pro Gly Ile Trp Thr Ala Pro Phe Ser Val Ser Glu Thr Ser Asp Val
        260             265             270

TTC AAC GAA CAT CCG GAC TGG GTA GTG AAG GAA AAC GGA GAG CCG AAG     864
Phe Asn Glu His Pro Asp Trp Val Val Lys Glu Asn Gly Glu Pro Lys
        275             280             285

ATG GCT TAC AGA AAC TGG AAC AAA AAG ATA TAC GCC CTC GAT CTT TCG     912
Met Ala Tyr Arg Asn Trp Asn Lys Lys Ile Tyr Ala Leu Asp Leu Ser
        290             295             300

AAA GAT GAG GTT CTG AAC TGG CTT TTC GAT CTC TTC TCA TCT CTG AGA     960
Lys Asp Glu Val Leu Asn Trp Leu Phe Asp Leu Phe Ser Ser Leu Arg
305             310             315             320

AAG ATG GGC TAC AGG TAC TTC AAG ATC GAC TTT CTC TTC GCG GGT GCC    1008
Lys Met Gly Tyr Arg Tyr Phe Lys Ile Asp Phe Leu Phe Ala Gly Ala
            325             330             335

GTT CCA GGA GAA AGA AAA AAG AAC ATA ACA CCA ATT CAG GCG TTC AGA    1056
Val Pro Gly Glu Arg Lys Lys Asn Ile Thr Pro Ile Gln Ala Phe Arg
        340             345             350

AAA GGG ATT GAG ACG ATC AGA AAA GCG GTG GGA GAA GAT TCT TTC ATC    1104
Lys Gly Ile Glu Thr Ile Arg Lys Ala Val Gly Glu Asp Ser Phe Ile
        355             360             365

CTC GGA TGC GGC TCT CCC CTT CTT CCC GCA GTG GGA TGC GTC GAC GGG    1152
Leu Gly Cys Gly Ser Pro Leu Leu Pro Ala Val Gly Cys Val Asp Gly
        370             375             380

ATG AGG ATA GGA CCT GAC ACT GCG CCG TTC TGG GGA GAA CAT ATA GAA    1200
Met Arg Ile Gly Pro Asp Thr Ala Pro Phe Trp Gly Glu His Ile Glu
385             390             395             400

GAC AAC GGA GCT CCC GCT GCA AGA TGG GCG CTG AGA AAC GCC ATA ACG    1248
Asp Asn Gly Ala Pro Ala Ala Arg Trp Ala Leu Arg Asn Ala Ile Thr
            405             410             415

AGG TAC TTC ATG CAC GAC AGG TTC TGG CTG AAC GAC CCC GAC TGT CTG    1296
Arg Tyr Phe Met His Asp Arg Phe Trp Leu Asn Asp Pro Asp Cys Leu
        420             425             430

ATA CTG AGA GAG GAG AAA ACG GAT CTC ACA CAG AAG GAA AAG GAG CTC    1344
Ile Leu Arg Glu Glu Lys Thr Asp Leu Thr Gln Lys Glu Lys Glu Leu
        435             440             445

TAC TCG TAC ACG TGT GGA GTG CTC GAC AAC ATG ATC ATA GAA AGC GAT    1392
Tyr Ser Tyr Thr Cys Gly Val Leu Asp Asn Met Ile Ile Glu Ser Asp
        450             455             460

GAT CTC TCG CTC GTC AGA GAT CAT GGA AAA AAG GTT CTG AAA GAA ACG    1440
Asp Leu Ser Leu Val Arg Asp His Gly Lys Lys Val Leu Lys Glu Thr
465             470             475             480

CTC GAA CTC CTC GGT GGA AGA CCA CGG GTT CAA AAC ATC ATG TCG GAG    1488
Leu Glu Leu Leu Gly Gly Arg Pro Arg Val Gln Asn Ile Met Ser Glu
            485             490             495

GAT CTG AGA TAC GAG ATC GTC TCG TCT GGC ACT CTC TCA GGA AAC GTC    1536
Asp Leu Arg Tyr Glu Ile Val Ser Ser Gly Thr Leu Ser Gly Asn Val
        500             505             510
```

FIG. 14b

THERMOTOGA MARITIMA ALPHA-GALACTOSIDASE
COMPLETE GENE SEQUENCE (3 OF 3)

| | | | | | | | | | | | | | | | |
|---|---|---|---|---|---|---|---|---|---|---|---|---|---|---|---|
| AAG | ATC | GTG | GTC | GAT | CTG | AAC | AGC | AGA | GAG | TAC | CAC | CTG | GAA | AAA | GAA | 1584 |
| Lys | Ile | Val | Val | Asp | Leu | Asn | Ser | Arg | Glu | Tyr | His | Leu | Glu | Lys | Glu |
| | | 515 | | | | | 520 | | | | | 525 | | | |
| GGA | AAG | TCC | TCC | CTG | AAA | AAA | AGA | GTC | GTC | AAA | AGA | GAA | GAC | GGA | AGA | 1632 |
| Gly | Lys | Ser | Ser | Leu | Lys | Lys | Arg | Val | Val | Lys | Arg | Glu | Asp | Gly | Arg |
| | 530 | | | | | 535 | | | | | 540 | | | | |
| AAC | TTC | TAC | TTC | TAC | GAA | GAG | GGT | GAG | AGA | GAA | TGA | | | | | 1668 |
| Asn | Phe | Tyr | Phe | Tyr | Glu | Glu | Gly | Glu | Arg | Glu | | | | | |
| 545 | | | | | 550 | | | | 555 | | | | | | |

FIG. 14c

THERMOTOGA MARITINA β-MANNANASE (6GP2)

```
ATG GGG ATT GGT GGC GAC GAC TCC TGG AGC CCG TCA GTA TCG GCG GAA        48
Met Gly Ile Gly Gly Asp Asp Ser Trp Ser Pro Ser Val Ser Ala Glu
 1            5                  10                 15

TTC CTT TTA TTG ATC GTT GAG CTC TCT TTC GTT CTC TTT GCA AGT GAC        96
Phe Leu Leu Leu Ile Val Glu Leu Ser Phe Val Leu Phe Ala Ser Asp
             20                  25                 30

GAG TTC GTG AAA GTG GAA AAC GGA AAA TTC GCT CTG AAC GGA AAA GAA       144
Glu Phe Val Lys Val Glu Asn Gly Lys Phe Ala Leu Asn Gly Lys Glu
             35                  40                 45

TTC AGA TTC ATT GGA AGC AAC AAC TAC TAC ATG CAC TAC AAG AGC AAC       192
Phe Arg Phe Ile Gly Ser Asn Asn Tyr Tyr Met His Tyr Lys Ser Asn
         50                  55                 60

GGA ATG ATA GAC AGT GTT CTG GAG AGT GCC AGA GAC ATG GGT ATA AAG       240
Gly Met Ile Asp Ser Val Leu Glu Ser Ala Arg Asp Met Gly Ile Lys
 65              70                  75                  80

GTC CTC AGA ATC TGG GGT TTC CTC GAC GGG GAG AGT TAC TGC AGA GAC       288
Val Leu Arg Ile Trp Gly Phe Leu Asp Gly Glu Ser Tyr Cys Arg Asp
                 85                  90                  95

AAG AAC ACC TAC ATG CAT CCT GAG CCC GGT GTT TTC GGG GTG CCA GAA       336
Lys Asn Thr Tyr Met His Pro Glu Pro Gly Val Phe Gly Val Pro Glu
                100                 105                110

GGA ATA TCG AAC GCC CAG AGC GGT TTC GAA AGA CTC GAC TAC ACA GTT       384
Gly Ile Ser Asn Ala Gln Ser Gly Phe Glu Arg Leu Asp Tyr Thr Val
            115                 120                 125

GCG AAA GCG AAA GAA CTC GGT ATA AAA CTT GTC ATT GTT CTT GTG AAC       432
Ala Lys Ala Lys Glu Leu Gly Ile Lys Leu Val Ile Val Leu Val Asn
        130                 135                 140

AAC TGG GAC GAC TTC GGT GGA ATG AAC CAG TAC GTG AGG TGG TTT GGA       480
Asn Trp Asp Asp Phe Gly Gly Met Asn Gln Tyr Val Arg Trp Phe Gly
145                 150                 155                 160

GGA ACC CAT CAC GAC GAT TTC TAC AGA GAT GAG AAG ATC AAA GAA GAG       528
Gly Thr His His Asp Asp Phe Tyr Arg Asp Glu Lys Ile Lys Glu Glu
                165                 170                 175

TAC AAA AAG TAC GTC TCC TTT CTC GTA AAC CAT GTC AAT ACC TAC ACG       576
Tyr Lys Lys Tyr Val Ser Phe Leu Val Asn His Val Asn Thr Tyr Thr
            180                 185                 190

GGA GTT CCT TAC AGG GAA GAG CCC ACC ATC ATG GCC TGG GAG CTT GCA       624
Gly Val Pro Tyr Arg Glu Glu Pro Thr Ile Met Ala Trp Glu Leu Ala
        195                 200                 205

AAC GAA CCG CGC TGT GAG ACG GAC AAA TCG GGG AAC ACG CTC GTT GAG       672
Asn Glu Pro Arg Cys Glu Thr Asp Lys Ser Gly Asn Thr Leu Val Glu
210                 215                 220

TGG GTG AAG GAG ATG AGC TCC TAC ATA AAG AGT CTG GAT CCC AAC CAC       720
Trp Val Lys Glu Met Ser Ser Tyr Ile Lys Ser Leu Asp Pro Asn His
225                 230                 235                 240

CTC GTG GCT GTG GGG GAC GAA GGA TTC TTC AGC AAC TAC GAA GGA TTC       768
Leu Val Ala Val Gly Asp Glu Gly Phe Phe Ser Asn Tyr Glu Gly Phe
                245                 250                 255
```

FIG. 15a

THERMOTOGA MARITINA β-MANNANASE (continued) (6GP2)

```
AAA CCT TAC GGT GGA GAA GCC GAG TGG GCC TAC AAC GGC TGG TCC GGT    816
Lys Pro Tyr Gly Gly Glu Ala Glu Trp Ala Tyr Asn Gly Trp Ser Gly
        260             265             270

GTT GAC TGG AAG AAG CTC CTT TCG ATA GAG ACG GTG GAC TTC GGC ACG    864
Val Asp Trp Lys Lys Leu Leu Ser Ile Glu Thr Val Asp Phe Gly Thr
        275             280             285

TTC CAC CTC TAT CCG TCC CAC TGG GGT GTC AGT CCA GAG AAC TAT GCC    912
Phe His Leu Tyr Pro Ser His Trp Gly Val Ser Pro Glu Asn Tyr Ala
        290             295             300

CAG TGG GGA GCG AAG TGG ATA GAA GAC CAC ATA AAG ATC GCA AAA GAG    960
Gln Trp Gly Ala Lys Trp Ile Glu Asp His Ile Lys Ile Ala Lys Glu
305             310             315             320

ATC GGA AAA CCC GTT GTT CTG GAA GAA TAT GGA ATT CCA AAG AGT GCG    1008
Ile Gly Lys Pro Val Val Leu Glu Glu Tyr Gly Ile Pro Lys Ser Ala
                325             330             335

CCA GTT AAC AGA ACG GCC ATC TAC AGA CTC TGG AAC GAT CTG GTC TAC    1056
Pro Val Asn Arg Thr Ala Ile Tyr Arg Leu Trp Asn Asp Leu Val Tyr
        340             345             350

GAT CTC GGT GGA GAT GGA GCG ATG TTC TGG ATG CTC GCG GGA ATC GGG    1104
Asp Leu Gly Gly Asp Gly Ala Met Phe Trp Met Leu Ala Gly Ile Gly
        355             360             365

GAA GGT TCG GAC AGA GAC GAG AGA GGG TAC TAT CCG GAC TAC GAC GGT    1152
Glu Gly Ser Asp Arg Asp Glu Arg Gly Tyr Tyr Pro Asp Tyr Asp Gly
370             375             380

TTC AGA ATA GTG AAC GAC GAC AGT CCA GAA GCG GAA CTG ATA AGA GAA    1200
Phe Arg Ile Val Asn Asp Asp Ser Pro Glu Ala Glu Leu Ile Arg Glu
385             390             395             400

TAC GCG AAG CTG TTC AAC ACA GGT GAA GAC ATA AGA GAA GAC ACC TGC    1248
Tyr Ala Lys Leu Phe Asn Thr Gly Glu Asp Ile Arg Glu Asp Thr Cys
        405             410             415

TCT TTC ATC CTT CCA AAA GAC GGC ATG GAG ATC AAA AAG ACC GTG GAA    1296
Ser Phe Ile Leu Pro Lys Asp Gly Met Glu Ile Lys Lys Thr Val Glu
        420             425             430

GTG AGG GCT GGT GTT TTC GAC TAC AGC AAC ACG TTT GAA AAG TTG TCT    1344
Val Arg Ala Gly Val Phe Asp Tyr Ser Asn Thr Phe Glu Lys Leu Ser
        435             440             445

GTC AAA GTC GAA GAT CTG GTT TTT GAA AAT GAG ATA GAG CAT CTC GGA    1392
Val Lys Val Glu Asp Leu Val Phe Glu Asn Glu Ile Glu His Leu Gly
450             455             460

TAC GGA ATT TAC GGC TTT GAT CTC GAC ACA ACC CGG ATC CCG GAT GGA    1440
Tyr Gly Ile Tyr Gly Phe Asp Leu Asp Thr Thr Arg Ile Pro Asp Gly
465             470             475             480

GAA CAT GAA ATG TTC CTT GAA GGC CAC TTT CAG GGA AAA ACG GTG AAA    1488
Glu His Glu Met Phe Leu Glu Gly His Phe Gln Gly Lys Thr Val Lys
        485             490             495

GAC TCT ATC AAA GCG AAA GTG GTG AAC GAA GCA CGG TAC GTG CTC GCA    1536
Asp Ser Ile Lys Ala Lys Val Val Asn Glu Ala Arg Tyr Val Leu Ala
        500             505             510
```

FIG. 15b

THERMOTOGA MARITIMA β-MANNANASE (continued) (6GP2)

```
GAG GAA GTT GAT TTT TCC TCT CCA GAA GAG GTG AAA AAC TGG TGG AAC     1584
Glu Glu Val Asp Phe Ser Ser Pro Glu Glu Val Lys Asn Trp Trp Asn
        515                 520                 525

AGC GGA ACC TGG CAG GCA GAG TTC GGG TCA CCT GAC ATT GAA TGG AAC     1632
Ser Gly Thr Trp Gln Ala Glu Phe Gly Ser Pro Asp Ile Glu Trp Asn
        530                 535                 540

GGT GAG GTG GGA AAT GGA GCA CTG CAG CTG AAC GTG AAA CTG CCC GGA     1680
Gly Glu Val Gly Asn Gly Ala Leu Gln Leu Asn Val Lys Leu Pro Gly
545                 550                 555                 560

AAG AGC GAC TGG GAA GAA GTG AGA GTA GCA AGG AAG TTC GAA AGA CTC     1728
Lys Ser Asp Trp Glu Glu Val Arg Val Ala Arg Lys Phe Glu Arg Leu
                565                 570                 575

TCA GAA TGT GAG ATC CTC GAG TAC GAC ATC TAC ATT CCA AAC GTC GAG     1776
Ser Glu Cys Glu Ile Leu Glu Tyr Asp Ile Tyr Ile Pro Asn Val Glu
        580                 585                 590

GGA CTC AAG GGA AGG TTG AGG CCG TAC GCG GTT CTG AAC CCC GGC TGG     1824
Gly Leu Lys Gly Arg Leu Arg Pro Tyr Ala Val Leu Asn Pro Gly Trp
        595                 600                 605

GTG AAG ATA GGC CTC GAC ATG AAC AAC GCG AAC GTG GAA AGT GCG GAG     1872
Val Lys Ile Gly Leu Asp Met Asn Asn Ala Asn Val Glu Ser Ala Glu
        610                 615                 620

ATC ATC ACT TTC GGC GGA AAA GAG TAC AGA AGA TTC CAT GTA AGA ATT     1920
Ile Ile Thr Phe Gly Gly Lys Glu Tyr Arg Arg Phe His Val Arg Ile
625                 630                 635                 640

GAG TTC GAC AGA ACA GCG GGG GTG AAA GAA CTT CAC ATA GGA GTT GTC     1968
Glu Phe Asp Arg Thr Ala Gly Val Lys Glu Leu His Ile Gly Val Val
                645                 650                 655

GGT GAT CAT CTG AGG TAC GAT GGA CCG ATT TTC ATC GAT AAT GTG AGA     2016
Gly Asp His Leu Arg Tyr Asp Gly Pro Ile Phe Ile Asp Asn Val Arg
            660                 665                 670

CTT TAT AAA AGA ACA GGA GGT ATG TGA                                  2043
Leu Tyr Lys Arg Thr Gly Gly Met
        675                 680
```

FIG. 15c

AEPII 1a β-MANNOSIDASE (63GB1)

```
ATG CTA CCA GAA GAG TTC CTA TGG GGC GTT GGG CAG TCA GGC TTT CAG          48
Met Leu Pro Glu Glu Phe Leu Trp Gly Val Gly Gln Ser Gly Phe Gln
 1               5                  10                  15

TTC GAA ATG GGC GAC AAG CTC AGG AGG CAC ATC GAT CCA AAT ACC GAC          96
Phe Glu Met Gly Asp Lys Leu Arg Arg His Ile Asp Pro Asn Thr Asp
             20                  25                  30

TGG TGG AAG TGG GTT CGC GAT CCT TTC AAC ATA AAA AAG GAG CTT GTG         144
Trp Trp Lys Trp Val Arg Asp Pro Phe Asn Ile Lys Lys Glu Leu Val
         35                  40                  45

AGT GGG GAC CTT CCC GAG GAC GGC ATC AAC AAC TAC GAA CTT TTT GAA         192
Ser Gly Asp Leu Pro Glu Asp Gly Ile Asn Asn Tyr Glu Leu Phe Glu
     50                  55                  60

AAC GAT CAC AAG CTC GCT AAA GGC CTT GGA CTC AAC GCA TAC AGG ATT         240
Asn Asp His Lys Leu Ala Lys Gly Leu Gly Leu Asn Ala Tyr Arg Ile
 65                  70                  75                  80

GGA ATA GAG TGG AGC AGA ATC TTT CCC TGG CCG ACG TGG ACG GTC GAT         288
Gly Ile Glu Trp Ser Arg Ile Phe Pro Trp Pro Thr Trp Thr Val Asp
             85                  90                  95

ACC GAG GTC GAG TTC GAC ACT TAC GGT TTA GTA AAG GAC GTT AAG ATA         336
Thr Glu Val Glu Phe Asp Thr Tyr Gly Leu Val Lys Asp Val Lys Ile
            100                 105                 110

GAC AAG TCC ACC CTT GCT GAA CTC GAC AGG CTG GCC AAC AAG GAG GAG         384
Asp Lys Ser Thr Leu Ala Glu Leu Asp Arg Leu Ala Asn Lys Glu Glu
            115                 120                 125

GTA ATG TAC TAC AGG CGC GTT ATT CAG CAT TTG AGG GAG CTC GGC TTC         432
Val Met Tyr Tyr Arg Arg Val Ile Gln His Leu Arg Glu Leu Gly Phe
    130                 135                 140

AAG GTC TTC GTT AAC CTC AAC CAC TTC ACG CTT CCA ATA TGG CTC CAC         480
Lys Val Phe Val Asn Leu Asn His Phe Thr Leu Pro Ile Trp Leu His
145                 150                 155                 160

GAC CCG ATA GTG GCA AGG GAG AAG GCC CTC ACA AAC GAC AGA ATC GGC         528
Asp Pro Ile Val Ala Arg Glu Lys Ala Leu Thr Asn Asp Arg Ile Gly
            165                 170                 175

TGG GTC TCC CAG AGG ACA GTT GTT GAG TTT GCC AAG TAT GCT GCT TAC         576
Trp Val Ser Gln Arg Thr Val Val Glu Phe Ala Lys Tyr Ala Ala Tyr
            180                 185                 190

ATC GCC CAT GCG CTC GGA GAC CTC GTG GAC ACA TGG AGC ACC TTC AAC         624
Ile Ala His Ala Leu Gly Asp Leu Val Asp Thr Trp Ser Thr Phe Asn
    195                 200                 205

GAA CCT ATG GTA GTT GTG GAG CTC GGC TAC CTC GCC CCC TAC TCA GGA         672
Glu Pro Met Val Val Val Glu Leu Gly Tyr Leu Ala Pro Tyr Ser Gly
210                 215                 220

TTT CCC CCG GGA GTC ATG AAC CCC GAG GCC GCG AAG CTG GCG ATC CTC         720
Phe Pro Pro Gly Val Met Asn Pro Glu Ala Ala Lys Leu Ala Ile Leu
225                 230                 235                 240

AAC ATG ATA AAC GCC CAC GCC TTG GCA TAT AAG ATG ATA AAG AGG TTC         768
Asn Met Ile Asn Ala His Ala Leu Ala Tyr Lys Met Ile Lys Arg Phe
            245                 250                 255
```

FIG. 16a

AKPII 1a β-MANNOSIDASE (63GB1) (continued)

```
GAC ACC AAG AAG GCC GAT GAG GAT AGC AAG TCC CCT GCG GAC GTT GGC      816
Asp Thr Lys Lys Ala Asp Glu Asp Ser Lys Ser Pro Ala Asp Val Gly
        260                 265                 270

ATA ATT TAC AAC AAC ATC GGT GTT GCC TAC CCT AAA GAC CCT AAC GAT      864
Ile Ile Tyr Asn Asn Ile Gly Val Ala Tyr Pro Lys Asp Pro Asn Asp
        275                 280                 285

CCC AAG GAC GTT AAA GCA GCC GAA AAC GAC AAC TAC TTC CAC AGC GGA      912
Pro Lys Asp Val Lys Ala Ala Glu Asn Asp Asn Tyr Phe His Ser Gly
        290                 295                 300

CTG TTC TTT GAT GCC ATC CAC AAG GGT AAG CTC AAC ATA GAG TTC GAC      960
Leu Phe Phe Asp Ala Ile His Lys Gly Lys Leu Asn Ile Glu Phe Asp
305                 310                 315                 320

GGC GAA AAC TTT GTA AAA GTT AGA CAC CTA AAA GGC AAT GAC TGG ATA     1008
Gly Glu Asn Phe Val Lys Val Arg His Leu Lys Gly Asn Asp Trp Ile
                325                 330                 335

GGC CTC AAC TAC TAC ACC CGC GAG GTT GTT AGA TAT TCG GAG CCC AAG     1056
Gly Leu Asn Tyr Tyr Thr Arg Glu Val Val Arg Tyr Ser Glu Pro Lys
                340                 345                 350

TTC CCA AGT ATA CCC CTC ATA TCC TTC AAG GGC GTT CCC AAC TAC GGC     1104
Phe Pro Ser Ile Pro Leu Ile Ser Phe Lys Gly Val Pro Asn Tyr Gly
            355                 360                 365

TAC TCC TGC AGG CCC GGC ACG ACC TCC GCC GAT GGC ATG CCC GTC AGC     1152
Tyr Ser Cys Arg Pro Gly Thr Thr Ser Ala Asp Gly Met Pro Val Ser
370                 375                 380

GAT ATC GGC TGG GAA GTC TAT CCC CAG GGA ATC TAC GAC TCG ATA GTC     1200
Asp Ile Gly Trp Glu Val Tyr Pro Gln Gly Ile Tyr Asp Ser Ile Val
385                 390                 395                 400

GAG GCC ACC AAG TAC AGT GTT CCT GTT TAC GTC ACC GAG AAC GGT GTT     1248
Glu Ala Thr Lys Tyr Ser Val Pro Val Tyr Val Thr Glu Asn Gly Val
                405                 410                 415

GCG GAT TCC GCG GAC ACG CTG AGG CCA TAC TAC ATA GTC AGC CAC GTC     1296
Ala Asp Ser Ala Asp Thr Leu Arg Pro Tyr Tyr Ile Val Ser His Val
                420                 425                 430

TCA AAG ATA GAG GAA GCC ATT GAG AAT GGA TAC CCC GTA AAA GGC TAC     1344
Ser Lys Ile Glu Glu Ala Ile Glu Asn Gly Tyr Pro Val Lys Gly Tyr
                435                 440                 445

ATG TAC TGG GCG CTT ACG GAT AAC TAC GAG TGG GCC CTC GGC TTC AGC     1392
Met Tyr Trp Ala Leu Thr Asp Asn Tyr Glu Trp Ala Leu Gly Phe Ser
        450                 455                 460

ATG AGG TTT GGT CTC TAC AAG GTC GAC CTC ATC TCC AAG GAG AGG ATC     1440
Met Arg Phe Gly Leu Tyr Lys Val Asp Leu Ile Ser Lys Glu Arg Ile
465                 470                 475                 480

CCG AGG GAG AGA AGC GTT GAG ATA TAT CGC AGG ATA GTG CAG TCC AAC     1488
Pro Arg Glu Arg Ser Val Glu Ile Tyr Arg Arg Ile Val Gln Ser Asn
                485                 490                 495

GGT GTT CCT AAG GAT ATC AAA GAG GAG TTC CTG AAG GGT GAG GAG AAA     1536
Gly Val Pro Lys Asp Ile Lys Glu Glu Phe Leu Lys Gly Glu Glu Lys
            500                 505                 510

TGA                                                                  1539
```

FIG. 16b

OC1/4V ENDOGLUCANASE (33GP1)

```
ATG GTA GAA AGA CAC TTC AGA TAT GTT CTT ATT TGC ACC CTG TTT CTT      48
Met Val Glu Arg His Phe Arg Tyr Val Leu Ile Cys Thr Leu Phe Leu
 1               5                  10                  15

GTT ATG CTC CTA ATC TCA TCC ACT CAG TGT GGA AAA AAT GAA CCA AAC      96
Val Met Leu Leu Ile Ser Ser Thr Gln Cys Gly Lys Asn Glu Pro Asn
                20                  25                  30

AAA AGA GTG AAT AGC ATG GAA CAG TCA GTT GCT GAA AGT GAT AGC AAC     144
Lys Arg Val Asn Ser Met Glu Gln Ser Val Ala Glu Ser Asp Ser Asn
             35                  40                  45

TCA GCA TTT GAA TAC AAC AAA ATG GTA GGT AAA GGA GTA AAT ATT GGA     192
Ser Ala Phe Glu Tyr Asn Lys Met Val Gly Lys Gly Val Asn Ile Gly
         50                  55                  60

AAT GCT TTA GAA GCT CCT TTC GAA GGA GCT TGG GGA GTA AGA ATT GAG     240
Asn Ala Leu Glu Ala Pro Phe Glu Gly Ala Trp Gly Val Arg Ile Glu
 65                  70                  75                  80

GAT GAA TAT TTT GAG ATA ATA AAG AAA AGG GGA TTT GAT TCT GTT AGG     288
Asp Glu Tyr Phe Glu Ile Ile Lys Lys Arg Gly Phe Asp Ser Val Arg
                 85                  90                  95

ATT CCC ATA AGA TGG TCA GCA CAT ATA TCC GAA AAG CCA CCA TAT GAT     336
Ile Pro Ile Arg Trp Ser Ala His Ile Ser Glu Lys Pro Pro Tyr Asp
                100                 105                 110

ATT GAC AGG AAT TTC CTC GAA AGA GTT AAC CAT GTT GTC GAT AGG GCT     384
Ile Asp Arg Asn Phe Leu Glu Arg Val Asn His Val Val Asp Arg Ala
            115                 120                 125

CTT GAG AAT AAT TTA ACA GTA ATC ATC AAT ACG CAC CAT TTT GAA GAA     432
Leu Glu Asn Asn Leu Thr Val Ile Ile Asn Thr His His Phe Glu Glu
        130                 135                 140

CTC TAT CAA GAA CCG GAT AAA TAC GGC GAT GTT TTG GTG GAA ATT TGG     480
Leu Tyr Gln Glu Pro Asp Lys Tyr Gly Asp Val Leu Val Glu Ile Trp
145                 150                 155                 160

AGA CAG ATT GCA AAA TTC TTT AAA GAT TAC CCG GAA AAT CTG TTC TTT     528
Arg Gln Ile Ala Lys Phe Phe Lys Asp Tyr Pro Glu Asn Leu Phe Phe
                165                 170                 175

GAA ATC TAC AAC GAG CCT GCT CAG AAC TTG ACA GCT GAA AAA TGG AAC     576
Glu Ile Tyr Asn Glu Pro Ala Gln Asn Leu Thr Ala Glu Lys Trp Asn
                180                 185                 190

GCA CTT TAT CCA AAA GTG CTC AAA GTT ATC AGG GAG AGC AAT CCA ACC     624
Ala Leu Tyr Pro Lys Val Leu Lys Val Ile Arg Glu Ser Asn Pro Thr
            195                 200                 205

CGG ATT GTC ATT ATC GAT GCT CCA AAC TGG GCA CAC TAT AGC GCA GTG     672
Arg Ile Val Ile Ile Asp Ala Pro Asn Trp Ala His Tyr Ser Ala Val
        210                 215                 220

AGA AGT CTA AAA TTA GTC AAC GAC AAA CGC ATC ATT GTT TCC TTC CAT     720
Arg Ser Leu Lys Leu Val Asn Asp Lys Arg Ile Ile Val Ser Phe His
225                 230                 235                 240

TAC TAC GAA CCT TTC AAA TTC ACA CAT CAG GGT GCC GAA TGG GTT AAT     768
Tyr Tyr Glu Pro Phe Lys Phe Thr His Gln Gly Ala Glu Trp Val Asn
                245                 250                 255
```

FIG. 17a

OC1/4V ENDOGLUCANASE (33GP1) (continued)

```
CCC ATC CCA CCT GTT AGG GTT AAG TGG AAT GGC GAG GAA TGG GAA ATT        816
Pro Ile Pro Pro Val Arg Val Lys Trp Asn Gly Glu Glu Trp Glu Ile
            260             265             270

AAC CAA ATC AGA AGT CAT TTC AAA TAC GTG AGT GAC TGG GCA AAG CAA        864
Asn Gln Ile Arg Ser His Phe Lys Tyr Val Ser Asp Trp Ala Lys Gln
        275             280             285

AAT AAC GTA CCA ATC TTT CTT GGT GAA TTC GGT GCT TAT TCA AAA GCA        912
Asn Asn Val Pro Ile Phe Leu Gly Glu Phe Gly Ala Tyr Ser Lys Ala
    290             295             300

GAC ATG GAC TCA AGG GTT AAG TGG ACC GAA AGT GTG AGA AAA ATG GCG        960
Asp Met Asp Ser Arg Val Lys Trp Thr Glu Ser Val Arg Lys Met Ala
305             310             315             320

GAA GAA TTT GGA TTT TCA TAC GCG TAT TGG GAA TTT TGT GCA GGA TTT       1008
Glu Glu Phe Gly Phe Ser Tyr Ala Tyr Trp Glu Phe Cys Ala Gly Phe
                325             330             335

GGC ATA TAC GAT AGA TGG TCT CAA AAC TGG ATC GAA CCA TTG GCA ACA       1056
Gly Ile Tyr Asp Arg Trp Ser Gln Asn Trp Ile Glu Pro Leu Ala Thr
            340             345             350

GCT GTG GTT GGC ACA GGC AAA GAG TAA                                   1083
Ala Val Val Gly Thr Gly Lys Glu
            355             360
```

FIG. 17b

Thermotoga maritima Pullulanase (6GP3)

```
                9              18             27             36             45             54
5'   ATG GAT CTT ACA AAG GTG GGG ATC ATA GTG AGG CTG AAC GAG TGG CAG GCA AAA
     --- --- --- --- --- --- --- --- --- --- --- --- --- --- --- --- --- ---
     Met Asp Leu Thr Lys Val Gly Ile Ile Val Arg Leu Asn Glu Trp Gln Ala Lys 63             72             81             90             99            108
     GAC GTG GCA AAA GAC AGG TTC ATA GAG ATA AAA GAC GGA AAG GCT GAA GTG TGG
     --- --- --- --- --- --- --- --- --- --- --- --- --- --- --- --- --- ---
     Asp Val Ala Lys Asp Arg Phe Ile Glu Ile Lys Asp Gly Lys Ala Glu Val Trp 117            126            135            144            153            162
     ATA CTC CAG GGA GTG GAA GAG ATT TTC TAC GAA AAA CCA GAC ACA TCT CCC AGA
     --- --- --- --- --- --- --- --- --- --- --- --- --- --- --- --- --- ---
     Ile Leu Gln Gly Val Glu Glu Ile Phe Tyr Glu Lys Pro Asp Thr Ser Pro Arg 171            180            189            198            207            216
     ATC TTC TTC GCA CAG GCA AGG TCG AAC AAG GTG ATC GAG GCT TTT CTG ACC AAT
     --- --- --- --- --- --- --- --- --- --- --- --- --- --- --- --- --- ---
     Ile Phe Phe Ala Gln Ala Arg Ser Asn Lys Val Ile Glu Ala Phe Leu Thr Asn 225            234            243            252            261            270
     CCT GTG GAT ACG AAA AAG AAA GAA CTC TTC AAG GTT ACT GTT GAC GGA AAA GAG
     --- --- --- --- --- --- --- --- --- --- --- --- --- --- --- --- --- ---
     Pro Val Asp Thr Lys Lys Lys Glu Leu Phe Lys Val Thr Val Asp Gly Lys Glu 279            288            297            306            315            324
     ATT CCC GTC TCA AGA GTG GAA AAG GCC GAT CCC ACG GAC ATA GAC GTG ACG AAC
     --- --- --- --- --- --- --- --- --- --- --- --- --- --- --- --- --- ---
     Ile Pro Val Ser Arg Val Glu Lys Ala Asp Pro Thr Asp Ile Asp Val Thr Asn 333            342            351            360            369            378
     TAC GTG AGA ATC GTC CTT TCT GAA TCC CTG AAA GAA GAA GAC CTC AGA AAA GAC
     --- --- --- --- --- --- --- --- --- --- --- --- --- --- --- --- --- ---
     Tyr Val Arg Ile Val Leu Ser Glu Ser Leu Lys Glu Glu Asp Leu Arg Lys Asp 387            396            405            414            423            432
     GTG GAA CTG ATC ATA GAA GGT TAC AAA CCG GCA AGA GTC ATC ATG ATG GAG ATC
     --- --- --- --- --- --- --- --- --- --- --- --- --- --- --- --- --- ---
     Val Glu Leu Ile Ile Glu Gly Tyr Lys Pro Ala Arg Val Ile Met Met Glu Ile 441            450            459            468            477            486
     CTG GAC GAC TAC TAT TAC GAT GGA GAG CTC GGA GCC GTA TAT TCT CCA GAG AAG
     --- --- --- --- --- --- --- --- --- --- --- --- --- --- --- --- --- ---
     Leu Asp Asp Tyr Tyr Tyr Asp Gly Glu Leu Gly Ala Val Tyr Ser Pro Glu Lys 495            504            513            522            531            540
     ACG ATA TTC AGA GTC TGG TCC CCC GTT TCT AAG TGG GTA AAG GTG CTT CTC TTC
     --- --- --- --- --- --- --- --- --- --- --- --- --- --- --- --- --- ---
     Thr Ile Phe Arg Val Trp Ser Pro Val Ser Lys Trp Val Lys Val Leu Leu Phe
```

Figure 18a

Thermotoga maritima Pullulanase (6GP3) (continued)

```
         549             558             567             576             585             594
AAA AAC GGA GAA GAC ACA GAA CCG TAC CAG GTT GTG AAC ATG GAA TAC AAG GGA
--- --- --- --- --- --- --- --- --- --- --- --- --- --- --- --- --- ---
Lys Asn Gly Glu Asp Thr Glu Pro Tyr Gln Val Val Asn Met Glu Tyr Lys Gly 603             612             621             630             639             648
AAC GGG GTC TGG GAA GCG GTT GTT GAA GGC GAT CTC GAC GGA GTG TTC TAC CTC
--- --- --- --- --- --- --- --- --- --- --- --- --- --- --- --- --- ---
Asn Gly Val Trp Glu Ala Val Val Glu Gly Asp Leu Asp Gly Val Phe Tyr Leu 657             666             675             684             693             702
TAT CAG CTG GAA AAC TAC GGA AAG ATC AGA ACA ACC GTC GAT CCT TAT TCG AAA
--- --- --- --- --- --- --- --- --- --- --- --- --- --- --- --- --- ---
Tyr Gln Leu Glu Asn Tyr Gly Lys Ile Arg Thr Thr Val Asp Pro Tyr Ser Lys 711             720             729             738             747             756
GCG GTT TAC GCA AAC AGC AAA AAG AGC GCC GTT GTG AAT CTT GCC AGG ACA AAC
--- --- --- --- --- --- --- --- --- --- --- --- --- --- --- --- --- ---
Ala Val Tyr Ala Asn Ser Lys Lys Ser Ala Val Val Asn Leu Ala Arg Thr Asn 765             774             783             792             801             810
CCA GAA GGA TGG GAA AAC GAC AGG GGA CCG AAA ATC GAA GGA TAC GAA GAC GCG
--- --- --- --- --- --- --- --- --- --- --- --- --- --- --- --- --- ---
Pro Glu Gly Trp Glu Asn Asp Arg Gly Pro Lys Ile Glu Gly Tyr Glu Asp Ala 819             828             837             846             855             864
ATA ATC TAT GAA ATA CAC ATA GCG GAC ATC ACA GGA CTC GAA AAC TCC GGG GTA
--- --- --- --- --- --- --- --- --- --- --- --- --- --- --- --- --- ---
Ile Ile Tyr Glu Ile His Ile Ala Asp Ile Thr Gly Leu Glu Asn Ser Gly Val 873             882             891             900             909             918
AAA AAC AAA GGC CTC TAT CTC GGG CTC ACC GAA GAA AAC ACG AAA GGA CCG GGC
--- --- --- --- --- --- --- --- --- --- --- --- --- --- --- --- --- ---
Lys Asn Lys Gly Leu Tyr Leu Gly Leu Thr Glu Glu Asn Thr Lys Gly Pro Gly 927             936             945             954             963             972
GGT GTG ACA ACA GGC CTT TCG CAC CTT GTG GAA CTC GGT GTT ACA CAC GTT CAT
--- --- --- --- --- --- --- --- --- --- --- --- --- --- --- --- --- ---
Gly Val Thr Thr Gly Leu Ser His Leu Val Glu Leu Gly Val Thr His Val His 981             990             999            1008            1017            1026
ATA CTT CCT TTC TTT GAT TTC TAC ACA GGC GAC GAA CTC GAT AAA GAT TTC GAG
--- --- --- --- --- --- --- --- --- --- --- --- --- --- --- --- --- ---
Ile Leu Pro Phe Phe Asp Phe Tyr Thr Gly Asp Glu Leu Asp Lys Asp Phe Glu 1035            1044            1053            1062            1071            1080
AAG TAC TAC AAC TGG GGT TAC GAT CCT TAC CTG TTC ATG GTT CCG GAG GGC AGA
--- --- --- --- --- --- --- --- --- --- --- --- --- --- --- --- --- ---
Lys Tyr Tyr Asn Trp Gly Tyr Asp Pro Tyr Leu Phe Met Val Pro Glu Gly Arg
```

Figure 18b

Thermotoga maritima Pullulanase (6GP3) (continued)

```
        1089        1098        1107        1116        1125        1134
TAC TCA ACC GAT CCC AAA AAC CCA CAC ACG AGA ATC AGA GAA GTC AAA GAA ATG
--- --- --- --- --- --- --- --- --- --- --- --- --- --- --- --- --- ---
Tyr Ser Thr Asp Pro Lys Asn Pro His Thr Arg Ile Arg Glu Val Lys Glu Met 1143        1152        1161        1170        1179        1188
GTC AAA GCC CTT CAC AAA CAC GGT ATA GGT GTG ATT ATG GAC ATG GTG TTC CCT
--- --- --- --- --- --- --- --- --- --- --- --- --- --- --- --- --- ---
Val Lys Ala Leu His Lys His Gly Ile Gly Val Ile Met Asp Met Val Phe Pro 1197        1206        1215        1224        1233        1242
CAC ACC TAC GGT ATA GGC GAA CTC TCT GCG TTC GAT CAG ACG GTG CCG TAC TAC
--- --- --- --- --- --- --- --- --- --- --- --- --- --- --- --- --- ---
His Thr Tyr Gly Ile Gly Glu Leu Ser Ala Phe Asp Gln Thr Val Pro Tyr Tyr 1251        1260        1269        1278        1287        1296
TTC TAC AGA ATC GAC AAG ACA GGT GCC TAT TTG AAC GAA AGC GGA TGT GGT AAC
--- --- --- --- --- --- --- --- --- --- --- --- --- --- --- --- --- ---
Phe Tyr Arg Ile Asp Lys Thr Gly Ala Tyr Leu Asn Glu Ser Gly Cys Gly Asn 1305        1314        1323        1332        1341        1350
GTC ATC GCA AGC GAA AGA CCC ATG ATG AGA AAA TTC ATA GTC GAT ACC GTC ACC
--- --- --- --- --- --- --- --- --- --- --- --- --- --- --- --- --- ---
Val Ile Ala Ser Glu Arg Pro Met Met Arg Lys Phe Ile Val Asp Thr Val Thr 1359        1368        1377        1386        1395        1404
TAC TGG GTA AAG GAG TAT CAC ATA GAC GGA TTC AGG TTC GAT CAG ATG GGT CTC
--- --- --- --- --- --- --- --- --- --- --- --- --- --- --- --- --- ---
Tyr Trp Val Lys Glu Tyr His Ile Asp Gly Phe Arg Phe Asp Gln Met Gly Leu 1413        1422        1431        1440        1449        1458
ATC GAC AAA AAG ACA ATG CTC GAA GTC GAA AGA GCT CTT CAT AAA ATC GAT CCA
--- --- --- --- --- --- --- --- --- --- --- --- --- --- --- --- --- ---
Ile Asp Lys Lys Thr Met Leu Glu Val Glu Arg Ala Leu His Lys Ile Asp Pro 1467        1476        1485        1494        1503        1512
ACT ATC ATT CTC TAC GGC GAA CCG TGG GGT GGA TGG GGA GCA CCG ATC AGG TTT
--- --- --- --- --- --- --- --- --- --- --- --- --- --- --- --- --- ---
Thr Ile Ile Leu Tyr Gly Glu Pro Trp Gly Gly Trp Gly Ala Pro Ile Arg Phe

1521       .1530        1539        1548        1557        1566
GGA AAG AGC GAT GTC GCC GGC ACA CAC GTG GCA GCT TTC AAC GAT GAG TTC AGA
--- --- --- --- --- --- --- --- --- --- --- --- --- --- --- --- --- ---
Gly Lys Ser Asp Val Ala Gly Thr His Val Ala Ala Phe Asn Asp Glu Phe Arg 1575        1584        1593        1602        1611        1620
GAC GCA ATA AGG GGT TCC GTG TTC AAC CCG AGC GTC AAG GGA TTC GTC ATG GGA
--- --- --- --- --- --- --- --- --- --- --- --- --- --- --- --- --- ---
Asp Ala Ile Arg Gly Ser Val Phe Asn Pro Ser Val Lys Gly Phe Val Met Gly
```

Figure 18c

Thermotoga maritima Pullulanase (6GP3) (continued)

```
          1629        1638        1647        1656        1665        1674
      GGA TAC GGA AAG GAA ACC AAG ATC AAA AGG GGT GTT GTT GGA AGC ATA AAC TAC
      --- --- --- --- --- --- --- --- --- --- --- --- --- --- --- --- --- ---
      Gly Tyr Gly Lys Glu Thr Lys Ile Lys Arg Gly Val Val Gly Ser Ile Asn Tyr 1683        1692        1701        1710        1719        1728
      GAC GGA AAA CTC ATC AAA AGT CTC GCC CTT GAT CCA GAA GAA ACT ATA AAC TAC
      --- --- --- --- --- --- --- --- --- --- --- --- --- --- --- --- --- ---
      Asp Gly Lys Leu Ile Lys Ser Leu Ala Leu Asp Pro Glu Glu Thr Ile Asn Tyr 1737        1746        1755        1764        1773        1782
      GCA GCG TGT CAC GAC AAC CAC ACA CTG TGG GAC AAG AAC TAC CTT GCC GCC AAA
      --- --- --- --- --- --- --- --- --- --- --- --- --- --- --- --- --- ---
      Ala Ala Cys His Asp Asn His Thr Leu Trp Asp Lys Asn Tyr Leu Ala Ala Lys 1791        1800        1809        1818        1827        1836
      GCT GAT AAG AAA AAG GAA TGG ACC GAA GAA GAA CTG AAA AAC GCC CAG AAA CTG
      --- --- --- --- --- --- --- --- --- --- --- --- --- --- --- --- --- ---
      Ala Asp Lys Lys Lys Glu Trp Thr Glu Glu Glu Leu Lys Asn Ala Gln Lys Leu 1845        1854        1863        1872        1881        1890
      GCT GGT GCG ATA CTT CTC ACT TCT CAA GGT GTT CCT TTC CTC CAC GGA GGG CAG
      --- --- --- --- --- --- --- --- --- --- --- --- --- --- --- --- --- ---
      Ala Gly Ala Ile Leu Leu Thr Ser Gln Gly Val Pro Phe Leu His Gly Gly Gln 1899        1908        1917        1926        1935        1944
      GAC TTC TGC AGG ACG AAG AAT TTC AAC GAC AAC TCC TAC AAC GCC CCT ATC TCG
      --- --- --- --- --- --- --- --- --- --- --- --- --- --- --- --- --- ---
      Asp Phe Cys Arg Thr Lys Asn Phe Asn Asp Asn Ser Tyr Asn Ala Pro Ile Ser 1953        1962        1971        1980        1989        1998
      ATA AAC GGC TTC GAT TAC GAA AGA AAA CTT CAG TTC ATA GAC GTG TTC AAT TAC
      --- --- --- --- --- --- --- --- --- --- --- --- --- --- --- --- --- ---
      Ile Asn Gly Phe Asp Tyr Glu Arg Lys Leu Gln Phe Ile Asp Val Phe Asn Tyr 2007        2016        2025        2034        2043        2052
      CAC AAG GGT CTC ATA AAA CTC AGA AAA GAA CAC CCT GCT TTC AGG CTG AAA AAC
      --- --- --- --- --- --- --- --- --- --- --- --- --- --- --- --- --- ---
      His Lys Gly Leu Ile Lys Leu Arg Lys Glu His Pro Ala Phe Arg Leu Lys Asn 2061        2070        2079        2088        2097        2106
      GCT GAA GAG ATC AAA AAA CAC CTG GAA TTT CTC CCG GGC GGG AGA AGA ATA GTT
      --- --- --- --- --- --- --- --- --- --- --- --- --- --- --- --- --- ---
      Ala Glu Glu Ile Lys Lys His Leu Glu Phe Leu Pro Gly Gly Arg Arg Ile Val 2115        2124        2133        2142        2151        2160
      GCG TTC ATG CTT AAA GAC CAC GCA GGT GGT GAT CCC TGG AAA GAC ATC GTG GTG
      --- --- --- --- --- --- --- --- --- --- --- --- --- --- --- --- --- ---
      Ala Phe Met Leu Lys Asp His Ala Gly Gly Asp Pro Trp Lys Asp Ile Val Val
```

Figure 18d

Thermotoga maritima Pullulanase (6GP3) (continued)

```
        2169        2178        2187        2196        2205        2214
ATT TAC AAT GGA AAC TTA GAG AAG ACA ACA TAC AAA CTG CCA GAA GGA AAA TGG
--- --- --- --- --- --- --- --- --- --- --- --- --- --- --- --- ---
Ile Tyr Asn Gly Asn Leu Glu Lys Thr Thr Tyr Lys Leu Pro Glu Gly Lys Trp 2223        2232        2241        2250        2259        2268
AAT GTG GTT GTG AAC AGC CAG AAA GCC GGA ACA GAA GTG ATA GAA ACC GTC GAA
--- --- --- --- --- --- --- --- --- --- --- --- --- --- --- --- ---
Asn Val Val Val Asn Ser Gln Lys Ala Gly Thr Glu Val Ile Glu Thr Val Glu 2277        2286        2295        2304        2313
GGA ACA ATA GAA CTC GAT CCG CTT TCC GCG TAC GTT CTG TAC AGA GAG TGA 3'
--- --- --- --- --- --- --- --- --- --- --- --- --- --- --- ---
Gly Thr Ile Glu Leu Asp Pro Leu Ser Ala Tyr Val Leu Tyr Arg Glu ***
```

Figure 18e

THERMOTOGA MARITIMA MSB8 (CLONE # 6GP2) GLYCOSIDASE

```
CTT TTA TTG ATC GTT GAG CTC TCT TTC GTT CTC TTT GCA AGT GAC GAG      48
Leu Leu Leu Ile Val Glu Leu Ser Phe Val Leu Phe Ala Ser Asp Glu
 1           5                  10                  15

TTC GTG AAA GTG GAA AAC GGA AAA TTC GCT CTG AAC GGA AAA GAA TTC      96
Phe Val Lys Val Glu Asn Gly Lys Phe Ala Leu Asn Gly Lys Glu Phe
            20                  25                  30

AGA TTC ATT GGA AGC AAC AAC TAC TAC ATG CAC TAC AAG AGC AAC GGA     144
Arg Phe Ile Gly Ser Asn Asn Tyr Tyr Met His Tyr Lys Ser Asn Gly
        35                  40                  45

ATG ATA GAC AGT GTT CTG GAG AGT GCC AGA GAC ATG GGT ATA AAG GTC     192
Met Ile Asp Ser Val Leu Glu Ser Ala Arg Asp Met Gly Ile Lys Val
    50                  55                  60

CTC AGA ATC TGG GGT TTC CTC GAC GGG GAG AGT TAC TGC AGA GAC AAG     240
Leu Arg Ile Trp Gly Phe Leu Asp Gly Glu Ser Tyr Cys Arg Asp Lys
65                  70                  75                  80

AAC ACC TAC ATG CAT CCT GAG CCC GGT GTT TTC GGG GTG CCA GAA GGA     288
Asn Thr Tyr Met His Pro Glu Pro Gly Val Phe Gly Val Pro Glu Gly
                85                  90                  95

ATA TCG AAC GCC CAG AGC GGT TTC GAA AGA CTC GAC TAC ACA GTT GCG     336
Ile Ser Asn Ala Gln Ser Gly Phe Glu Arg Leu Asp Tyr Thr Val Ala
            100                 105                 110

AAA GCG AAA GAA CTC GGT ATA AAA CTT GTC ATT GTT CTT GTG AAC AAC     384
Lys Ala Lys Glu Leu Gly Ile Lys Leu Val Ile Val Leu Val Asn Asn
        115                 120                 125

TGG GAC GAC TTC GGT GGA ATG AAC CAG TAC GTG AGG TGG TTT GGA GGA     432
Trp Asp Asp Phe Gly Gly Met Asn Gln Tyr Val Arg Trp Phe Gly Gly
    130                 135                 140

ACC CAT CAC GAC GAT TTC TAC AGA GAT GAG AAG ATC AAA GAA GAG TAC     480
Thr His His Asp Asp Phe Tyr Arg Asp Glu Lys Ile Lys Glu Glu Tyr
145                 150                 155                 160

AAA AAG TAC GTC TCC TTT CTC GTA AAC CAT GTC AAT ACC TAC ACG GGA     528
Lys Lys Tyr Val Ser Phe Leu Val Asn His Val Asn Thr Tyr Thr Gly
                165                 170                 175

GTT CCT TAC AGG GAA GAG CCC ACC ATC ATG GCC TGG GAG CTT GCA AAC     576
Val Pro Tyr Arg Glu Glu Pro Thr Ile Met Ala Trp Glu Leu Ala Asn
            180                 185                 190

GAA CCG CGC TGT GAG ACG GAC AAA TCG GGG AAC ACG CTC GTT GAG TGG     624
Glu Pro Arg Cys Glu Thr Asp Lys Ser Gly Asn Thr Leu Val Glu Trp
        195                 200                 205

GTG AAG GAG ATG AGC TCC TAC ATA AAG AGT CTG GAT CCC AAC CAC CTC     672
Val Lys Glu Met Ser Ser Tyr Ile Lys Ser Leu Asp Pro Asn His Leu
    210                 215                 220

GTG GCT GTG GGG GAC GAA GGA TTC TTC AGC AAC TAC GAA GGA TTC AAA     720
Val Ala Val Gly Asp Glu Gly Phe Phe Ser Asn Tyr Glu Gly Phe Lys
225                 230                 235                 240

CCT TAC GGT GGA GAA GCC GAG TGG GCC TAC AAC GGC TGG TCC GGT GTT     768
Pro Tyr Gly Gly Glu Ala Glu Trp Ala Tyr Asn Gly Trp Ser Gly Val
```

FIG. 19a

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 245 |     |     |     | 250 |     |     |     | 255 |     |     |     |
| GAC | TGG | AAG | AAG | CTC | CTT | TCG | ATA | GAG | ACG | GTG | GAC | TTC | GGC | ACG | TTC | 816 |
| Asp | Trp | Lys | Lys | Leu | Leu | Ser | Ile | Glu | Thr | Val | Asp | Phe | Gly | Thr | Phe |
|     |     |     | 260 |     |     |     |     | 265 |     |     |     |     | 270 |     |     |
| CAC | CTC | TAT | CCG | TCC | CAC | TGG | GGT | GTC | AGT | CCA | GAG | AAC | TAT | GCC | CAG | 864 |
| His | Leu | Tyr | Pro | Ser | His | Trp | Gly | Val | Ser | Pro | Glu | Asn | Tyr | Ala | Gln |
|     |     | 275 |     |     |     |     | 280 |     |     |     |     | 285 |     |     |     |
| TGG | GGA | GCG | AAG | TGG | ATA | GAA | GAC | CAC | ATA | AAG | ATC | GCA | AAA | GAG | ATC | 912 |
| Trp | Gly | Ala | Lys | Trp | Ile | Glu | Asp | His | Ile | Lys | Ile | Ala | Lys | Glu | Ile |
|     | 290 |     |     |     |     | 295 |     |     |     |     | 300 |     |     |     |     |
| GGA | AAA | CCC | GTT | GTT | CTG | GAA | GAA | TAT | GGA | ATT | CCA | AAG | AGT | GCG | CCA | 960 |
| Gly | Lys | Pro | Val | Val | Leu | Glu | Glu | Tyr | Gly | Ile | Pro | Lys | Ser | Ala | Pro |
| 305 |     |     |     |     | 310 |     |     |     |     | 315 |     |     |     |     | 320 |
| GTT | AAC | AGA | ACG | GCC | ATC | TAC | AGA | CTC | TGG | AAC | GAT | CTG | GTC | TAC | GAT | 1008 |
| Val | Asn | Arg | Thr | Ala | Ile | Tyr | Arg | Leu | Trp | Asn | Asp | Leu | Val | Tyr | Asp |
|     |     |     |     | 325 |     |     |     |     | 330 |     |     |     |     | 335 |     |
| CTC | GGT | GGA | GAT | GGA | GCG | ATG | TTC | TGG | ATG | CTC | GCG | GGA | ATC | GGG | GAA | 1056 |
| Leu | Gly | Gly | Asp | Gly | Ala | Met | Phe | Trp | Met | Leu | Ala | Gly | Ile | Gly | Glu |
|     |     |     | 340 |     |     |     |     | 345 |     |     |     |     | 350 |     |     |
| GGT | TCG | GAC | AGA | GAC | GAG | AGA | GGG | TAC | TAT | CCG | GAC | TAC | GAC | GGT | TTC | 1104 |
| Gly | Ser | Asp | Arg | Asp | Glu | Arg | Gly | Tyr | Tyr | Pro | Asp | Tyr | Asp | Gly | Phe |
|     |     | 355 |     |     |     |     | 360 |     |     |     |     | 365 |     |     |     |
| AGA | ATA | GTG | AAC | GAC | GAC | AGT | CCA | GAA | GCG | GAA | CTG | ATA | AGA | GAA | TAC | 1152 |
| Arg | Ile | Val | Asn | Asp | Asp | Ser | Pro | Glu | Ala | Glu | Leu | Ile | Arg | Glu | Tyr |
|     | 370 |     |     |     |     | 375 |     |     |     |     | 380 |     |     |     |     |
| GCG | AAG | CTG | TTC | AAC | ACA | GGT | GAA | GAC | ATA | AGA | GAA | GAC | ACC | TGC | TCT | 1200 |
| Ala | Lys | Leu | Phe | Asn | Thr | Gly | Glu | Asp | Ile | Arg | Glu | Asp | Thr | Cys | Ser |
| 385 |     |     |     |     | 390 |     |     |     |     | 395 |     |     |     |     | 400 |
| TTC | ATC | CTT | CCA | AAA | GAC | GGC | ATG | GAG | ATC | AAA | AAG | ACC | GTG | GAA | GTG | 1248 |
| Phe | Ile | Leu | Pro | Lys | Asp | Gly | Met | Glu | Ile | Lys | Lys | Thr | Val | Glu | Val |
|     |     |     |     | 405 |     |     |     |     | 410 |     |     |     |     | 415 |     |
| AGG | GCT | GGT | GTT | TTC | GAC | TAC | AGC | AAC | ACG | TTT | GAA | AAG | TTG | TCT | GTC | 1296 |
| Arg | Ala | Gly | Val | Phe | Asp | Tyr | Ser | Asn | Thr | Phe | Glu | Lys | Leu | Ser | Val |
|     |     |     | 420 |     |     |     |     | 425 |     |     |     |     | 430 |     |     |
| AAA | GTC | GAA | GAT | CTG | GTT | TTT | GAA | AAT | GAG | ATA | GAG | CAT | CTC | GGA | TAC | 1344 |
| Lys | Val | Glu | Asp | Leu | Val | Phe | Glu | Asn | Glu | Ile | Glu | His | Leu | Gly | Tyr |
|     |     | 435 |     |     |     |     | 440 |     |     |     |     | 445 |     |     |     |
| GGA | ATT | TAC | GGC | TTT | GAT | CTC | GAC | ACA | ACC | CGG | ATC | CCG | GAT | GGA | GAA | 1392 |
| Gly | Ile | Tyr | Gly | Phe | Asp | Leu | Asp | Thr | Thr | Arg | Ile | Pro | Asp | Gly | Glu |
|     | 450 |     |     |     |     | 455 |     |     |     |     | 460 |     |     |     |     |
| CAT | GAA | ATG | TTC | CTT | GAA | GGC | CAC | TTT | CAG | GGA | AAA | ACG | GTG | AAA | GAC | 1440 |
| His | Glu | Met | Phe | Leu | Glu | Gly | His | Phe | Gln | Gly | Lys | Thr | Val | Lys | Asp |
| 465 |     |     |     |     | 470 |     |     |     |     | 475 |     |     |     |     | 480 |
| TCT | ATC | AAA | GCG | AAA | GTG | GTG | AAC | GAA | GCA | CGG | TAC | GTG | CTC | GCA | GAG | 1488 |
| Ser | Ile | Lys | Ala | Lys | Val | Val | Asn | Glu | Ala | Arg | Tyr | Val | Leu | Ala | Glu |
|     |     |     |     | 485 |     |     |     |     | 490 |     |     |     |     | 495 |     |

FIG. 19b

```
GAA GTT GAT TTT TCC TCT CCA GAA GAG GTG AAA AAC TGG TGG AAC AGC   1536
Glu Val Asp Phe Ser Ser Pro Glu Glu Val Lys Asn Trp Trp Asn Ser
            500             505             510

GGA ACC TGG CAG GCA GAG TTC GGG TCA CCT GAC ATT GAA TGG AAC GGT   1584
Gly Thr Trp Gln Ala Glu Phe Gly Ser Pro Asp Ile Glu Trp Asn Gly
        515             520             525

GAG GTG GGA AAT GGA GCA CTG CAG CTG AAC GTG AAA CTG CCC GGA AAG   1632
Glu Val Gly Asn Gly Ala Leu Gln Leu Asn Val Lys Leu Pro Gly Lys
    530             535             540

AGC GAC TGG GAA GAA GTG AGA GTA GCA AGG AAG TTC GAA AGA CTC TCA   1680
Ser Asp Trp Glu Glu Val Arg Val Ala Arg Lys Phe Glu Arg Leu Ser
545             550             555             560

GAA TGT GAG ATC CTC GAG TAC GAC ATC TAC ATT CCA AAC GTC GAG GGA   1728
Glu Cys Glu Ile Leu Glu Tyr Asp Ile Tyr Ile Pro Asn Val Glu Gly
            565             570             575

CTC AAG GGA AGG TTG AGG CCG TAC GCG GTT CTG AAC CCC GGC TGG GTG   1776
Leu Lys Gly Arg Leu Arg Pro Tyr Ala Val Leu Asn Pro Gly Trp Val
        580             585             590

AAG ATA GGC CTC GAC ATG AAC AAC GCG AAC GTG GAA AGT GCG GAG ATC   1824
Lys Ile Gly Leu Asp Met Asn Asn Ala Asn Val Glu Ser Ala Glu Ile
        595             600             605

ATC ACT TTC GGC GGA AAA GAG TAC AGA AGA TTC CAT GTA AGA ATT GAG   1872
Ile Thr Phe Gly Gly Lys Glu Tyr Arg Arg Phe His Val Arg Ile Glu
    610             615             620

TTC GAC AGA ACA GCG GGG GTG AAA GAA CTT CAC ATA GGA GTT GTC GGT   1920
Phe Asp Arg Thr Ala Gly Val Lys Glu Leu His Ile Gly Val Val Gly
625             630             635             640

GAT CAT CTG AGG TAC GAT GGA CCG ATT TTC ATC GAT AAT GTG AGA CTT   1968
Asp His Leu Arg Tyr Asp Gly Pro Ile Phe Ile Asp Asn Val Arg Leu
            645             650             655

TAT AAA AGA ACA GGA GGT ATG TGA                                   1992
Tyr Lys Arg Thr Gly Gly Met
            660
```

FIG. 19c

THERMOTOGA MARITIMA MSB8 (6gb4)

| | | | | | | | | | | | | | | | | |
|---|---|---|---|---|---|---|---|---|---|---|---|---|---|---|---|---|
| ATG | AAA | AGA | ATC | GAC | CTG | AAT | GGT | TTC | TGG | AGC | GTT | AGG | GAT | AAC | GAA | 48 |
| Met | Lys | Arg | Ile | Asp | Leu | Asn | Gly | Phe | Trp | Ser | Val | Arg | Asp | Asn | Glu | |
| 1 | | | | 5 | | | | | 10 | | | | | 15 | | |
| GGG | AGA | TTT | TCG | TTT | GAA | GGG | ACT | GTG | CCA | GGG | GTT | GTC | CAG | GCA | GAT | 96 |
| Gly | Arg | Phe | Ser | Phe | Glu | Gly | Thr | Val | Pro | Gly | Val | Val | Gln | Ala | Asp | |
| | | | 20 | | | | | 25 | | | | | 30 | | | |
| CTG | GTC | AGA | AAA | GGT | CTT | CTT | CCA | CAC | CCG | TAC | GTT | GGG | ATG | AAC | GAA | 144 |
| Leu | Val | Arg | Lys | Gly | Leu | Leu | Pro | His | Pro | Tyr | Val | Gly | Met | Asn | Glu | |
| | | 35 | | | | | 40 | | | | | 45 | | | | |
| GAT | CTC | TTC | AAG | GAA | ATA | GAA | GAC | AGA | GAG | TGG | ATC | TAC | GAG | AGG | GAG | 192 |
| Asp | Leu | Phe | Lys | Glu | Ile | Glu | Asp | Arg | Glu | Trp | Ile | Tyr | Glu | Arg | Glu | |
| | 50 | | | | | 55 | | | | | 60 | | | | | |
| TTC | GAG | TTC | AAA | GAA | GAT | GTG | AAA | GAG | GGG | GAA | CGT | GTC | GAT | CTC | GTT | 240 |
| Phe | Glu | Phe | Lys | Glu | Asp | Val | Lys | Glu | Gly | Glu | Arg | Val | Asp | Leu | Val | |
| 65 | | | | 70 | | | | | 75 | | | | | 80 | | |
| TTT | GAG | GGC | GTC | GAC | ACG | CTG | TCG | GAT | GTT | TAT | CTG | AAC | GGT | GTT | TAC | 288 |
| Phe | Glu | Gly | Val | Asp | Thr | Leu | Ser | Asp | Val | Tyr | Leu | Asn | Gly | Val | Tyr | |
| | | | 85 | | | | | 90 | | | | | 95 | | | |
| CTT | GGA | AGC | ACC | GAA | GAC | ATG | TTC | ATC | GAG | TAT | CGC | TTC | GAT | GTC | ACG | 336 |
| Leu | Gly | Ser | Thr | Glu | Asp | Met | Phe | Ile | Glu | Tyr | Arg | Phe | Asp | Val | Thr | |
| | | | 100 | | | | | 105 | | | | | 110 | | | |
| AAC | GTG | TTG | AAA | GAA | AAG | AAT | CAC | CTG | AAG | GTG | TAC | ATA | AAA | TCT | CCC | 384 |
| Asn | Val | Leu | Lys | Glu | Lys | Asn | His | Leu | Lys | Val | Tyr | Ile | Lys | Ser | Pro | |
| | | 115 | | | | | 120 | | | | | 125 | | | | |
| ATC | AGA | GTT | CCG | AAA | ACT | CTC | GAG | CAG | AAC | TAC | GGG | GTC | CTC | GGC | GGT | 432 |
| Ile | Arg | Val | Pro | Lys | Thr | Leu | Glu | Gln | Asn | Tyr | Gly | Val | Leu | Gly | Gly | |
| | 130 | | | | | 135 | | | | | 140 | | | | | |
| CCT | GAA | GAT | CCC | ATC | AGA | GGA | TAC | ATA | AGA | AAA | GCC | CAG | TAT | TCG | TAC | 480 |
| Pro | Glu | Asp | Pro | Ile | Arg | Gly | Tyr | Ile | Arg | Lys | Ala | Gln | Tyr | Ser | Tyr | |
| 145 | | | | | 150 | | | | | 155 | | | | | 160 | |
| GGA | TGG | GAC | TGG | GGT | GCC | AGA | ATC | GTT | ACA | AGC | GGT | ATT | TGG | AAA | CCC | 528 |
| Gly | Trp | Asp | Trp | Gly | Ala | Arg | Ile | Val | Thr | Ser | Gly | Ile | Trp | Lys | Pro | |
| | | | 165 | | | | | 170 | | | | | 175 | | | |
| GTC | TAC | CTC | GAG | GTG | TAC | AGG | GCA | CGT | CTT | CAG | GAT | TCA | ACG | GCT | TAT | 576 |
| Val | Tyr | Leu | Glu | Val | Tyr | Arg | Ala | Arg | Leu | Gln | Asp | Ser | Thr | Ala | Tyr | |
| | | | 180 | | | | | 185 | | | | | 190 | | | |
| CTG | TTG | GAA | CTT | GAG | GGG | AAA | GAT | GCC | CTT | GTG | AGG | GTG | AAC | GGT | TTC | 624 |
| Leu | Leu | Glu | Leu | Glu | Gly | Lys | Asp | Ala | Leu | Val | Arg | Val | Asn | Gly | Phe | |
| | | 195 | | | | | 200 | | | | | 205 | | | | |
| GTA | CAC | GGG | GAA | GGA | AAT | CTC | ATT | GTG | GAA | GTT | TAT | GTA | AAC | GGT | GAA | 672 |
| Val | His | Gly | Glu | Gly | Asn | Leu | Ile | Val | Glu | Val | Tyr | Val | Asn | Gly | Glu | |
| | 210 | | | | | 215 | | | | | 220 | | | | | |
| AAG | ATA | GGG | GAG | TTT | CCT | GTT | CTT | GAA | AAG | AAC | GGA | GAA | AAG | CTC | TTC | 720 |
| Lys | Ile | Gly | Glu | Phe | Pro | Val | Leu | Glu | Lys | Asn | Gly | Glu | Lys | Leu | Phe | |
| 225 | | | | | 230 | | | | | 235 | | | | | 240 | |
| GAT | GGA | GTG | TTC | CAC | CTG | AAA | GAT | GTG | AAA | CTA | TGG | TAT | CCG | TGG | AAC | 768 |
| Asp | Gly | Val | Phe | His | Leu | Lys | Asp | Val | Lys | Leu | Trp | Tyr | Pro | Trp | Asn | |
| | | | 245 | | | | | 250 | | | | | 255 | | | |

FIG. 20a

```
GTG GGG AAA CCG TAC CTG TAC GAT TTC GTT TTC GTG TTG AAA GAC TTA         816
Val Gly Lys Pro Tyr Leu Tyr Asp Phe Val Phe Val Leu Lys Asp Leu
            260                 265                 270

AAC GGA GAG ATC TAC AGA GAA GAA AAG AAA ATC GGT TTG AGA AGA GTC         864
Asn Gly Glu Ile Tyr Arg Glu Glu Lys Lys Ile Gly Leu Arg Arg Val
            275                 280                 285

AGA ATC GTT CAG GAG CCC GAT GAA GAA GGA AAA ACT TTC ATA TTC GAA         912
Arg Ile Val Gln Glu Pro Asp Glu Glu Gly Lys Thr Phe Ile Phe Glu
        290                 295                 300

ATC AAC GGT GAG AAA GTC TTC GCT AAG GGT GCT AAC TGG ATT CCC TCA         960
Ile Asn Gly Glu Lys Val Phe Ala Lys Gly Ala Asn Trp Ile Pro Ser
305                 310                 315                 320

GAA AAC ATC CTC ACG TGG TTG AAG GAG GAA GAT TAC GAA AAG CTC GTC        1008
Glu Asn Ile Leu Thr Trp Leu Lys Glu Glu Asp Tyr Glu Lys Leu Val
            325                 330                 335

AAA ATG GCA AGG AGT GCC AAT ATG AAC ATG CTC AGG GTC TGG GGA GGA        1056
Lys Met Ala Arg Ser Ala Asn Met Asn Met Leu Arg Val Trp Gly Gly
            340                 345                 350

GGA ATC TAC GAG AGA GAG ATC TTC TAC AGA CTC TGT GAT GAA CTC GGT        1104
Gly Ile Tyr Glu Arg Glu Ile Phe Tyr Arg Leu Cys Asp Glu Leu Gly
            355                 360                 365

ATC ATG GTG TGG CAG GAT TTC ATG TAC GCG TGT CTT GAA TAT CCG GAT        1152
Ile Met Val Trp Gln Asp Phe Met Tyr Ala Cys Leu Glu Tyr Pro Asp
370                 375                 380

CAT CTT CCG TGG TTC AGA AAA CTC GCG AAC GAA GAG GCA AGA AAG ATT        1200
His Leu Pro Trp Phe Arg Lys Leu Ala Asn Glu Glu Ala Arg Lys Ile
385                 390                 395                 400

GTG AGA AAA CTC AGA TAC CAT CCC TCC ATT GTT CTC TGG TGC GGA AAC        1248
Val Arg Lys Leu Arg Tyr His Pro Ser Ile Val Leu Trp Cys Gly Asn
            405                 410                 415

AAC GAA AAC AAC TGG GGA TTC GAT GAA TGG GGA AAT ATG GCC AGA AAA        1296
Asn Glu Asn Asn Trp Gly Phe Asp Glu Trp Gly Asn Met Ala Arg Lys
            420                 425                 430

GTG GAT GGT ATC AAC CTC GGA AAC AGG CTC TAC CTC TTC GAT TTT CCT        1344
Val Asp Gly Ile Asn Leu Gly Asn Arg Leu Tyr Leu Phe Asp Phe Pro
            435                 440                 445

GAG ATT TGT GCC GAA GAA GAC CCG TCC ACT CCC TAT TGG CCA TCC AGT        1392
Glu Ile Cys Ala Glu Glu Asp Pro Ser Thr Pro Tyr Trp Pro Ser Ser
450                 455                 460

CCA TAC GGC GGT GAA AAA GCG AAC AGC GAA AAG GAA GGA GAC AGG CAC        1440
Pro Tyr Gly Gly Glu Lys Ala Asn Ser Glu Lys Glu Gly Asp Arg His
465                 470                 475                 480

GTC TGG TAC GTG TGG AGT GGC TGG ATG AAC TAC GAA AAC TAC GAA AAA        1488
Val Trp Tyr Val Trp Ser Gly Trp Met Asn Tyr Glu Asn Tyr Glu Lys
            485                 490                 495

GAC ACC GGA AGG TTC ATC AGC GAG TTT GGA TTT CAG GGT GCT CCC CAT        1536
Asp Thr Gly Arg Phe Ile Ser Glu Phe Gly Phe Gln Gly Ala Pro His
            500                 505                 510
```

FIG. 20b

```
CCA GAG ACG ATA GAG TTC TTT TCA AAA CCC GAG GAA AGA GAG ATA TTC    1584
Pro Glu Thr Ile Glu Phe Phe Ser Lys Pro Glu Glu Arg Glu Ile Phe
        515                 520                 525

CAT CCC GTC ATG CTG AAG CAC AAC AAA CAG GTG GAA GGA CAG GAA AGA    1632
His Pro Val Met Leu Lys His Asn Lys Gln Val Glu Gly Gln Glu Arg
        530                 535                 540

TTG ATC AGG TTC ATA TTC GGA AAT TTT GGA AAG TGT AAA GAT TTC GAC    1680
Leu Ile Arg Phe Ile Phe Gly Asn Phe Gly Lys Cys Lys Asp Phe Asp
545                 550                 555                 560

AGT TTT GTG TAT CTG TCC CAG CTC AAC CAG GCG GAG GCG ATC AAG TTC    1728
Ser Phe Val Tyr Leu Ser Gln Leu Asn Gln Ala Glu Ala Ile Lys Phe
                565                 570                 575

GGT GTT GAA CAC TGG CGA AGC AGG AAG TAC AAA ACG GCC GGC GCT CTC    1776
Gly Val Glu His Trp Arg Ser Arg Lys Tyr Lys Thr Ala Gly Ala Leu
            580                 585                 590

TTC TGG CAG TTC AAC GAC AGC TGG CCG GTC TTC AGC TGG TCC GCA GTC    1824
Phe Trp Gln Phe Asn Asp Ser Trp Pro Val Phe Ser Trp Ser Ala Val
        595                 600                 605

GAT TAC TTC AAA AGG CCC AAA GCT CTC TAC TAC TAT GCG AGA AGA TTC    1872
Asp Tyr Phe Lys Arg Pro Lys Ala Leu Tyr Tyr Tyr Ala Arg Arg Phe
        610                 615                 620

TTC GCT GAA GTT CTA CCC GTT TTG AAG AAG AGA GAC AAC AAA ATA GAA    1920
Phe Ala Glu Val Leu Pro Val Leu Lys Lys Arg Asp Asn Lys Ile Glu
625                 630                 635                 640

CTG CTG GTG GGT GAG CGA TCT GAG GGA GAC AAA AGA AGT CTC TCT CAG    1968
Leu Leu Val Gly Glu Arg Ser Glu Gly Asp Lys Arg Ser Leu Ser Gln
                645                 650                 655

GCT TGC AGC CTA CGA GAA GAA GGG AGA AAA GGT ATT CGA AAA GAC TTA    2016
Ala Cys Ser Leu Arg Glu Glu Gly Arg Lys Gly Ile Arg Lys Asp Leu
                660                 665                 670

CAG AAC GGT ACT CCC AGC AGA CGG TGT GAG TTT GGT TGA                2055
Gln Asn Gly Thr Pro Ser Arg Arg Cys Glu Phe Gly
        675                 680
```

FIG. 20c

BANKIA GOULDI (37gp4)

| | | | | | | | | | | | | | | | | |
|---|---|---|---|---|---|---|---|---|---|---|---|---|---|---|---|---|
| ATG | AAA | AAA | AAT | CTA | CTA | ATG | TTT | AAA | AGG | CTT | ACG | TAT | CTA | CCT | TTG | 48 |
| Met | Lys | Lys | Asn | Leu | Leu | Met | Phe | Lys | Arg | Leu | Thr | Tyr | Leu | Pro | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TTT | TTA | ATG | CTG | CTC | TCA | CTA | AGT | TCA | GTA | GCT | CAA | TCT | CCT | GTA | GAA | 96 |
| Phe | Leu | Met | Leu | Leu | Ser | Leu | Ser | Ser | Val | Ala | Gln | Ser | Pro | Val | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| AAA | CAT | GGC | CGT | TTA | CAA | GTT | GAC | GGA | AAC | CGC | ATT | CTT | AAT | GCG | TCT | 144 |
| Lys | His | Gly | Arg | Leu | Gln | Val | Asp | Gly | Asn | Arg | Ile | Leu | Asn | Ala | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| GGA | GAA | ATT | ACG | AGC | TTA | GCT | GGT | AAC | AGC | CTC | TTT | TGG | AGT | AAT | GCT | 192 |
| Gly | Glu | Ile | Thr | Ser | Leu | Ala | Gly | Asn | Ser | Leu | Phe | Trp | Ser | Asn | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| GGA | GAC | ACC | TCC | GAT | TTT | TAT | AAT | GCA | GAA | ACT | GTT | GAT | TTT | TTA | GCA | 240 |
| Gly | Asp | Thr | Ser | Asp | Phe | Tyr | Asn | Ala | Glu | Thr | Val | Asp | Phe | Leu | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GAA | AAC | TGG | AAT | AGC | TCA | CTT | ATT | AGA | ATA | GCT | ATG | GGC | GTA | AAA | GAA | 288 |
| Glu | Asn | Trp | Asn | Ser | Ser | Leu | Ile | Arg | Ile | Ala | Met | Gly | Val | Lys | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| AAT | TGG | GAT | GGC | GGA | AAT | GGC | TAT | ATT | GAT | AGT | CCG | CAG | GAG | CAA | GAA | 336 |
| Asn | Trp | Asp | Gly | Gly | Asn | Gly | Tyr | Ile | Asp | Ser | Pro | Gln | Glu | Gln | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| GCT | AAA | ATT | AGA | AAA | GTT | ATT | GAT | GCA | GCT | ATT | GCT | AAC | GGC | ATA | TAT | 384 |
| Ala | Lys | Ile | Arg | Lys | Val | Ile | Asp | Ala | Ala | Ile | Ala | Asn | Gly | Ile | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| GTA | ATA | ATA | GAC | TGG | CAC | ACT | CAC | GAA | GCA | GAG | TTA | TAC | ACA | GAT | GAG | 432 |
| Val | Ile | Ile | Asp | Trp | His | Thr | His | Glu | Ala | Glu | Leu | Tyr | Thr | Asp | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| GCT | GTT | GAC | TTT | TTT | ACC | AGA | ATG | GCA | GAC | CTA | TAC | GGA | GAT | ACT | CCC | 480 |
| Ala | Val | Asp | Phe | Phe | Thr | Arg | Met | Ala | Asp | Leu | Tyr | Gly | Asp | Thr | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| AAT | GTA | ATG | TAT | GAA | ATT | TAT | AAC | GAG | CCT | ATA | TAC | CAA | AGT | TGG | CCT | 528 |
| Asn | Val | Met | Tyr | Glu | Ile | Tyr | Asn | Glu | Pro | Ile | Tyr | Gln | Ser | Trp | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| GTT | ATT | AAG | AAT | TAT | GCA | GAG | CAA | GTA | ATT | GCT | GGT | ATA | CGT | TCT | AAA | 576 |
| Val | Ile | Lys | Asn | Tyr | Ala | Glu | Gln | Val | Ile | Ala | Gly | Ile | Arg | Ser | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| GAC | CCA | GAT | AAT | TTA | ATA | ATT | GTA | GGT | ACT | AGC | AAT | TAT | TCT | CAG | CAA | 624 |
| Asp | Pro | Asp | Asn | Leu | Ile | Ile | Val | Gly | Thr | Ser | Asn | Tyr | Ser | Gln | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| GTT | GAT | GTA | GCA | TCA | GCA | GAC | CCA | ATA | TCT | GAT | ACT | AAT | GTG | GCA | TAT | 672 |
| Val | Asp | Val | Ala | Ser | Ala | Asp | Pro | Ile | Ser | Asp | Thr | Asn | Val | Ala | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| ACT | TTA | CAT | TTT | TAT | GCA | GCA | TTT | AAC | CCG | CAT | GAT | AAC | TTA | AGA | AAT | 720 |
| Thr | Leu | His | Phe | Tyr | Ala | Ala | Phe | Asn | Pro | His | Asp | Asn | Leu | Arg | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GTA | GCA | CAG | ACA | GCA | TTA | GAT | AAT | AAT | GTT | GCT | TTG | TTT | GTT | ACA | GAA | 768 |
| Val | Ala | Gln | Thr | Ala | Leu | Asp | Asn | Asn | Val | Ala | Leu | Phe | Val | Thr | Glu | |
| | | | | 245 | | | | | 250 | | | | | 255 | | |

FIG. 21a

```
TGG GGT ACA ATT TTA AAT ACC GGA CAA GGA GAA CCA GAC AAA GAA AGC    816
Trp Gly Thr Ile Leu Asn Thr Gly Gln Gly Glu Pro Asp Lys Glu Ser
            260             265             270

ACT AAT ACT TGG ATG GCC TTT TTG AAA GAA AAA GGT ATA AGT CAC GCT    864
Thr Asn Thr Trp Met Ala Phe Leu Lys Glu Lys Gly Ile Ser His Ala
            275             280             285

AAT TGG TCT TTG AGT GAC AAA GCT TTT CCT GAA ACA GGG TCT GTA GTT    912
Asn Trp Ser Leu Ser Asp Lys Ala Phe Pro Glu Thr Gly Ser Val Val
    290             295             300

CAA GCA GGA CAA GGT GTA TCT GGT TTA ATT AGC AAT AAA CTT ACA GCC    960
Gln Ala Gly Gln Gly Val Ser Gly Leu Ile Ser Asn Lys Leu Thr Ala
305             310             315             320

TCT GGT GAA ATT GTA AAA AAC ATC ATC CAA AAC TGG GAT ACA GAG ACC   1008
Ser Gly Glu Ile Val Lys Asn Ile Ile Gln Asn Trp Asp Thr Glu Thr
                325             330             335

TCT ACA GGA CCT AAA ACA ACA CAA TGT AGT ACT ATA GAA TGT ATT AGA   1056
Ser Thr Gly Pro Lys Thr Thr Gln Cys Ser Thr Ile Glu Cys Ile Arg
            340             345             350

GCT GCA ATG GAA ACA GCA CAA GCA GGA GAT GAA ATT ATA ATT GCC CCT   1104
Ala Ala Met Glu Thr Ala Gln Ala Gly Asp Glu Ile Ile Ile Ala Pro
            355             360             365

GGA AAC TAC AAT TTT CAA GAC AAG ATA CAA GGT GCC TTT AAC CGT AGT   1152
Gly Asn Tyr Asn Phe Gln Asp Lys Ile Gln Gly Ala Phe Asn Arg Ser
    370             375             380

GTT TAC CTT TAT GGT AGT GCT AAC GGA AAC AGT ACA AAC CCT ATT ATA   1200
Val Tyr Leu Tyr Gly Ser Ala Asn Gly Asn Ser Thr Asn Pro Ile Ile
385             390             395             400

TTA AGA GGC GAA AGC GCT ACA AAC CCT CCT GTT TTC TCA GGA TTA GAT   1248
Leu Arg Gly Glu Ser Ala Thr Asn Pro Pro Val Phe Ser Gly Leu Asp
                405             410             415

TAT AAC AAT GGC TAC CTA TTA AGT ATT GAA GGT GAT TAT TGG AAT ATT   1296
Tyr Asn Asn Gly Tyr Leu Leu Ser Ile Glu Gly Asp Tyr Trp Asn Ile
            420             425             430

AAA GAT ATA GAG TTT AAA ACT GGG TCT AAA GGT ATT GTT CTT GAC AAT   1344
Lys Asp Ile Glu Phe Lys Thr Gly Ser Lys Gly Ile Val Leu Asp Asn
            435             440             445

TCT AAT GGT AGT AAA TTA AAA AAC CTT GTT GTT CAT GAT ATT GGA GAA   1392
Ser Asn Gly Ser Lys Leu Lys Asn Leu Val Val His Asp Ile Gly Glu
450             455             460

GAA GCT ATT CAC TTG CGT GAT GGA TCT AGC AAT AAT AGT ATA GAT GGT   1440
Glu Ala Ile His Leu Arg Asp Gly Ser Ser Asn Asn Ser Ile Asp Gly
465             470             475             480

TGC ACT ATA TAC AAT ACA GGT AGA ACT AAA CCT GGT TTT GGT GAA GGT   1488
Cys Thr Ile Tyr Asn Thr Gly Arg Thr Lys Pro Gly Phe Gly Glu Gly
            485             490             495

TTA TAT GTA GGC TCA GAT AAA GGA CAA CAT GAC ACT TAT GAA AGA GCT   1536
Leu Tyr Val Gly Ser Asp Lys Gly Gln His Asp Thr Tyr Glu Arg Ala
            500             505             510
```

FIG. 21b

```
TGT AAC AAT AAC ACT ATT GAA AAC TGT ACC GTT GGA CCC AAT GTA ACA    1584
Cys Asn Asn Asn Thr Ile Glu Asn Cys Thr Val Gly Pro Asn Val Thr
        515                 520                 525

GCA GAA GGC GTA GAT GTT AAG GAA GGT ACA ATG AAC ACT ATT ATA AGA    1632
Ala Glu Gly Val Asp Val Lys Glu Gly Thr Met Asn Thr Ile Ile Arg
        530                 535                 540

AAT TGC GTG TTT TCT GCA GAA GGA ATT TCA GGA GAA AAT AGC TCA GAT    1680
Asn Cys Val Phe Ser Ala Glu Gly Ile Ser Gly Glu Asn Ser Ser Asp
545                 550                 555                 560

GCT TTT ATT GAT TTA AAA GGA GCC TAT GGT TTT GTA TAC AGA AAC ACG    1728
Ala Phe Ile Asp Leu Lys Gly Ala Tyr Gly Phe Val Tyr Arg Asn Thr
                565                 570                 575

TTT AAT GTT GAT GGT TCT GAA GTA ATA AAT ACT GGA GTA GAC TTT TTA    1776
Phe Asn Val Asp Gly Ser Glu Val Ile Asn Thr Gly Val Asp Phe Leu
        580                 585                 590

GAT AGA GGT ACA GGA TTT AAT ACA GGT TTT AGA AAT GCA ATA TTT GAA    1824
Asp Arg Gly Thr Gly Phe Asn Thr Gly Phe Arg Asn Ala Ile Phe Glu
        595                 600                 605

AAT ACA TAT AAC CTT GGC AGT AGA GCT TCA GAA ATT TCA ACT GCT CGT    1872
Asn Thr Tyr Asn Leu Gly Ser Arg Ala Ser Glu Ile Ser Thr Ala Arg
        610                 615                 620

AAA AAA CAA GGT TCT CCT GAA CAA ACT CAC GTT TGG GAT AAT ATT AGA    1920
Lys Lys Gln Gly Ser Pro Glu Gln Thr His Val Trp Asp Asn Ile Arg
625                 630                 635                 640

AAC CCT AAT TCT GTT GAT TTT CCA ATA AGT GAT GGT ACA GAA AAT CTA    1968
Asn Pro Asn Ser Val Asp Phe Pro Ile Ser Asp Gly Thr Glu Asn Leu
                645                 650                 655

GTA AAT AAA TTC TGC CCA GAT TGG AAT ATA GAA CCA TGT AAT CCT GTA    2016
Val Asn Lys Phe Cys Pro Asp Trp Asn Ile Glu Pro Cys Asn Pro Val
        660                 665                 670

GAC GAA ACC AAC CAA GCA CCT ACA ATA AGC TTC CTA TCT CCT GTT AAC    2064
Asp Glu Thr Asn Gln Ala Pro Thr Ile Ser Phe Leu Ser Pro Val Asn
        675                 680                 685

AAT ATT ACT TTA GTT GAA GGT TAT AAT TTA CAA GTT GAA GTT AAT GCT    2112
Asn Ile Thr Leu Val Glu Gly Tyr Asn Leu Gln Val Glu Val Asn Ala
        690                 695                 700

ACT GAT GCA GAT GGA ACT ATT GAT AAT GTA AAA CTT TAT ATA GAT AAC    2160
Thr Asp Ala Asp Gly Thr Ile Asp Asn Val Lys Leu Tyr Ile Asp Asn
705                 710                 715                 720

AAT TTA GTT AGG CAA ATA AAT TCT ACT TCA TAT AAA TGG GGC CAT TCT    2208
Asn Leu Val Arg Gln Ile Asn Ser Thr Ser Tyr Lys Trp Gly His Ser
                725                 730                 735

GAT TCT CCA AAT ACA GAT GAA CTT AAT GGT CTT ACA GAA GGA ACT TAT    2256
Asp Ser Pro Asn Thr Asp Glu Leu Asn Gly Leu Thr Glu Gly Thr Tyr
        740                 745                 750

ACC TTA AAA GCA ATT GCA ACT GAT AAC GAC GGG GCT TCT ACA GAA ACG    2304
Thr Leu Lys Ala Ile Ala Thr Asp Asn Asp Gly Ala Ser Thr Glu Thr
        755                 760                 765
```

FIG. 21c

```
CAA TTT ACG TTA ACT GTA ATA ACA GAA CAA AGT CCG TCT GAG AAT TGT      2352
Gln Phe Thr Leu Thr Val Ile Thr Glu Gln Ser Pro Ser Glu Asn Cys
770             775                 780

GAC TTT AAT ACA CCT TCT TCA ACT GGT TTA GAA GAT TTT GAC ATT AAA      2400
Asp Phe Asn Thr Pro Ser Ser Thr Gly Leu Glu Asp Phe Asp Ile Lys
785             790                 795                 800

AAG TTT TCT AAC GTT TTT GAG TTA GGA TCT GGC GGA CCA TCT TTA AGT      2448
Lys Phe Ser Asn Val Phe Glu Leu Gly Ser Gly Gly Pro Ser Leu Ser
                805                 810                 815

AAT TTA AAA ACA TTT ACT ATT AAT TGG AAT TCG CAA TAC AAT GGG TTA      2496
Asn Leu Lys Thr Phe Thr Ile Asn Trp Asn Ser Gln Tyr Asn Gly Leu
        820                 825                 830

TAT CAA TTT TCA ATA AAC ACA AAC AAC GGT GTA CCT GAT TAT TAT ATA      2544
Tyr Gln Phe Ser Ile Asn Thr Asn Asn Gly Val Pro Asp Tyr Tyr Ile
        835                 840                 845

AAT TTA AAA CCA AAA ATT ACC TTT CAG TTT AAA AAT GCA AAT CCA GAA      2592
Asn Leu Lys Pro Lys Ile Thr Phe Gln Phe Lys Asn Ala Asn Pro Glu
850                 855                 860

ATA TCT ATT AGC AAT AGC TTA ATT CCT AAT TTT GAT GGT GAT TAC TGG      2640
Ile Ser Ile Ser Asn Ser Leu Ile Pro Asn Phe Asp Gly Asp Tyr Trp
865                 870                 875                 880

GTA ACA TCA GAT AAC GGT AAT TTT GTG ATG GTA TCT AAA ACT AAT AAT      2688
Val Thr Ser Asp Asn Gly Asn Phe Val Met Val Ser Lys Thr Asn Asn
                885                 890                 895

TTT ACG ATA TAC TTT AGT AAT GAC GCT ACT GCT CCT ATT TGT AAT GTT      2736
Phe Thr Ile Tyr Phe Ser Asn Asp Ala Thr Ala Pro Ile Cys Asn Val
                900                 905                 910

ACG CCT AGT AAC CAA ATA AGT AAA ATT ACT GAT GAT TCT AGT ATT AAT      2784
Thr Pro Ser Asn Gln Ile Ser Lys Ile Thr Asp Asp Ser Ser Ile Asn
        915                 920                 925

TTT AAG CTT TAC CCT AAT CCT GCT TTA GAC GAA ACT ATT TTT GTG AGC      2832
Phe Lys Leu Tyr Pro Asn Pro Ala Leu Asp Glu Thr Ile Phe Val Ser
    930                 935                 940

GCT GAA GAT GAA AAA CTA GCT TTG GTG CTT GTA CC AGT                   2870
Ala Glu Asp Glu Lys Leu Ala Leu Val Leu Val Pro
945                 950                 955
```

FIG. 21d

PYROCOCCUS FURIOSUS VC1 (7EG1)

```
ATG AGC AAG AAA AAG TTC GTC ATC GTA TCT ATC TTA ACA ATC CTT TTA     48
Met Ser Lys Lys Lys Phe Val Ile Val Ser Ile Leu Thr Ile Leu Leu
 1               5                  10                  15

GTA CAG GCA ATA TAT TTT GTA GAA AAG TAT CAT ACC TCT GAG GAC AAG     96
Val Gln Ala Ile Tyr Phe Val Glu Lys Tyr His Thr Ser Glu Asp Lys
                 20                  25                  30

TCA ACT TCA AAT ACC TCA TCT ACA CCA CCC CAA ACA ACA CTT TCC ACT    144
Ser Thr Ser Asn Thr Ser Ser Thr Pro Pro Gln Thr Thr Leu Ser Thr
             35                  40                  45

ACC AAG GTT CTC AAG ATT AGA TAC CCT GAT GAC GGT GAG TGG CCA GGA    192
Thr Lys Val Leu Lys Ile Arg Tyr Pro Asp Asp Gly Glu Trp Pro Gly
         50                  55                  60

GCT CCT ATT GAT AAG GAT GGT GAT GGG AAC CCA GAA TTC TAC ATT GAA    240
Ala Pro Ile Asp Lys Asp Gly Asp Gly Asn Pro Glu Phe Tyr Ile Glu
 65                  70                  75                  80

ATA AAC CTA TGG AAC ATT CTT AAT GCT ACT GGA TTT GCT GAG ATG ACG    288
Ile Asn Leu Trp Asn Ile Leu Asn Ala Thr Gly Phe Ala Glu Met Thr
                 85                  90                  95

TAC AAT TTA ACC AGC GGC GTC CTT CAC TAC GTC CAA CAA CTT GAC AAC    336
Tyr Asn Leu Thr Ser Gly Val Leu His Tyr Val Gln Gln Leu Asp Asn
            100                 105                 110

ATT GTC TTG AGG GAT AGA AGT AAT TGG GTG CAT GGA TAC CCC GAA ATA    384
Ile Val Leu Arg Asp Arg Ser Asn Trp Val His Gly Tyr Pro Glu Ile
        115                 120                 125

TTC TAT GGA AAC AAG CCA TGG AAT GCA AAC TAC GCA ACT GAT GGC CCA    432
Phe Tyr Gly Asn Lys Pro Trp Asn Ala Asn Tyr Ala Thr Asp Gly Pro
    130                 135                 140

ATA CCA TTA CCC AGT AAA GTT TCA AAC CTA ACA GAC TTC TAT CTA ACA    480
Ile Pro Leu Pro Ser Lys Val Ser Asn Leu Thr Asp Phe Tyr Leu Thr
145                 150                 155                 160

ATC TCC TAT AAA CTT GAG CCC AAG AAC GGC CTG CCA ATT AAC TTC GCA    528
Ile Ser Tyr Lys Leu Glu Pro Lys Asn Gly Leu Pro Ile Asn Phe Ala
                165                 170                 175

ATA GAA TCC TGG TTA ACG AGA GAA GCT TGG AGA ACA ACA GGA ATT AAC    576
Ile Glu Ser Trp Leu Thr Arg Glu Ala Trp Arg Thr Thr Gly Ile Asn
            180                 185                 190

AGC GAT GAG CAA GAA GTA ATG ATA TGG ATT TAC TAT GAC GGA TTA CAA    624
Ser Asp Glu Gln Glu Val Met Ile Trp Ile Tyr Tyr Asp Gly Leu Gln
        195                 200                 205

CCG GCT GGC TCC AAA GTT AAG GAG ATT GTA GTC CCA ATA ATA GTT AAC    672
Pro Ala Gly Ser Lys Val Lys Glu Ile Val Val Pro Ile Ile Val Asn
    210                 215                 220

GGA ACA CCA GTA AAT GCT ACA TTT GAA GTA TGG AAG GCA AAC ATT GGT    720
Gly Thr Pro Val Asn Ala Thr Phe Glu Val Trp Lys Ala Asn Ile Gly
225                 230                 235                 240

TGG GAG TAT GTT GCA TTT AGA ATA AAG ACC CCA ATC AAA GAG GGA ACA    768
Trp Glu Tyr Val Ala Phe Arg Ile Lys Thr Pro Ile Lys Glu Gly Thr
                245                 250                 255
```

FIG. 22a

```
GTG ACA ATT CCA TAC GGA GCA TTT ATA AGT GTT GCA GCC AAC ATT TCA          816
Val Thr Ile Pro Tyr Gly Ala Phe Ile Ser Val Ala Ala Asn Ile Ser
            260                 265                 270

AGC TTA CCA AAT TAC ACA GAA CTT TAC TTA GAG GAC GTG GAG ATT GGA          864
Ser Leu Pro Asn Tyr Thr Glu Leu Tyr Leu Glu Asp Val Glu Ile Gly
            275                 280                 285

ACT GAG TTT GGA ACG CCA AGC ACT ACC TCC GCC CAC CTA GAG TGG TGG          912
Thr Glu Phe Gly Thr Pro Ser Thr Thr Ser Ala His Leu Glu Trp Trp
            290                 295                 300

ATC ACA AAC ATA ACA CTA ACT CCT CTA GAT AGA CCT CTT ATT TCC TAA          960
Ile Thr Asn Ile Thr Leu Thr Pro Leu Asp Arg Pro Leu Ile Ser
305                 310                 315
```

FIG. 22b

SEQUENCE LISTING

<160> NUMBER OF SEQ ID NOS: 72

<210> SEQ ID NO 1
<211> LENGTH: 1446
<212> TYPE: DNA
<213> ORGANISM: Desulfurococcus sp.

<400> SEQUENCE: 1

| | | | | | |
|---|---|---|---|---|---|
| ttgaaattcc | ccaaagactt | catgataggc | tactcatctt | caccgtttca | atttgaagct | 60 |
| ggtattcccg | ggtccgagga | tccgaatagt | gattggtggg | tatgggtgca | tgatccggag | 120 |
| aacacagcag | ctggactagt | cagcggcgat | tttcccgaga | acggcccagg | ttactggaat | 180 |
| ttaaaccaaa | atgaccacga | cctggctgag | aagctggggg | ttaacactat | tagagtaggc | 240 |
| gttgagtgga | gtaggatttt | tccaaagcca | actttcaatg | ttaaagtccc | tgtagagaga | 300 |
| gatgagaacg | gcagcattgt | tcacgtagat | gtcgatgata | aagcggttga | aagacttgat | 360 |
| gaattagcca | acaaggaggc | cgtaaaccat | tacgtagaaa | tgtataaaga | ctgggttgaa | 420 |
| agaggtagaa | aacttatact | caatttatac | cattggcccc | tgcctctctg | gcttcacaac | 480 |
| ccaatcatgg | tgagaagaat | gggcccggac | agagcgccct | caggctggct | taacgaggag | 540 |
| tccgtggtgg | agtttgccaa | atacgccgca | tacattgctt | ggaaaatggg | cgagctacct | 600 |
| gttatgtgga | gcaccatgaa | cgaacccaac | gtcgtttatg | agcaaggata | catgttcgtt | 660 |
| aaaggggggtt | tcccacccgg | ctacttgagt | ttggaagctg | ctgataaggc | caggagaaat | 720 |
| atgatccagg | ctcatgcacg | ggcctatgac | aatattaaac | gcttcagtaa | gaaacctgtt | 780 |
| ggactaatat | acgctttcca | atggttcgaa | ctattagagg | gtccagcaga | agtatttgat | 840 |
| aagtttaaga | gctctaagtt | atactatttc | acagacatag | tatcgaaggg | tagttcaatc | 900 |
| atcaatgttg | aatacaggag | agatcttgcc | aataggctag | actggttggg | cgttaactac | 960 |
| tatagccgtt | tagtctacaa | aatcgtcgat | gacaaaccta | taatcctgca | cgggtatgga | 1020 |
| ttcctttgta | cacctggggg | gatcagcccg | gctgaaaatc | cttgtagcga | ttttgggtgg | 1080 |
| gaggtgtatc | ctgaaggact | ctacctactt | ctaaaagaac | tttacaaccg | atacgggta | 1140 |
| gacttgatcg | tgaccgagaa | cggtgtttca | gacagcaggg | atgcgttgag | accggcatac | 1200 |
| ctggtctcgc | atgtttacag | cgtatggaaa | gccgctaacg | agggcattcc | cgtcaaaggc | 1260 |
| tacctccact | ggagcttgac | agacaattac | gagtgggccc | agggcttcag | gcagaaattc | 1320 |
| ggtttagtca | tggttgactt | caaaactaag | aaaaggtatc | tccgcccaag | cgccctagtg | 1380 |
| ttccgggaga | tcgcaacgca | taacggaata | ccggatgagc | tacagcatct | tacactgatc | 1440 |
| cagtaa | | | | | | 1446 |

<210> SEQ ID NO 2
<211> LENGTH: 1317
<212> TYPE: DNA
<213> ORGANISM: Thermotoga sp.

<400> SEQUENCE: 2

| | | | | | |
|---|---|---|---|---|---|
| atgataagaa | ggtccgattt | tccaaaagat | tttatcttcg | gaacggctac | ggcagcatac | 60 |
| cagattgaag | gtgcagcaaa | cgaagatggc | agagggccat | caatttggga | tgtcttttca | 120 |
| cacacgcctg | gcaaaaccct | gaacggtgac | acaggagacg | ttgcgtgtga | ccattatcac | 180 |
| cgatacaagg | aagatatcca | gctgatgaaa | gaaataggt | tagacgctta | caggttctct | 240 |
| atctcctggc | ccagaattat | gccagatggg | aagaacatca | accaaaaggg | tgtggatttc | 300 |

-continued

```
tacaacagac tcgttgatga gcttttgaag aatgatatca taccattcgt aacactctat        360
cactgggact tacc ctacgc actttatgaa aaggtggat g gcttaaccc agatatagcg        420 ctctatttca gagcatacgc aacgtttatg ttcaacgaac tcggtgatcg tgtgaaacat        480
tggattacac tgaacgaacc atggtgttct tctttctcgg gttattacac gggagagcat        540
gccccgggtc atcaaaattt acaagaagcg ataatcgcgg cgcacaacct gttgagggaa        600
catggacatg ccgtccaggc gtccagagaa gaagtaaaag atggggaagt tggcttaacc        660
aacgttgtga tgaaaataga accgggcgat gcaaaacccg aaagtttctt ggtcgcaagt        720
cttgttgata agttcgttaa tgcatggtcc catgaccctg ttgttttcgg aaaatatccc        780
gaagaagcag ttgcactttta tacgaaaaaa gggttgcaag ttctcgatag cgatatgaat        840
attatttcga ctcctataga cttctttggt gtgaattatt acacaagaac acttgttgtt        900
tttgatatga caatcctct g gatttttcg tatgttcagg gagaccttcc caaaacggag        960
atgggatggg aaatctaccc gcagggatta tttgatatgc tggtctatct gaaggaaaga       1020
tataaactac cactttatat cacagagaac gggatggctg gacctgataa attggaaaac       1080
ggaagagttc atgataatta ccgaattgaa tatttggaaa agcactttga aaaagcactt       1140
gaagcaatca atgcagatgt tgatttgaaa ggttacttca tttggtcttt gatggataac       1200
ttcgaatggg cgtgcggata ctccaaacgt tcggtataa tctacgtaga ttacaatacc         1260
ccaaaaagga tattgaaaga ttcagcgatg tggttgaagg aatttctaaa atcttaa          1317
```

```
<210> SEQ ID NO 3
<211> LENGTH: 1266
<212> TYPE: DNA
<213> ORGANISM: Staphylothermus marinus

<400> SEQUENCE: 3
```

```
ttgataaggt ttcctgatta tttcttgttt ggaacagcta catcatcgca ccagatcgag         60
ggtaataaca tatttaatga ttggtgggag tgggagacta aaggcaggat taaggtgaga        120
tcgggtaagg catgtaatca ttgggaactc tataaagaag acatagagct tatggctgag       180
ctgggatata atgcttatag gttctccata gagtggagta gaatatttcc cagaaaagat        240
catatagatt atgagtcgct taataagtat aaggaaatag ttaatctact tagaaaatac        300
gggatagaac ctgtaatcac tcttcaccac ttcacaaacc cgcaatggtt tatgaaaatt        360
ggtggatgga ctagggaaga gaacataaaa tattttataa aatatgtaga acttatagct        420
tccgagataa aagacgtgaa aatatggatc actattaatg aaccaataat atatgtttta        480
caaggatata tttccggcga atggccacct ggaattaaaa atttaaaaat agctgatcaa        540
gtaactaaga atctttttaaa agcacataat gaagcctata atatacttca taaacacggt       600
attgtaggca tagctaaaaa catgatagca tttaaaccag atctaatag aggaaaagac        660 attaatattt atcataaagt cgataaagca ttcaactggg gatttctcaa cggaatatta        720 agggagaac tagaaactct ccgtggaaaa taccgagttg agcccggaaa tattgatttc         780
ataggcataa actattattc atcatatatt gtaaaatata cttggaatcc ttttaaacta        840
catattaaag tcgaaccatt agatacaggt ctatggacaa ctatgggtta ctgcatatat        900
cctagaggaa tatgaagt tgtaatgaaa actcatgaga aatacggcaa agaaataatc         960
attacagaga acggtgttgc agtagaaaat gatgaattaa ggattttatc cattatcagg        1020
cacttacaat acttatataa agccatgaat gaaggagcaa aggtgaaagg atatttctac       1080
```

```
tggagcttca tggataattt tgagtgggat aaaggattta accaaaggtt cggactagta    1140
gaagttgatt ataagacttt tgagagaaaa cctagaaaaa gcgcatatgt atatagtcaa    1200
atagcacgta ccaagactat aagtgatgaa tacctagaaa aatatggatt aaagaacctc    1260
gaataa                                                                1266
```

<210> SEQ ID NO 4
<211> LENGTH: 1530
<212> TYPE: DNA
<213> ORGANISM: Thermococcus sp.

<400> SEQUENCE: 4

```
atgctaccag aaggctttct ctggggcgtg tcccagtccg gctttcagtt cgagatgggc     60
gacaagctca ggaggaacat tgatccgaac acagactggt ggaagtgggt cagggatccc    120
ttcaacataa agagggaact cgtcagcggc gacctgcccg aggagggat aaacaactac     180 gaactttacg agaaggatca ccgcctcgcc agagacctcg gtctgaacgt ttacaggatt    240
ggaatagagt ggagcaggat ctttccctgg ccaacgtggt tgtggaggt tgacgttgag    300 cgggacagct acggactcgt gaaggacgtc aaaatcgata agacacgct cgaagagctc     360 gacgagatag cgaatcatca ggagatagcc tactaccgcc gcgttataga gcacctcagg     420
gagctgggct caaggtcat cgtgaacctc aaccacttca cgctccccct ctggcttcac     480
gatccgataa tcgcgaggga aaggccctc accaacggta ggattggctg gtcgggcag     540 gagagcgtgg tggagttcgc caagtacgcg gcgtacatcg cgaacgcact cggggacctc    600
gttgatatgt ggagcaccett caacgagccg atggtcgttg tggagctcgg ttacctcgcg    660
ccctactccg gctttccgcc gggggttatg aaccccgagg cggcaaagct ggcaatcctc    720
aacatgataa acgcccacgc actggcctac aagatgataa agaagttcga cagggtaaag    780
gccgataagg attcccgctc cgaggccgag gtcgggataa tctacaacaa cataggcgtt    840
gcctatccat acgactccaa cgacccaaag gacgtgaaag ctgcagaaaa cgacaactac    900
ttccacagcg ggctcttctt cgacgcaatc cacaagggca agctcaacat cgagttcgac    960
ggtgagacct tcgtcaaagt tcggcatctc agggggaacg actggatagg cgttaactac    1020
tacacgagag aagtcgtcag gtattcggag cccaagttcc cgagcatacc cctgatatcc    1080
ttccggggag ttcacaacta cggctacgcc tgcaggcccg ggagttcttc cgccgacgga    1140
aggcccgtaa gcgacatcgg ctgggagatc tatccggagg ggatctacga ctcgataaga    1200
gaggccaaca aatacgggt cccggtttac gtcaccgaaa acggaatagc cgattcaact    1260
gacaccctgc ggccgtacta cctcgcgagc catgtagcga agattgagga ggcgtacgag    1320
gcgggttacg acgtcagggg ctacctctac tgggcgctga ccgacaacta cgagtgggcc    1380
ctcggtttca ggatgaggtt cggcctctat aaagtggatc tcataaccaa ggagagaaca    1440 ccgcggagg aaagcgtaaa ggtttatagg ggcatcgtgg agaacaacgg agtgagcaag    1500
gaaatccggg agaagttcgg acttgggtga                                      1530
```

<210> SEQ ID NO 5
<211> LENGTH: 2166
<212> TYPE: DNA
<213> ORGANISM: Thermotoga maritima

<400> SEQUENCE: 5

```
atggaagga tcgatgaaat tctctctcag ttaactacag aggaaaaggt gaagctcgtt     60
gtgggggttg gtcttccagg acttttttggg aacccacatt ccagagtggc gggtgcggct    120
```

```
ggagaaacac atcccgttcc aagacttgga attcctgcgt ttgtcctggc agatggtccc    180
gcaggactca gaataaatcc cacaagggaa acgatgaaa acacttacta cacgacggca     240
tttcccgttg aaatcatgct cgcttctacc tggaacagag accttctgga agaagtggga    300
aaagccatgg gagaagaagt tagggaatac ggtgtcgatg tgcttcttgc acctgcgatg    360
aacattcaca gaaccctct ttgtggaagg aatttcgagt actactcaga agatcctgtc     420
cttttccggtg aaatggcttc agcctttgtc aagggagttc aatctcaagg ggtgggagcc   480
tgcataaaac actttgtcgc gaacaaccag gaaacgaaca ggatggtagt ggacacgatc    540
gtgtccgagc gagccctcag agaaatatat ctgaaaggtt ttgaaattgc tgtcaagaaa    600
gcaagaccct ggaccgtgat gagcgcttac aacaaactga atggaaaata ctgttcacag    660
aacgaatggc ttttgaagaa ggttctcagg gaagaatggg gatttggcgg tttcgtgatg    720
agcgactggt acgcgggaga caaccctgta aacagctca aggccggaaa cgatatgatc     780
atgcctggga aagcgtatca ggtgaacaca gaaagaagag atgaaataga agaaatcatg    840
gaggcgttga aggagggaaa attgagtgag gaggttctcg atgagtgtgt gagaaacatt    900
ctcaaagttc ttgtgaacgc gccttccttc aaagggtaca ggtactcaaa caagccggat    960
ctcgaatctc acgcggaagt cgcctacgaa gcaggtgcgg agggtgttgt ccttcttgag    1020
aacaacggtg ttcttccgtt cgatgaaaat acccatgtcg ccgtctttgg caccggtcaa    1080
atcgaaacaa taagggggagg aacgggaagt ggagacaccc atccgagata cacgatctct   1140
atccttgaag gcataaaaga aagaaacatg aagttcgacg aagaactcgc ttccacttat    1200
gaggagtaca taaaaagat gagagaaaca gaggaatata aacccagaac cgactcttgg     1260
ggaacggtca taaaaccgaa actcccagag aatttcctct cagaaaaaga gataaagaaa    1320
cctccaaaga aaaacgatgt tgcagttgtt gtgatcagta ggatctccgg tgagggatac    1380
gacagaaagc cggtgaaagg tgacttctac ctctccgatg acgagctgga actcataaaa    1440
accgtctcga aagaattcca cgatcagggt aagaaagttg tggttcttct gaacatcgga    1500
agtcccatcg aagtcgcaag ctggagagac cttgtggatg gaattcttct cgtctggcag    1560
gcgggacagg agatgggaag aatagtggcc gatgttcttg tgggaaagat taatccctcc    1620
ggaaaacttc caacgacctt cccgaaggat tactcggacg ttccatcctg gacgttccca    1680
ggagagccaa aggacaatcc gcaaagagtg gtgtacgagg aagacatcta cgtgggatac    1740
aggtactacg cacccttcgg tgtggaacct gcctacgaat tcggctacgg cctctcttac    1800
acaaagtttg aatacaaaga tttaaaaatc gctatcgacg gtgagacgct cagagtgtcg    1860
tacacgatca caaacactgg ggacagagct ggaaaggaag tctcacaggt ctacatcaaa    1920
gctccaaaag gaaaaataga caaacccttc caggagctga aagcgtttca caaaacaaaa    1980
cttttgaacc cggggtgaatc agaagaaatc tccttggaaa ttcctctcag agatcttgcg   2040
agtttcgatg ggaaagaatg ggttgtcgag tcaggagaat acgaggtcag ggtcggtgca    2100
tcttcgaggg atataaggtt gagagatatt tttctggttg agggagagaa gagattcaaa    2160
ccatga                                                              2166
```

<210> SEQ ID NO 6
<211> LENGTH: 1365
<212> TYPE: DNA
<213> ORGANISM: Thermococcus alcaliphilus

<400> SEQUENCE: 6

-continued

```
atgatccact gcccggttaa agggattata tctgaggctc gcggcataac catcacaata      60
gatttaagtt ttcaaggcca aataaataat ttggtgaatg ctatgattgt ctttccggag     120
ttcttcctct ttggaaccgc cacatcttct catcagatcg agggagataa taaatggaac     180
gactggtggt attatgagga gataggtaag ctcccctaca aatccggtaa agcctgcaat     240
cactgggagc tttacaggga agatatagag ctaatggcac agctcggcta caatgcctac     300
cgcttttcga tagagtggag ccgtctcttc ccggaagagg gcaaattcaa tgaagaagcc     360
ttcaaccgct accgtgaaat aattgaaatc ctccttgaga agggattac tccaaacgtt      420
acactgcacc acttcacatc accgctgtgg ttcatgcgga agggaggctt tttgaaggaa     480
gaaaacctca agtactggga gcagtacgtt gataaagccg cggagctcct caagggagtc     540
aagcttgtag ctacattcaa cgagccgatg gtctatgtta tgatgggcta cctcacagcc     600
tactggccgc ccttcatcaa gagtcccttt aaagccttta agttgccgc aaacctcctt      660
aaggcccatg caatggcata tgatatcctc catggtaact ttgatgtggg gatagttaaa     720
aacatcccca taatgctccc tgcaagcaac agagagaaag acgtagaagc tgcccaaaag     780
gcggataacc tctttaactg gaacttcctt gatgcaatat ggagcggaaa atataaagga     840
gcttttggaa cttacaaaac tccagaaagc gatgcagact catagggat aaactactac      900
acagccagcg aggtaaggca tagctggaat ccgctaaagt ttttcttcga tgccaagctt     960
gcagacttaa gcgagagaaa aacagatatg ggttggagtg tctatccaaa gggcatatac    1020
gaagctatag caaaggtttc acactacgga aagccaatgt acatcacgga aaacgggata    1080
gctaccttag acgatgagtg gaggatagag tttatcatcc agcacctcca gtacgttcac    1140
aaagccttaa acgatggctt tgacttgaga ggctacttct attggtcttt tatggataac    1200
ttcgagtggg ctgagggttt tagaccacgc tttgggctgg tcgaggtgga ctacacgacc    1260
ttcaagagga gaccgagaaa gagtgcttac atatatggag aaattgcaag ggaaaagaaa    1320
ataaaagacg aactgctggc aaagtatggg cttccggagc tatga                    1365
```

<210> SEQ ID NO 7
<211> LENGTH: 1536
<212> TYPE: DNA
<213> ORGANISM: Thermococcus chitonophagus

<400> SEQUENCE: 7

```
ttgcttccag agaactttct ctggggagtt tcacagtccg gattccagtt tgaaatgggg      60
gacagactga ggaggcacat tgatccaaac acagattggt ggtactgggt aagagatgaa    120
tataatatca aaaaggact agtaagtggg gatcttcccg aagacggtat aaattcatat     180
gaattatatg agagagacca agaaattgca aaggatttag ggctcaacac atataggatc    240
ggaattgaat ggagcagagt atttccatgg ccaacgactt tgtcgacgt ggagtatgaa      300
attgatgagt cttacgggtt ggtaaggat gtgaagattt ctaaagacgc attagaaaaa     360
cttgatgaaa tcgctaacca aagggaaata atatattata ggaacctaat aaattcccta    420
agaaagaggg gttttaaggt aatactaaac ctaaatcatt ttaccctccc aatatggctt    480
catgatccta tcgaatctag agaaaaagcc ctgaccaata agagaaacgg atgggtaagc    540
gaaaggagtg ttatagagtt tgcaaaattt gccgcgtatt tagcatataa attcggagac    600
atagtagaca tgtggagcac atttaatgaa cctatggtgg tcgccgagtt gggtatttta    660
gccccatact caggattccc cccgggagtc atgaatccag aagcagcaaa gttagttatg    720
ctacatatga taaacgccca tgctttagca tataggatga taaagaaatt tgacagaaaa    780
```

```
aaagctgatc cagaatcaaa agaaccagct gaaataggaa ttatatacaa taacatcggc    840
gtcacatatc cgtttaatcc gaaagactca aggatctac  aagcatccga taatgccaat    900
ttcttccaca gtgggctatt cttaacggct atccacaggg gaaaattaaa tatcgaattt    960
gacggagaga catttgttta ccttccatat ttaaagggca atgattggct gggagtgaat   1020
tattatacaa gagaagtcgt taaataccaa gatcccatgt ttccaagtat ccctctcata   1080
agcttcaagg gcgttccaga ttatggatac ggatgtagac caggaacgac gtcaaaggac   1140
ggtaatcctg ttagtgacat tggatgggag gtatatccca aggcatgta  cgactctata   1200 gtagctgcca atgaatatgg agttcctgta tacgtaacag aaaacggaat agcagattca   1260
aaagatgtat taaggcccta ttacatcgca tctcacattg aagccatgga agaggcttac   1320
gaaaatggtt atgacgtgag aggatactta cactgggcat taaccgataa ttacgaatgg   1380
gccttagggt tcagaatgag gtttggcttg tacgaagtaa acttgataac caaagagaga   1440
aaacccagga aaagagtgt  aagagtattc agagagatag ttattaataa tgggctaaca   1500
agcaacatca ggaaagagat cttagaggag gggtag                             1536
```

<210> SEQ ID NO 8
<211> LENGTH: 1533
<212> TYPE: DNA
<213> ORGANISM: Pyrococcus furiosus

<400> SEQUENCE: 8

```
atgttccctg aaagttcct  ttggggtgtg gcacaatcgg gttttcagtt tgaaatgggg     60
gataaactca ggaggaatat tgacactaac actgattggt ggcactgggt aagggataag    120
acaaatatag agaaaggcct cgttagtgga gatcttcccg aggaggggat taacaattac    180
gagctttatg agaaggacca tgagattgca agaaagctgg gtcttaatgc ttacagaata    240
ggcatagagt ggagcagaat attcccatgg ccaacgacat ttattgatgt tgattatagc    300
tataatgaat catataacct tatagaagat gtaaagatca ccaaggacac tttggaggag    360
ttagatgaga tcgccaacaa gagggaggtg gcctactata ggtcagtcat aaacagcctg    420
aggagcaagg ggtttaaggt tatagttaat ctaaatcact tcacccttcc atattggttg    480
catgatccca ttgaggctag ggagagggcg ttaactaata gaggaacgg  ctgggttaac    540 ccaagaacag ttatagagtt tgcaaagtat gccgcttaca tagcctataa gtttggagat    600
atagtggata tgtggagcac gtttaatgag cctatggtgg ttgttgagct tggctaccta    660 gcccctact  ctggcttccc tccagggggtt ctaaatccag aggccgcaaa gctggcgata    720
cttcacatga taaatgcaca tgctttagct tataggcaga taagaagtt  tgacactgag    780 aaagctgata aggattctaa agagcctgca gaagttggta tatttacaa  caacattgga    840 gttgcttatc ccaaggatcc gaacgattcc aaggatgtta aggcagcaga aaacgacaac    900
ttcttccact cagggctgtt cttcgaggcc atacacaaag gaaaacttaa tatagagttt    960
gacggtgaaa cgtttataga tgccccctat ctaaagggca atgactggat agggttaat   1020 tactacacaa gggaagtagt tacgtatcag gaaccaatgt ttccttcaat cccgctgatc   1080
acctttaagg gagttcaagg atatggctat gcctgcagac ctggaactct gtcaaaggat   1140
gacagacccg tcagcgacat aggatgggaa ctctatccag aggggatgta cgattcaata   1200
gttgaagctc acaagtacgg cgttccagtt tacgtgacgg agaacggaat agcggattca   1260
aaggacatcc taagacctta ctacatagcg agccacataa agatgataga gaaggccttt   1320
```

-continued

| | |
|---|---|
| gaggatgggt atgaagttaa gggctacttc cactgggcat taactgacaa cttcgagtgg | 1380 |
| gctctcgggt ttagaatgcg ctttggcctc tacgaagtca acctaattac aaaggagaga | 1440 |
| attcccaggg agaagagcgt gtcgatattc agagagatag tagccaataa tggtgttacg | 1500 |
| aaaaagattg aagaggaatt gctgagggga tga | 1533 |

<210> SEQ ID NO 9
<211> LENGTH: 1614
<212> TYPE: DNA
<213> ORGANISM: Bankia gouldi

<400> SEQUENCE: 9

| | |
|---|---|
| atgagaatac gtttagcgac gctcgcgctc tgcgcagcgc tgagcccagt cacctttgca | 60 |
| gataatgtaa ccgtacaaat cgacgccgac ggcggtaaaa aactcatcag ccgagcccct | 120 |
| tacggcatga taactccaa cgcagaaagc cttaccgata ctgactggca gcgttttcgc | 180 |
| gatgcaggtg tgcgcatgct gcgggaaaat ggcggcaaca acagcaccaa atataactgg | 240 |
| caactgcacc tgagcagtca tccggattgg tacaacaatg tctacgccgg caacaacaac | 300 |
| tgggacaacc gggtagccct gattcaggaa aacctgcccg cgccgacac catgtgggca | 360 |
| ttccagctca tcggtaaggt cgcggcgact tctgcctaca actttaacga ttgggaattc | 420 |
| aaccagtcgc aatggtggac cggcgtcgct cagaatctcg ctggcggcgg tgaacccaat | 480 |
| ctggacggcg gcggcgaagc gctggttgaa ggagacccca atctctacct catggattgg | 540 |
| tcgccagccg acactgtggg tattctcgac cactggtttg gcgtaaacgg gctgggcgtg | 600 |
| cggcgtggca agccaaata ctggagtatg ataacgagc ccggcatctg ggttggcacc | 660 |
| cacgacgatg tagtgaaaga acaaacgccg gtagaagatt tcctgcacac ctatttcgaa | 720 |
| accgccaaaa aagcccgcgc caaatttccc ggtattaaaa tcaccggtcc ggtgcccgct | 780 |
| aatgagtggc agtggtatgc ctgggcggt ttctcggtac cccaggaaca agggtttatg | 840 |
| agctggatgg agtatttcat caagcgggtg tctgaagagc aacgcgcaag tggtgttcgc | 900 |
| ctcctcgatg tactcgatct gcactactac cccggcgctt acaatgcgga agatatcgtg | 960 |
| caattacatc gcacgttctt cgaccgcgac tttgtttcac tggatgccaa cggggtgaaa | 1020 |
| atggtagaag gtggctggga tgacagcatc aacaaggaat atattttcgg gcgagtgaac | 1080 |
| gattggctcg aggaatatat ggggccagac catggtgtaa ccctgggctt aaccgaaatg | 1140 |
| tgcgtgcgca atgtgaatcc gatgactacc gccatctggt atgcctccat gctcggcacc | 1200 |
| ttcgcggata acggcgtcga aatattcacc ccatggtgct ggaacaccgg aatgtgggaa | 1260 |
| acactccacc tcttcagccg ctacaacaaa ccttatcggg tcgcctccag ctccagtctt | 1320 |
| gaagagtttg tcagcgccta cagctccatt aacgaagcag aagacgccat gacggtactt | 1380 |
| ctggtgaatc gttccactag cgagacccac accgccactg tcgctatcga cgatttccca | 1440 |
| ctggatggcc cctaccgcac cctgcgctta cacaacctgc cggggagga aaccttcgta | 1500 |
| tctcaccgag acaacgcccct ggaaaaaggt acagtgcgcg ccagcgacaa tacggtaaca | 1560 |
| ctggagttgc cccctctgtc cgttactgca atattgctca aggcccggcc ctaa | 1614 |

<210> SEQ ID NO 10
<211> LENGTH: 1668
<212> TYPE: DNA
<213> ORGANISM: Thermotoga maritima

<400> SEQUENCE: 10

| | |
|---|---|
| gtgatctgtg tggaaatatt cggaaagacc ttcagagagg gaagattcgt tctcaaagag | 60 |

-continued

```
aaaaacttca cagttgagtt cgcggtggag aagatacacc ttggctggaa gatctccggc      120
agggtgaagg gaagtccggg aaggcttgag gttcttcgaa cgaaagcacc ggaaaaggta      180
cttgtgaaca actggcagtc ctggggaccg tgcagggtgg tcgatgcctt ttctttcaaa      240
ccacctgaaa tagatccgaa ctggagatac accgcttcgg tggtgcccga tgtacttgaa      300
aggaacctcc agagcgacta tttcgtggct gaagaaggaa agtgtacgg ttttctgagt       360 tcgaaaatcg cacatccttt cttcgctgtg aagatgggg aacttgtggc atacctcgaa       420
tatttcgatg tcgagttcga cgactttgtt cctcttgaac ctctcgttgt actcgaggat      480
cccaacacac cccttcttct ggagaaatac gcggaactcg tcggaatgga aaacaacgcg      540
agagttccaa acacacacc cactggatgg tgcagctggt accattactt ccttgatctc       600
acctgggaag agaccctcaa gaacctgaag ctcgcgaaga atttcccgtt cgaggtcttc      660
cagatagacg acgcctacga aaaggacata ggtgactggc tcgtgacaag aggagacttt      720
ccatcggtgg aagagatggc aaaagttata gcggaaaacg gtttcatccc gggcatatgg      780
accgccccgt tcagtgtttc tgaaacctcg gatgtattca acgaacatcc ggactgggta      840
gtgaaggaaa acggagagcc gaagatggct tacagaaact ggaacaaaaa gatatacgcc      900
ctcgatcttt cgaaagatga ggttctgaac tggcttttcg atctcttctc atctctgaga      960
aagatgggct acaggtactt caagatcgac tttctcttcg cgggtgccgt tccaggagaa     1020
agaaaaaaga acataacacc aattcaggcg ttcagaaaag ggattgagac gatcagaaaa     1080
gcggtgggag aagattcttt catcctcgga tgcggctctc cccttcttcc cgcagtggga     1140
tgcgtcgacg ggatgaggat aggacctgac actgcgccgt tctggggaga acatatagaa     1200
gacaacggag ctcccgctgc aagatgggcg ctgagaaacg ccataacgag gtacttcatg     1260
cacgacaggt tctggctgaa cgaccccgac tgtctgatac tgagagagga gaaaacggat     1320
ctcacacaga aggaaaagga gctctactcg tacacgtgtg gagtgctcga caacatgatc     1380
atagaaagcg atgatctctc gctcgtcaga gatcatggaa aaaaggttct gaaagaaacg     1440
ctcgaactcc tcggtggaag accacgggtt caaaacatca tgtcggagga tctgagatac     1500
gagatcgtct cgtctggcac tctctcagga aacgtcaaga tcgtggtcga tctgaacagc     1560
agagagtacc acctggaaaa agaaggaaag tcctccctga aaaaaagagt cgtcaaaaga     1620
gaagacggaa gaaacttcta cttctacgaa gagggtgaga gagaatga                  1668
```

<210> SEQ ID NO 11
<211> LENGTH: 2043
<212> TYPE: DNA
<213> ORGANISM: Thermotoga maritima

<400> SEQUENCE: 11

```
atggggattg gtggcgacga ctcctggagc ccgtcagtat cggcggaatt ccttttattg       60
atcgttgagc tctctttcgt tctctttgca agtgacgagt tcgtgaaagt ggaaaacgga      120
aaattcgctc tgaacggaaa agaattcaga ttcattggaa gcaacaacta ctacatgcac      180
tacaagagca acggaatgat agacagtgtt ctggagagtg ccagagacat gggtataaag      240
gtcctcagaa tctggggttt cctcgacggg gagagttact gcagagacaa gaacaccctac    300 atgcatcctg agcccggtgt tttcggggtg ccagaaggaa tatcgaacgc ccagagcggt      360
ttcgaaagac tcgactacac agttgcgaaa gcgaaagaac tcggtataaa acttgtcatt      420
gttcttgtga caactgggga cgacttcggt ggaatgaacc agtacgtgag gtggtttgga      480
```

```
ggaacccatc acgacgattt ctacagagat gagaagatca aagaagagta caaaaagtac      540 gtctccttc tcgtaaacca tgtcaatacc tacacgggag ttccttacag ggaagagccc       600
accatcatgg cctgggagct tgcaaacgaa ccgcgctgtg agacggacaa atcggggaac      660
acgctcgttg agtgggtgaa ggagatgagc tcctacataa agagtctgga tcccaaccac     720
ctcgtggctg tggggacga aggattcttc agcaactacg aaggattcaa accttacggt      780
ggagaagccg agtgggccta caacggctgg tccggtgttg actggaagaa gctcctttcg     840
atagagacgg tggacttcgg cacgttccac ctctatccgt cccactgggg tgtcagtcca     900
gagaactatg cccagtgggg agcgaagtgg atagaagacc acataaagat cgcaaaagag     960
atcggaaaac ccgttgttct ggaagaatat ggaattccaa agagtgcgcc agttaacaga    1020
acggccatct acagactctg gaacgatctg gtctacgatc tcggtggaga tggagcgatg    1080
ttctggatgc tcgcgggaat cggggaaggt tcggacagag acgagagagg gtactatccg    1140
gactacgacg gtttcagaat agtgaacgac gacagtccag aagcggaact gataagagaa    1200
tacgcgaagc tgttcaacac aggtgaagac ataagagaag cacctgctc tttcatcctt     1260 ccaaaagacg gcatggagat caaaaagacc gtggaagtga gggctggtgt tttcgactac    1320
agcaacacgt ttgaaaagtt gtctgtcaaa gtcgaagatc tggtttttga aaatgagata    1380
gagcatctcg gatacggaat ttacggcttt gatctcgaca caacccggat cccggatgga    1440
gaacatgaaa tgttccttga aggccacttt cagggaaaaa cggtgaaaga ctctatcaaa    1500
gcgaaagtgg tgaacgaagc acggtacgtg ctcgcagagg aagttgattt ttcctctcca    1560
gaagaggtga aaaactggtg gaacagcgga acctggcagg cagagttcgg gtcacctgac    1620
attgaatgga acggtgaggt gggaaatgga gcactcagc tgaacgtgaa actgcccgga     1680
aagagcgact gggaagaagt gagagtagca aggaagttcg aaagactctc agaatgtgag    1740
atcctcgagt acgacatcta cattccaaac gtcgagggac tcaagggaag gttgaggccg    1800
tacgcggttc tgaaccccgg ctgggtgaag ataggcctcg acatgaacaa cgcgaacgtg    1860
gaaagtgcgg agatcatcac tttcggcgga aaagagtaca aagattcca tgtaagaatt    1920 gagttcgaca gaacagcggg ggtgaaagaa cttcacatag gagttgtcgg tgatcatctg    1980
aggtacgatg gaccgatttt catcgataat gtgagacttt ataaaagaac aggaggtatg    2040
tga                                                                 2043
```

<210> SEQ ID NO 12  
<211> LENGTH: 1539  
<212> TYPE: DNA  
<213> ORGANISM: Thermococcus chitonophagus

<400> SEQUENCE: 12

```
atgctaccag aagagttcct atggggcgtt gggcagtcag gctttcagtt cgaaatgggc       60
gacaagctca ggaggcacat cgatccaaat accgactggt ggaagtgggt tcgcgatcct      120
ttcaacataa aaaggagct tgtgagtggg gaccttcccg aggacggcat caacaactac       180
gaactttttg aaaacgatca caagctcgct aaaggccttg gactcaacgc atacaggatt      240
ggaatagagt ggagcagaat cttcccctgg ccgacgtgga cggtcgatac cgaggtcgag      300
ttcgacactt acggtttagt aaaggacgtt aagatagaca agtccaccct tgctgaactc      360
gacaggctgg ccaacaagga ggaggtaatg tactacaggc gcgttattca gcatttgagg      420
gagctcggct tcaaggtctt cgttaacctc aaccacttca cgcttccaat atggctccac      480
gacccgatag tggcaaggga gaaggccctc acaaacgaca gaatcggctg gtctcccag       540
```

-continued

```
aggacagttg ttgagtttgc caagtatgct gcttacatcg cccatgcgct cggagacctc    600
gtggacacat ggagcacctt caacgaacct atggtagttg tggagctcgg ctacctcgcc    660
ccctactcag gatttccccc gggagtcatg aaccccgagg ccgcgaagct ggcgatcctc    720
aacatgataa acgcccacgc cttggcatat aagatgataa agaggttcga caccaagaag    780
gccgatgagg atagcaagtc ccctgcggac gttggcataa tttacaacaa catcggtgtt    840
gcctacccta agaccctaac gatcccaag gacgttaaag cagccgaaaa cgacaactac    900
ttccacagcg gactgttctt tgatgccatc acaagggta agctcaacat agagttcgac    960
ggcgaaaact ttgtaaaagt tagacaccta aaaggcaatg actggatagg cctcaactac   1020
tacacccgcg aggttgttag atattcggag cccaagttcc caagtatacc cctcatatcc   1080
ttcaagggcg ttcccaacta cggctactcc tgcaggcccg gcacgacctc cgccgatggc   1140
atgcccgtca gcgatatcgg ctgggaagtc tatccccagg gaatctacga ctcgatagtc   1200
gaggccacca agtacagtgt tcctgtttac gtcaccgaga acggtgttgc ggattccgcg   1260
gacacgctga ggccatacta catagtcagc cacgtctcaa agatagagga agccattgag   1320
aatggatacc ccgtaaaagg ctacatgtac tgggcgctta cggataacta cgagtgggcc   1380
ctcggcttca gcatgaggtt tggtctctac aaggtcgacc tcatctccaa ggagaggatc   1440
ccgagggaga gaagcgttga gatatatcgc aggatagtgc agtccaacgg tgttcctaag   1500
gatatcaaag aggagttcct gaagggtgag gagaaatga                          1539
```

<210> SEQ ID NO 13
<211> LENGTH: 1083
<212> TYPE: DNA
<213> ORGANISM: Thermotoga sp.

<400> SEQUENCE: 13

```
atggtagaaa gacacttcag atatgttctt atttgcaccc tgtttcttgt tatgctccta     60
atctcatcca ctcagtgtgg aaaaaatgaa ccaaacaaaa gagtgaatag catggaacag    120
tcagttgctg aaagtgatag caactcagca tttgaataca caaaatggt aggtaaagga    180 gtaaatattg gaaatgcttt agaagctcct ttcgaaggag cttggggagt aagaattgag    240
gatgaatatt ttgagataat aaagaaaagg ggatttgatt ctgttaggat tcccataaga    300
tggtcagcac atatatccga aaagccacca tatgatattg acaggaattt cctcgaaaga    360
gttaaccatg ttgtcgatag ggctcttgag aataatttaa cagtaatcat caatacgcac    420
cattttgaag aactctatca agaaccggat aaatacggcg atgttttggt ggaaatttgg    480
agacagattg caaattctt taagattac ccggaaaatc tgttctttga atctacaac    540 gagcctgctc agaacttgac agctgaaaaa tggaacgcac tttatccaaa agtgctcaaa    600
gttatcaggg agagcaatcc aacccggatt gtcattatcg atgctccaaa ctgggcacac    660
tatagcgcag tgagaagtct aaaattagtc aacgacaaac gcatcattgt ttccttccat    720
tactacgaac ctttcaaatt cacacatcag ggtgccgaat gggttaatcc catcccacct    780
gttagggtta agtggaatgg cgaggaatgg gaaattaacc aaatcagaag tcatttcaaa    840
tacgtgagtg actgggcaaa gcaaataac gtaccaatct ttcttggtga attcggtgct    900
tattcaaaag cagacatgga ctcaagggtt aagtggaccg aaagtgtgag aaaaatggcg    960
gaagaatttg gattttcata cgcgtattgg gaattttgtg caggatttgg catatacgat   1020
agatggtctc aaaactggat cgaaccattg gcaacagctg tggttggcac aggcaaagag   1080
```

-continued

| | |
|---|---|
| taa | 1083 |

<210> SEQ ID NO 14
<211> LENGTH: 2319
<212> TYPE: DNA
<213> ORGANISM: Thermotoga maritima

<400> SEQUENCE: 14

| | |
|---|---|
| atggatctta caaaggtggg gatcatagtg aggctgaacg agtggcaggc aaaagacgtg | 60 |
| gcaaaagaca ggttcataga gataaaagac ggaaaggctg aagtgtggat actccaggga | 120 |
| gtggaagaga ttttctacga aaaaccagac acatctccca gaatcttctt cgcacaggca | 180 |
| aggtcgaaca aggtgatcga ggcttttctg accaatcctg tggatacgaa aaagaaagaa | 240 |
| ctcttcaagg ttactgttga cggaaaagag attcccgtct caagagtgga aaaggccgat | 300 |
| cccacggaca tagacgtgac gaactacgtg agaatcgtcc tttctgaatc cctgaaagaa | 360 |
| gaagacctca gaaagacgt ggaactgatc atagaaggtt acaaaccggc aagagtcatc | 420 |
| atgatggaga tcctggacga ctactattac gatggagagc tcggagccgt atattctcca | 480 |
| gagaagacga tattcagagt ctggtccccc gtttctaagt gggtaaaggt gcttctcttc | 540 |
| aaaaacggag aagacacaga accgtaccag gttgtgaaca tggaatacaa gggaaacggg | 600 |
| gtctgggaag cggttgttga aggcgatctc gacggagtgt tctacctcta tcagctggaa | 660 |
| aactacggaa agatcagaac aaccgtcgat ccttattcga aagcggttta cgcaaacagc | 720 |
| aaaaagagcg ccgttgtgaa tcttgccagg acaaacccag aaggatggga aaacgacagg | 780 |
| ggaccgaaaa tcgaaggata cgaagacgcg ataatctatg aaatacacat agcggacatc | 840 |
| acaggactcg aaaactccgg ggtaaaaaac aaaggcctct atctcgggct caccgaagaa | 900 |
| aacacgaaag gaccgggcgg tgtgacaaca ggcctttcgc accttgtgga actcggtgtt | 960 |
| acacacgttc atatacttcc tttctttgat ttctacacag gcgacgaact cgataaagat | 1020 |
| ttcgagaagt actacaactg gggttacgat ccttacctgt tcatggttcc ggagggcaga | 1080 |
| tactcaaccg atcccaaaaa cccacacacg agaatcagag aagtcaaaga atggtcaaa | 1140 |
| gcccttcaca aacacggtat aggtgtgatt atggacatgg tgttccctca cacctacggt | 1200 |
| ataggcgaac tctctgcgtt cgatcagacg gtgccgtact acttctacag aatcgacaag | 1260 |
| acaggtgcct atttgaacga aagcggatgt ggtaacgtca tcgcaagcga aagacccatg | 1320 |
| atgagaaaat tcatagtcga taccgtcacc tactgggtaa aggagtatca catagacgga | 1380 |
| ttcaggttcg atcagatggg tctcatcgac aaaaagacaa tgctcgaagt cgaaagagct | 1440 |
| cttcataaaa tcgatccaac tatcattctc tacggcgaac cgtgggggtgg atggggagca | 1500 |
| ccgatcaggt ttggaaagag cgatgtcgcc ggcacacacg tggcagcttt caacgatgag | 1560 |
| ttcagagacg caataagggg ttccgtgttc aacccgagcg tcaagggatt cgtcatggga | 1620 |
| ggatacggaa aggaaaccaa gatcaaaagg ggtgttgttg aagcataaa ctacgacgga | 1680 |
| aaactcatca aaagtctcgc ccttgatcca gaagaaacta taactacgc agcgtgtcac | 1740 |
| gacaaccaca cactgtggga caagaactac cttgccgcca agctgataaa gaaaaaggaa | 1800 |
| tggaccgaag aagaactgaa aaacgcccag aaactggctg gtgcgatact tctcacttct | 1860 |
| caaggtgttc ctttcctcca cggagggcag gacttctgca ggacgaagaa tttcaacgac | 1920 |
| aactcctaca cgcccctat ctcgataaac ggcttcgatt acgaaagaaa acttcagttc | 1980 |
| atagacgtgt tcaattacca aagggtctc ataaaactca gaaagaaca ccctgctttc | 2040 |
| aggctgaaaa acgctgaaga gatcaaaaaa cacctggaat ttctcccggg cgggagaaga | 2100 |

```
atagttgcgt tcatgcttaa agaccacgca ggtggtgatc cctggaaaga catcgtggtg   2160
atttacaatg gaaacttaga gaagacaaca tacaaactgc cagaaggaaa atggaatgtg   2220
gttgtgaaca gccagaaagc cggaacagaa gtgatagaaa ccgtcgaagg aacaatagaa   2280
ctcgatccgc tttccgcgta cgttctgtac agagagtga                          2319
```

<210> SEQ ID NO 15
<211> LENGTH: 481
<212> TYPE: PRT
<213> ORGANISM: Desulfurococcus sp.

<400> SEQUENCE: 15

```
Leu Lys Phe Pro Lys Asp Phe Met Ile Gly Tyr Ser Ser Pro Phe
 1               5                  10                  15

Gln Phe Glu Ala Gly Ile Pro Gly Ser Glu Asp Pro Asn Ser Asp Trp
             20                  25                  30

Trp Val Trp Val His Asp Pro Glu Asn Thr Ala Ala Gly Leu Val Ser
         35                  40                  45

Gly Asp Phe Pro Glu Asn Gly Pro Gly Tyr Trp Asn Leu Asn Gln Asn
     50                  55                  60

Asp His Asp Leu Ala Glu Lys Leu Gly Val Asn Thr Ile Arg Val Gly
 65                  70                  75                  80

Val Glu Trp Ser Arg Ile Phe Pro Lys Pro Thr Phe Asn Val Lys Val
                 85                  90                  95

Pro Val Glu Arg Asp Glu Asn Gly Ser Ile Val His Val Asp Val Asp
            100                 105                 110

Asp Lys Ala Val Glu Arg Leu Asp Glu Leu Ala Asn Lys Glu Ala Val
        115                 120                 125

Asn His Tyr Val Glu Met Tyr Lys Asp Trp Val Glu Arg Gly Arg Lys
    130                 135                 140

Leu Ile Leu Asn Leu Tyr His Trp Pro Leu Pro Leu Trp Leu His Asn
145                 150                 155                 160

Pro Ile Met Val Arg Arg Met Gly Pro Asp Arg Ala Pro Ser Gly Trp
                165                 170                 175

Leu Asn Glu Glu Ser Val Val Glu Phe Ala Lys Tyr Ala Ala Tyr Ile
            180                 185                 190

Ala Trp Lys Met Gly Glu Leu Pro Val Met Trp Ser Thr Met Asn Glu
        195                 200                 205

Pro Asn Val Val Tyr Glu Gln Gly Tyr Met Phe Val Lys Gly Gly Phe
    210                 215                 220

Pro Pro Gly Tyr Leu Ser Leu Glu Ala Ala Asp Lys Ala Arg Arg Asn
225                 230                 235                 240

Met Ile Gln Ala His Ala Arg Ala Tyr Asp Asn Ile Lys Arg Phe Ser
                245                 250                 255

Lys Lys Pro Val Gly Leu Ile Tyr Ala Phe Gln Trp Phe Glu Leu Leu
            260                 265                 270

Glu Gly Pro Ala Glu Val Phe Asp Lys Phe Lys Ser Ser Lys Leu Tyr
        275                 280                 285

Tyr Phe Thr Asp Ile Val Ser Lys Gly Ser Ser Ile Ile Asn Val Glu
    290                 295                 300

Tyr Arg Arg Asp Leu Ala Asn Arg Leu Asp Trp Leu Gly Val Asn Tyr
305                 310                 315                 320

Tyr Ser Arg Leu Val Tyr Lys Ile Val Asp Asp Lys Pro Ile Ile Leu
                325                 330                 335
```

-continued

His Gly Tyr Gly Phe Leu Cys Thr Pro Gly Gly Ile Ser Pro Ala Glu
            340                 345                 350

Asn Pro Cys Ser Asp Phe Gly Trp Glu Val Tyr Pro Glu Gly Leu Tyr
            355                 360                 365

Leu Leu Leu Lys Glu Leu Tyr Asn Arg Tyr Gly Val Asp Leu Ile Val
        370                 375                 380

Thr Glu Asn Gly Val Ser Asp Ser Arg Asp Ala Leu Arg Pro Ala Tyr
385                 390                 395                 400

Leu Val Ser His Val Tyr Ser Val Trp Lys Ala Ala Asn Glu Gly Ile
            405                 410                 415

Pro Val Lys Gly Tyr Leu His Trp Ser Leu Thr Asp Asn Tyr Glu Trp
            420                 425                 430

Ala Gln Gly Phe Arg Gln Lys Phe Gly Leu Val Met Val Asp Phe Lys
        435                 440                 445

Thr Lys Lys Arg Tyr Leu Arg Pro Ser Ala Leu Val Phe Arg Glu Ile
450                 455                 460

Ala Thr His Asn Gly Ile Pro Asp Glu Leu Gln His Leu Thr Leu Ile
465                 470                 475                 480

Gln

<210> SEQ ID NO 16
<211> LENGTH: 438
<212> TYPE: PRT
<213> ORGANISM: Thermotoga sp.

<400> SEQUENCE: 16

Met Ile Arg Arg Ser Asp Phe Pro Lys Asp Phe Ile Phe Gly Thr Ala
1               5                   10                  15

Thr Ala Ala Tyr Gln Ile Glu Gly Ala Ala Asn Glu Asp Gly Arg Gly
            20                  25                  30

Pro Ser Ile Trp Asp Val Phe Ser His Thr Pro Gly Lys Thr Leu Asn
        35                  40                  45

Gly Asp Thr Gly Asp Val Ala Cys Asp His Tyr His Arg Tyr Lys Glu
    50                  55                  60

Asp Ile Gln Leu Met Lys Glu Ile Gly Leu Asp Ala Tyr Arg Phe Ser
65                  70                  75                  80

Ile Ser Trp Pro Arg Ile Met Pro Asp Gly Lys Asn Ile Asn Gln Lys
            85                  90                  95

Gly Val Asp Phe Tyr Asn Arg Leu Val Asp Glu Leu Leu Lys Asn Asp
            100                 105                 110

Ile Ile Pro Phe Val Thr Leu Tyr His Trp Asp Leu Pro Tyr Ala Leu
        115                 120                 125

Tyr Glu Lys Gly Gly Trp Leu Asn Pro Asp Ile Ala Leu Tyr Phe Arg
    130                 135                 140

Ala Tyr Ala Thr Phe Met Phe Asn Glu Leu Gly Asp Arg Val Lys His
145                 150                 155                 160

Trp Ile Thr Leu Asn Glu Pro Trp Cys Ser Ser Phe Ser Gly Tyr Tyr
            165                 170                 175

Thr Gly Glu His Ala Pro Gly His Gln Asn Leu Gln Glu Ala Ile Ile
            180                 185                 190

Ala Ala His Asn Leu Leu Arg Glu His Gly His Ala Val Gln Ala Ser
        195                 200                 205

Arg Glu Glu Val Lys Asp Gly Glu Val Gly Leu Thr Asn Val Val Met
    210                 215                 220

-continued

```
Lys Ile Glu Pro Gly Asp Ala Lys Pro Glu Ser Phe Leu Val Ala Ser
225                 230                 235                 240

Leu Val Asp Lys Phe Val Asn Ala Trp Ser His Asp Pro Val Val Phe
            245                 250                 255

Gly Lys Tyr Pro Glu Ala Val Ala Leu Tyr Thr Glu Lys Gly Leu
            260                 265                 270

Gln Val Leu Asp Ser Asp Met Asn Ile Ile Ser Thr Pro Ile Asp Phe
            275                 280                 285

Phe Gly Val Asn Tyr Tyr Thr Arg Thr Leu Val Val Phe Asp Met Asn
290                 295                 300

Asn Pro Leu Gly Phe Ser Tyr Val Gln Gly Asp Leu Pro Lys Thr Glu
305                 310                 315                 320

Met Gly Trp Glu Ile Tyr Pro Gln Gly Leu Phe Asp Met Leu Val Tyr
                325                 330                 335

Leu Lys Glu Arg Tyr Lys Leu Pro Leu Tyr Ile Thr Glu Asn Gly Met
                340                 345                 350

Ala Gly Pro Asp Lys Leu Glu Asn Gly Arg Val His Asp Asn Tyr Arg
                355                 360                 365

Ile Glu Tyr Leu Glu Lys His Phe Glu Lys Ala Leu Glu Ala Ile Asn
                370                 375                 380

Ala Asp Val Asp Leu Lys Gly Tyr Phe Ile Trp Ser Leu Met Asp Asn
385                 390                 395                 400

Phe Glu Trp Ala Cys Gly Tyr Ser Lys Arg Phe Gly Ile Ile Tyr Val
                405                 410                 415

Asp Tyr Asn Thr Pro Lys Arg Ile Leu Lys Asp Ser Ala Met Trp Leu
                420                 425                 430

Lys Glu Phe Leu Lys Ser
                435
```

<210> SEQ ID NO 17
<211> LENGTH: 421
<212> TYPE: PRT
<213> ORGANISM: Staphylothermus marinus

<400> SEQUENCE: 17

```
Leu Ile Arg Phe Pro Asp Tyr Phe Leu Phe Gly Thr Ala Thr Ser Ser
1               5                   10                  15

His Gln Ile Glu Gly Asn Asn Ile Phe Asn Asp Trp Glu Trp Glu
            20                  25                  30

Thr Lys Gly Arg Ile Lys Val Arg Ser Gly Lys Ala Cys Asn His Trp
            35                  40                  45

Glu Leu Tyr Lys Glu Asp Ile Glu Leu Met Ala Glu Leu Gly Tyr Asn
    50                  55                  60

Ala Tyr Arg Phe Ser Ile Glu Trp Ser Arg Ile Phe Pro Arg Lys Asp
65                  70                  75                  80

His Ile Asp Tyr Glu Ser Leu Asn Lys Tyr Lys Glu Ile Val Asn Leu
                85                  90                  95

Leu Arg Lys Tyr Gly Ile Glu Pro Val Ile Thr Leu His His Phe Thr
            100                 105                 110

Asn Pro Gln Trp Phe Met Lys Ile Gly Gly Trp Thr Arg Glu Glu Asn
            115                 120                 125

Ile Lys Tyr Phe Ile Lys Tyr Val Glu Leu Ile Ala Ser Glu Ile Lys
            130                 135                 140

Asp Val Lys Ile Trp Ile Thr Ile Asn Glu Pro Ile Ile Tyr Val Leu
```

```
                145                 150                 155                 160
Gln Gly Tyr Ile Ser Gly Glu Trp Pro Pro Gly Ile Lys Asn Leu Lys
                    165                 170                 175
Ile Ala Asp Gln Val Thr Lys Asn Leu Leu Lys Ala His Asn Glu Ala
                180                 185                 190
Tyr Asn Ile Leu His Lys His Gly Ile Val Gly Ile Ala Lys Asn Met
            195                 200                 205
Ile Ala Phe Lys Pro Gly Ser Asn Arg Gly Lys Asp Ile Asn Ile Tyr
        210                 215                 220
His Lys Val Asp Lys Ala Phe Asn Trp Gly Phe Leu Asn Gly Ile Leu
225                 230                 235                 240
Arg Gly Glu Leu Glu Thr Leu Arg Gly Lys Tyr Arg Val Glu Pro Gly
                245                 250                 255
Asn Ile Asp Phe Ile Gly Ile Asn Tyr Tyr Ser Tyr Ile Val Lys
                260                 265                 270
Tyr Thr Trp Asn Pro Phe Lys Leu His Ile Lys Val Glu Pro Leu Asp
            275                 280                 285
Thr Gly Leu Trp Thr Thr Met Gly Tyr Cys Ile Tyr Pro Arg Gly Ile
        290                 295                 300
Tyr Glu Val Val Met Lys Thr His Glu Lys Tyr Gly Lys Glu Ile Ile
305                 310                 315                 320
Ile Thr Glu Asn Gly Val Ala Val Glu Asn Asp Glu Leu Arg Ile Leu
                325                 330                 335
Ser Ile Ile Arg His Leu Gln Tyr Leu Tyr Lys Ala Met Asn Glu Gly
            340                 345                 350
Ala Lys Val Lys Gly Tyr Phe Tyr Trp Ser Phe Met Asp Asn Phe Glu
        355                 360                 365
Trp Asp Lys Gly Phe Asn Gln Arg Phe Gly Leu Val Glu Val Asp Tyr
    370                 375                 380
Lys Thr Phe Glu Arg Lys Pro Arg Lys Ser Ala Tyr Val Tyr Ser Gln
385                 390                 395                 400
Ile Ala Arg Thr Lys Thr Ile Ser Asp Glu Tyr Leu Glu Lys Tyr Gly
                405                 410                 415
Leu Lys Asn Leu Glu
            420

<210> SEQ ID NO 18
<211> LENGTH: 509
<212> TYPE: PRT
<213> ORGANISM: Thermococcus sp.

<400> SEQUENCE: 18

Met Leu Pro Glu Gly Phe Leu Trp Gly Val Ser Gln Ser Gly Phe Gln
1               5                   10                  15
Phe Glu Met Gly Asp Lys Leu Arg Arg Asn Ile Asp Pro Asn Thr Asp
                20                  25                  30
Trp Trp Lys Trp Val Arg Asp Pro Phe Asn Ile Lys Arg Glu Leu Val
            35                  40                  45
Ser Gly Asp Leu Pro Glu Glu Gly Ile Asn Asn Tyr Glu Leu Tyr Glu
        50                  55                  60
Lys Asp His Arg Leu Ala Arg Asp Leu Gly Leu Asn Val Tyr Arg Ile
65                  70                  75                  80
Gly Ile Glu Trp Ser Arg Ile Phe Pro Trp Pro Thr Trp Phe Val Glu
                85                  90                  95
```

-continued

```
Val Asp Val Glu Arg Asp Ser Tyr Gly Leu Val Lys Asp Val Lys Ile
            100                 105                 110

Asp Lys Asp Thr Leu Glu Glu Leu Asp Glu Ile Ala Asn His Gln Glu
            115                 120                 125

Ile Ala Tyr Tyr Arg Arg Val Ile Glu His Leu Arg Glu Leu Gly Phe
            130                 135                 140

Lys Val Ile Val Asn Leu Asn His Phe Thr Leu Pro Leu Trp Leu His
145                 150                 155                 160

Asp Pro Ile Ile Ala Arg Glu Lys Ala Leu Thr Asn Gly Arg Ile Gly
                165                 170                 175

Trp Val Gly Gln Glu Ser Val Val Glu Phe Ala Lys Tyr Ala Ala Tyr
                180                 185                 190

Ile Ala Asn Ala Leu Gly Asp Leu Val Asp Met Trp Ser Thr Phe Asn
            195                 200                 205

Glu Pro Met Val Val Glu Leu Gly Tyr Leu Ala Pro Tyr Ser Gly
            210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Lys Phe
                245                 250                 255

Asp Arg Val Lys Ala Asp Lys Asp Ser Arg Ser Glu Ala Glu Val Gly
            260                 265                 270

Ile Ile Tyr Asn Asn Ile Gly Val Ala Tyr Pro Tyr Asp Ser Asn Asp
            275                 280                 285

Pro Lys Asp Val Lys Ala Ala Glu Asn Asp Asn Tyr Phe His Ser Gly
            290                 295                 300

Leu Phe Phe Asp Ala Ile His Lys Gly Lys Leu Asn Ile Glu Phe Asp
305                 310                 315                 320

Gly Glu Thr Phe Val Lys Val Arg His Leu Arg Gly Asn Asp Trp Ile
                325                 330                 335

Gly Val Asn Tyr Tyr Thr Arg Glu Val Val Arg Tyr Ser Glu Pro Lys
                340                 345                 350

Phe Pro Ser Ile Pro Leu Ile Ser Phe Arg Gly Val His Asn Tyr Gly
            355                 360                 365

Tyr Ala Cys Arg Pro Gly Ser Ser Ser Ala Asp Gly Arg Pro Val Ser
            370                 375                 380

Asp Ile Gly Trp Glu Ile Tyr Pro Glu Gly Ile Tyr Asp Ser Ile Arg
385                 390                 395                 400

Glu Ala Asn Lys Tyr Gly Val Pro Val Tyr Val Thr Glu Asn Gly Ile
                405                 410                 415

Ala Asp Ser Thr Asp Thr Leu Arg Pro Tyr Tyr Leu Ala Ser His Val
            420                 425                 430

Ala Lys Ile Glu Glu Ala Tyr Glu Ala Gly Tyr Asp Val Arg Gly Tyr
            435                 440                 445

Leu Tyr Trp Ala Leu Thr Asp Asn Tyr Glu Trp Ala Leu Gly Phe Arg
            450                 455                 460

Met Arg Phe Gly Leu Tyr Lys Val Asp Leu Ile Thr Lys Glu Arg Thr
465                 470                 475                 480

Pro Arg Glu Glu Ser Val Lys Val Tyr Arg Gly Ile Val Glu Asn Asn
                485                 490                 495

Gly Val Ser Lys Glu Ile Arg Glu Lys Phe Gly Leu Gly
            500                 505
```

<210> SEQ ID NO 19
<211> LENGTH: 721
<212> TYPE: PRT
<213> ORGANISM: Thermotoga maritima

<400> SEQUENCE: 19

| Met | Glu | Arg | Ile | Asp | Glu | Ile | Leu | Ser | Gln | Leu | Thr | Thr | Glu | Glu | Lys |
|-----|-----|-----|-----|-----|-----|-----|-----|-----|-----|-----|-----|-----|-----|-----|-----|
| 1 | | | | 5 | | | | | 10 | | | | | 15 | |

| Val | Lys | Leu | Val | Val | Gly | Val | Gly | Leu | Pro | Gly | Leu | Phe | Gly | Asn | Pro |
| | | | 20 | | | | | 25 | | | | | 30 | | |

| His | Ser | Arg | Val | Ala | Gly | Ala | Ala | Gly | Glu | Thr | His | Pro | Val | Pro | Arg |
| | | 35 | | | | | 40 | | | | | 45 | | | |

| Leu | Gly | Ile | Pro | Ala | Phe | Val | Leu | Ala | Asp | Gly | Pro | Ala | Gly | Leu | Arg |
| | 50 | | | | | 55 | | | | | 60 | | | | |

| Ile | Asn | Pro | Thr | Arg | Glu | Asn | Asp | Glu | Asn | Thr | Tyr | Tyr | Thr | Thr | Ala |
| 65 | | | | | 70 | | | | | 75 | | | | | 80 |

| Phe | Pro | Val | Glu | Ile | Met | Leu | Ala | Ser | Thr | Trp | Asn | Arg | Asp | Leu | Leu |
| | | | | 85 | | | | | 90 | | | | | 95 | |

| Glu | Glu | Val | Gly | Lys | Ala | Met | Gly | Glu | Glu | Val | Arg | Glu | Tyr | Gly | Val |
| | | | 100 | | | | | 105 | | | | | 110 | | |

| Asp | Val | Leu | Leu | Ala | Pro | Ala | Met | Asn | Ile | His | Arg | Asn | Pro | Leu | Cys |
| | | | 115 | | | | | 120 | | | | | 125 | | |

| Gly | Arg | Asn | Phe | Glu | Tyr | Tyr | Ser | Glu | Asp | Pro | Val | Leu | Ser | Gly | Glu |
| | 130 | | | | | 135 | | | | | 140 | | | | |

| Met | Ala | Ser | Ala | Phe | Val | Lys | Gly | Val | Gln | Ser | Gln | Gly | Val | Gly | Ala |
| 145 | | | | | 150 | | | | | 155 | | | | | 160 |

| Cys | Ile | Lys | His | Phe | Val | Ala | Asn | Asn | Gln | Glu | Thr | Asn | Arg | Met | Val |
| | | | | 165 | | | | | 170 | | | | | 175 | |

| Val | Asp | Thr | Ile | Val | Ser | Glu | Arg | Ala | Leu | Arg | Glu | Ile | Tyr | Leu | Lys |
| | | | 180 | | | | | 185 | | | | | 190 | | |

| Gly | Phe | Glu | Ile | Ala | Val | Lys | Lys | Ala | Arg | Pro | Trp | Thr | Val | Met | Ser |
| | | | 195 | | | | | 200 | | | | | 205 | | |

| Ala | Tyr | Asn | Lys | Leu | Asn | Gly | Lys | Tyr | Cys | Ser | Gln | Asn | Glu | Trp | Leu |
| | 210 | | | | | 215 | | | | | 220 | | | | |

| Leu | Lys | Lys | Val | Leu | Arg | Glu | Glu | Trp | Gly | Phe | Gly | Phe | Val | Met |
| 225 | | | | | 230 | | | | | 235 | | | | | 240 |

| Ser | Asp | Trp | Tyr | Ala | Gly | Asp | Asn | Pro | Val | Glu | Gln | Leu | Lys | Ala | Gly |
| | | | 245 | | | | | 250 | | | | | 255 | | |

| Asn | Asp | Met | Ile | Met | Pro | Gly | Lys | Ala | Tyr | Gln | Val | Asn | Thr | Glu | Arg |
| | | | 260 | | | | | 265 | | | | | 270 | | |

| Arg | Asp | Glu | Ile | Glu | Glu | Ile | Met | Glu | Ala | Leu | Lys | Glu | Gly | Lys | Leu |
| | 275 | | | | | 280 | | | | | 285 | | | | |

| Ser | Glu | Glu | Val | Leu | Asp | Glu | Cys | Val | Arg | Asn | Ile | Leu | Lys | Val | Leu |
| | 290 | | | | | 295 | | | | | 300 | | | | |

| Val | Asn | Ala | Pro | Ser | Phe | Lys | Gly | Tyr | Arg | Tyr | Ser | Asn | Lys | Pro | Asp |
| 305 | | | | | 310 | | | | | 315 | | | | | 320 |

| Leu | Glu | Ser | His | Ala | Glu | Val | Ala | Tyr | Glu | Ala | Gly | Ala | Glu | Gly | Val |
| | | | | 325 | | | | | 330 | | | | | 335 | |

| Val | Leu | Leu | Glu | Asn | Asn | Gly | Val | Leu | Pro | Phe | Asp | Glu | Asn | Thr | His |
| | | | 340 | | | | | 345 | | | | | 350 | | |

| Val | Ala | Val | Phe | Gly | Thr | Gly | Gln | Ile | Glu | Thr | Ile | Lys | Gly | Gly | Thr |
| | | | 355 | | | | | 360 | | | | | 365 | | |

| Gly | Ser | Gly | Asp | Thr | His | Pro | Arg | Tyr | Thr | Ile | Ser | Ile | Leu | Glu | Gly |
| | 370 | | | | | 375 | | | | | 380 | | | | |

```
Ile Lys Glu Arg Asn Met Lys Phe Asp Glu Glu Leu Ala Ser Thr Tyr
385                 390                 395                 400

Glu Glu Tyr Ile Lys Lys Met Arg Glu Thr Glu Tyr Lys Pro Arg
            405                 410                 415

Thr Asp Ser Trp Gly Thr Val Ile Lys Pro Lys Leu Pro Glu Asn Phe
                420                 425                 430

Leu Ser Glu Lys Glu Ile Lys Lys Pro Pro Lys Lys Asn Asp Val Ala
            435                 440                 445

Val Val Val Ile Ser Arg Ile Ser Gly Glu Gly Tyr Asp Arg Lys Pro
450                 455                 460

Val Lys Gly Asp Phe Tyr Leu Ser Asp Asp Glu Leu Glu Leu Ile Lys
465                 470                 475                 480

Thr Val Ser Lys Glu Phe His Asp Gln Gly Lys Lys Val Val Val Leu
                485                 490                 495

Leu Asn Ile Gly Ser Pro Ile Glu Val Ala Ser Trp Arg Asp Leu Val
            500                 505                 510

Asp Gly Ile Leu Leu Val Trp Gln Ala Gly Gln Glu Met Gly Arg Ile
        515                 520                 525

Val Ala Asp Val Leu Val Gly Lys Ile Asn Pro Ser Gly Lys Leu Pro
530                 535                 540

Thr Thr Phe Pro Lys Asp Tyr Ser Asp Val Pro Ser Trp Thr Phe Pro
545                 550                 555                 560

Gly Glu Pro Lys Asp Asn Pro Gln Arg Val Val Tyr Glu Glu Asp Ile
                565                 570                 575

Tyr Val Gly Tyr Arg Tyr Tyr Asp Thr Phe Gly Val Glu Pro Ala Tyr
            580                 585                 590

Glu Phe Gly Tyr Gly Leu Ser Tyr Thr Lys Phe Glu Tyr Lys Asp Leu
        595                 600                 605

Lys Ile Ala Ile Asp Gly Glu Thr Leu Arg Val Ser Tyr Thr Ile Thr
610                 615                 620

Asn Thr Gly Asp Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
            645                 650                 655

His Lys Thr Lys Leu Leu Asn Pro Gly Glu Ser Glu Glu Ile Ser Leu
        660                 665                 670

Glu Ile Pro Leu Arg Asp Leu Ala Ser Phe Asp Gly Lys Glu Trp Val
    675                 680                 685

Val Glu Ser Gly Glu Tyr Glu Val Arg Val Gly Ala Ser Ser Arg Asp
690                 695                 700

Ile Arg Leu Arg Asp Ile Phe Leu Val Glu Gly Lys Arg Phe Lys
705                 710                 715                 720

Pro

<210> SEQ ID NO 20
<211> LENGTH: 454
<212> TYPE: PRT
<213> ORGANISM: Thermococcus alcaliphilus

<400> SEQUENCE: 20

Met Ile His Cys Pro Val Lys Gly Ile Ile Ser Glu Ala Arg Gly Ile
1               5                   10                  15

Thr Ile Thr Ile Asp Leu Ser Phe Gln Gly Gln Ile Asn Asn Leu Val
                20                  25                  30
```

-continued

```
Asn Ala Met Ile Val Phe Pro Glu Phe Phe Leu Phe Gly Thr Ala Thr
     35                  40                  45

Ser Ser His Gln Ile Glu Gly Asp Asn Lys Trp Asn Asp Trp Trp Tyr
     50                  55                  60

Tyr Glu Glu Ile Gly Lys Leu Pro Tyr Lys Ser Gly Lys Ala Cys Asn
 65                  70                  75                  80

His Trp Glu Leu Tyr Arg Glu Asp Ile Glu Leu Met Ala Gln Leu Gly
                 85                  90                  95

Tyr Asn Ala Tyr Arg Phe Ser Ile Glu Trp Ser Arg Leu Phe Pro Glu
                100                 105                 110

Glu Gly Lys Phe Asn Glu Glu Ala Phe Asn Arg Tyr Arg Glu Ile Ile
            115                 120                 125

Glu Ile Leu Leu Glu Lys Gly Ile Thr Pro Asn Val Thr Leu His His
130                 135                 140

Phe Thr Ser Pro Leu Trp Phe Met Arg Lys Gly Gly Phe Leu Lys Glu
145                 150                 155                 160

Glu Asn Leu Lys Tyr Trp Glu Gln Tyr Val Asp Lys Ala Ala Glu Leu
                165                 170                 175

Leu Lys Gly Val Lys Leu Val Ala Thr Phe Asn Glu Pro Met Val Tyr
            180                 185                 190

Val Met Met Gly Tyr Leu Thr Ala Tyr Trp Pro Pro Phe Ile Lys Ser
            195                 200                 205

Pro Phe Lys Ala Phe Lys Val Ala Ala Asn Leu Leu Lys Ala His Ala
            210                 215                 220

Met Ala Tyr Asp Ile Leu His Gly Asn Phe Asp Val Gly Ile Val Lys
225                 230                 235                 240

Asn Ile Pro Ile Met Leu Pro Ala Ser Asn Arg Glu Lys Asp Val Glu
                245                 250                 255

Ala Ala Gln Lys Ala Asp Asn Leu Phe Asn Trp Asn Phe Leu Asp Ala
            260                 265                 270

Ile Trp Ser Gly Lys Tyr Lys Gly Ala Phe Gly Thr Tyr Lys Thr Pro
            275                 280                 285

Glu Ser Asp Ala Asp Phe Ile Gly Ile Asn Tyr Tyr Thr Ala Ser Glu
            290                 295                 300

Val Arg His Ser Trp Asn Pro Leu Lys Phe Phe Phe Asp Ala Lys Leu
305                 310                 315                 320

Ala Asp Leu Ser Glu Arg Lys Thr Asp Met Gly Trp Ser Val Tyr Pro
                325                 330                 335

Lys Gly Ile Tyr Glu Ala Ile Ala Lys Val Ser His Tyr Gly Lys Pro
            340                 345                 350

Met Tyr Ile Thr Glu Asn Gly Ile Ala Thr Leu Asp Asp Glu Trp Arg
            355                 360                 365

Ile Glu Phe Ile Ile Gln His Leu Gln Tyr Val His Lys Ala Leu Asn
370                 375                 380

Asp Gly Phe Asp Leu Arg Gly Tyr Phe Tyr Trp Ser Phe Met Asp Asn
385                 390                 395                 400

Phe Glu Trp Ala Glu Gly Phe Arg Pro Arg Phe Gly Leu Val Glu Val
                405                 410                 415

Asp Tyr Thr Thr Phe Lys Arg Arg Pro Arg Lys Ser Ala Tyr Ile Tyr
            420                 425                 430

Gly Glu Ile Ala Arg Glu Lys Lys Ile Lys Asp Glu Leu Leu Ala Lys
            435                 440                 445

Tyr Gly Leu Pro Glu Leu
```

<210> SEQ ID NO 21
<211> LENGTH: 511
<212> TYPE: PRT
<213> ORGANISM: Thermococcus chitonophagus

<400> SEQUENCE: 21

| | | | | | | | | | | | | | | |
|---|---|---|---|---|---|---|---|---|---|---|---|---|---|---|
| Leu | Leu | Pro | Glu | Asn | Phe | Leu | Trp | Gly | Val | Ser | Gln | Ser | Gly | Phe | Gln |
| 1 | | | | 5 | | | | | 10 | | | | | 15 | |
| Phe | Glu | Met | Gly | Asp | Arg | Leu | Arg | Arg | His | Ile | Asp | Pro | Asn | Thr | Asp |
| | | | 20 | | | | | 25 | | | | | 30 | | |
| Trp | Trp | Tyr | Trp | Val | Arg | Asp | Glu | Tyr | Asn | Ile | Lys | Lys | Gly | Leu | Val |
| | | | 35 | | | | | 40 | | | | | 45 | | |
| Ser | Gly | Asp | Leu | Pro | Glu | Asp | Gly | Ile | Asn | Ser | Tyr | Glu | Leu | Tyr | Glu |
| | 50 | | | | | 55 | | | | | 60 | | | | |
| Arg | Asp | Gln | Glu | Ile | Ala | Lys | Asp | Leu | Gly | Leu | Asn | Thr | Tyr | Arg | Ile |
| 65 | | | | | 70 | | | | | 75 | | | | | 80 |
| Gly | Ile | Glu | Trp | Ser | Arg | Val | Phe | Pro | Trp | Pro | Thr | Thr | Phe | Val | Asp |
| | | | | 85 | | | | | 90 | | | | | 95 | |
| Val | Glu | Tyr | Glu | Ile | Asp | Glu | Ser | Tyr | Gly | Leu | Val | Lys | Asp | Val | Lys |
| | | | | 100 | | | | | 105 | | | | | 110 | |
| Ile | Ser | Lys | Asp | Ala | Leu | Glu | Lys | Leu | Asp | Glu | Ile | Ala | Asn | Gln | Arg |
| | | | 115 | | | | | 120 | | | | | 125 | | |
| Glu | Ile | Ile | Tyr | Tyr | Arg | Asn | Leu | Ile | Asn | Ser | Leu | Arg | Lys | Arg | Gly |
| | 130 | | | | | 135 | | | | | 140 | | | | |
| Phe | Lys | Val | Ile | Leu | Asn | Leu | Asn | His | Phe | Thr | Leu | Pro | Ile | Trp | Leu |
| 145 | | | | | 150 | | | | | 155 | | | | | 160 |
| His | Asp | Pro | Ile | Glu | Ser | Arg | Glu | Lys | Ala | Leu | Thr | Asn | Lys | Arg | Asn |
| | | | | 165 | | | | | 170 | | | | | 175 | |
| Gly | Trp | Val | Ser | Glu | Arg | Ser | Val | Ile | Glu | Phe | Ala | Lys | Phe | Ala | Ala |
| | | | 180 | | | | | 185 | | | | | 190 | | |
| Tyr | Leu | Ala | Tyr | Lys | Phe | Gly | Asp | Ile | Val | Asp | Met | Trp | Ser | Thr | Phe |
| | 195 | | | | | 200 | | | | | 205 | | | | |
| Asn | Glu | Pro | Met | Val | Val | Ala | Glu | Leu | Gly | Tyr | Leu | Ala | Pro | Tyr | Ser |
| 210 | | | | | 215 | | | | | 220 | | | | | |
| Gly | Phe | Pro | Pro | Gly | Val | Met | Asn | Pro | Glu | Ala | Ala | Lys | Leu | Val | Met |
| 225 | | | | | 230 | | | | | 235 | | | | | 240 |
| Leu | His | Met | Ile | Asn | Ala | His | Ala | Leu | Ala | Tyr | Arg | Met | Ile | Lys | Lys |
| | | | | 245 | | | | | 250 | | | | | 255 | |
| Phe | Asp | Arg | Lys | Lys | Ala | Asp | Pro | Glu | Ser | Lys | Glu | Pro | Ala | Glu | Ile |
| | | | 260 | | | | | 265 | | | | | 270 | | |
| Gly | Ile | Ile | Tyr | Asn | Asn | Ile | Gly | Val | Thr | Tyr | Pro | Phe | Asn | Pro | Lys |
| | 275 | | | | | 280 | | | | | 285 | | | | |
| Asp | Ser | Lys | Asp | Leu | Gln | Ala | Ser | Asp | Asn | Ala | Asn | Phe | Phe | His | Ser |
| | 290 | | | | | 295 | | | | | 300 | | | | |
| Gly | Leu | Phe | Leu | Thr | Ala | Ile | His | Arg | Gly | Lys | Leu | Asn | Ile | Glu | Phe |
| 305 | | | | | 310 | | | | | 315 | | | | | 320 |
| Asp | Gly | Glu | Thr | Phe | Val | Tyr | Leu | Pro | Tyr | Leu | Lys | Gly | Asn | Asp | Trp |
| | | | | 325 | | | | | 330 | | | | | 335 | |
| Leu | Gly | Val | Asn | Tyr | Tyr | Thr | Arg | Glu | Val | Val | Lys | Tyr | Gln | Asp | Pro |
| | | | 340 | | | | | 345 | | | | | 350 | | |
| Met | Phe | Pro | Ser | Ile | Pro | Leu | Ile | Ser | Phe | Lys | Gly | Val | Pro | Asp | Tyr |
| | | | 355 | | | | | 360 | | | | | 365 | | |

```
Gly Tyr Gly Cys Arg Pro Gly Thr Thr Ser Lys Asp Gly Asn Pro Val
    370                 375                 380

Ser Asp Ile Gly Trp Glu Val Tyr Pro Lys Gly Met Tyr Asp Ser Ile
385                 390                 395                 400

Val Ala Ala Asn Glu Tyr Gly Val Pro Tyr Val Thr Glu Asn Gly
                405                 410                 415

Ile Ala Asp Ser Lys Asp Val Leu Arg Pro Tyr Tyr Ile Ala Ser His
            420                 425                 430

Ile Glu Ala Met Glu Glu Ala Tyr Glu Asn Gly Tyr Asp Val Arg Gly
            435                 440                 445

Tyr Leu His Trp Ala Leu Thr Asp Asn Tyr Glu Trp Ala Leu Gly Phe
    450                 455                 460

Arg Met Arg Phe Gly Leu Tyr Glu Val Asn Leu Ile Thr Lys Glu Arg
465                 470                 475                 480

Lys Pro Arg Lys Lys Ser Val Arg Val Phe Arg Glu Ile Val Ile Asn
                485                 490                 495

Asn Gly Leu Thr Ser Asn Ile Arg Lys Glu Ile Leu Glu Glu Gly
            500                 505                 510

<210> SEQ ID NO 22
<211> LENGTH: 510
<212> TYPE: PRT
<213> ORGANISM: Pyrococcus furiosus

<400> SEQUENCE: 22

Met Phe Pro Glu Lys Phe Leu Trp Gly Val Ala Gln Ser Gly Phe Gln
1               5                   10                  15

Phe Glu Met Gly Asp Lys Leu Arg Arg Asn Ile Asp Thr Asn Thr Asp
                20                  25                  30

Trp Trp His Trp Val Arg Asp Lys Thr Asn Ile Glu Lys Gly Leu Val
            35                  40                  45

Ser Gly Asp Leu Pro Glu Glu Gly Ile Asn Asn Tyr Glu Leu Tyr Glu
    50                  55                  60

Lys Asp His Glu Ile Ala Arg Lys Leu Gly Leu Asn Ala Tyr Arg Ile
65                  70                  75                  80

Gly Ile Glu Trp Ser Arg Ile Phe Pro Trp Pro Thr Thr Phe Ile Asp
                85                  90                  95

Val Asp Tyr Ser Tyr Asn Glu Ser Tyr Asn Leu Ile Glu Asp Val Lys
                100                 105                 110

Ile Thr Lys Asp Thr Leu Glu Glu Leu Asp Glu Ile Ala Asn Lys Arg
            115                 120                 125

Glu Val Ala Tyr Tyr Arg Ser Val Ile Asn Ser Leu Arg Ser Lys Gly
    130                 135                 140

Phe Lys Val Ile Val Asn Leu Asn His Phe Thr Leu Pro Tyr Trp Leu
145                 150                 155                 160

His Asp Pro Ile Glu Ala Arg Glu Arg Ala Leu Thr Asn Lys Arg Asn
                165                 170                 175

Gly Trp Val Asn Pro Arg Thr Val Ile Glu Phe Ala Lys Tyr Ala Ala
            180                 185                 190

Tyr Ile Ala Tyr Lys Phe Gly Asp Ile Val Asp Met Trp Ser Thr Phe
    195                 200                 205

Asn Glu Pro Met Val Val Glu Leu Gly Tyr Leu Ala Pro Tyr Ser
210                 215                 220

Gly Phe Pro Pro Gly Val Leu Asn Pro Glu Ala Ala Lys Leu Ala Ile
225                 230                 235                 240
```

```
Leu His Met Ile Asn Ala His Ala Leu Ala Tyr Arg Gln Ile Lys Lys
                245                 250                 255

Phe Asp Thr Glu Lys Ala Asp Lys Asp Ser Lys Glu Pro Ala Glu Val
            260                 265                 270

Gly Ile Ile Tyr Asn Asn Ile Gly Val Ala Tyr Pro Lys Asp Pro Asn
        275                 280                 285

Asp Ser Lys Asp Val Lys Ala Ala Glu Asn Asp Asn Phe Phe His Ser
    290                 295                 300

Gly Leu Phe Phe Glu Ala Ile His Lys Gly Lys Leu Asn Ile Glu Phe
305                 310                 315                 320

Asp Gly Glu Thr Phe Ile Asp Ala Pro Tyr Leu Lys Gly Asn Asp Trp
                325                 330                 335

Ile Gly Val Asn Tyr Tyr Thr Arg Glu Val Val Thr Tyr Gln Glu Pro
            340                 345                 350

Met Phe Pro Ser Ile Pro Leu Ile Thr Phe Lys Gly Val Gln Gly Tyr
        355                 360                 365

Gly Tyr Ala Cys Arg Pro Gly Thr Leu Ser Lys Asp Asp Arg Pro Val
    370                 375                 380

Ser Asp Ile Gly Trp Glu Leu Tyr Pro Glu Gly Met Tyr Asp Ser Ile
385                 390                 395                 400

Val Glu Ala His Lys Tyr Gly Val Pro Val Tyr Val Thr Glu Asn Gly
                405                 410                 415

Ile Ala Asp Ser Lys Asp Ile Leu Arg Pro Tyr Tyr Ile Ala Ser His
            420                 425                 430

Ile Lys Met Ile Glu Lys Ala Phe Glu Asp Gly Tyr Glu Val Lys Gly
        435                 440                 445

Tyr Phe His Trp Ala Leu Thr Asp Asn Phe Glu Trp Ala Leu Gly Phe
    450                 455                 460

Arg Met Arg Phe Gly Leu Tyr Glu Val Asn Leu Ile Thr Lys Glu Arg
465                 470                 475                 480

Ile Pro Arg Glu Lys Ser Val Ser Ile Phe Arg Glu Ile Val Ala Asn
                485                 490                 495

Asn Gly Val Thr Lys Lys Ile Glu Glu Glu Leu Leu Arg Gly
            500                 505                 510

<210> SEQ ID NO 23
<211> LENGTH: 537
<212> TYPE: PRT
<213> ORGANISM: Bankia gouldi

<400> SEQUENCE: 23

Met Arg Ile Arg Leu Ala Thr Leu Ala Leu Cys Ala Ala Leu Ser Pro
1               5                   10                  15

Val Thr Phe Ala Asp Asn Val Thr Val Gln Ile Asp Ala Asp Gly Gly
            20                  25                  30

Lys Lys Leu Ile Ser Arg Ala Leu Tyr Gly Met Asn Asn Ser Asn Ala
        35                  40                  45

Glu Ser Leu Thr Asp Thr Asp Trp Gln Arg Phe Arg Asp Ala Gly Val
    50                  55                  60

Arg Met Leu Arg Glu Asn Gly Asn Asn Ser Thr Lys Tyr Asn Trp
65                  70                  75                  80

Gln Leu His Leu Ser Ser His Pro Asp Trp Tyr Asn Asn Val Tyr Ala
                85                  90                  95

Gly Asn Asn Asn Trp Asp Asn Arg Val Ala Leu Ile Gln Glu Asn Leu
```

-continued

```
            100                 105                 110
Pro Gly Ala Asp Thr Met Trp Ala Phe Gln Leu Ile Gly Lys Val Ala
        115                 120                 125

Ala Thr Ser Ala Tyr Asn Phe Asn Asp Trp Glu Phe Asn Gln Ser Gln
        130                 135                 140

Trp Trp Thr Gly Val Ala Gln Asn Leu Ala Gly Gly Glu Pro Asn
145                 150                 155                 160

Leu Asp Gly Gly Gly Glu Ala Leu Val Glu Gly Asp Pro Asn Leu Tyr
                165                 170                 175

Leu Met Asp Trp Ser Pro Ala Asp Thr Val Gly Ile Leu Asp His Trp
            180                 185                 190

Phe Gly Val Asn Gly Leu Gly Val Arg Arg Gly Lys Ala Lys Tyr Trp
                195                 200                 205

Ser Met Asp Asn Glu Pro Gly Ile Trp Val Gly Thr His Asp Asp Val
        210                 215                 220

Val Lys Glu Gln Thr Pro Val Glu Asp Phe Leu His Thr Tyr Phe Glu
225                 230                 235                 240

Thr Ala Lys Lys Ala Arg Ala Lys Phe Pro Gly Ile Lys Ile Thr Gly
                245                 250                 255

Pro Val Pro Ala Asn Glu Trp Gln Trp Tyr Ala Trp Gly Gly Phe Ser
            260                 265                 270

Val Pro Gln Glu Gln Gly Phe Met Ser Trp Met Glu Tyr Phe Ile Lys
            275                 280                 285

Arg Val Ser Glu Glu Gln Arg Ala Ser Gly Val Arg Leu Leu Asp Val
        290                 295                 300

Leu Asp Leu His Tyr Tyr Pro Gly Ala Tyr Asn Ala Glu Asp Ile Val
305                 310                 315                 320

Gln Leu His Arg Thr Phe Phe Asp Arg Asp Phe Val Ser Leu Asp Ala
                325                 330                 335

Asn Gly Val Lys Met Val Glu Gly Gly Trp Asp Ser Ile Asn Lys
            340                 345                 350

Glu Tyr Ile Phe Gly Arg Val Asn Asp Trp Leu Glu Glu Tyr Met Gly
        355                 360                 365

Pro Asp His Gly Val Thr Leu Gly Leu Thr Glu Met Cys Val Arg Asn
370                 375                 380

Val Asn Pro Met Thr Thr Ala Ile Trp Tyr Ala Ser Met Leu Gly Thr
385                 390                 395                 400

Phe Ala Asp Asn Gly Val Glu Ile Phe Thr Pro Trp Cys Trp Asn Thr
                405                 410                 415

Gly Met Trp Glu Thr Leu His Leu Phe Ser Arg Tyr Asn Lys Pro Tyr
            420                 425                 430

Arg Val Ala Ser Ser Ser Leu Glu Glu Phe Val Ser Ala Tyr Ser
        435                 440                 445

Ser Ile Asn Glu Ala Glu Asp Ala Met Thr Val Leu Leu Val Asn Arg
        450                 455                 460

Ser Thr Ser Glu Thr His Thr Ala Thr Val Ala Ile Asp Asp Phe Pro
465                 470                 475                 480

Leu Asp Gly Pro Tyr Arg Thr Leu Arg Leu His Asn Leu Pro Gly Glu
                485                 490                 495

Glu Thr Phe Val Ser His Arg Asp Asn Ala Leu Glu Lys Gly Thr Val
            500                 505                 510

Arg Ala Ser Asp Asn Thr Val Thr Leu Glu Leu Pro Pro Leu Ser Val
        515                 520                 525
```

Thr Ala Ile Leu Leu Lys Ala Arg Pro
    530                 535

<210> SEQ ID NO 24
<211> LENGTH: 555
<212> TYPE: PRT
<213> ORGANISM: Thermotoga maritima

<400> SEQUENCE: 24

Val Ile Cys Val Glu Ile Phe Gly Lys Thr Phe Arg Glu Gly Arg Phe
  1               5                  10                  15

Val Leu Lys Glu Lys Asn Phe Thr Val Glu Phe Ala Val Glu Lys Ile
             20                  25                  30

His Leu Gly Trp Lys Ile Ser Gly Arg Val Lys Gly Ser Pro Gly Arg
         35                  40                  45

Leu Glu Val Leu Arg Thr Lys Ala Pro Glu Lys Val Leu Val Asn Asn
     50                  55                  60

Trp Gln Ser Trp Gly Pro Cys Arg Val Val Asp Ala Phe Ser Phe Lys
 65                  70                  75                  80

Pro Pro Glu Ile Asp Pro Asn Trp Arg Tyr Thr Ala Ser Val Val Pro
                 85                  90                  95

Asp Val Leu Glu Arg Asn Leu Gln Ser Asp Tyr Phe Val Ala Glu Glu
            100                 105                 110

Gly Lys Val Tyr Gly Phe Leu Ser Ser Lys Ile Ala His Pro Phe Phe
        115                 120                 125

Ala Val Glu Asp Gly Glu Leu Val Ala Tyr Leu Glu Tyr Phe Asp Val
    130                 135                 140

Glu Phe Asp Asp Phe Val Pro Leu Glu Pro Leu Val Val Leu Glu Asp
145                 150                 155                 160

Pro Asn Thr Pro Leu Leu Leu Glu Lys Tyr Ala Glu Leu Val Gly Met
                165                 170                 175

Glu Asn Asn Ala Arg Val Pro Lys His Thr Pro Thr Gly Trp Cys Ser
            180                 185                 190

Trp Tyr His Tyr Phe Leu Asp Leu Thr Trp Glu Glu Thr Leu Lys Asn
        195                 200                 205

Leu Lys Leu Ala Lys Asn Phe Pro Phe Glu Val Phe Gln Ile Asp Asp
    210                 215                 220

Ala Tyr Glu Lys Asp Ile Gly Asp Trp Leu Val Thr Arg Gly Asp Phe
225                 230                 235                 240

Pro Ser Val Glu Glu Met Ala Lys Val Ile Ala Glu Asn Gly Phe Ile
                245                 250                 255

Pro Gly Ile Trp Thr Ala Pro Phe Ser Val Ser Glu Thr Ser Asp Val
            260                 265                 270

Phe Asn Glu His Pro Asp Trp Val Lys Glu Asn Gly Glu Pro Lys
        275                 280                 285

Met Ala Tyr Arg Asn Trp Asn Lys Lys Ile Tyr Ala Leu Asp Leu Ser
    290                 295                 300

Lys Asp Glu Val Leu Asn Trp Leu Phe Asp Leu Phe Ser Ser Leu Arg
305                 310                 315                 320

Lys Met Gly Tyr Arg Tyr Phe Lys Ile Asp Phe Leu Phe Ala Gly Ala
                325                 330                 335

Val Pro Gly Glu Arg Lys Lys Asn Ile Thr Pro Ile Gln Ala Phe Arg
            340                 345                 350

Lys Gly Ile Glu Thr Ile Arg Lys Ala Val Gly Glu Asp Ser Phe Ile

-continued

```
                355                 360                 365
Leu Gly Cys Gly Ser Pro Leu Leu Pro Ala Val Gly Cys Val Asp Gly
        370                 375                 380

Met Arg Ile Gly Pro Asp Thr Ala Pro Phe Trp Gly Glu His Ile Glu
385                 390                 395                 400

Asp Asn Gly Ala Pro Ala Ala Arg Trp Ala Leu Arg Asn Ala Ile Thr
                405                 410                 415

Arg Tyr Phe Met His Asp Arg Phe Trp Leu Asn Asp Pro Asp Cys Leu
                420                 425                 430

Ile Leu Arg Glu Glu Lys Thr Asp Leu Thr Gln Lys Glu Lys Glu Leu
            435                 440                 445

Tyr Ser Tyr Thr Cys Gly Val Leu Asp Asn Met Ile Ile Glu Ser Asp
450                 455                 460

Asp Leu Ser Leu Val Arg Asp His Gly Lys Lys Val Leu Lys Glu Thr
465                 470                 475                 480

Leu Glu Leu Leu Gly Gly Arg Pro Arg Val Gln Asn Ile Met Ser Glu
                485                 490                 495

Asp Leu Arg Tyr Glu Ile Val Ser Ser Gly Thr Leu Ser Gly Asn Val
            500                 505                 510

Lys Ile Val Val Asp Leu Asn Ser Arg Glu Tyr His Leu Glu Lys Glu
            515                 520                 525

Gly Lys Ser Ser Leu Lys Lys Arg Val Val Lys Arg Glu Asp Gly Arg
        530                 535                 540

Asn Phe Tyr Phe Tyr Glu Glu Gly Glu Arg Glu
545                 550                 555

<210> SEQ ID NO 25
<211> LENGTH: 680
<212> TYPE: PRT
<213> ORGANISM: Thermotoga maritima

<400> SEQUENCE: 25

Met Gly Ile Gly Gly Asp Asp Ser Trp Ser Pro Ser Val Ser Ala Glu
1               5                   10                  15

Phe Leu Leu Leu Ile Val Glu Leu Ser Phe Val Leu Phe Ala Ser Asp
                20                  25                  30

Glu Phe Val Lys Val Glu Asn Gly Lys Phe Ala Leu Asn Gly Lys Glu
            35                  40                  45

Phe Arg Phe Ile Gly Ser Asn Asn Tyr Tyr Met His Tyr Lys Ser Asn
    50                  55                  60

Gly Met Ile Asp Ser Val Leu Glu Ser Ala Arg Asp Met Gly Ile Lys
65                  70                  75                  80

Val Leu Arg Ile Trp Gly Phe Leu Asp Gly Glu Ser Tyr Cys Arg Asp
                85                  90                  95

Lys Asn Thr Tyr Met His Pro Glu Pro Gly Val Phe Gly Val Pro Glu
            100                 105                 110

Gly Ile Ser Asn Ala Gln Ser Gly Phe Glu Arg Leu Asp Tyr Thr Val
        115                 120                 125

Ala Lys Ala Lys Glu Leu Gly Ile Lys Leu Val Ile Leu Val Asn
    130                 135                 140

Asn Trp Asp Asp Phe Gly Gly Met Asn Gln Tyr Val Arg Trp Phe Gly
145                 150                 155                 160

Gly Thr His His Asp Asp Phe Tyr Arg Asp Glu Lys Ile Lys Glu Glu
                165                 170                 175
```

```
Tyr Lys Lys Tyr Val Ser Phe Leu Val Asn His Val Asn Thr Tyr Thr
            180             185             190
Gly Val Pro Tyr Arg Glu Glu Pro Thr Ile Met Ala Trp Glu Leu Ala
        195             200             205
Asn Glu Pro Arg Cys Glu Thr Asp Lys Ser Gly Asn Thr Leu Val Glu
    210             215             220
Trp Val Lys Glu Met Ser Ser Tyr Ile Lys Ser Leu Asp Pro Asn His
225             230             235             240
Leu Val Ala Val Gly Asp Glu Gly Phe Phe Ser Asn Tyr Glu Gly Phe
            245             250             255
Lys Pro Tyr Gly Gly Glu Ala Glu Trp Ala Tyr Asn Gly Trp Ser Gly
        260             265             270
Val Asp Trp Lys Lys Leu Leu Ser Ile Glu Thr Val Asp Phe Gly Thr
    275             280             285
Phe His Leu Tyr Pro Ser His Trp Gly Val Ser Pro Glu Asn Tyr Ala
    290             295             300
Gln Trp Gly Ala Lys Trp Ile Glu Asp His Ile Lys Ile Ala Lys Glu
305             310             315             320
Ile Gly Lys Pro Val Val Leu Glu Glu Tyr Gly Ile Pro Lys Ser Ala
            325             330             335
Pro Val Asn Arg Thr Ala Ile Tyr Arg Leu Trp Asn Asp Leu Val Tyr
        340             345             350
Asp Leu Gly Gly Asp Gly Ala Met Phe Trp Met Leu Ala Gly Ile Gly
        355             360             365
Glu Gly Ser Asp Arg Asp Glu Arg Gly Tyr Tyr Pro Asp Tyr Asp Gly
    370             375             380
Phe Arg Ile Val Asn Asp Asp Ser Pro Glu Ala Glu Leu Ile Arg Glu
385             390             395             400
Tyr Ala Lys Leu Phe Asn Thr Gly Glu Asp Ile Arg Glu Asp Thr Cys
            405             410             415
Ser Phe Ile Leu Pro Lys Asp Gly Met Glu Ile Lys Lys Thr Val Glu
        420             425             430
Val Arg Ala Gly Val Phe Asp Tyr Ser Asn Thr Phe Glu Lys Leu Ser
        435             440             445
Val Lys Val Glu Asp Leu Val Phe Glu Asn Glu Ile Glu His Leu Gly
    450             455             460
Tyr Gly Ile Tyr Gly Phe Asp Leu Asp Thr Thr Arg Ile Pro Asp Gly
465             470             475             480
Glu His Glu Met Phe Leu Glu Gly His Phe Gln Gly Lys Thr Val Lys
            485             490             495
Asp Ser Ile Lys Ala Lys Val Val Asn Glu Ala Arg Tyr Val Leu Ala
        500             505             510
Glu Glu Val Asp Phe Ser Ser Pro Glu Glu Val Lys Asn Trp Trp Asn
    515             520             525
Ser Gly Thr Trp Gln Ala Glu Phe Gly Ser Pro Asp Ile Glu Trp Asn
530             535             540
Gly Glu Val Gly Asn Gly Ala Leu Gln Leu Asn Val Lys Leu Pro Gly
545             550             555             560
Lys Ser Asp Trp Glu Glu Val Arg Val Ala Arg Lys Phe Glu Arg Leu
            565             570             575
Ser Glu Cys Glu Ile Leu Glu Tyr Asp Ile Tyr Ile Pro Asn Val Glu
        580             585             590
Gly Leu Lys Gly Arg Leu Arg Pro Tyr Ala Val Leu Asn Pro Gly Trp
```

```
                595                 600                 605
Val Lys Ile Gly Leu Asp Met Asn Asn Ala Asn Val Glu Ser Ala Glu
        610                 615                 620

Ile Ile Thr Phe Gly Gly Lys Glu Tyr Arg Arg Phe His Val Arg Ile
625                 630                 635                 640

Glu Phe Asp Arg Thr Ala Gly Val Lys Glu Leu His Ile Gly Val Val
                645                 650                 655

Gly Asp His Leu Arg Tyr Asp Gly Pro Ile Phe Ile Asp Asn Val Arg
                660                 665                 670

Leu Tyr Lys Arg Thr Gly Gly Met
            675                 680

<210> SEQ ID NO 26
<211> LENGTH: 512
<212> TYPE: PRT
<213> ORGANISM: Thermococcus chitonophagus

<400> SEQUENCE: 26

Met Leu Pro Glu Glu Phe Leu Trp Gly Val Gly Gln Ser Gly Phe Gln
1               5                   10                  15

Phe Glu Met Gly Asp Lys Leu Arg Arg His Ile Asp Pro Asn Thr Asp
                20                  25                  30

Trp Trp Lys Trp Val Arg Asp Pro Phe Asn Ile Lys Lys Glu Leu Val
            35                  40                  45

Ser Gly Asp Leu Pro Glu Asp Gly Ile Asn Asn Tyr Glu Leu Phe Glu
        50                  55                  60

Asn Asp His Lys Leu Ala Lys Gly Leu Gly Leu Asn Ala Tyr Arg Ile
65                  70                  75                  80

Gly Ile Glu Trp Ser Arg Ile Phe Pro Trp Pro Thr Trp Thr Val Asp
                85                  90                  95

Thr Glu Val Glu Phe Asp Thr Tyr Gly Leu Val Lys Asp Val Lys Ile
                100                 105                 110

Asp Lys Ser Thr Leu Ala Glu Leu Asp Arg Leu Ala Asn Lys Glu Glu
            115                 120                 125

Val Met Tyr Tyr Arg Arg Val Ile Gln His Leu Arg Glu Leu Gly Phe
130                 135                 140

Lys Val Phe Val Asn Leu Asn His Phe Thr Leu Pro Ile Trp Leu His
145                 150                 155                 160

Asp Pro Ile Val Ala Arg Glu Lys Ala Leu Thr Asn Asp Arg Ile Gly
                165                 170                 175

Trp Val Ser Gln Arg Thr Val Val Glu Phe Ala Lys Tyr Ala Ala Tyr
            180                 185                 190

Ile Ala His Ala Leu Gly Asp Leu Val Asp Thr Trp Ser Thr Phe Asn
        195                 200                 205

Glu Pro Met Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Arg Phe
                245                 250                 255

Asp Thr Lys Lys Ala Asp Glu Asp Ser Lys Ser Pro Ala Asp Val Gly
            260                 265                 270

Ile Ile Tyr Asn Asn Ile Gly Val Ala Tyr Pro Lys Asp Pro Asn Asp
        275                 280                 285
```

```
Pro Lys Asp Val Lys Ala Ala Glu Asn Asp Asn Tyr Phe His Ser Gly
        290                 295                 300

Leu Phe Phe Asp Ala Ile His Lys Gly Lys Leu Asn Ile Glu Phe Asp
305                 310                 315                 320

Gly Glu Asn Phe Val Lys Val Arg His Leu Lys Gly Asn Asp Trp Ile
                325                 330                 335

Gly Leu Asn Tyr Tyr Thr Arg Glu Val Val Arg Tyr Ser Glu Pro Lys
                340                 345                 350

Phe Pro Ser Ile Pro Leu Ile Ser Phe Lys Gly Val Pro Asn Tyr Gly
                355                 360                 365

Tyr Ser Cys Arg Pro Gly Thr Thr Ser Ala Asp Gly Met Pro Val Ser
        370                 375                 380

Asp Ile Gly Trp Glu Val Tyr Pro Gln Gly Ile Tyr Asp Ser Ile Val
385                 390                 395                 400

Glu Ala Thr Lys Tyr Ser Val Pro Val Tyr Val Thr Glu Asn Gly Val
                405                 410                 415

Ala Asp Ser Ala Asp Thr Leu Arg Pro Tyr Tyr Ile Val Ser His Val
                420                 425                 430

Ser Lys Ile Glu Glu Ala Ile Glu Asn Gly Tyr Pro Val Lys Gly Tyr
                435                 440                 445

Met Tyr Trp Ala Leu Thr Asp Asn Tyr Glu Trp Ala Leu Gly Phe Ser
450                 455                 460

Met Arg Phe Gly Leu Tyr Lys Val Asp Leu Ile Ser Lys Glu Arg Ile
465                 470                 475                 480

Pro Arg Glu Arg Ser Val Glu Ile Tyr Arg Arg Ile Val Gln Ser Asn
                485                 490                 495

Gly Val Pro Lys Asp Ile Lys Glu Glu Phe Leu Lys Gly Glu Glu Lys
                500                 505                 510

<210> SEQ ID NO 27
<211> LENGTH: 360
<212> TYPE: PRT
<213> ORGANISM: Thermotoga sp.

<400> SEQUENCE: 27

Met Val Glu Arg His Phe Arg Tyr Val Leu Ile Cys Thr Leu Phe Leu
1               5                   10                  15

Val Met Leu Leu Ile Ser Ser Thr Gln Cys Gly Lys Asn Glu Pro Asn
                20                  25                  30

Lys Arg Val Asn Ser Met Glu Gln Ser Val Ala Glu Ser Asp Ser Asn
            35                  40                  45

Ser Ala Phe Glu Tyr Asn Lys Met Val Gly Lys Gly Val Asn Ile Gly
        50                  55                  60

Asn Ala Leu Glu Ala Pro Phe Glu Gly Ala Trp Gly Val Arg Ile Glu
65                  70                  75                  80

Asp Glu Tyr Phe Glu Ile Ile Lys Lys Arg Gly Phe Asp Ser Val Arg
                85                  90                  95

Ile Pro Ile Arg Trp Ser Ala His Ile Ser Glu Lys Pro Pro Tyr Asp
                100                 105                 110

Ile Asp Arg Asn Phe Leu Glu Arg Val Asn His Val Asp Arg Ala
                115                 120                 125

Leu Glu Asn Asn Leu Thr Val Ile Ile Asn Thr His His Phe Glu Glu
            130                 135                 140

Leu Tyr Gln Glu Pro Asp Lys Tyr Gly Asp Val Leu Val Glu Ile Trp
145                 150                 155                 160
```

-continued

```
Arg Gln Ile Ala Lys Phe Phe Lys Asp Tyr Pro Glu Asn Leu Phe Phe
                165                 170                 175

Glu Ile Tyr Asn Glu Pro Ala Gln Asn Leu Thr Ala Glu Lys Trp Asn
            180                 185                 190

Ala Leu Tyr Pro Lys Val Leu Lys Val Ile Arg Glu Ser Asn Pro Thr
        195                 200                 205

Arg Ile Val Ile Asp Ala Pro Asn Trp Ala His Tyr Ser Ala Val
    210                 215                 220

Arg Ser Leu Lys Leu Val Asn Asp Lys Arg Ile Ile Val Ser Phe His
225                 230                 235                 240

Tyr Tyr Glu Pro Phe Lys Phe Thr His Gln Gly Ala Glu Trp Val Asn
                245                 250                 255

Pro Ile Pro Pro Val Arg Val Lys Trp Asn Gly Glu Glu Trp Glu Ile
            260                 265                 270

Asn Gln Ile Arg Ser His Phe Lys Tyr Val Ser Asp Trp Ala Lys Gln
        275                 280                 285

Asn Asn Val Pro Ile Phe Leu Gly Glu Phe Gly Ala Tyr Ser Lys Ala
    290                 295                 300

Asp Met Asp Ser Arg Val Lys Trp Thr Glu Ser Val Arg Lys Met Ala
305                 310                 315                 320

Glu Glu Phe Gly Phe Ser Tyr Ala Tyr Trp Glu Phe Cys Ala Gly Phe
                325                 330                 335

Gly Ile Tyr Asp Arg Trp Ser Gln Asn Trp Ile Glu Pro Leu Ala Thr
            340                 345                 350

Ala Val Val Gly Thr Gly Lys Glu
        355                 360

<210> SEQ ID NO 28
<211> LENGTH: 772
<212> TYPE: PRT
<213> ORGANISM: Thermotoga maritima

<400> SEQUENCE: 28

Met Asp Leu Thr Lys Val Gly Ile Ile Val Arg Leu Asn Glu Trp Gln
 1               5                  10                  15

Ala Lys Asp Val Ala Lys Asp Arg Phe Ile Glu Ile Lys Asp Gly Lys
            20                  25                  30

Ala Glu Val Trp Ile Leu Gln Gly Val Glu Glu Ile Phe Tyr Glu Lys
        35                  40                  45

Pro Asp Thr Ser Pro Arg Ile Phe Ala Gln Ala Arg Ser Asn Lys
    50                  55                  60

Val Ile Glu Ala Phe Leu Thr Asn Pro Val Asp Thr Lys Lys Lys Glu
65                  70                  75                  80

Leu Phe Lys Val Thr Val Asp Gly Lys Glu Ile Pro Val Ser Arg Val
                85                  90                  95

Glu Lys Ala Asp Pro Thr Asp Ile Asp Val Thr Asn Tyr Val Arg Ile
            100                 105                 110

Val Leu Ser Glu Ser Leu Lys Glu Asp Leu Arg Lys Asp Val Glu
        115                 120                 125

Leu Ile Ile Glu Gly Tyr Lys Pro Ala Arg Val Ile Met Met Glu Ile
    130                 135                 140

Leu Asp Asp Tyr Tyr Asp Gly Glu Leu Gly Ala Val Tyr Ser Pro
145                 150                 155                 160

Glu Lys Thr Ile Phe Arg Val Trp Ser Pro Val Ser Lys Trp Val Lys
```

-continued

```
                165                 170                 175
Val Leu Leu Phe Lys Asn Gly Glu Asp Thr Glu Pro Tyr Gln Val Val
                180                 185                 190
Asn Met Glu Tyr Lys Gly Asn Gly Val Trp Glu Ala Val Val Glu Gly
                195                 200                 205
Asp Leu Asp Gly Val Phe Tyr Leu Tyr Gln Leu Glu Asn Tyr Gly Lys
                210                 215                 220
Ile Arg Thr Thr Val Asp Pro Tyr Ser Lys Ala Val Tyr Ala Asn Ser
225                 230                 235                 240
Lys Lys Ser Ala Val Val Asn Leu Ala Arg Thr Asn Pro Glu Gly Trp
                245                 250                 255
Glu Asn Asp Arg Gly Pro Lys Ile Glu Gly Tyr Glu Asp Ala Ile Ile
                260                 265                 270
Tyr Glu Ile His Ile Ala Asp Ile Thr Gly Leu Glu Asn Ser Gly Val
                275                 280                 285
Lys Asn Lys Gly Leu Tyr Leu Gly Leu Thr Glu Glu Asn Thr Lys Gly
                290                 295                 300
Pro Gly Gly Val Thr Thr Gly Leu Ser His Leu Val Glu Leu Gly Val
305                 310                 315                 320
Thr His Val His Ile Leu Pro Phe Phe Asp Phe Tyr Thr Gly Asp Glu
                325                 330                 335
Leu Asp Lys Asp Phe Glu Lys Tyr Tyr Asn Trp Gly Tyr Asp Pro Tyr
                340                 345                 350
Leu Phe Met Val Pro Glu Gly Arg Tyr Ser Thr Asp Pro Lys Asn Pro
                355                 360                 365
His Thr Arg Ile Arg Glu Val Lys Glu Met Val Lys Ala Leu His Lys
                370                 375                 380
His Gly Ile Gly Val Ile Met Asp Met Val Phe Pro His Thr Tyr Gly
385                 390                 395                 400
Ile Gly Glu Leu Ser Ala Phe Asp Gln Thr Val Pro Tyr Tyr Phe Tyr
                405                 410                 415
Arg Ile Asp Lys Thr Gly Ala Tyr Leu Asn Glu Ser Gly Cys Gly Asn
                420                 425                 430
Val Ile Ala Ser Glu Arg Pro Met Met Arg Lys Phe Ile Val Asp Thr
                435                 440                 445
Val Thr Tyr Trp Val Lys Glu Tyr His Ile Asp Gly Phe Arg Phe Asp
                450                 455                 460
Gln Met Gly Leu Ile Asp Lys Lys Thr Met Leu Glu Val Glu Arg Ala
465                 470                 475                 480
Leu His Lys Ile Asp Pro Thr Ile Ile Leu Tyr Gly Glu Pro Trp Gly
                485                 490                 495
Gly Trp Gly Ala Pro Ile Arg Phe Gly Lys Ser Asp Val Ala Gly Thr
                500                 505                 510
His Val Ala Ala Phe Asn Asp Glu Phe Arg Asp Ala Ile Arg Gly Ser
                515                 520                 525
Val Phe Asn Pro Ser Val Lys Gly Phe Val Met Gly Gly Tyr Gly Lys
                530                 535                 540
Glu Thr Lys Ile Lys Arg Gly Val Val Gly Ser Ile Asn Tyr Asp Gly
545                 550                 555                 560
Lys Leu Ile Lys Ser Leu Ala Leu Asp Pro Glu Glu Thr Ile Asn Tyr
                565                 570                 575
Ala Ala Cys His Asp Asn His Thr Leu Trp Asp Lys Asn Tyr Leu Ala
                580                 585                 590
```

```
Ala Lys Ala Asp Lys Lys Glu Trp Thr Glu Glu Leu Lys Asn
        595                 600                 605

Ala Gln Lys Leu Ala Gly Ala Ile Leu Leu Thr Ser Gln Gly Val Pro
    610                 615                 620

Phe Leu His Gly Gly Gln Asp Phe Cys Arg Thr Lys Asn Phe Asn Asp
625                 630                 635                 640

Asn Ser Tyr Asn Ala Pro Ile Ser Ile Asn Gly Phe Asp Tyr Glu Arg
                645                 650                 655

Lys Leu Gln Phe Ile Asp Val Phe Asn Tyr His Lys Gly Leu Ile Lys
            660                 665                 670

Leu Arg Lys Glu His Pro Ala Phe Arg Leu Lys Asn Ala Glu Glu Ile
        675                 680                 685

Lys Lys His Leu Glu Phe Leu Pro Gly Gly Arg Arg Ile Val Ala Phe
    690                 695                 700

Met Leu Lys Asp His Ala Gly Gly Asp Pro Trp Lys Asp Ile Val Val
705                 710                 715                 720

Ile Tyr Asn Gly Asn Leu Glu Lys Thr Thr Tyr Lys Leu Pro Glu Gly
                725                 730                 735

Lys Trp Asn Val Val Asn Ser Gln Lys Ala Gly Thr Glu Val Ile
            740                 745                 750

Glu Thr Val Glu Gly Thr Ile Glu Leu Asp Pro Leu Ser Ala Tyr Val
        755                 760                 765

Leu Tyr Arg Glu
    770

<210> SEQ ID NO 29
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 29
ccgagaattc attaaagagg agaaattaac tatggtgaat gctatgattg tc         52

<210> SEQ ID NO 30
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 30
atacccgaag gcctcgatac ttctagaagg c                                31

<210> SEQ ID NO 31
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 31
ccgagaattc attaaagagg agaaattaac tatgataaga aggtccgatt ttcc       54

<210> SEQ ID NO 32
<211> LENGTH: 31
<212> TYPE: DNA
<213> ORGANISM: Artificial sequence
<220> FEATURE:
```

<223> OTHER INFORMATION: synthetically generated oligonucleotide

<400> SEQUENCE: 32
ttccttaaag attttagaat ttctagaagg c                                31

<210> SEQ ID NO 33
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 33
ccgagaattc attaaagagg agaaattaac tatgctacca gaaggctttc tc         52

<210> SEQ ID NO 34
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 34
ctcttcaagc ctgaacccac tccatggagg c                                31

<210> SEQ ID NO 35
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 35
ccgagaattc attaaagagg agaaattaac tatgataagg tttcctgatt at         52

<210> SEQ ID NO 36
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 36
cctaatttct tggagcttat ttctagaagg c                                31

<210> SEQ ID NO 37
<211> LENGTH: 57
<212> TYPE: DNA
<213> ORGANISM: Artificial sequence
<220> FEATURE:
<223> OTHER INFORMATION: synthetically generated oligonucleotide

<400> SEQUENCE: 37
ccgagaattc attcattaaa gaggagaaat taactatgct tccaggagaa ctttctc    57

<210> SEQ ID NO 38
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 38
ctctagaatc tcctccccat ccctaggagg c                                31

<210> SEQ ID NO 39
<211> LENGTH: 40
<212> TYPE: DNA
<213> ORGANISM: Artificial sequence
<220> FEATURE:
<223> OTHER INFORMATION: synthetically generated oligonucleotide

<400> SEQUENCE: 39
ataatctaga gcatgcaatt ccccaaagac ttcatgatag                    40

<210> SEQ ID NO 40
<211> LENGTH: 32
<212> TYPE: DNA
<213> ORGANISM: Artificial sequence
<220> FEATURE:
<223> OTHER INFORMATION: synthetically generated oligonucleotide

<400> SEQUENCE: 40
tcgtagaatg tgactaggtc attcgaaaat aa                            32

<210> SEQ ID NO 41
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 41
ccgacaattg attaaagagg agaaattaac tatggaaagg atcgatgaaa tt       52

<210> SEQ ID NO 42
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 42
ctcttctcta agtttggtac tccatggagg c                             31

<210> SEQ ID NO 43
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 43
ccgacaattg attaaagagg agaaattaac tatgttccct gaaaagttcc tt       52

<210> SEQ ID NO 44
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 44
ctccttaacg actcccctac tccatggagg c                             31

<210> SEQ ID NO 45
<211> LENGTH: 27
<212> TYPE: DNA
<213> ORGANISM: Artificial sequence
<220> FEATURE:
<223> OTHER INFORMATION: synthetically generated oligonucleotide

```
<400> SEQUENCE: 45
aataaggatc cgtttagcga cgctcgc                                              27

<210> SEQ ID NO 46
<211> LENGTH: 35
<212> TYPE: DNA
<213> ORGANISM: Artificial sequence
<220> FEATURE:
<223> OTHER INFORMATION: synthetically generated oligonucleotide

<400> SEQUENCE: 46
cggataatgg cgacatgttg ggccttcgaa aataa                                     35

<210> SEQ ID NO 47
<211> LENGTH: 60
<212> TYPE: DNA
<213> ORGANISM: Artificial sequence
<220> FEATURE:
<223> OTHER INFORMATION: synthetically generated oligonucleotide

<400> SEQUENCE: 47
tttattgaat tcattaaaga ggagaaatta actatgatct gtgtggaaat attcggaaag          60

<210> SEQ ID NO 48
<211> LENGTH: 40
<212> TYPE: DNA
<213> ORGANISM: Artificial sequence
<220> FEATURE:
<223> OTHER INFORMATION: primer sequence

<400> SEQUENCE: 48
gaagatgctt ctcccactct ctcttacttt cgaaatatct                                40

<210> SEQ ID NO 49
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 49
tttattcaat tgattaaaga ggagaaatta actatgggga ttggtggcga cgac                54

<210> SEQ ID NO 50
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 50
cctccataca cttatacttt tctattcgaa ttattt                                    36

<210> SEQ ID NO 51
<211> LENGTH: 60
<212> TYPE: DNA
<213> ORGANISM: Artificial sequence
<220> FEATURE:
<223> OTHER INFORMATION: synthetically generated oligonucleotide

<400> SEQUENCE: 51
tttattgaat tcattaaaga ggagaaatta actatgctac cagaagagtt cctatggggc          60

<210> SEQ ID NO 52
<211> LENGTH: 39
```

```
<212> TYPE: DNA
<213> ORGANISM: Artificial sequence
<220> FEATURE:
<223> OTHER INFORMATION: synthetically generated oligonucleotide

<400> SEQUENCE: 52
ctttacttct ggtatcggca actactcttc gaattattt                             39

<210> SEQ ID NO 53
<211> LENGTH: 68
<212> TYPE: DNA
<213> ORGANISM: Artificial sequence
<220> FEATURE:
<223> OTHER INFORMATION: synthetically generated oligonucleotide

<400> SEQUENCE: 53
aaaaaacaat tgaattcatt aaagaggaga aattaactat ggtagaaaga cacttcagat      60
atgttctt                                                              68

<210> SEQ ID NO 54
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 54
gtccgtttct catttacttc ttaacctagg cttttt                               36

<210> SEQ ID NO 55
<211> LENGTH: 56
<212> TYPE: DNA
<213> ORGANISM: Artificial sequence
<220> FEATURE:
<223> OTHER INFORMATION: synthetically generated oligonucleotide

<400> SEQUENCE: 55
ttttggaatt cattaaagag gagaaattaa ctatggaact gatcatagaa ggttac         56

<210> SEQ ID NO 56
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 56
cgcatgcaag acatgtctct cacttttcga agaata                               36

<210> SEQ ID NO 57
<211> LENGTH: 1992
<212> TYPE: DNA
<213> ORGANISM: Thermotoga maritima

<400> SEQUENCE: 57
cttttattga tcgtttgagct ctctttcgtt ctctttgcaa gtgacgagtt cgtgaaagtg      60
gaaaacggaa aattcgctct gaacggaaaa gaattcagat tcattggaag caacaactac     120
tacatgcact acaagagcaa cggaatgata gacagtgttc tggagagtgc cagagacatg     180
ggtataaagg tcctcagaat ctggggtttc ctcgacgggg agagttactg cagagacaag     240
aacacctaca tgcatcctga gcccggtgtt tcggggtgc cagaaggaat atcgaacgcc      300
cagagcggtt tcgaaagact cgactacaca gttgcgaaag cgaagaact cggtataaaa     360
```

-continued

```
cttgtcattg ttcttgtgaa caactgggac gacttcggtg gaatgaacca gtacgtgagg    420
tggtttggag gaacccatca cgacgatttc tacagagatg agaagatcaa agaagagtac    480
aaaaagtacg tctcctttct cgtaaaccat gtcaatacct acacgggagt tccttacagg    540
gaagagccca ccatcatggc ctgggagctt gcaaacgaac cgcgctgtga gacggacaaa    600
tcggggaaca cgctcgttga gtgggtgaag gagatgagct cctacataaa gagtctggat    660
cccaaccacc tcgtggctgt gggggacgaa ggattcttca gcaactacga aggattcaaa    720
ccttacggtg gagaagccga gtgggcctac aacggctggt ccgtgttga ctggaagaag    780
ctccttcga tagagacggt ggacttcggc acgttccacc tctatccgtc ccactggggt    840
gtcagtccag agaactatgc ccagtgggga gcgaagtgga tagaagacca cataaagatc    900
gcaaaagaga tcgaaaaacc cgttgttctg gaagaatatg gaattccaaa gagtgcgcca    960
gttaacagaa cggccatcta cagactctgg aacgatctgg tctacgatct cggtggagat   1020
ggagcgatgt tctggatgct cgcgggaatc ggggaaggtt cggacagaga cgagagaggg   1080
tactatccgg actacgacgg tttcagaata gtgaacgacg acagtccaga agcggaactg   1140
ataagagaat acgcgaagct gttcaacaca ggtgaagaca tagagaagaa cacctgctct   1200
ttcatccttc caaaagacgg catggagatc aaaaagaccg tggaagtgag ggctggtgtt   1260
ttcgactaca gcaacacgtt tgaaaagttg tctgtcaaag tcgaagatct ggtttttgaa   1320
aatgagatag agcatctcgg atacggaatt tacggctttg atctcgacac aacccggatc   1380
ccggatggag aacatgaaat gttccttgaa ggccactttc agggaaaaac ggtgaaagac   1440
tctatcaaag cgaaagtggt gaacgaagca cggtacgtgc tcgcagagga agttgatttt   1500
tcctctccag aagaggtgaa aaactggtgg aacagcggaa cctggcaggc agagttcggg   1560
tcacctgaca ttgaatggaa cggtgaggtg ggaaatggag cactgcagct gaacgtgaaa   1620
ctgcccggaa agagcgactg ggaagaagtg agagtagcaa ggaagttcga aagactctca   1680
gaatgtgaga tcctcgagta cgacatctac attccaaacg tcgagggact caagggaagg   1740
ttgaggccgt acgcggttct gaaccccggc tgggtgaaga taggcctcga catgaacaac   1800
gcgaacgtgg aaagtgcgga gatcatcact ttcggcggaa aagagtacag aagattccat   1860
gtaagaattg agttcgacag aacagcgggg gtgaaagaac ttcacatagg agttgtcggt   1920
gatcatctga ggtacgatgg accgattttc atcgataatg tgagactta taaaagaaca   1980
ggaggtatgt ga                                                       1992
```

<210> SEQ ID NO 58
<211> LENGTH: 2055
<212> TYPE: DNA
<213> ORGANISM: Thermotoga maritima

<400> SEQUENCE: 58

```
atgaaaagaa tcgacctgaa tggtttctgg agcgttaggg ataacgaagg gagattttcg     60
tttgaaggga ctgtgccagg ggttgtccag gcagatctgg tcagaaaagg tcttcttcca    120
cacccgtacg ttgggatgaa cgaagatctc ttcaaggaaa tagaagacag agagtggatc    180
tacgagaggg agttcgagtt caaagaagat gtgaaagagg gggaacgtgt cgatctcgtt    240
tttgagggcg tcgacacgct gtcggatgtt tatctgaacg tgtttaccct tggaagcacc    300
gaagacatgt tcatcgagta tcgcttcgat gtcacgaacg tgttgaaaga aaagaatcac    360
ctgaaggtgt acataaaatc tcccatcaga gttccgaaaa ctctcgagca gaactacggg    420
gtcctcggcg gtcctgaaga tcccatcaga ggatacataa gaaaagccca gtattcgtac    480
```

-continued

```
ggatgggact ggggtgccag aatcgttaca agcggtattt ggaaacccgt ctacctcgag    540
gtgtacaggg cacgtcttca ggattcaacg gcttatctgt tggaacttga ggggaaagat    600
gcccttgtga gggtgaacgg tttcgtacac ggggaaggaa atctcattgt ggaagtttat    660
gtaaacggtg aaaagatagg ggagtttcct gttcttgaaa agaacggaga aaagctcttc    720
gatggagtgt tccacctgaa agatgtgaaa ctatggtatc cgtggaacgt ggggaaaccg    780
tacctgtacg atttcgtttt cgtgttgaaa gacttaaacg gagagatcta cagagaagaa    840
aagaaaatcg gtttgagaag agtcagaatc gttcaggagc ccgatgaaga aggaaaaact    900
ttcatattcg aaatcaacgg tgagaaagtc ttcgctaagg gtgctaactg gattccctca    960
gaaaacatcc tcacgtggtt gaaggaggaa gattacgaaa agctcgtcaa aatggcaagg   1020
agtgccaata tgaacatgct cagggtctgg ggaggaggaa tctacgagag agagatcttc   1080
tacagactct gtgatgaact cggtatcatg gtgtggcagg atttcatgta cgcgtgtctt   1140
gaatatccgg atcatcttcc gtggttcaga aaactcgcga acgaagaggc aagaaagatt   1200
gtgagaaaac tcagatacca tccctccatt gttctctggt gcggaaacaa cgaaaacaac   1260
tggggattcg atgaatgggg aaatatggcc agaaaagtgg atggtatcaa cctcggaaac   1320
aggctctacc tcttcgattt tcctgagatt tgtgccgaag aagacccgtc cactccctat   1380
tggccatcca gtccatacgg cggtgaaaaa gcgaacagcg aaaaggaagg agacaggcac   1440
gtctggtacg tgtggagtgg ctggatgaac tacgaaaact acgaaaaaga caccggaagg   1500
ttcatcagcg agtttggatt tcagggtgct ccccatccag agacgataga gttcttttca   1560
aaacccgagg aaagagagat attccatccc gtcatgctga agcacaacaa acaggtggaa   1620
ggacaggaaa gattgatcag gttcatattc ggaaattttg gaaagtgtaa agatttcgac   1680
agttttgtgt atctgtccca gctcaaccag gcggaggcga tcaagttcgg tgttgaacac   1740
tggcgaagca ggaagtacaa aacggccggc gctctcttct ggcagttcaa cgacagctgg   1800
ccggtcttca gctggtccgc agtcgattac ttcaaaaggc ccaaagctct ctactactat   1860
gcgagaagat tcttcgctga agttctaccc gttttgaaga agagagacaa caaaatagaa   1920
ctgctggtgg gtgagcgatc tgagggagac aaaagaagtc tctctcaggc ttgcagccta   1980
cgagaagaag ggagaaaagg tattcgaaaa gacttacaga acggtactcc cagcagacgg   2040
tgtgagtttg gttga                                                   2055
```

<210> SEQ ID NO 59
<211> LENGTH: 2870
<212> TYPE: DNA
<213> ORGANISM: Bankia gouldi

<400> SEQUENCE: 59

```
atgaaaaaaa atctactaat gtttaaaagg cttacgtatc taccttttgtt tttaatgctg     60 ctctcactaa gttcagtagc tcaatctcct gtagaaaaac atggccgttt acaagttgac    120
ggaaaccgca ttcttaatgc gtctggagaa attacgagct tagctggtaa cagcctcttt    180
tggagtaatg ctggagacac ctccgatttt tataatgcag aaactgttga ttttttagca    240
gaaaactgga atagctcact tattagaata gctatgggcg taaagaaaaa ttgggatggc    300
ggaaatggct atattgatag tccgcaggag caagaagcta aaattagaaa agttattgat    360
gcagctattg ctaacggcat atatgtaata atagactggc acactcacga agcagagtta    420
tacacagatg aggctgttga cttttttacc agaatggcag acctatacgg agatactccc    480
```

-continued

| | |
|---|---|
| aatgtaatgt atgaaattta taacgagcct atataccaaa gttggcctgt tattaagaat | 540 |
| tatgcagagc aagtaattgc tggtatacgt tctaaagacc cagataattt aataattgta | 600 |
| ggtactagca attattctca gcaagttgat gtagcatcag cagacccaat atctgatact | 660 |
| aatgtggcat atactttaca tttttatgca gcatttaacc cgcatgataa cttaagaaat | 720 |
| gtagcacaga cagcattaga taataatgtt gctttgtttg ttacagaatg gggtacaatt | 780 |
| ttaaataccg gacaaggaga accagacaaa gaaagcacta atacttggat ggccttttg | 840 |
| aaagaaaaag gtataagtca cgctaattgg tctttgagtg acaaagcttt tcctgaaaca | 900 |
| gggtctgtag ttcaagcagg acaaggtgta tctggtttaa ttagcaataa acttacagcc | 960 |
| tctggtgaaa ttgtaaaaaa catcatccaa aactgggata cagagacctc tacaggacct | 1020 |
| aaaacaacac aatgtagtac tatagaatgt attagagctg caatggaaac agcacaagca | 1080 |
| ggagatgaaa ttataattgc ccctggaaac tacaattttc aagacaagat acaaggtgcc | 1140 |
| tttaaccgta gtgtttacct ttatggtagt gctaacggaa acagtacaaa ccctattata | 1200 |
| ttaagaggcg aaagcgctac aaaccctcct gttttctcag gattagatta taacaatggc | 1260 |
| tacctattaa gtattgaagg tgattattgg aatattaaag atatagagtt taaaactggg | 1320 |
| tctaaaggta ttgttcttga caattctaat ggtagtaaat taaaaaaccct tgttgttcat | 1380 |
| gatattggag aagaagctat tcacttgcgt gatggatcta gcaataatag tatagatggt | 1440 |
| tgcactatat acaatacagg tagaactaaa cctggttttg gtgaaggttt atatgtaggc | 1500 |
| tcagataaag gacaacatga cacttatgaa agagcttgta acaataacac tattgaaaac | 1560 |
| tgtaccgttg gacccaatgt aacagcagaa ggcgtagatg ttaaggaagg tacaatgaac | 1620 |
| actattataa gaaattgcgt gttttctgca gaaggaattt caggagaaaa tagctcagat | 1680 |
| gcttttattg atttaaaagg agcctatggt tttgtataca gaaacacgtt taatgttgat | 1740 |
| ggttctgaag taataaatac tggagtagac ttttagata gaggtacagg atttaataca | 1800 |
| ggttttagaa atgcaatatt tgaaaataca tataaccttg gcagtagagc ttcagaaatt | 1860 |
| tcaactgctc gtaaaaaaca aggttctcct gaacaaactc acgtttggga taatattaga | 1920 |
| aaccctaatt ctgttgattt tccaataagt gatggtacag aaaatctagt aaataaattc | 1980 |
| tgcccagatt ggaatataga accatgtaat cctgtagacg aaaccaacca agcacctaca | 2040 |
| ataagcttcc tatctcctgt taacaatatt actttagttg aaggttataa tttacaagtt | 2100 |
| gaagttaatg ctactgatgc agatggaact attgataatg taaaacttta tatagataac | 2160 |
| aatttagtta ggcaaataaa ttctacttca tataaatggg gccattctga ttctccaaat | 2220 |
| acagatgaac ttaatggtct tacagaagga acttatacct taaaagcaat tgcaactgat | 2280 |
| aacgacgggg cttctacaga aacgcaattt acgttaactg taataacaga acaaagtccg | 2340 |
| tctgagaatt gtgactttaa tacaccttct tcaactggtt tagaagattt tgacattaaa | 2400 |
| aagttttcta cgtttttga gttaggatct ggcggaccat ctttaagtaa tttaaaaaca | 2460 |
| tttactatta attggaattc gcaatacaat gggttatatc aattttcaat aaacacaaac | 2520 |
| aacggtgtac ctgattatta tataaattta aaaccaaaaa ttacctttca gtttaaaaat | 2580 |
| gcaaatccag aaatatctat tagcaatagc ttaattccta attttgatgg tgattactgg | 2640 |
| gtaacatcag ataacggtaa ttttgtgatg gtatctaaaa ctaataattt tacgatatac | 2700 |
| tttagtaatg acgctactgc tcctatttgt aatgttacgc ctagtaacca aataagtaaa | 2760 |
| attactgatg attctagtat taattttaag ctttaccccta atcctgcttt agacgaaact | 2820 |
| atttttgtga gcgctgaaga tgaaaaacta gctttggtgc ttgtaccagt | 2870 |

-continued

```
<210> SEQ ID NO 60
<211> LENGTH: 960
<212> TYPE: DNA
<213> ORGANISM: Pyrococcus furiosus

<400> SEQUENCE: 60
atgagcaaga aaaagttcgt catcgtatct atcttaacaa tcctttagt acaggcaata      60 tattttgtag aaaagtatca tacctctgag acaagtcaa cttcaaatac ctcatctaca     120
ccaccccaaa caacactttc cactaccaag gttctcaaga ttagataccc tgatgacggt     180
gagtggccag gagctcctat tgataaggat ggtgatggga acccagaatt ctacattgaa     240
ataaacctat ggaacattct taatgctact ggatttgctg agatgacgta caatttaacc     300
agcggcgtcc ttcactacgt ccaacaactt gacaacattg tcttgaggga tagaagtaat     360
tgggtgcatg gataccccga aatattctat ggaaacaagc catggaatgc aaactacgca     420
actgatggcc aataccatt acccagtaaa gtttcaaacc taacagactt ctatctaaca      480
atctcctata aacttgagcc caagaacggc ctgccaatta acttcgcaat gaatcctgg      540 ttaacgagag aagcttggag aacaacagga attaacagcg atgagcaaga agtaatgata     600
tggatttact atgacggatt acaaccggct ggctccaaag ttaaggagat tgtagtccca     660
ataatagtta acggaacacc agtaaatgct acatttgaag tatggaaggc aaacattggt     720
tgggagtatg ttgcatttag aataaagacc ccaatcaaag agggaacagt gacaattcca     780
tacggagcat ttataagtgt tgcagccaac atttcaagct taccaaatta cacagaactt     840
tacttagagg acgtggagat tggaactgag tttggaacgc aagcactac ctccgcccac      900 ctagagtggt ggatcacaaa cataacacta actcctctag atagacctct tatttcctaa     960

<210> SEQ ID NO 61
<211> LENGTH: 663
<212> TYPE: PRT
<213> ORGANISM: Thermotoga maritima

<400> SEQUENCE: 61

Leu Leu Leu Ile Val Glu Leu Ser Phe Val Leu Phe Ala Ser Asp Glu
 1               5                  10                  15

Phe Val Lys Val Glu Asn Gly Lys Phe Ala Leu Asn Gly Lys Glu Phe
            20                  25                  30

Arg Phe Ile Gly Ser Asn Asn Tyr Tyr Met His Tyr Lys Ser Asn Gly
        35                  40                  45

Met Ile Asp Ser Val Leu Glu Ser Ala Arg Asp Met Gly Ile Lys Val
    50                  55                  60

Leu Arg Ile Trp Gly Phe Leu Asp Gly Glu Ser Tyr Cys Arg Asp Lys
65                  70                  75                  80

Asn Thr Tyr Met His Pro Glu Pro Gly Val Phe Gly Val Pro Glu Gly
                85                  90                  95

Ile Ser Asn Ala Gln Ser Gly Phe Glu Arg Leu Asp Tyr Thr Val Ala
            100                 105                 110

Lys Ala Lys Glu Leu Gly Ile Lys Leu Val Ile Val Leu Val Asn Asn
        115                 120                 125

Trp Asp Asp Phe Gly Gly Met Asn Gln Tyr Val Arg Trp Phe Gly Gly
    130                 135                 140

Thr His His Asp Asp Phe Tyr Arg Asp Glu Lys Ile Lys Glu Glu Tyr
145                 150                 155                 160
```

```
Lys Lys Tyr Val Ser Phe Leu Val Asn His Val Asn Thr Tyr Thr Gly
                165                 170                 175
Val Pro Tyr Arg Glu Pro Thr Ile Met Ala Trp Glu Leu Ala Asn
            180                 185                 190
Glu Pro Arg Cys Glu Thr Asp Lys Ser Gly Asn Thr Leu Val Glu Trp
            195                 200                 205
Val Lys Glu Met Ser Ser Tyr Ile Lys Ser Leu Asp Pro Asn His Leu
225 210                 215                 220
Val Ala Val Gly Asp Glu Gly Phe Phe Ser Asn Tyr Glu Gly Phe Lys
225                 230                 235                 240
Pro Tyr Gly Gly Glu Ala Glu Trp Ala Tyr Asn Gly Trp Ser Gly Val
                245                 250                 255
Asp Trp Lys Lys Leu Leu Ser Ile Glu Thr Val Asp Phe Gly Thr Phe
                260                 265                 270
His Leu Tyr Pro Ser His Trp Gly Val Ser Pro Glu Asn Tyr Ala Gln
                275                 280                 285
Trp Gly Ala Lys Trp Ile Glu Asp His Ile Lys Ile Ala Lys Glu Ile
            290                 295                 300
Gly Lys Pro Val Val Leu Glu Glu Tyr Gly Ile Pro Lys Ser Ala Pro
305                 310                 315                 320
Val Asn Arg Thr Ala Ile Tyr Arg Leu Trp Asn Asp Leu Val Tyr Asp
                325                 330                 335
Leu Gly Gly Asp Gly Ala Met Phe Trp Met Leu Ala Gly Ile Gly Glu
                340                 345                 350
Gly Ser Asp Arg Asp Glu Arg Gly Tyr Tyr Pro Asp Tyr Asp Gly Phe
            355                 360                 365
Arg Ile Val Asn Asp Asp Ser Pro Glu Ala Glu Leu Ile Arg Glu Tyr
            370                 375                 380
Ala Lys Leu Phe Asn Thr Gly Glu Asp Ile Arg Glu Asp Thr Cys Ser
385                 390                 395                 400
Phe Ile Leu Pro Lys Asp Gly Met Glu Ile Lys Lys Thr Val Glu Val
                405                 410                 415
Arg Ala Gly Val Phe Asp Tyr Ser Asn Thr Phe Glu Lys Leu Ser Val
                420                 425                 430
Lys Val Glu Asp Leu Val Phe Glu Asn Glu Ile Glu His Leu Gly Tyr
            435                 440                 445
Gly Ile Tyr Gly Phe Asp Leu Asp Thr Thr Arg Ile Pro Asp Gly Glu
450                 455                 460
His Glu Met Phe Leu Glu Gly His Phe Gln Gly Lys Thr Val Lys Asp
465                 470                 475                 480
Ser Ile Lys Ala Lys Val Val Asn Glu Ala Arg Tyr Val Leu Ala Glu
                485                 490                 495
Glu Val Asp Phe Ser Ser Pro Glu Val Lys Asn Trp Trp Asn Ser
                500                 505                 510
Gly Thr Trp Gln Ala Glu Phe Gly Ser Pro Asp Ile Glu Trp Asn Gly
            515                 520                 525
Glu Val Gly Asn Gly Ala Leu Gln Leu Asn Val Lys Leu Pro Gly Lys
            530                 535                 540
Ser Asp Trp Glu Glu Val Arg Val Ala Arg Lys Phe Glu Arg Leu Ser
545                 550                 555                 560
Glu Cys Glu Ile Leu Glu Tyr Asp Ile Tyr Ile Pro Asn Val Glu Gly
                565                 570                 575
Leu Lys Gly Arg Leu Arg Pro Tyr Ala Val Leu Asn Pro Gly Trp Val
```

-continued

```
            580                 585                 590
Lys Ile Gly Leu Asp Met Asn Asn Ala Asn Val Glu Ser Ala Glu Ile
            595                 600                 605

Ile Thr Phe Gly Gly Lys Glu Tyr Arg Arg Phe His Val Arg Ile Glu
610                 615                 620

Phe Asp Arg Thr Ala Gly Val Lys Glu Leu His Ile Gly Val Val Gly
625                 630                 635                 640

Asp His Leu Arg Tyr Asp Gly Pro Ile Phe Ile Asp Asn Val Arg Leu
                    645                 650                 655

Tyr Lys Arg Thr Gly Gly Met
            660

<210> SEQ ID NO 62
<211> LENGTH: 684
<212> TYPE: PRT
<213> ORGANISM: Thermotoga maritima

<400> SEQUENCE: 62

Met Lys Arg Ile Asp Leu Asn Gly Phe Trp Ser Val Arg Asp Asn Glu
1               5                   10                  15

Gly Arg Phe Ser Phe Glu Gly Thr Val Pro Gly Val Val Gln Ala Asp
                20                  25                  30

Leu Val Arg Lys Gly Leu Leu Pro His Pro Tyr Val Gly Met Asn Glu
            35                  40                  45

Asp Leu Phe Lys Glu Ile Glu Asp Arg Glu Trp Ile Tyr Glu Arg Glu
    50                  55                  60

Phe Glu Phe Lys Glu Asp Val Lys Glu Gly Glu Arg Val Asp Leu Val
65                  70                  75                  80

Phe Glu Gly Val Asp Thr Leu Ser Asp Val Tyr Leu Asn Gly Val Tyr
                85                  90                  95

Leu Gly Ser Thr Glu Asp Met Phe Ile Glu Tyr Arg Phe Asp Val Thr
            100                 105                 110

Asn Val Leu Lys Glu Lys Asn His Leu Lys Val Tyr Ile Lys Ser Pro
        115                 120                 125

Ile Arg Val Pro Lys Thr Leu Glu Gln Asn Tyr Gly Val Leu Gly Gly
    130                 135                 140

Pro Glu Asp Pro Ile Arg Gly Tyr Ile Arg Lys Ala Gln Tyr Ser Tyr
145                 150                 155                 160

Gly Trp Asp Trp Gly Ala Arg Ile Val Thr Ser Gly Ile Trp Lys Pro
                165                 170                 175

Val Tyr Leu Glu Val Tyr Arg Ala Arg Leu Gln Asp Ser Thr Ala Tyr
            180                 185                 190

Leu Leu Glu Leu Glu Gly Lys Asp Ala Leu Val Arg Val Asn Gly Phe
        195                 200                 205

Val His Gly Glu Gly Asn Leu Ile Val Glu Val Tyr Val Asn Gly Glu
    210                 215                 220

Lys Ile Gly Glu Phe Pro Val Leu Glu Lys Asn Gly Glu Lys Leu Phe
225                 230                 235                 240

Asp Gly Val Phe His Leu Lys Asp Val Lys Leu Trp Tyr Pro Trp Asn
                245                 250                 255

Val Gly Lys Pro Tyr Leu Tyr Asp Phe Val Phe Val Leu Lys Asp Leu
            260                 265                 270

Asn Gly Glu Ile Tyr Arg Glu Glu Lys Lys Ile Gly Leu Arg Arg Val
        275                 280                 285
```

```
Arg Ile Val Gln Glu Pro Asp Glu Glu Gly Lys Thr Phe Ile Phe Glu
            290                 295                 300

Ile Asn Gly Glu Lys Val Phe Ala Lys Gly Ala Asn Trp Ile Pro Ser
305                 310                 315                 320

Glu Asn Ile Leu Thr Trp Leu Lys Glu Glu Asp Tyr Glu Lys Leu Val
                    325                 330                 335

Lys Met Ala Arg Ser Ala Asn Met Asn Met Leu Arg Val Trp Gly Gly
                340                 345                 350

Gly Ile Tyr Glu Arg Glu Ile Phe Tyr Arg Leu Cys Asp Glu Leu Gly
            355                 360                 365

Ile Met Val Trp Gln Asp Phe Met Tyr Ala Cys Leu Glu Tyr Pro Asp
370                 375                 380

His Leu Pro Trp Phe Arg Lys Leu Ala Asn Glu Glu Ala Arg Lys Ile
385                 390                 395                 400

Val Arg Lys Leu Arg Tyr His Pro Ser Ile Val Leu Trp Cys Gly Asn
                405                 410                 415

Asn Glu Asn Asn Trp Gly Phe Asp Glu Trp Gly Asn Met Ala Arg Lys
                420                 425                 430

Val Asp Gly Ile Asn Leu Gly Asn Arg Leu Tyr Leu Phe Asp Phe Pro
            435                 440                 445

Glu Ile Cys Ala Glu Glu Asp Pro Ser Thr Pro Tyr Trp Pro Ser Ser
450                 455                 460

Pro Tyr Gly Gly Glu Lys Ala Asn Ser Glu Lys Glu Gly Asp Arg His
465                 470                 475                 480

Val Trp Tyr Val Trp Ser Gly Trp Met Asn Tyr Glu Asn Tyr Glu Lys
                485                 490                 495

Asp Thr Gly Arg Phe Ile Ser Glu Phe Gly Phe Gln Gly Ala Pro His
            500                 505                 510

Pro Glu Thr Ile Glu Phe Phe Ser Lys Pro Glu Glu Arg Glu Ile Phe
            515                 520                 525

His Pro Val Met Leu Lys His Asn Lys Gln Val Glu Gly Gln Glu Arg
            530                 535                 540

Leu Ile Arg Phe Ile Phe Gly Asn Phe Gly Lys Cys Lys Asp Phe Asp
545                 550                 555                 560

Ser Phe Val Tyr Leu Ser Gln Leu Asn Gln Ala Glu Ala Ile Lys Phe
                565                 570                 575

Gly Val Glu His Trp Arg Ser Arg Lys Tyr Lys Thr Ala Gly Ala Leu
                580                 585                 590

Phe Trp Gln Phe Asn Asp Ser Trp Pro Val Phe Ser Trp Ser Ala Val
            595                 600                 605

Asp Tyr Phe Lys Arg Pro Lys Ala Leu Tyr Tyr Ala Arg Arg Phe
610                 615                 620

Phe Ala Glu Val Leu Pro Val Leu Lys Lys Arg Asp Asn Lys Ile Glu
625                 630                 635                 640

Leu Leu Val Gly Glu Arg Ser Glu Gly Asp Lys Arg Ser Leu Ser Gln
                645                 650                 655

Ala Cys Ser Leu Arg Glu Glu Gly Lys Gly Ile Arg Lys Asp Leu
                660                 665                 670

Gln Asn Gly Thr Pro Ser Arg Arg Cys Glu Phe Gly
            675                 680

<210> SEQ ID NO 63
<211> LENGTH: 956
<212> TYPE: PRT
```

<213> ORGANISM: Bankia gouldi

<400> SEQUENCE: 63

```
Met Lys Lys Asn Leu Leu Met Phe Lys Arg Leu Thr Tyr Leu Pro Leu
 1               5                  10                  15
Phe Leu Met Leu Leu Ser Leu Ser Ser Val Ala Gln Ser Pro Val Glu
             20                  25                  30
Lys His Gly Arg Leu Gln Val Asp Gly Asn Arg Ile Leu Asn Ala Ser
         35                  40                  45
Gly Glu Ile Thr Ser Leu Ala Gly Asn Ser Leu Phe Trp Ser Asn Ala
 50                  55                  60
Gly Asp Thr Ser Asp Phe Tyr Asn Ala Glu Thr Val Asp Phe Leu Ala
 65                  70                  75                  80
Glu Asn Trp Asn Ser Ser Leu Ile Arg Ile Ala Met Gly Val Lys Glu
                 85                  90                  95
Asn Trp Asp Gly Gly Asn Gly Tyr Ile Asp Ser Pro Gln Glu Gln Glu
            100                 105                 110
Ala Lys Ile Arg Lys Val Ile Asp Ala Ala Ile Ala Asn Gly Ile Tyr
        115                 120                 125
Val Ile Ile Asp Trp His Thr His Glu Ala Glu Leu Tyr Thr Asp Glu
130                 135                 140
Ala Val Asp Phe Phe Thr Arg Met Ala Asp Leu Tyr Gly Asp Thr Pro
145                 150                 155                 160
Asn Val Met Tyr Glu Ile Tyr Asn Glu Pro Ile Tyr Gln Ser Trp Pro
                165                 170                 175
Val Ile Lys Asn Tyr Ala Glu Gln Val Ile Ala Gly Ile Arg Ser Lys
            180                 185                 190
Asp Pro Asp Asn Leu Ile Ile Val Gly Thr Ser Asn Tyr Ser Gln Gln
        195                 200                 205
Val Asp Val Ala Ser Ala Asp Pro Ile Ser Asp Thr Asn Val Ala Tyr
210                 215                 220
Thr Leu His Phe Tyr Ala Ala Phe Asn Pro His Asp Asn Leu Arg Asn
225                 230                 235                 240
Val Ala Gln Thr Ala Leu Asp Asn Asn Val Ala Leu Phe Val Thr Glu
                245                 250                 255
Trp Gly Thr Ile Leu Asn Thr Gly Gln Gly Glu Pro Asp Lys Glu Ser
            260                 265                 270
Thr Asn Thr Trp Met Ala Phe Leu Lys Glu Lys Gly Ile Ser His Ala
        275                 280                 285
Asn Trp Ser Leu Ser Asp Lys Ala Phe Pro Glu Thr Gly Ser Val Val
290                 295                 300
Gln Ala Gly Gln Gly Val Ser Gly Leu Ile Ser Asn Lys Leu Thr Ala
305                 310                 315                 320
Ser Gly Glu Ile Val Lys Asn Ile Ile Gln Asn Trp Asp Thr Glu Thr
                325                 330                 335
Ser Thr Gly Pro Lys Thr Thr Gln Cys Ser Thr Ile Glu Cys Ile Arg
            340                 345                 350
Ala Ala Met Glu Thr Ala Gln Ala Gly Asp Glu Ile Ile Ile Ala Pro
        355                 360                 365
Gly Asn Tyr Asn Phe Gln Asp Lys Ile Gln Gly Ala Phe Asn Arg Ser
370                 375                 380
Val Tyr Leu Tyr Gly Ser Ala Asn Gly Asn Ser Thr Asn Pro Ile Ile
385                 390                 395                 400
```

-continued

```
Leu Arg Gly Glu Ser Ala Thr Asn Pro Pro Val Phe Ser Gly Leu Asp
            405                 410                 415
Tyr Asn Asn Gly Tyr Leu Leu Ser Ile Glu Gly Asp Tyr Trp Asn Ile
        420                 425                 430
Lys Asp Ile Glu Phe Lys Thr Gly Ser Lys Gly Ile Val Leu Asp Asn
            435                 440                 445
Ser Asn Gly Ser Lys Leu Lys Asn Leu Val Val His Asp Ile Gly Glu
450                 455                 460
Glu Ala Ile His Leu Arg Asp Gly Ser Ser Asn Asn Ser Ile Asp Gly
465                 470                 475                 480
Cys Thr Ile Tyr Asn Thr Gly Arg Thr Lys Pro Gly Phe Gly Glu Gly
                485                 490                 495
Leu Tyr Val Gly Ser Asp Lys Gly Gln His Asp Thr Tyr Glu Arg Ala
            500                 505                 510
Cys Asn Asn Thr Ile Glu Asn Cys Thr Val Gly Pro Asn Val Thr
            515                 520                 525
Ala Glu Gly Val Asp Val Lys Glu Gly Thr Met Asn Thr Ile Ile Arg
        530                 535                 540
Asn Cys Val Phe Ser Ala Glu Gly Ile Ser Gly Glu Asn Ser Ser Asp
545                 550                 555                 560
Ala Phe Ile Asp Leu Lys Gly Ala Tyr Gly Phe Val Tyr Arg Asn Thr
                565                 570                 575
Phe Asn Val Asp Gly Ser Glu Val Ile Asn Thr Gly Val Asp Phe Leu
            580                 585                 590
Asp Arg Gly Thr Gly Phe Asn Thr Gly Phe Arg Asn Ala Ile Phe Glu
        595                 600                 605
Asn Thr Tyr Asn Leu Gly Ser Arg Ala Ser Glu Ile Ser Thr Ala Arg
        610                 615                 620
Lys Lys Gln Gly Ser Pro Glu Gln Thr His Val Trp Asp Asn Ile Arg
625                 630                 635                 640
Asn Pro Asn Ser Val Asp Phe Pro Ile Ser Asp Gly Thr Glu Asn Leu
                645                 650                 655
Val Asn Lys Phe Cys Pro Asp Trp Asn Ile Glu Pro Cys Asn Pro Val
            660                 665                 670
Asp Glu Thr Asn Gln Ala Pro Thr Ile Ser Phe Leu Ser Pro Val Asn
        675                 680                 685
Asn Ile Thr Leu Val Glu Gly Tyr Asn Leu Gln Val Glu Val Asn Ala
        690                 695                 700
Thr Asp Ala Asp Gly Thr Ile Asp Asn Val Lys Leu Tyr Ile Asp Asn
705                 710                 715                 720
Asn Leu Val Arg Gln Ile Asn Ser Thr Ser Tyr Lys Trp Gly His Ser
                725                 730                 735
Asp Ser Pro Asn Thr Asp Glu Leu Asn Gly Leu Thr Glu Gly Thr Tyr
            740                 745                 750
Thr Leu Lys Ala Ile Ala Thr Asp Asn Asp Gly Ala Ser Thr Glu Thr
        755                 760                 765
Gln Phe Thr Leu Thr Val Ile Thr Glu Gln Ser Ser Glu Asn Cys
        770                 775                 780
Asp Phe Asn Thr Pro Ser Ser Thr Gly Leu Glu Asp Phe Asp Ile Lys
785                 790                 795                 800
Lys Phe Ser Asn Val Phe Glu Leu Gly Ser Gly Pro Ser Leu Ser
                805                 810                 815
Asn Leu Lys Thr Phe Thr Ile Asn Trp Asn Ser Gln Tyr Asn Gly Leu
```

```
                    820                 825                 830
Tyr Gln Phe Ser Ile Asn Thr Asn Asn Gly Val Pro Asp Tyr Tyr Ile
            835                 840                 845

Asn Leu Lys Pro Lys Ile Thr Phe Gln Phe Lys Asn Ala Asn Pro Glu
850                 855                 860

Ile Ser Ile Ser Asn Ser Leu Ile Pro Asn Phe Asp Gly Asp Tyr Trp
865                 870                 875                 880

Val Thr Ser Asp Asn Gly Asn Phe Val Met Val Ser Lys Thr Asn Asn
                885                 890                 895

Phe Thr Ile Tyr Phe Ser Asn Asp Ala Thr Ala Pro Ile Cys Asn Val
            900                 905                 910

Thr Pro Ser Asn Gln Ile Ser Lys Ile Thr Asp Asp Ser Ser Ile Asn
            915                 920                 925

Phe Lys Leu Tyr Pro Asn Pro Ala Leu Asp Glu Thr Ile Phe Val Ser
        930                 935                 940

Ala Glu Asp Glu Lys Leu Ala Leu Val Leu Val Pro
945                 950                 955

<210> SEQ ID NO 64
<211> LENGTH: 319
<212> TYPE: PRT
<213> ORGANISM: Pyrococcus furiosus

<400> SEQUENCE: 64

Met Ser Lys Lys Phe Val Ile Val Ser Ile Leu Thr Ile Leu Leu
1               5                   10                  15

Val Gln Ala Ile Tyr Phe Val Glu Lys Tyr His Thr Ser Glu Asp Lys
                20                  25                  30

Ser Thr Ser Asn Thr Ser Ser Thr Pro Pro Gln Thr Thr Leu Ser Thr
            35                  40                  45

Thr Lys Val Leu Lys Ile Arg Tyr Pro Asp Asp Gly Glu Trp Pro Gly
50                  55                  60

Ala Pro Ile Asp Lys Asp Gly Asp Gly Asn Pro Glu Phe Tyr Ile Glu
65                  70                  75                  80

Ile Asn Leu Trp Asn Ile Leu Asn Ala Thr Gly Phe Ala Glu Met Thr
                85                  90                  95

Tyr Asn Leu Thr Ser Gly Val Leu His Tyr Val Gln Gln Leu Asp Asn
            100                 105                 110

Ile Val Leu Arg Asp Arg Ser Asn Trp Val His Gly Tyr Pro Glu Ile
        115                 120                 125

Phe Tyr Gly Asn Lys Pro Trp Asn Ala Asn Tyr Ala Thr Asp Gly Pro
    130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175

Ile Glu Ser Trp Leu Thr Arg Glu Ala Trp Arg Thr Thr Gly Ile Asn
            180                 185                 190

Ser Asp Glu Gln Glu Val Met Ile Trp Ile Tyr Tyr Asp Gly Leu Gln
        195                 200                 205

Pro Ala Gly Ser Lys Val Lys Glu Ile Val Val Pro Ile Ile Val Asn
    210                 215                 220

Gly Thr Pro Val Asn Ala Thr Phe Glu Val Trp Lys Ala Asn Ile Gly
225                 230                 235                 240
```

```
Trp Glu Tyr Val Ala Phe Arg Ile Lys Thr Pro Ile Lys Glu Gly Thr
                245                 250                 255

Val Thr Ile Pro Tyr Gly Ala Phe Ile Ser Val Ala Ala Asn Ile Ser
            260                 265                 270

Ser Leu Pro Asn Tyr Thr Glu Leu Tyr Leu Glu Asp Val Glu Ile Gly
        275                 280                 285

Thr Glu Phe Gly Thr Pro Ser Thr Thr Ser Ala His Leu Glu Trp Trp
    290                 295                 300

Ile Thr Asn Ile Thr Leu Thr Pro Leu Asp Arg Pro Leu Ile Ser
305                 310                 315

<210> SEQ ID NO 65
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 65
ccgacaattg attaaagagg agaaattaac tatggaaagg atcgatgaaa tt              52

<210> SEQ ID NO 66
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 66
ctcttctcta gtttggtac tccatggagg c                                     31

<210> SEQ ID NO 67
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 67
ccgacaattg attaaagagg agaaattaac tatgttccct gaaaagttcc tt              52

<210> SEQ ID NO 68
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 68
ctccttaacg actcccctac tccatggagg c                                    31

<210> SEQ ID NO 69
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 69
aataaggatc cgtttagcga cgctcgc                                         27

<210> SEQ ID NO 70
<211> LENGTH: 35
<212> TYPE: DNA
```

```
<213> ORGANISM: Artificial Sequence
<220> FEATURE:
<223> OTHER INFORMATION: synthetically generated oligonucleotide

<400> SEQUENCE: 70
cggataatgg cgacatgttg ggccttcgaa aataa                              35

<210> SEQ ID NO 71
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 71
aataacaatt gaaggaggaa tttaaatggc ttatcatacc tctgaggaca ag           52

<210> SEQ ID NO 72
<211> LENGTH: 32
<212> TYPE: DNA
<213> ORGANISM: Artificial Sequence
<220> FEATURE:
<223> OTHER INFORMATION: synthetically generated oligonucleotide

<400> SEQUENCE: 72
ctatctggag aataaaggat tcagctgaat aa                                 32
```

ENZYMES HAVING GLYCOSIDASE ACTIVITY AND METHODS OF USE THEREOF

RELATED APPLICATIONS

This application is a continuation of U.S. application Ser. No. 09/910,579 filed Jul. 20, 2001, now abandoned which is a continuation-in-part of U.S. patent application Ser. No. 09/134,078, filed Aug. 13, 1998, issued as U.S. Pat. No. 6,368,844, on Apr. 9, 2002; which is a continuation of U.S. application Ser. No. 08/949,026, filed Oct. 10, 1997, now abandoned; which claims benefit of priority under 35 U.S.C. § 119(e) of U.S. Provisional Application No. 60/056,916, filed Dec. 6, 1996, all of which are herein incorporated by reference in their entirety. The application is also related to U.S. application Ser. No. 08/583,787, filed Jan. 11, 1996, now abandoned; which is hereby incorporated by reference in its entirety.

FIELD OF THE INVENTION

This invention relates generally to enzymes, polynucleotides encoding the enzymes, the use of such polynucleotides and polypeptides, and more specifically to enzymes having glycosidase activity.

BACKGROUND

The glycosidic bond of β-galactosides can be cleaved by different classes of enzymes: (i) phospho-β-galactosidases (EC3.2.1.85) are specific for a phosphorylated substrate generated via phosphoenolpyruvate phosphotransferase system (PTS)-dependent uptake; (ii) typical β-galactosidases (EC3.2.1.23), represented by the *Escherichia coli* LacZ enzyme, which are relatively specific for β-galactosides; and (iii) β-glucosidases (EC 3.2.1.21) such as the enzymes of *Agrobacterium faecalis*, *Clostridium thermocellum*, *Pyrococcus furiosus* or *Sulfolobus solfataricus* (Day, A. G. and Withers, S. G., (1986) Purification and characterization of a β-glucosidase from *Alcaligenes faecalis*. Can. J. Biochem. Cell. Biol. 64, 914-922; Kengen, S. W. M., et al. (1993) Eur. J. Biochem., 213, 305-312; Ait, N., Cruezet, N. and Cattaneo, J. (1982) Properties of β-glucosidase purified from *Clostridium thermocellum*. J. Gen. Microbiol. 128, 569-577; Grogan, D. W. (1991) Evidence that β-galactosidase of *Sulfolobus solfataricus* is only one of several activities of a thermostable β-glycodiase. Appl. Environ. Microbiol. 57, 1644-1649). Members of the latter group, although highly specific with respect to the β-anomeric configuration of the glycosidic linkage, often display a rather relaxed substrate specificity and hydrolyse β-glucosides as well as β-fucosides and β-galactosides.

Generally, α-galactosidases are enzymes that catalyze the hydrolysis of galactose groups on a polysaccharide backbone or hydrolyze the cleavage of di- or oligosaccharides comprising galactose.

Generally, β-mannanases are enzymes that catalyze the hydrolysis of mannose groups internally on a polysaccharide backbone or hydrolyze the cleavage of di- or oligosaccharides comprising mannose groups. β-mannosidases hydrolyze non-reducing, terminal mannose residues on a mannose-containing polysaccharide and the cleavage of di- or oligosaccaharides comprising mannose groups.

Guar gum is a branched galactomannan polysaccharide composed of β-1,4 linked mannose backbone with a-1,6 linked galactose sidechains. The enzymes required for the degradation of guar are β-mannanase, β-mannosidase and α-galactosidase. β-mannanase hydrolyses the mannose backbone internally and β-mannosidase hydrolyses non-reducing, terminal mannose residues. α-galactosidase hydrolyses α-linked galactose groups.

Galactomannan polysaccharides and the enzymes that degrade them have a variety of applications. Guar is commonly used as a thickening agent in food and is utilized in hydraulic fracturing in oil and gas recovery. Consequently, galactomannanases are industrially relevant for the degradation and modification of guar. Furthermore, a need exists for thermostable galactomannases that are active in extreme conditions associated with drilling and well stimulation.

There are other applications for these enzymes in various industries, such as in the beet sugar industry. 20-30% of the domestic U.S. sucrose consumption is sucrose from sugar beets. Raw beet sugar can contain a small amount of raffinose when the sugar beets are stored before processing and rotting begins to set in. Raffinose inhibits the crystallization of sucrose and also constitutes a hidden quantity of sucrose. Thus, there is merit to eliminating raffinose from raw beet sugar. α-Galactosidase has also been used as a digestive aid to break down raffinose, stachyose, and verbascose in such foods as beans and other gassy foods.

β-Galactosidases which are active and stable at high temperatures appear to be superior enzymes for the production of lactose-free dietary milk products (Chaplin, M. F. and Bucke, C. (1990) In: Enzyme Technology, pp. 159-160, Cambridge University Press, Cambridge, UK). Also, several studies have demonstrated the applicability of β-galactosidases to the enzymatic synthesis of oligosaccharides via transglycosylation reactions (Nilsson, K. G. I. (1998) Enzymatic synthesis of oligosaccharides. Trends Biotechnol. 6, 156-264; Cote, G. L. and Tao, B. Y. (1990) Oligosaccharide synthesis by enzymatic transglycosylation. Glycoconjugate J. 7, 145-162). Despite the commercial potential, only a few β-galactosidases of thermophiles have been characterized so far. Two genes reported are β-galactoside-cleaving enzymes of the hyperthermophilic bacterium *Thermotoga maritima*, one of the most themiophilic organotrophic eubacteria described to date (Huber, R., Langworthy, T. A., König, H., Thomm, M., Woese, C. R., Sleytr, U. B. and Stetter, K. O. (1986) *T. martima* sp. nov. represents a new genus of unique extremely thermophilic eubacteria growing up to 90° C., Arch. Microbiol. 144, 324-333) one of the most thermophilic organotrophic eubacteria described to date. The gene products have been identified as a β-galactosidase and a β-glucosidase.

Pullulanase is well known as a debranching enzyme of pullulan and starch. The enzyme hydrolyzes α-1,6-glucosidic linkages on these polymers. Starch degradation for the production or sweeteners (glucose or maltose) is a very important industrial application of this enzyme. The degradation of starch is developed in two stages. The first stage involves the liquefaction of the substrate with α-amylase, and the second stage, or saccharification stage, is performed by β-amylase with pullalanase added as a debranching enzyme, to obtain better yields.

Endoglucanases can be used in a variety of industrial applications. For instance, the endoglucanases of the present invention can hydrolyze the internal β-1,4-glycosidic bonds in cellulose, which may be used for the conversion of plant biomass into fuels and chemicals. Endoglucanases also have applications in detergent formulations, the textile industry, in animal feed, in waste treatment, and in the fruit juice and brewing industry for the clarification and extraction of juices.

The polynucleotides and polypeptides of the present invention have been identified as glucosidases, α-galactosidases, β-galactosidases, β-mannosidases, β-mannanases, endoglucanases, and pullalanases as a result of their enzymatic activity.

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

The invention provides an isolated nucleic acid having a sequence as set forth in SEQ ID Nos.: 1, 2, 3, 4, 5, 6, 7, 8, 9, 10, 11, 12, 13, 14, 57, 58, 59, 60, and variants thereof having at least 50% sequence identity to SEQ ID Nos.: 1, 2, 3, 4, 5, 6, 7, 8, 9, 10, 11, 12, 13, 14, 57, 58, 59 and 60, and encoding polypeptides having glycosidase activity.

One aspect of the invention is an isolated nucleic acid having a sequence as set forth in SEQ ID Nos.: 1, 2, 3, 4, 5, 6, 7, 8, 9, 10, 11, 12, 13, 14, 57, 58, 59, 60 (hereinafter referred to as "Group A nucleic acid sequences"), sequences substantially identical thereto, and sequences complementary thereto.

Another aspect of the invention is an isolated nucleic acid including at least 10 consecutive bases of a sequence as set forth in Group A nucleic acid sequences, sequences substantially identical thereto, and the sequences complementary thereto.

In yet another aspect, the invention provides an isolated nucleic acid encoding a polypeptide having a sequence as set forth in SEQ ID Nos.: 9, 10, 11, 12, 13, 14, 15, 16, 39, 40, 41, 42, 43, 44, 61, 62, 63, 64, and variants thereof encoding a polypeptide having glycosidase activity and having at least 50% sequence identity to such sequences.

Another aspect of the invention is an isolated nucleic acid encoding a polypeptide or a functional fragment thereof having a sequence as set forth in SEQ ID Nos.: 15, 16, 17, 18, 19, 20, 21, 22, 23, 24, 25, 26, 27, 28, 61, 62, 63, 64 (hereinafter referred to as "Group B amino acid sequences"), and sequences substantially identical thereto.

Another aspect of the invention is an isolated nucleic acid encoding a polypeptide having at least 10 consecutive amino acids of a sequence as set forth in Group B amino acid sequences, and sequences substantially identical thereto.

In yet another aspect, the invention provides a purified polypeptide having a sequence as set forth in Group B amino acid sequences, and sequences substantially identical thereto.

Another aspect of the invention is an isolated or purified antibody that specifically binds to a polypeptide having a sequence as set forth in Group B amino acid sequences, and sequences substantially identical thereto.

Another aspect of the invention is an isolated or purified antibody or binding fragment thereof, which specifically binds to a polypeptide having at least 10 consecutive amino acids of one of the polypeptides of Group B amino acid sequences, and sequences substantially identical thereto.

Another aspect of the invention is a method of making a polypeptide having a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in Group A nucleic acid sequences, sequences substantially identical thereto, sequences complementary to the sequences of Group A nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in Group A nucleic acid sequences, and sequences substantially identical thereto, or a polypeptide sequence as set forth in Group B amino acid sequences, and sequences substantially identical thereto.

Another aspect of the invention is a computer system including a processor and a data storage device wherein the data storage device has stored thereon a sequence as set forth in Group A nucleic acid sequences, and sequences substantially identical thereto, or a polypeptide having a sequence as set forth in Group B amino acid sequences, and sequences substantially identical thereto.

Another aspect of the invention is a method for comparing a first sequence to a reference sequence wherein the first sequence is a nucleic acid having a sequence as set forth in Group A nucleic acid sequences, and sequences substantially identical thereto, or a polypeptide code of Group B amino acid sequences, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in Group A nucleic acid sequences, and sequences substantially identical thereto, or a polypeptide having a sequence as set forth in Group B amino acid sequences, and sequences substantially identical thereto, including reading the sequence through the use of a computer program which identifies features in sequences; and identifying features in the sequence with the computer program.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. The assay includes contacting the polypeptide of Group B amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

BRIEF DESCRIPTION OF THE DRAWINGS

The following drawings are illustrative of embodiments of the invention and are not meant to limit the scope of the invention as encompassed by the claims.

FIG. 5 is an illustration of the full length DNA sequence (SEQ ID NO: 1) and the corresponding deduced amino acid sequence (SEQ ID NO: 15) of M11TL glycosidase (29G).

FIG. 6 is an illustration of the full length DNA sequence (SEQ ID NO: 2) and the corresponding deduced amino acid sequence (SEQ ID NO: 16) of OC1/4 glycosidase-33B/G.

FIG. 7 is an illustration of the full length DNA sequence (SEQ ID NO: 3) and the corresponding deduced amino acid sequence (SEQ ID NO: 17) of *Staphylothermus marinus* glycosidase-12G.

FIG. 8 is an illustration of the full length DNA sequence (SEQ ID NO: 4) and the corresponding deduced amino acid sequence (SEQ ID NO: 18) of *Thermococcus* 9N2 glycosidase-31 B/G.

FIG. 9 is an illustration of the full length DNA sequence (SEQ ID NO: 5) and the corresponding deduced amino acid sequence (SEQ ID NO: 19) of MSB8-6G.

FIG. 10 is an illustration of the full length DNA sequence (SEQ ID NO: 6) and the corresponding deduced amino acid sequence (SEQ ID NO: 20) of *Thermococcus* AEDII12RA glycosidase-18B/G.

FIG. 11 is an illustration of the full length DNA sequence (SEQ ID NO: 7) and the corresponding deduced amino acid sequence (SEQ ID NO: 21) of *Thermococcus chitonophagus* glycosidase-22G.

FIG. 12 is an illustration of the full length DNA sequence (SEQ ID NO: 8) and the corresponding deduced amino acid sequence (SEQ ID NO: 22) of *Pyrococcus furiosus* glycosidase-7G1.

FIG. 13 is an illustration of the full length DNA sequence (SEQ ID NO: 9) and the corresponding deduced amino acid sequence (SEQ ID NO: 23) of *Bankis gouldi* endoglucanase-37GP1.

FIG. 14 is an illustration of the full length DNA sequence (SEQ ID NO: 10) and the corresponding deduced amino acid sequence (SEQ ID NO: 24) of *Thermotoga maritima* alpha-galactosidase-6GC2.

FIG. 15 is an illustration of the full length DNA sequence (SEQ ID NO: 11) and the corresponding deduced amino acid sequence (SEQ ID NO: 25) of *Thermotoga maritima* beta-mannase-6GP2.

FIG. 16 is an illustration of the full length DNA sequence (SEQ ID NO: 12) and the corresponding deduced amino acid sequence (SEQ ID NO: 26) of AEPII 1 a beta-manosidase-63 GB 1.

FIG. 17 is an illustration of the full length DNA sequence (SEQ ID NO: 13) and the corresponding deduced amino acid sequence (SEQ ID NO: 27) of OC1/4V endoglucanase-33GP1.

FIG. 18 is an illustration of the full length DNA sequence (SEQ ID) NO: 14) and the corresponding deduced amino acid sequence (SEQ ID NO: 28) of *Thermotoga maritima pullulanase*-6GP3 (plasmid 6GP3 deposited with the American Type Culture Collection (ATCC), 10801 University Blvd., Manassas, Va. on Jan. 20, 2004, and having patent deposit desisgnation PTA-5788).

FIG. 19 is an illustration of the full-length DNA sequence (SEQ ID NO: 57) and the corresponding deduced amino acid sequence (SEQ ID NO: 61) of *Thermotoga maritima* MSB8-6GP2.

FIG. 20 is an illustration of the full-length DNA sequence (SEQ ID NO: 58) and the corresponding amino acid sequence (SEQ ID NO: 62) of *Thermotoga maritima* MSB8-6GP4.

FIG. 21 is an illustration of the full-length DNA sequence (SEQ ID NO: 59) and the corresponding deduced amino acid sequence (SEQ ID NO: 63) of *Bankis gouldi* 37GP4.

FIG. 22 is an illustration of the full-length DNA sequence (SEQ ID NO: 60) and the corresponding deduced amino acid sequence (SEQ ID NO: 64) of *Pyrococcus furiosus* VC1-7EG1.

DETAILED DESCRIPTION OF THE INVENTION

Figure 1:
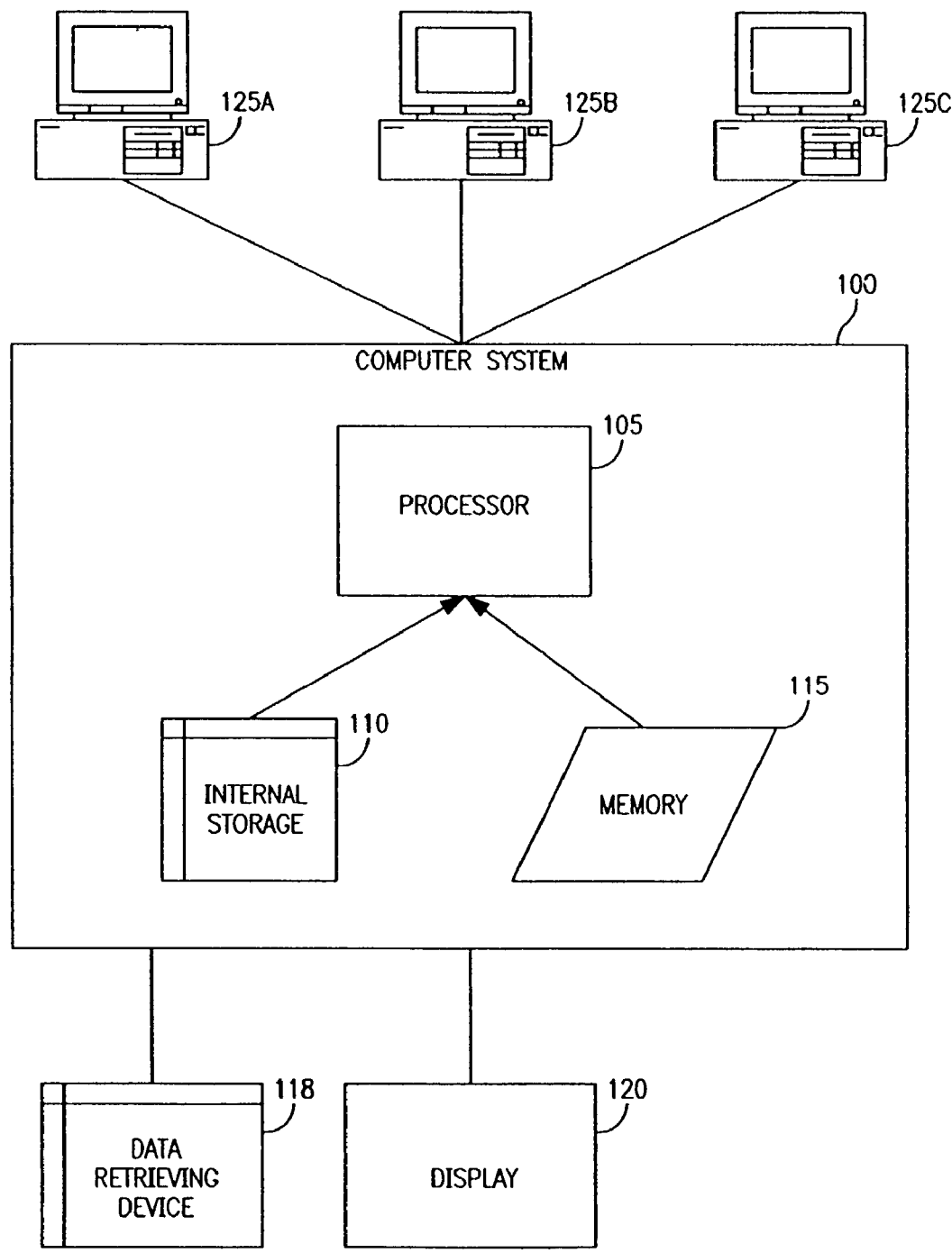
FIG. 1 is a block diagram of a computer system.

The present invention relates to glycosidases and polynucleotides encoding them. As used herein, the term "glycosidase" encompasses enzymes having hydrolase activity, for example, enzymes capable of hydrolyzing glycosidic linkages present in starch.

The polynucleotides of the invention have been identified as encoding polypeptides having glycosidase activity.

Definitions

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least 104-106 fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431 A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein axe commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37°C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucin, valine, leucine, or methionine, for another, or substitution of one polar amino acid for another, such as substitution of arginine for lysine, glutamic acid for aspartic acid or glutamine for asparagine). One or more amino acids can be deleted, for example, from a glycosidase polypeptide, resulting in modification of the structure of the polypeptide, without significantly altering its biological activity. For example, amino- or carboxyl-terminal amino acids that are not required for glycosidase biological activity can be removed. Modified polypeptide sequences of the invention can be assayed for glycosidase biological activity by any number of methods, including contacting the modified polypeptide sequence with an glycosidase substrate and determining whether the modified polypeptide decreases the amount of specific substrate in the assay or increases the bioproducts of the enzymatic reaction of a functional glycosidase polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an glycosidase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds.

Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174, herein incorporated by reference in its entirety).

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over 10100 different chimeras. Conceivably, synthetic gene reassembly can even be used to generate libraries comprised of over 101000 different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The glycosidases of the present invention can be mutagenized in accordance with the methods described herein.

Thus according to one aspect of the invention, the sequences of a plurality of progenitor nucleic acid templates (e.g., polynucleotides of Group A nucleic acid sequences) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, According to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made, intron-containing gene and a nucleic acid, which serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid glycosidases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, such as glycosidases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as *Eubacteria* and *Archaebacteria*, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., *Molecular Cloning: A Laboratory Manual, 2nd Ed.*, Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;

2) growing the host cell under conditions which promote sequence reorganization resulting in a hybrid polynucleotide in operable linkage;

3) expressing a hybrid polypeptide encoded by the hybrid polynucleotide;

4) screening the hybrid polypeptide under conditions which promote identification of enhanced biological activity; and 5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
   a) Primers that include a poly-A head and poly-T tail which when made single-stranded would provide orientation can be utilized. This is accomplished by having the first few bases of the primers made from RNA and hence easily removed RNAseH.
   b) Primers that include unique restriction cleavage sites can be utilized. Multiple sites, a battery of unique sequences, and repeated synthesis and ligation steps would be required.
   c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
   1) The use of vectors only stably maintained when the construct is reduced in complexity.
   2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, viron, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acelylated or deacetylated 4'-fluro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[α]anthracene ("BMA"), tris(2,3-dibromopropyl) phosphate ("Tris-BP"), 1,2-dibromo-3-chloropropane ("DBCP"), 2-bromoacrolein (2BA), benzo[α]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids a teach position, and a library of polypeptides encoded thereby.

One aspect of the invention is an isolated nucleic acid comprising one of the sequences of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Group A nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the Group A nucleic acid sequences, and sequences substantially identical thereto, may be used to prepare one of the polypeptides of a Group B amino acid sequence, and sequences substantially identical thereto, or fragments comprising at least 5, 10, 15, 20, 25, 30, 35, 40, 50, 75, 100, or 150 consecutive amino acids of one of the polypeptides of Group B amino acid sequences, and sequences substantially identical thereto.

Accordingly, another aspect of the invention is an isolated nucleic acid which encodes one of the polypeptides of Group B amino acid sequences, and sequences substantially identical thereto, or fragments comprising at least 5, 10, 15, 20, 25, 30, 35, 40, 50, 75, 100, or 150 consecutive amino acids of one of the polypeptides of the Group B amino acid sequences. The coding sequences of these nucleic acids may be identical to one of the coding sequences of one of the nucleic acids of Group A nucleic acid sequences, or a fragment thereof or may be different coding sequences which encode one of the polypeptides of Group B amino acid sequences, sequences substantially identical thereto, and fragments having at least 5, 10, 15, 20, 25, 30, 35, 40, 50, 75, 100, or 150 consecutive amino acids of one of the polypeptides of Group B amino acid sequences, as a result of the redundancy or degeneracy of the genetic code. The genetic code is well known to those of skill in the art and can be obtained, for example, on page 214 of B. Lewin, *Genes VI*, Oxford University Press, 1997, the disclosure of which is incorporated herein by reference.

The isolated nucleic acid which encodes one of the polypeptides bf Group B amino acid sequences, and sequences substantially identical thereto, may include, but is not limited to: only the coding sequence of one of Group A nucleic acid sequences, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of Group A nucleic acid sequences, and sequences substantially identical thereto, may be mutagenized using conventional techniques, such as site directed mutagenesis, or other techniques familiar to those skilled in the art, to introduce silent changes into the polynucleotides of Group A nucleic acid sequences, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of Group B amino acid sequences, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto (or the sequences complementary thereto) under conditions of high, moderate, or low stringency as provided herein.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. *Current Protocols in Molecular Biology*, John Wiley 503 Sons, Inc. (1997)and Sambrook et al., *Molecular Cloning: A Laboratory Manual 2nd Ed.*, Cold Spring Harbor Laboratory Press (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification-an Isothermal in vitro DNA Amplification Technique", *Nucleic Acid Research* 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an interculator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of Group A nucleic acid sequences, and sequences substantially identical thereto, may also be used in chromosome walking procedures to identify clones containing genomic sequences located adjacent to the sequences of Group A nucleic acid sequences, and sequences substantially identical thereto. Such methods allow the isolation of genes which encode additional proteins from the host organism.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2×10^7$ cpm (specific activity $4-9×10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m$–10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log [Na+])+0.41$ (fraction G+C)–(600/N) where N is the length of the probe.

If the hybridization is carried out in a solution containing formamide, the melting temperature may be calculated using the equation: $T_m=81.5+16.6(\log [Na+])+0.41$(fraction G+C)–(0.63% formamide)–(600/N) where N is the length of the probe.

Prehybridization may be carried out in 6×SSC, 5×Denhardt's reagent, 0.5% SDS, 100 μg denatured fragmented salmon sperm DNA or 6×SSC, 5×Denhardt's reagent, 0.5% SDS, 100 μg denatured fragmented salmon sperm DNA, 50% formamide. The formulas for SSC and Denhardt's solutions are listed in Sambrook et al, supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v.

AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.1 5M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 70%, at least 65%, at least 60%, at least 55%, or at least 50% homology to a nucleic acid sequence selected from the group consisting of one of the sequences of Group A nucleic acid sequences, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of Group A nucleic acid sequences or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide having the sequence of one of Group B amino acid sequences, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of Group A nucleic acid sequences, and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene.

In some embodiments, the nucleic acid encoding one of the polypeptides of Group B amino acid sequences, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., *Molecular Cloning: A Laboratory Manual 2nd Ed.*, Cold Spring Harbor Laboratory Press (1989), the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., *Molecular Cloning: A Laboratory Manual, 2nd Ed.*, Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the *genera Pseudomonas, Streptomyces,* and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of Group B amino acid sequences, and sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of Group B amino acid sequences, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11-15, 1989) and Caldwell, R. C. & Joyce G. F., PCR Methods Applic., 2:28-33, 1992, the disclosure of which is incorporated herein by reference in its entirety. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747-10751, 1994, the disclosure of which is incorporated herein by reference. Briefly, in such procedures a plurality of nucleic acids to be recombined are digested with DNAse to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis)

developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815,1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D.C., Biotechnology Research, 11:1548-1552, 1993, the disclosure of which incorporated herein by reference in its entirety. Random and site-directed mutagenesis are described in Arnold, F. H., Current Opinion in Biotechnology, 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of Group B amino acid sequences may be variants in which one or more of the amino acid residues of the polypeptides of the Group B amino acid sequences are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the Group B amino acid sequences includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of Group B amino acid sequences, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of Group B amino acid sequences, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. For example the fragments or variants of said polypeptides, may be used to catalyze biochemical reactions, which indicate that the fragment or variant retains the enzymatic activity of the polypeptides in the Group B amino acid sequences.

The assay for determining if fragments of variants retain the enzymatic activity of the polypeptides of Group B amino acid sequences, and sequences substantially identical thereto includes the steps of: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of Group B amino acid sequences, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of Group B amino acid sequences, and sequences substantially identical thereto or polynucleotides encoding such polypeptides for hydrolyzing glycosidic linkages. In such procedures, a substance containing a glycosidic linkage (e.g., a starch) is contacted with one of the polypeptides of Group B amino acid sequences, or sequences substantially identical thereto under conditions which facilitate the hydrolysis of the glycosidic linkage.

The polypeptides of Group B amino acid sequences, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of Group B amino acid sequences, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of Group B amino acid sequences, and sequences substantially identical thereto, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87-116, which is hereby incorporated by reference in its entirety.

As used herein the term "nucleic acid sequence as set forth in SEQ ID Nos.: 1, 2, 3, 4, 5, 6, 7, 8, 9, 10, 11, 12, 13, 14, 57, 58, 59 and 60" encompasses the nucleotide sequences of Group A nucleic acid sequences, and sequences substantially identical thereto, as well as sequences homologous to Group A nucleic acid sequences, and fragments thereof and sequences complementary to all of the preceding sequences. The fragments include portions of SEQ ID Nos.: 1, 2, 3, 4, 5, 6, 7, 8, 9, 10, 11, 12, 13, 14, 57, 58, 59 and 60 comprising at least 10, 15, 20, 25, 30, 35, 40, 50, 75, 100, 150, 200, 300, 400, or 500 consecutive nucleotides of Group A nucleic acid sequences, and sequences substantially identical thereto. Homologous sequences and fragments of Group A nucleic acid sequences, and sequences substantially identical thereto, refer to a sequence having at least 99%, 98%, 97%, 96%, 95%, 90%, 85%, 80%, 75%, 70%, 65%, 60%, 55%, or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the Group A nucleic acid sequences. The homologous sequences may be obtained using any of the procedures described herein or may result from the correction of a sequencing error. It will be appreciated that the nucleic acid sequences as set forth in Group A nucleic acid sequences, and sequences substantially identical thereto, can be represented in the traditional single character format (See the inside back cover of Stryer, Lubert. *Biochemistry* 3rd Ed., W. H Freeman & Co., New York.) or in any other format which records the identity of the nucleotides in a sequence.

As used herein the term "a polypeptide sequence as set forth in SEQ ID Nos.: 15, 16, 17, 18, 19, 20, 21, 22, 23, 24, 25, 26, 27, 28, 61, 62, 63 and 64" encompasses the polypeptide sequence of Group B amino acid sequences, and sequences substantially identical thereto, which are encoded by a sequence as set forth in SEQ ID Nos.:1, 2, 3, 4, 5, 6, 7, 8, 9, 10, 11, 12, 13, 14, 57, 58, 59 and 60, polypeptide sequences homologous to the polypeptides of Group B amino acid sequences, and sequences substantially identical thereto, or fragments of any of the preceding sequences.

Homologous polypeptide sequences refer to a polypeptide sequence having at least 99%, 98%, 97%, 96%, 95%, 90%, 85%, 80%, 75%, 70%, 65%, 60%, 55% or 50% homology to one of the polypeptide sequences of the Group B amino acid sequences. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of Group B amino acid sequences, and sequences substantially identical thereto. It will be appreciated that the polypeptide codes as set forth in Group B amino acid sequences, and sequences substantially identical thereto, can be represented in the traditional single character format or three letter format (See the inside back cover of Stryer, Lubert. *Biochemistry, 3rd Ed.*, W. H Freeman & Co., New York.) or in any other format which relates the identity of the polypeptides in a sequence.

It will be appreciated by those skilled in the art that a nucleic acid sequence as set forth in SEQ ID Nos.:1, 2, 3, 4, 5, 6, 7, 8, 9, 10, 11, 12, 13, 14, 57, 58, 59 and 60 and a polypeptide sequence as set forth in SEQ ID Nos.: 15, 16, 17, 18, 19, 20, 21, 22, 23, 24, 25, 26, 27, 28, 61, 62, 63 and 64 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in Group A nucleic acid sequences, and sequences substantially identical thereto, one or more of the polypeptide sequences as set forth in Group B amino acid sequences, and sequences substantially identical thereto. Another aspect of the invention is a computer readable medium having recorded thereon at least 2, 5, 10, 15, or 20 nucleic acid sequences as set forth in Group A nucleic acid sequences, and sequences substantially identical thereto.

Another aspect of the invention is a computer readable medium having recorded thereon one or more of the nucleic acid sequences as set forth in Group A nucleic acid sequences, and sequences substantially identical thereto. Another aspect of the invention is a computer readable medium having recorded thereon one or more of the polypeptide sequences as set forth in Group B amino acid sequences, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components, and data storage components used to analyze a nucleotide sequence of a nucleic acid sequence as set forth in Group A nucleic acid sequences, and sequences substantially identical thereto, or a polypeptide sequence as set forth in the Group B amino acid sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to reference sequences stored on a computer readable medium to identify homologies or structural motifs. Various sequence comparison programs identified elsewhere in this patent specification arc particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group. 575 Science Dr., Madison, Wis.), or by manual alignment and visual inspection. Other algorithms for determining homology or identity include, for example. in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCQR, BIOSCAN (Biological Sequence Comparative Analysis Node), BLIMPS (BLocks IMproved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, *M. genitalium* (Fraser et al., 1995), M. jannaschii (Bult et al., 1996), *H. influenzae* (Fleischmann et al., 1995), *E. coil* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a ward of the same length in a database sequence. T is referred to as the neighborhood word score threshold (Altschul et al., supra). These initial neighborhood word hits act as seeds for initiating searches to find longer HSPs containing them. The word hits are extended in both directions along each sequence far as ft as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

Figure 2:
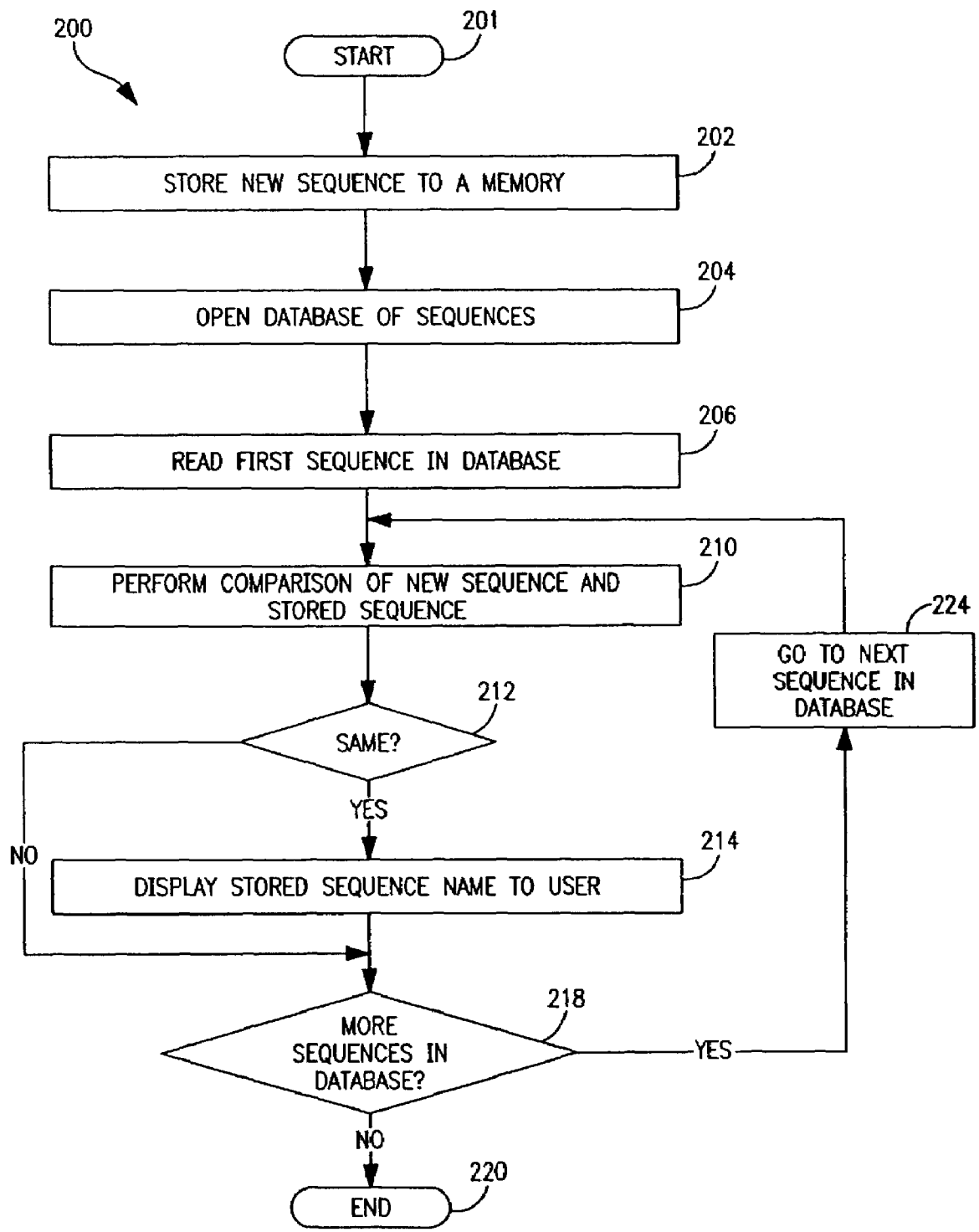
FIG. 2 is a flow diagram illustrating one embodiment of a process for comparing a new nucleotide or protein sequence with a database of sequences in order to determine the homology levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in Group A nucleic acid sequences, and sequences substantially identical thereto, or a polypeptide sequence as set forth in Group B amino acid sequences, and sequences substantially identical thereto, a data storage device having retrievably stored thereon reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto, and a sequence comparer for conducting the comparison. The sequence comparer may indicate a homology level between the sequences compared or identify structural motifs in the above described nucleic acid code of Group A nucleic acid sequences, and sequences substantially identical thereto, or a polypeptide sequence as set forth in Group B amino acid sequences, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in Group A nucleic acid sequences, and sequences substantially identical thereto, or the polypeptide sequences as set forth in Group B amino acid sequences, and sequences substantially identical thereto.

Another aspect of the invention is a method for determining the level of homology between a nucleic acid sequence as set forth in Group A nucleic acid sequences, and sequences substantially identical thereto, or a polypeptide sequence as set forth in Group B amino acid sequences, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the Group A nucleic acid sequences, or the polypeptide sequences as set forth in the Group B amino acid sequences through use of the computer program and determining homology between the nucleic acid codes or polypeptide codes and reference nucleotide sequences or polypeptide sequences.

Figure 3:
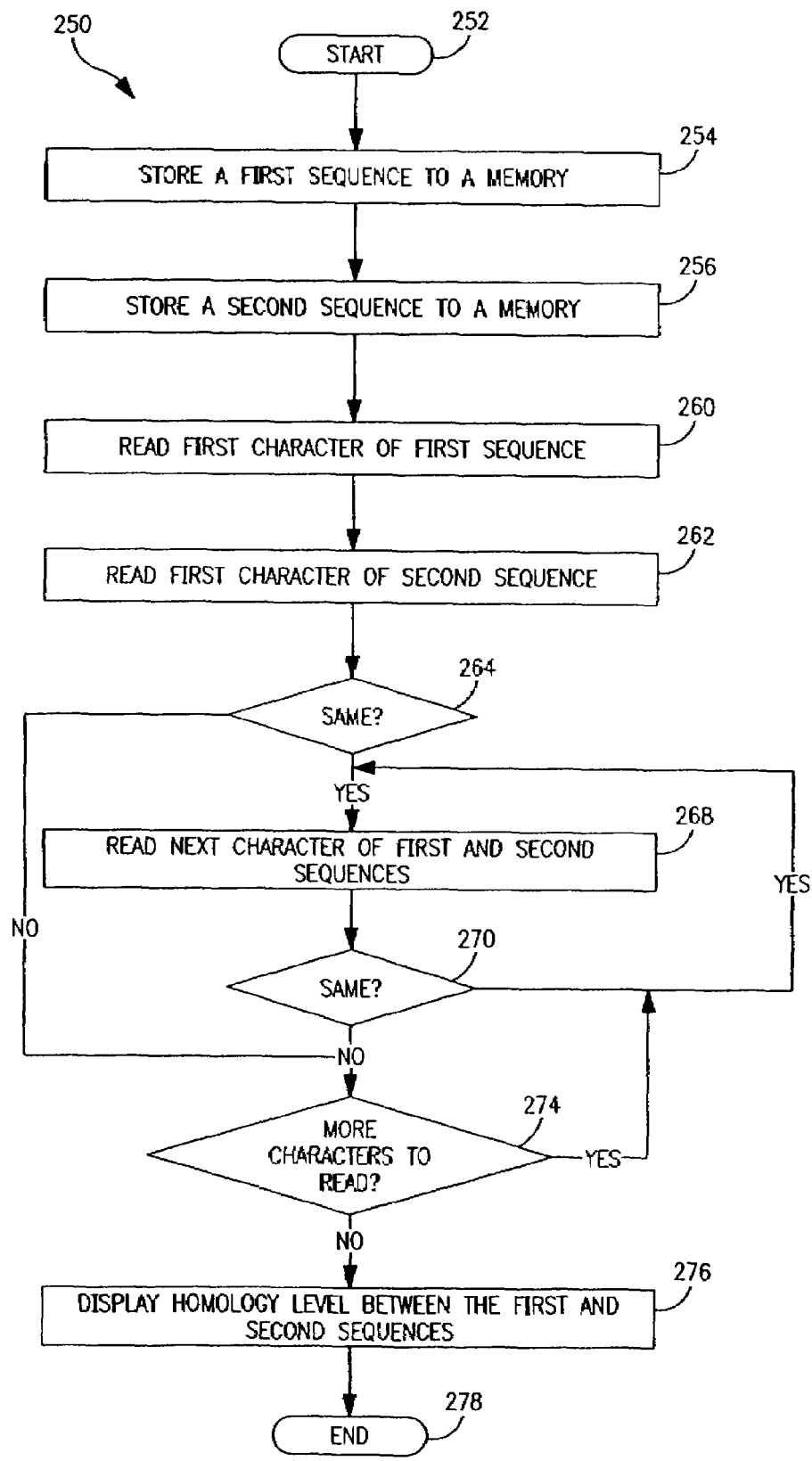
FIG. 3 is a flow diagram illustrating one embodiment of a process in a computer for determining whether two sequences are homologous.
Figure 4:
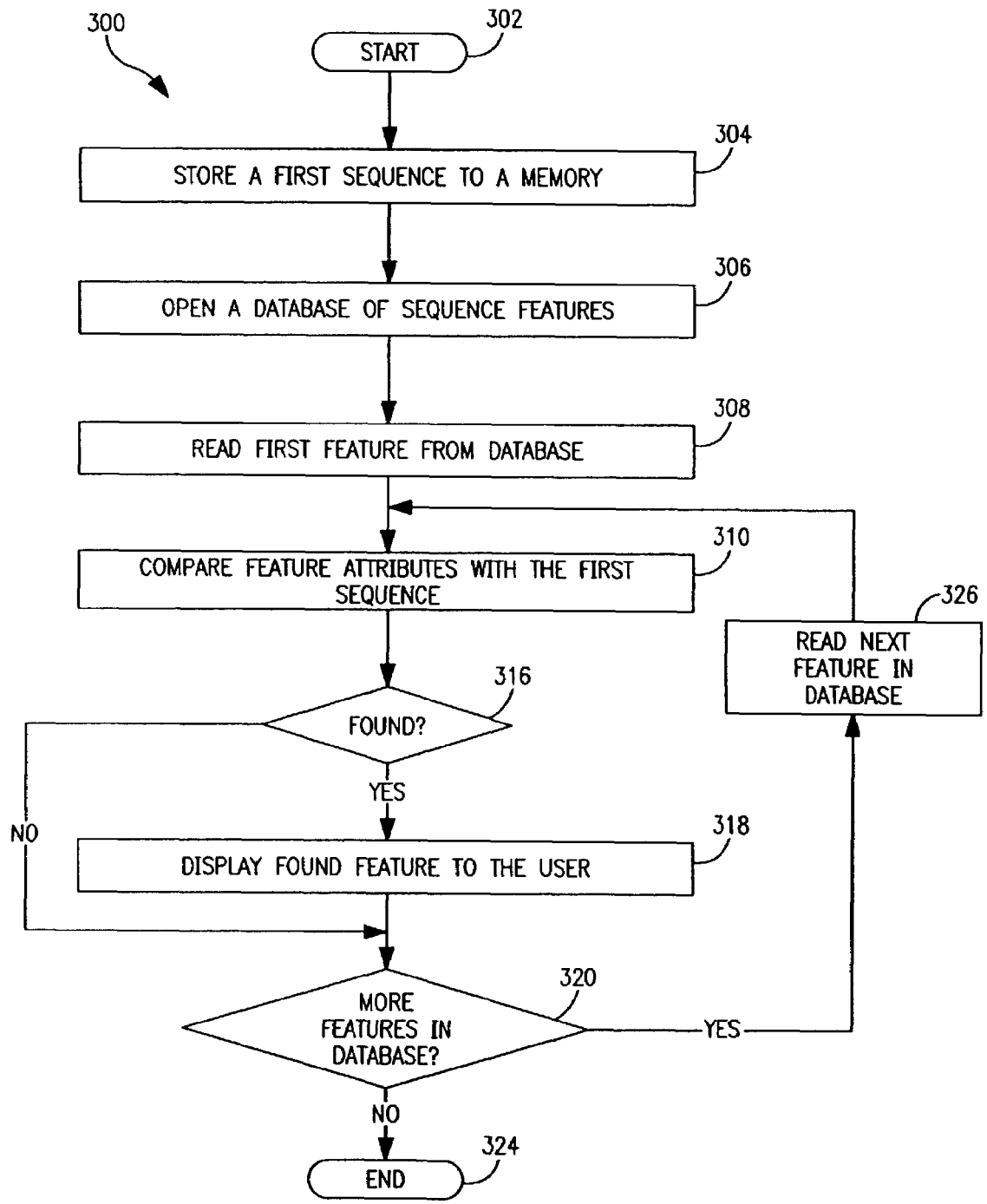
FIG. 4 is a flow diagram illustrating one embodiment of an identifier process 300 for detecting the presence of a feature in a sequence.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of Group A nucleic acid sequences, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in Group A nucleic acid sequences, and sequences substantially identical thereto. In one embodiment, the computer program may be a program which determines whether a nucleic acid sequence as set forth in Group A nucleic acid sequences, and sequences substantially identical thereto, contains a single nucleotide polymorphism (SNP) with respect to a reference nucleotide sequence.

Accordingly, another aspect of the invention is a method for determining whether a nucleic acid sequence as set forth in Group A nucleic acid sequences, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in Group A nucleic acid sequences, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the Group A nucleic acid sequences or a polypeptide sequence as set forth in Group B amino acid sequences, and sequences substantially identical thereto.

An "identifier" refers to one or more programs which identifies certain features within a nucleic acid sequence as set forth in Group A nucleic acid sequences, and sequences substantially identical thereto, or a polypeptide sequence as set forth in Group B amino acid sequences, and sequences substantially identical thereto. In one embodiment, the identifier may comprise a program which identifies an open reading frame in a nucleic acid sequence as set forth in Group A nucleic acid sequences, and sequences substantially identical thereto.

FIG. 5 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in Group A nucleic acid sequences, and sequences substantially identical thereto, or a polypeptide sequence as set forth in Group B amino acid sequences, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in Group A nucleic acid sequences, and sequences substantially identical thereto, or the polypeptide sequences as set forth in Group B amino acid sequences, and sequences substantially identical thereto, through the use of the computer program and identifying features within the nucleic acid codes or polypeptide codes with the computer program.

A nucleic acid sequence as set forth in Group A nucleic acid sequences, and sequences substantially identical thereto, or a polypeptide sequence as set forth in Group B amino acid sequences, and sequences substantially identical thereto, may be stored and manipulated in a variety of data processor programs in a variety of formats. For example, a nucleic acid sequence as set forth in Group A nucleic acid sequences, and sequences substantially identical thereto, or a polypeptide sequence as set forth in Group B amino acid sequences, and sequences substantially identical thereto, may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto. The following list is intended not to limit the invention but to provide guidance to programs and databases which are useful with the nucleic acid sequences as set forth in Group A nucleic acid sequences, and sequences substantially identical thereto, or the polypeptide sequences as set forth in Group B amino acid sequences, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMM (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds.

Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular embodiment, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library, and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

The invention will be further described with reference to the following examples; however, it is to be understood that the invention is not limited to such examples.

EXAMPLES

Example 1

Bacterial Expression and Purification of Glycosidase Enzymes

DNA encoding the enzymes of the present invention, SEQ ID NOS: 1-14 and 57-60 were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The 5' and 3' primer sequences for the respective genes are as follows:

```
Thermococcus AEDIII2RA-18B/G
5'CCGAGAATTCATTAAAGAGGAGAAATTAACTATGGTGAATGCTATGATTGTC 3'          (SEQ ID NO:29)
3'CGGAAGATCTTCATAGCTCCGGAAGCCCATA 5'                                (SEQ ID NO:30)
Vector: pQE12; and contains the following restriction enzyme sites 5'
EcoRI and 3' Big II.

OC1/4V-33B/G
5'CCGAGAATTCATTAAAGAGGAGAAATTAACTATGATAAGAAGGTCCGATTTTCC 3'         (SEQ ID NO:31)
3'CGGAAGATCTTTAAGATTTTAGAAATTCCTT 5'                                (SEQ ID NO:32)
Vector: pQE12; and contains the following restriction enzyme sites 5'
EcoRI and 3' Bgl II.

Thermococcus 9N2-31B/G
5'CCGAGAATTCATTAAAGAGGAGAAATTAACTATGCTACCAGAAGGCTTTCTC 3'           (SEQ ID NO:33)
3'CGGAGGTACCTCACCCAAGTCCGAACTTCTC 5;                                (SEQ ID NO:34)
Vector: pQE30; and contains the following restriction enzyme sites 5;
EcoRI and 3' KpnI.

Staphylothermus marinus F1-12G
5 CCGAGAATTCATTAAAGAGGAGAAATTAACTATGATAAGGTTTCCTGATTAT 3'           (SEQ ID NO:35)
3'CGGAAGATCTTTATTCGAGGTTCTTTAATCC 5'                                (SEQ ID NO:36)
Vector: pQE12; and contains the following restriction enzyme sites 5'
EcoRI and 3' Bld II.

Thermococcus chitonophagus GC74-22G
5'CCGAGAATTCATTCATTAAAGAGGAGAAATTAACTATGCTTCGAGGAGAACTTTCTC 3'      (SEQ ID NO:37)
3'CGGAGGATCCCTACCCCTCCTCTAAGATGTC 5'                                (SEQ ID NO:38)
Vector: pQE12; and contains the following restriction enzyme sites 5'
EcoRI and 3' BamHI.
```

-continued

M11TL
5'ATAATCTAGAGCATGCAATTCCCCAAAGACTTCATGATAG 3' (SEQ ID NO:39)
3'AATAAAAGCTTACTGGATCAGTGTAAGATGCT 5' (SEQ ID NO:40)
Vector: pQE70; and contains the following restriction enzyme sites 5'
SphI and 3' Hind III.

*Thermotoga maritime* MSB8-6G
5'CCGACAATTGATTAAAGAGGAGAAATTAACTATGGAAAGGATCGATGAAATT 3' (SEQ ID NO:41)
3'CGGAGGTACCTCATGGTTTGAATCTCTTCTC 5' (SEQ ID NO:42)
Vector: pQE12; and contains the following restriction enzyme sites 5'
EcoRI and 3' KpnI.

*Pyrococcus furiosus* VC1-7G1
5'CCGACAATTGATTAAAGAGGAGAAATTAACTATGTTCCCTGAAAAGTTCCTT 3' (SEQ ID NO:43)
3'CGGAGGTACCTCATCCCCTCAGCAATTCCTC 5' (SEQ ID NO:44)
Vector: pQE12; and contains the following restriction enzyme sites 5'
EcoRI and 3' KpnI.

*Bankia gouldi* endoglucanase (37GP1)
5'AATAAGGATCCGTTTAGCGACGCTCGC 3' (SEQ ID NO:45)
3'AATAAAAGCTTCCGGGTTGTACAGCGGTAATAGGC 5' (SEQ ID NO:46)
Vector: pQE52; and contains the following restriction enzyme sites 5'
Bam HI and 3' Hind III.

*Thermotoga maritima* α-galactosidase (6GC2)
5'TTTATTGAATTCATTAAAGAGGAGAAATTAACTATGATCTGTGTGGAAATATTCGGAAAG 3' (SEQ ID NO:47)
3'TCTATAAAGCTTTCATTCTCTCTCACCCTCTTCGTAGAAG 5' (SEQ ID NO:48)
Vector: pQET; and contains the following restriction enzyme sites 5'
EcoRI and 3' Hind III.

*Thermotoga maritima* α-galactosidase (6GP2)
5'TTTATTCAATTGATTAAAGAGGAGAAATTAACTATGGGGATTGGTGGGACGAC 3' (SEQ ID NO:49)
3'TTTATTAAGCTTATCTTTTCATATTCACATACCTCC 5' (SEQ ID NO:50)
Vector: pQEt; and contains the following restriction enzyme sites 5' Hind
III and 3' EcoRI.

*AEPII 1αβ-mannanase (63GB1)*
5'TTTATTGAATTCATTAAAGAGGAGAAATTAACTATGCTACCAGAAGAGTTCCTATGGGC 3' (SEQ ID NO:51)
3'TTTATTAAGCTTCTCATCAACGGCTATGGTCTTCATTTC 5' (SEQ ID NO:52)
Vector: pQEt; and contains the following restriction enzyme sites 5' Hind
III and 3' EcoRI.

*OC1/4V endoglucanase (33GP1)*
5'AAAAAACAATTGAATTCATTAAAGAGGAGAAATTAACTATGGTAGAAAGACACTTCAGATATGTTCTT 3' (SEQ ID NO:53)
3'TTTTTCGGATCCAATTCTTCATTTACTCTTTGCCTG 5' (SEQ ID NO:54)
Vector: pQEt; and contains the following restriction enzyme sites 5'
BamHI and 3' EcoRI.

*Thermotoga maritima* pullalanase (6GP3)
5'TTTTGGAATTCATTAAAGAGGAGAAATTAACTATGGAACTGATCATAGAAGGTTAC 3' (SEQ ID NO:55)
3'ATAAGAAGCTTTTCACTCTCTGTACAGAACGTACGC 5' (SEQ ID NO:56)
Vector: pQEt; and contains the following restriction enzyme sites 5'
EcoRI and 3' Hind III.

*Thermotoga maritima* MSB8-6GP2
5'CCGACAATTGATTAAAGAGGAGAAATTAACTATGGAAAGGATCGATGAAATT 3' (SEQ ID NO:65)
3'CGGAGGTACCTCATGGTTTGAATCTCTTCTC 5' (SEQ ID NO:66)
Vector: pQE12; and contains the following restriction enzyme sites 5'
EcoRI and 3' KpnI.

*Pyrococcus furiosus* VC1-7EG1
5'CCGACAATTGATTAAAGAGGAGAAATTAACTATGTTCCCTGAAAAGTTCCTT 3' (SEQ ID NO:67)
3'CGGAGGTACCTCATCCCCTCAGCAATTCCTC 5' (SEQ ID NO:68)
Vector: pQE12; and contains the following restriction enzyme sites 5'
EcoRI and 3' Kpn I.

*Bankia gouldi* endoglucanase (37GP4)
5'AATAAGGATCCGTTTAGCGACGCTCGC 3' (SEQ ID NO:69)
3'AATAAAAGCTTCCGGGTTGTACAGCGGTAATAGGC 5' (SEQ ID NO:70)
Vector: pQE52; and contains the following restriction enzyme sites 5'
BamHI and 3' Hind III.

Thermotoga maritime MSB8-6GP4
AATAACAATTGAAGGAGGAATTTAAATGGCTTATCATACCTCTGAGGACAAG (SEQ ID NO:71)
AATAAGTCGACTTAGGAAATAAGAGGTCTATC (SEQ ID NO:72)
Vector: and contains the following restriction enzyme sites 5' and 3'.

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp'), a bacterial origin of replication (ori), an IPTG-regulatable promoter operator (P/O), a ribosome binding site (RBS), a 6-His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance (Kan'). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 µg/ml) and Kan (25 µg/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Example 2

Isolation of a Selected Clone from the Deposited Genomic Clones

A clone is isolated directly by screening the deposited material using the oligonucleotide primers set forth in Example 1 for the particular gene desired to be isolated. The specific oligonucleotides are synthesized using an Applied Biosystems DNA synthesizer. The oligonucleotides are labeled with $^{32}$P-ATP using T4 polynucleotide kinase and purified according to a standard protocol (Maniatis et al., Molecular Cloning: A Laboratory Manual, Cold Spring Harbor Press, Cold Spring, N.Y., 1982). The deposited clones in the pBluescript vectors may be employed to transform bacterial hosts which are then plated on 1.5% agar plates to the density of 20,000-50,000 pfu/150 mm plate. These plates are screened using Nylon membranes according to the standard screening protocol (Stratagene, 1993). Specifically, the Nylon membrane with denatured and fixed DNA is prehybridized in 6×SSC, 20 mM NaJ$_2$PO$_4$, 0.4% SDS, 5×Denhardt's 500 µg/ml denatured, sonicated salmon sperm DNA; and 6×SSC, 0.1% SDS. After one hour of prehybridization, the membrane is hybridized with hybridization buffer 6×SSC, 20 mM NaH$_2$PO$_4$, 0.4% SDS, 500 ug/ml denatured, sonicated salmon sperm DNA with 1×10$^6$ cpm/ml $^{32}$P-probe overnight at 42° C. The membrane is washed at 45-50° C. with washing buffer 6 ×SSC, 0.1% SDS for 20-30 minutes dried and exposed to Kodak X-ray film overnight. Positive clones are isolated and purified by secondary and tertiary screening the purified clone is sequenced to verify its identity to the primer source.

Once the clone is isolated, the two oligonucleotide primers corresponding to the gene of interest are used to amplify the gene from the deposited material. A polymerase chain reaction is carried out in 25 µl of reaction mixture with 0.5 ug of the DNA of the gene of interest. The reaction mixture is 1.5-5 mM MgCl$_2$ 0.01% (w/v) gelatin, 20 µM each of dATP, dCTP, dGTP dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with the Perkin-Elmer Cetus automated thermal cycler. The amplified product is analyzed by agarose gel electrophoresis and the DNA band with expected molecular weight is excised and purified. The PCR product is verified to be the gene of interest by subcloning and sequencing the DNA product. The ends of the newly purified genes are nucleotide sequenced to identify full length sequences. Complete sequencing of full length genes is then performed by Exonuclease III digestion or primer walking.

Example 3

Screening for Galactosidase Activity

Screening procedures for α-galactosidase protein activity may be assayed for as follows:

Substrate plates were provided by a standard plating procedure. Dilute LX1-Blue MRF E. coli host of (Stratagene Cloning Systems, La Jolla, Calif.) of O.D.$_{600}$=1.0 with NZY media. In 15 ml tubes, inoculate 200 µl diluted host cells with phage. Mix gently and incubate tubes at 37° C. for 15 min. Add approximately 3.5 ml LB top agarose (0.7%) containing 1 mM IPTG to each tube and pour onto all NYZ plate surface. Allow to cool and incubate at 37° C. overnight. The assay plates arc obtained as substrate p-Nitrophenyl α-galactosidase (Sigma) (200 ml/100 ml)(100 mM NaCl, 100 mM Potassium-Phosphate) 1% (w/v) agarose. The plaques are overlayed with nitrocellulose and incubated at 4° C. for 30 minutes whereupon the nitrocellulose is removed and overlayed onto the substrate plates. The substrate plates are then incubated at 70° C. for 20 minutes.

Example 4

Screening of Clones for Mannanase Activity

A solid phase screening assay was utilized as a primary screening method to test clones for β-mannanase activity.

A culture solution of the Y1090-E. coli host strain (Stratagene Cloning Systems, La Jolla, Calif.) was diluted to O.D.$_{600}$=1.0 with NZY media. The amplified library from Thermotoga maritima lambda gtl 1 library was diluted in SM (phage dilution buffer): 5×10$^7$ pfu/µl diluted 1:1000 then 1:100 to 5×10$^2$ pfu/µl. Then 8 µl of phage dilution (5×10$^2$ pfu/µl) was plated in 200 µl host cells. They were then incubated in 15 ml tubes at 37° C. for 15 minutes.

Approximately 4 ml of molten, LP top agarose (0.7%) at approximately 52° C. was added to each tube and the mixture was poured onto the surface of LP agar plates. The agar plates were then incubated at 37° C. for five hours. The plates were replicated and induced with 10 mM IPTG-soaked Duralon-UVTM nylon membranes (Stratagene Cloning Systems, La Jolla, Calif.) overnight. The nylon membranes and plates were marked with a needle to keep their orientation and the nylon membranes were then removed and stored at 4° C.

An Azo-galactomannan overlay was applied to the LB plates containing the lambda plaques. The overlay contains 1% agarose, 50 mM potassium-phosphate buffer pH 7, 0.4%

Azocarob-galactomannan. (Megazyme, Australia). The plates were incubated at 72° C. The Azocarob-galactomannan treated plates were observed after 4 hours then returned to incubation overnight. Putative positives were identified by clearing zones on the Azocarob-galactomannan plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 µl SM (phage dilution buffer) and 25 µl CHCl$_3$.

Example 5

Screening for Clones for Mannosidase Activity

A solid phase screening assay was utilized as a primary screening method to test clones for β-mannosidase activity. A culture solution of the Y1090-*E. coli* host strain (Stratagene Cloning Systems, La Jolla, Calif.) was diluted to O.D.$_{600}$=1.0 with NZY media. The amplified library from AEPII la lambda gtl 1 library was diluted in SM (phage dilution buffer): 5×10$^7$ pfu/µl diluted 1:1000 then 1:100 to 5×10$^2$ pfu/µl. Then 8 µl of phage dilution (5×10$^2$ pfu/µl) was plated in 200 µl host cells. They were then incubated in 15 ml tubes at 37° C. for 15 minutes.

Approximately 4 ml of molten, LP top agarose (0.7%) at approximately 52° C. was added to each tube and the mixture was poured onto the surface of LP agar plates. The agar plates were then incubated at 37° C. for five hours. The plates were replicated and induced with 10 mM IPTG-soaked Duralon-UV™ nylon membranes (Stratagene Cloning Systems, La Jolla, Calif.) overnight. The nylon membranes and plates were marked with a needle to keep their orientation and the nylon membranes were then removed and stored at 4° C.

A p-nitrophenyl-β-manno-pyranoside overlay was applied to the LB plates containing the lambda plaques. The overlay contains 1% agarose, 50 mM potassium-phosphate buffer pH 7, 0.4% p-nitrophenyl-β-manno-pyranoside. (Megazyme, Australia). The plates were incubated at 72° C. The p-nitrophenyl-β-manno-pyranoside treated plates were observed after 4 hours then returned to incubation overnight. Putative positives were identified by clearing zones on the p-nitrophenyl-β-manno-pyranoside plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 µl SM (phage dilution buffer) and 25 µl CHCl$_3$.

Example 6

Screening for Pullulanase Activity

Screening procedures for pullulanase protein activity may be assayed for as follows:
Substrate plates were provided by a standard plating procedure. Host cells are diluted to O.D.$_{600}$=1.0 with NZY media. In 15 ml tubes, inoculate 200 µl diluted host cells with phage. Mix gently and incubate tubes at 37° C. for 15 minutes. Add approximately 3.5 ml LB top agarose (0.7%) is added to each tube and the mixture is plated, allowed to cool, and incubated at 37° C. for 28 hours. Overlays of 4.5 mls of the following substrate are poured:

| 100 ml total volume | |
|---|---|
| 0.5 g | Red Pullulan Red (Megazyme, Australia) |
| 1.0 g | Agarose |
| 5 ml | Buffer (Tris-HCL pH 7.2 @ 75° C.) |
| 2 ml | 5M NaCl |
| 5 ml | CaCl$_2$ (100 mM) |
| 85 ml | dH$_2$O |

Plates are cooled at room temperature, and then incubated at 75° C. for 2 hours. Positives are observed as showing substrate degradation.

Example 7

Screening for Endoglucanase Activity

Screening procedures for endoglucanase protein activity may be assayed for as follows:

i. The gene library is plated onto 6 LB/GelRite/0.1% CMC/NZY agar plates (~4,800 plaque forming units/plate) in *E. coli* host with LP agarose as top agarose. The plates are incubated at 37° C. overnight.

ii. Plates are chilled at 4° C. for one hour.

iii. The plates are overlayed with Duralon membranes (Stratagene) at room temperature for one hour and the membranes are oriented and lifted off the plates and stored at 4° C.

iv. The top agarose layer is removed and plates are incubated at 37° C. for ~3 hours.

v. The plate surface is rinsed with NaCl.

vi. The plate is stained with 0.1% Congo Red for 15 minutes.

vii. The plate is destained with 1M NaCl viii. The putative positives identified on plate are isolated from the Duralon membrane (positives are identified by clearing zones around clones). The phage is eluted from the membrane by incubating 500 µl SM+25 µl CHCl$_3$ to elute.

ix. Insert DNA is subcloned into any appropriate cloning vector and subclones are reassayed for CMCase activity using the following protocol:

a) Spin 1 ml overnight miniprep of clone at maximum speed for 3 minutes.

b) Decant the supernatant and use it to fill "wells" that have been made in an LB/GelRite/0.1% CMC plate.

c) Incubate at 37° C. for 2 hours.

d) Stain with 0.1% Congo Red for 15 minutes.

e) Destain with 1 M NaCl for 15 minutes.

f) Identify positives by clearing zone around clone.

While the invention has been described in detail with reference to certain preferred embodiments thereof, it will be understood that modifications and variations are within the spirit and scope of that which is described and claimed.

What is claimed is:

1. An isolated, synthetic or recombinant nucleic acid comprising a sequence that encodes a polypeptide having glycosidase activity, wherein said sequence is selected from the group consisting of:
   (a) a nucleic acid comprising the sequence SEQ ID NO:14, or an active fragment thereof;
   (b) a nucleic acid comprising a sequence having at least 95% sequence identity to the sequence SEQ ID NO: 14, or an active fragment thereof;
   (c) a nucleic acid comprising a sequence having at least 96% sequence identity to the sequence SEQ ID NO:14, or an active fragment thereof;
   (d) a nucleic acid comprising a sequence having at least 97% sequence identity to the sequence SEQ ID NO:14, or an active fragment thereof;
   (e) a nucleic acid comprising a sequence having at least 98% sequence identity to the sequence SEQ ID NO: 14, or an active fragment thereof;
   (f) a nucleic acid comprising a sequence having at least 99% sequence identity to the sequence SEQ ID NO: 14, or an active fragment thereof, and,
   (g) sequences fully complementary to the nucleic acids of (a) through (f).

2. An isolated, synthetic or recombinant nucleic acid encoding a polypeptide having glycosidase activity, comprising (a) a nucleic acid sequence that hybridizes under high stringency conditions to the nucleic acid sequence SEQ ID NO: 14, or (b) sequences complementary to the sequence of (a).

3. The isolated, synthetic or recombinant nucleic acid of claim 1, wherein the sequence identity is determined by a sequence comparison algorithm comprising FASTA version 3.0t78 with the default parameters.

4. A method of producing a polypeptide having a glycosidase activity comprising: (a) introducing any one of the nucleic acids of claim 1(a) through 1(f) into an isolated host cell, (b) culturing the host cell, (c) expressing from the host cell a polypeptide encoded by said nucleic acid, wherein the polypeptide has glycosidase activity, and (d) isolating the polypeptide.

5. A method of producing a polypeptide having glycosidase activity comprising: (a) introducing the nucleic acid of claim 3a into an isolated host cell, (b) culturing the host cell, (c) expressing from the host cell a polypeptide encoded by said nucleic acid, wherein the polypeptide has glycosidase activity, and (d) isolating the polypeptide.

6. A nucleic acid probe for isolation or identification of glycosidase genes consisting of an oligonucleotide from about 15 to 50 nucleotides in length, wherein the probe hybridizes to a nucleic acid having the sequence SEQ ID NO:14 under high stringency conditions.

7. The probe of claim 6, wherein the oligonucleotide comprises DNA or RNA.

8. A nucleic acid probe for isolation or identification of glycosidase genes consisting of an oligonucleotide from about 15 to 50 nucleotides in length that has at least 95% sequence identity over about 15 to 50 nucleotides of a nucleic acid having the sequence SEQ ID NO: 14, wherein the probe hybridizes to the nucleic acid under high stringency conditions.

9. The probe of claim 8, wherein the sequence identity is at least 97%.

10. The probe of claim 8, wherein the 15 to 50 nucleotides is fully complementary to the nucleic acid.

11. The probe of claim 6, wherein the oligonucleotide is 20-50 bases in length.

12. The probe of claim 6, wherein the probe further comprises a detectable isotopic or non-isotopic label.

13. The probe of claim 8, wherein the probe further comprises a detectable isotopic or non-isotopic label.

14. A nucleic acid probe for isolation or identification of glycosidase genes consisting of an oligonucleotide from about 25 to 50 nucleotides in length, wherein the probe hybridizes to a nucleic acid having the sequence SEQ ID NO:14 under high stringency conditions.

15. A nucleic acid probe for isolation or identification of glycosidase genes consisting of an oligonucleotide from about 25 to 50 nucleotides in length having at least 95% sequence identity over about 25 to 50 nucleotides of a nucleic acid having the sequence SEQ ID NO:14, wherein the probe hybridizes to the nucleic acid under high stringency conditions.

16. A nucleic acid probe for isolation or identification of glycosidase genes consisting of an oligonucleotide from about 25 to 50 nucleotides in length having at least 97% sequence identity over about 25 to 50 nucleotides of a nucleic acid having the sequence SEQ ID NO:14, wherein the probe hybridizes to the nucleic acid under high stringency conditions.

17. A nucleic acid probe for isolation or identification of glycosidase genes consisting of a polynucleotide comprising at least 15 consecutive nucleotides of a nucleic acid having the sequence SEQ ID NO:14, wherein the probe hybridizes to the nucleic acid under high stringency conditions.

18. The nucleic acid probe of claim 15, wherein the probe is used for isolation or identification of pullulanase genes.

19. The probe of claim 12 or claim 13, wherein the detectable non-isotopic label comprises a fluorescent molecule, a chemiluminescent molecule, an enzyme, a cofactor, an enzyme substrate, a hapten or a combination thereof.

20. The probe of claim 14, wherein the probe further comprises a detectable isotopic or non-isotopic label.

21. The probe of claim 17, wherein the probe further comprises a detectable isotopic or non-isotopic label.

22. The probe of claim 20 or claim 21, wherein the detectable non-isotopic label comprises a fluorescent molecule, a chemiluminescent molecule, an enzyme, a cofactor, an enzyme substrate, a hapten or a combination thereof.

23. The isolated, synthetic or recombinant nucleic acid of claim 1(a) through 1(f), wherein the glycosidase activity comprises a pullulanase activity.

24. The isolated, synthetic or recombinant nucleic acid of claim 2, wherein the glycosidase activity comprises a Pullulanase activity.

25. The nucleic acid probe of claim 16, wherein the a probe is used for isolation or identification of pullulanase genes.

26. The method of claim 4, wherein the glycosidase activity comprises a pullulanase activity.

27. The method of claim 5, wherein the glycosidase activity comprises a pullulanase activity.

28. The nucleic acid probe of claim 6, wherein the probe is used for isolation or identification of pullulanase genes.

29. The nucleic acid probe of claim 14, wherein the probe is used for isolation or identification of pullulanase genes.

30. A vector comprising the nucleic acid of claim 1.

31. An isolated host cell comprising the vector of claim 30.

32. The nucleic acid probe of claim 17, wherein the probe is used for isolation or identification of pullulanase genes.

33. An isolated, synthetic or recombinant nucleic acid comprising a sequence that encodes a polypeptide having glycosidase activity, wherein said polypeptide is selected from the group consisting of:
  (a) a polypeptide comprising the sequence SEQ ID NO:28, or an active fragment thereof;
  (b) a polypeptide comprising a sequence having at least 95% sequence identity to the sequence SEQ ID NO: 28, or an active fragment thereof;
  (c) polypeptide comprising a sequence having at least 96% sequence identity to the sequence SEQ ID NO: 28, or an active fragment thereof;
  (d) a polypeptide comprising a sequence having at least 97% sequence identity to the sequence SEQ ID NO: 28, or an active fragment thereof;
  (e) polypeptide comprising a sequence having at least 98% sequence identity to the sequence SEQ ID NO: 28, or an active fragment thereof; and
  (f) a polypeptide comprising a sequence having at least 99% sequence identity to the sequence SEQ ID NO: 28, or an active fragment-thereof.

34. A method of producing a polypeptide having glycosidase activity comprising: (a) introducing any one of the nucleic acids of claim 33 into an isolated host cell, (b) culturing the host cell, (c) expressing from the host cell a polypeptide encoded by said nucleic acid, wherein the polypeptide has glycosidase activity, and (d) isolating the polypeptide.

35. An isolated, synthetic or recombinant nucleic acid encoding a polypeptide having glycosidase activity, comprising (a) a nucleic acid sequence that hybridizes under high stringency conditions to a nucleic acid encoding a polypeptide having the amino sequence SEQ ID NO:28, or (b) a nucleic acid sequence that hybridizes under high stringency conditions to the complement of a nucleic acid encoding a polypeptide having the amino sequence SEQ ID NO:28.

36. A method of producing a polypeptide having glycosidase activity comprising: (a) introducing the nucleic acid of claim 35 into an isolated host cell, (b) culturing the host cell, (c) expressing from the host cell a polypeptide encoded by said nucleic acid, wherein the polypeptide has glycosidase activity, and (d) isolating the polypeptide.

37. The isolated, synthetic or recombinant nucleic acid of claim 33, wherein the glycosidase activity comprises pullulanase activity.

38. The isolated, synthetic or recombinant nucleic acid of claim 34, wherein the glycosidase activity comprises pullulanase activity.

39. The isolated, synthetic or recombinant nucleic acid of claim 35, wherein the glycosidase activity comprises pullulanase activity.

40. The isolated, synthetic or recombinant nucleic acid of claim 36, wherein the glycosidase activity comprises pullulanase activity.

41. A vector comprising the nucleic acid of claim 2.

42. A vector comprising the nucleic acid of claim 33.

43. A vector comprising the nucleic acid of claim 35.

44. An isolated host cell comprising the vector of claim 41.

45. An isolated host cell comprising the vector of claim 42.

46. An isolated host cell comprising the vector of claim 43.

47. The nucleic acid probe of claim 11, wherein the probe is used for isolation or identification of pullulanase genes.

48. The nucleic acid probe of claim 11, wherein the probe is used for isolation or identification of pullulanase genes.

49. The probe of claim 11, wherein the probe further comprises a detectable isotopic or non-isotopic label.

50. The probe of claim 49, wherein the detectable non-isotopic label comprises a fluorescent molecule, a chemiluminescent molecule, an enzyme, a cofactor, an enzyme substrate, a hapten or a combination thereof.

* * * * *